US008604278B2

(12) United States Patent
Heim et al.

(10) Patent No.: US 8,604,278 B2
(45) **Date of Patent: *Dec. 10, 2013**

(54) EXPRESSION CASSETTES FOR TRANSGENIC EXPRESSION OF NUCLEIC ACIDS

(75) Inventors: Ute Heim, Gatersleben (DE); Helke Hillebrand, Mannheim (DE); Irene Kunze, Gatersleben (DE); Karin Herbers, Neustadt (DE); Uwe Sonnewald, Quedlinburg (DE); Eric Glickmann, Ditfurt (DE); Wolfgang Lein, Potsdam (DE); Rüdiger Hell, Quedlinburg (DE); Ricarda Jost, Quedlinburg (DE)

(73) Assignee: SunGene GmbH & Co. KGaA, Gatersleben (DE)

( * ) Notice: Subject to any disclaimer, the term of this patent is extended or adjusted under 35 U.S.C. 154(b) by 85 days.

This patent is subject to a terminal disclaimer.

(21) Appl. No.: 13/113,615

(22) Filed: May 23, 2011

(65) Prior Publication Data

US 2011/0289622 A1 Nov. 24, 2011

Related U.S. Application Data

(60) Division of application No. 10/755,677, filed on Jan. 13, 2004, now Pat. No. 8,022,272, which is a continuation-in-part of application No. PCT/EP02/07527, filed on Jul. 5, 2002.

(30) Foreign Application Priority Data

| | | |
|---|---|---|
| Jul. 13, 2001 | (DE) | 101 33 407 |
| Dec. 4, 2001 | (DE) | 101 59 455 |
| Feb. 22, 2002 | (DE) | 102 07 582 |

(51) Int. Cl.

| | |
|---|---|
| ***A01H 5/00*** | (2006.01) |
| ***C12N 15/63*** | (2006.01) |
| ***C12N 15/82*** | (2006.01) |
| ***C12N 15/87*** | (2006.01) |
| ***C12N 5/14*** | (2006.01) |
| ***C07H 21/00*** | (2006.01) |
| ***C07H 21/04*** | (2006.01) |

(52) U.S. Cl.
USPC ........ 800/295; 800/278; 800/289; 435/320.1; 435/419; 435/468; 536/23.6; 536/24.1

(58) Field of Classification Search
None
See application file for complete search history.

(56) References Cited

U.S. PATENT DOCUMENTS

| | | | | |
|---|---|---|---|---|
| 4,237,224 | A | 12/1980 | Cohen et al. | |
| 4,987,071 | A | 1/1991 | Cech et al. | |
| 5,463,175 | A | 10/1995 | Barry et al. | |
| 5,510,471 | A | 4/1996 | Lebrun et al. | |
| 5,612,472 | A | 3/1997 | Wilson et al. | |
| 5,627,061 | A | 5/1997 | Barry et al. | |
| 5,633,435 | A | 5/1997 | Barry et al. | |
| 5,776,760 | A | 7/1998 | Barry et al. | |
| 5,864,425 | A | 1/1999 | Filas | |
| 5,990,387 | A * | 11/1999 | Tomes et al. | 800/293 |
| 6,110,736 | A | 8/2000 | Hodges et al. | |
| 6,169,226 | B1 | 1/2001 | Ek et al. | |
| 6,225,105 | B1 * | 5/2001 | Sathasivan et al. | 435/252.2 |
| 6,229,067 | B1 | 5/2001 | Sonnewald et al. | |
| 2002/0160378 | A1 * | 10/2002 | Harper et al. | 435/6 |
| 2011/0191912 | A1 * | 8/2011 | Alexandrov et al. | 800/298 |

FOREIGN PATENT DOCUMENTS

| | | | |
|---|---|---|---|
| EP | 0 120 516 | A2 | 10/1984 |
| EP | 0 218 571 | A2 | 4/1987 |
| EP | 0 257 993 | A2 | 3/1988 |
| EP | 0 291 533 | A1 | 11/1988 |
| EP | 0 321 201 | A2 | 6/1989 |
| EP | 0 360 257 | A2 | 3/1990 |
| EP | 0 601 092 | A1 | 6/1994 |
| EP | 0 807 836 | A2 | 11/1997 |
| WO | WO-91/13991 | A1 | 9/1991 |
| WO | WO-97/12983 | A1 | 4/1997 |
| WO | WO-97/25346 | A1 | 7/1997 |
| WO | WO-97/41228 | A2 | 11/1997 |
| WO | WO-97/42326 | A2 | 11/1997 |
| WO | WO-98/11240 | A2 | 3/1998 |
| WO | WO-98/26045 | A1 | 6/1998 |
| WO | WO-98/45456 | A1 | 10/1998 |
| WO | WO-98/50561 | A1 | 11/1998 |
| WO | WO-99/04013 | A2 | 1/1999 |
| WO | WO-99/05902 | A1 | 2/1999 |
| WO | WO-99 06580 | A2 | 2/1999 |
| WO | WO-99/27116 | A2 | 6/1999 |

(Continued)

OTHER PUBLICATIONS

Kim et al. (Plant Molecular Biology, 24:105-117, 1994).*
Benfey et al., Science 250:959-966, 1990.*
De Block et al. (The EMBO Journal, 6:2513-2518, 1987).*
Jost et al. (GenBank Accession No. AJ272027, Published Feb. 9, 2000).*
Jost et al. (Gene, 253: 237-247, 2000).*
Holtorf, S., et al., "Comparison of Different Constitutive and Inducible Promoters for the Overexpression of Transgenes in *Arabidopsis thaliana*", Plant Molecular Biology, vol. 29, (1995), pp. 637-646.
Elliott, R. C., et al., "cis-Acting Elements for Light Regulation of Pea Ferredoxin I Gene Expression are Located within Transcribed Sequences", Plant Cell, vol. 1, (1989), pp. 691-698.
Luebberstedt, T., et al., "Promoters from Genes for Plastid Proteins Possess Regions with Different Sensitivities Toward Red and Blue Light", Plant Physiology, vol. 104, (1994), pp. 997-1006.

(Continued)

*Primary Examiner* — Vinod Kumar
(74) *Attorney, Agent, or Firm* — Novak Druce Connolly Bove + Quigg LLP

(57) ABSTRACT

The invention relates to expression cassettes and vectors which contain constitutive promoters of plants and to the use of these expression cassettes or vectors for transgenic expression of nucleic acid sequences, preferably selection markers, in organisms, preferably in plants. The invention further relates to transgenic plants which have been transformed with the expression cassettes or vectors, to cultures, parts or propagation material derived from these plants, and to the use of these plants for the production of food and animal feedstuffs, seed, pharmaceuticals, or fine chemicals.

29 Claims, 8 Drawing Sheets

(56) References Cited

FOREIGN PATENT DOCUMENTS

| | | | |
|---|---|---|---|
| WO | WO-99/31258 | A1 | 6/1999 |
| WO | WO-99/32619 | A1 | 7/1999 |
| WO | WO-99/45456 | A1 | 9/1999 |
| WO | WO-99/53050 | A1 | 10/1999 |
| WO | WO-00/00512 | A2 | 1/2000 |
| WO | WO-00/37662 | A2 | 6/2000 |
| WO | WO-00/44895 | A1 | 8/2000 |
| WO | WO-00/44914 | A1 | 8/2000 |
| WO | WO-00/49035 | A1 | 8/2000 |
| WO | WO-00/63364 | A2 | 10/2000 |
| WO | WO-00/68374 | A1 | 11/2000 |

OTHER PUBLICATIONS

Petracek, M. E., et al., "Light-Regulated Changes in Abundance and Polyribosome Association of Ferredoxin mRNA are Dependent on Photosynthesis", Plant Cell, vol. 9, (1997), pp. 2291-2300.
Gallo-Meagher, M., et al., "The Pea Ferredoxin I Gene Exhibits Different Light Responses in Pea and Tobacco", Plant Cell, vol. 4, (1992), pp. 383-388.
GeneBank Accession No. Z97337, Jun. 29, 1999.
GeneBank Accession No. AB011474, Feb. 14, 2004.
GeneBank Accession No. A19545, Apr. 26, 1994.
GeneBank Accession No. A19546, Apr. 26, 1994.
GeneBank Accession No. A19547, Apr. 26, 1994.
GeneBank Accession No. A19451, Jun. 10, 1994.
GeneBank Accession No. AF017451, Jul. 3, 2001.
GeneBank Accession No. AB006698, Feb. 14, 2004.
GeneBank Accession No. AB025109, Mar. 27, 1999.
GeneBank Accession No. AB044391, Jun. 9, 2000.
GeneBank Accession No. AB045592, Jun. 2, 2001.
GeneBank Accession No. AB045593, Jun. 2, 2001.
GeneBank Accession No. AB049823, Apr. 14, 2001.
GeneBank Accession No. AB061022, May 3, 2001.
GeneBank Accession No. AF078796, Dec. 11, 1998.
GeneBank Accession No. AF080389, Jul. 21, 1999.
GeneBank Accession No. AF080390, Jul. 21, 1999.
GeneBank Accession No. AF094326, Nov. 1, 1998.
GeneBank Accession No. AF234298, Apr. 24, 2000.
GeneBank Accession No, AF234299, Apr. 24, 2000.
GeneBank Accession No. AF234300, Apr. 24, 2000.
GeneBank Accession No. AF234301, Apr. 24, 2000.
GeneBank Accession No. AF234314, Apr. 24, 2000.
GeneBank Accession No. AF234315, Apr. 24, 2000.
GeneBank Accession No. AF234316, Apr. 24, 2000.
GeneBank Accession No. AF276302, Jul. 2, 2001.
GeneBank Accession No. AF294981, May 24, 2002.
GeneBank Accession No. AF354045, Apr. 16, 2001.
GeneBank Accession No. AF354046, Apr. 16, 2001.
GeneBank Accession No. AJ222980, May 24, 2002.
GeneBank Accession No. AL133315, Dec. 2, 1999.
GeneBank Accession No. AR123356, May 16, 2001.
GeneBank Accession No. AX022820, Sep. 7, 2000.
GeneBank Accession No. AX022822, Sep. 7, 2000.
GeneBank Accession No. E01313, Sep. 29, 1997.
GeneBank Accession No. AF306348, Apr. 9, 2001.
GeneBank Accession No. I05373, Dec. 2, 1994.
GeneBank Accession No. I05376, Dec. 2, 1994.
GeneBank Accession No. L25042, Feb. 6, 1997.
GeneBank Accession No. M22827, Jul. 14, 1993.
GeneBank Accession No. S78423, Sep. 27, 1995.
GeneBank Accession No. U00004, May 18, 1994.
GeneBank Accession No. U32624, Jan. 20, 1996.
GeneBank Accession No. U77378, Mar. 20, 1997.
GeneBank Accession No. X05822, Feb. 10, 1999.
GeneBank Accession No. X07644, Sep. 12, 1993.
GeneBank Accession No. X07645, Sep. 12, 1993.
GeneBank Accession No. X14074, May 9, 1995.
GeneBank Accession No. X17220, Sep. 12, 1993.
GeneBank Accession No. X51366, Feb. 10, 1999.
GeneBank Accession No. X51370, Feb. 23, 1995.
GeneBank Accession No. X51514, Sep. 12, 1993.
GeneBank Accession No. X63374, Sep. 4, 1996.
GeneBank Accession No. X65876, Jul. 7, 2002.
GeneBank Accession No. X72592, Nov. 15, 1993.
GeneBank Accession No. X74985, Nov. 21, 1996.
GeneBank Accession No. X78815, Apr. 11, 1997.
GeneBank Accession No. Y14032, Jun. 27, 1997.
GeneBank Accession No. Z26489, May 12, 1995.
Al-Kaff, N. S., et al., "Plants Rendered Herbicide-Susceptible by Cauliflower Mosaic Virus-Elicited Suppression of a 35S Promoter-Regulated Transgene", Nature Biotechnology, vol. 18, (2000), pp. 995-999.
An, G., et al., "New Cloning Vehicles for Transformation of Higher Plants", The EMBO Journal, vol. 4, No. 2, (1985), pp. 277-284.
Atanassova, R., et al., "Functional Analysis of the Promoter Region of a Maize (*Zea mays* L.) H3 Histone Gene in Transgenic *Arabidopsis thaliana*", Plant Molecular Biology, vol. 37, (1998), pp. 275-285.
Battraw, M.J., et al., "Histochemical Analysis of CaMV 35S Promoter-β-Glucuronidase Gene Expression in Transgenic Rice Plants", Plant Molecular Biology, vol. 15, (1990), pp. 527-538.
Banerji, A., et al., "1,3-Dipolar Cycloadditions: Part II-Cycloaddition of 1-Pyrroline 1-Oxide to 1-Cinnamoyl Piperidine and 1-(4'-Chlorocinnamoyl) Piperidine", Indian Journal of Chemistry, vol. 37B, (1998), pp. 15-22.
Bartel, D. P., et al., "Isolation of New Ribozymes from a Large Pool of Random Sequences", Science, vol. 261, (1993), pp. 1411-1418.
Bayley, C. C., et al., "Exchange of Gene Activity in Transgenic Plants Catalyzed by the Cre-*lox* Site-Specific Recombination System", Plant Molecular Biology, vol. 18, (1992), pp. 353-361.
Beaudoin, F., et al., "Heterologous Reconstitution in Yeast of the Polyunsaturated Fatty Acid Biosynthetic Pathway", PNAS, vol. 97, No. 12, (2000), pp. 6421-6426.
Becker, D., et al., Fertile Transgenic Wheat from Microprojectile Bombardment of Scutellar Tissue, The Plant Journal, vol. 5, No. 2, (1994), pp. 299-307.
Beerli, R. R., et al., "Positivie and Negative Regulation of Endogenous Genes by Designed Transcription Factors", PNAS, vol. 97, No. 4, (2000), pp. 1495-1500.
Benfey, P., et al., "Tissue-Specific Expression from CaMV 35S Enhancer Subdomains in Early Stages of Plant Development", The EMBO Journal, vol. 9, No. 6, (1990), pp. 1677-1684.
Bevan, M., "Binary *Agrobacterium* Vectors for Plant Transformation", Nucleic Acids Research, vol. 12, No. 22, (1984), pp. 8711-8721.
Bolivar, F., et al., "Construction and Characterization of New Cloning Vehicles. II. A Multipurpose Cloning System", Gene, vol. 2, (1997), pp. 95-113.
Broglie, K., et al., "Transgenic Plants with Enhanced Resistance to the Fungal Pathogen *Rhizoctonia solani*", Science, vol. 254, (1991), pp. 1194-1997.
Callis, J., et al., "Ubiquitin Extension Proteins of *Arabidopsis thaliana*: Structure, Localization, and Expression of their Promoters in Transgenic Tobacco", The Journal of Biological Chemistry, vol. 265, No. 21, (1990), pp. 12486-12493.
Cheng, X., et al., "*Agrobacterium*-Transformed Rice Plants Expressing Synthetic *crylA*(*b*) and *ctylA*(*c*) Genes are Highly Toxic to Striped Stem Borer and Yellow Stem Borer", Proc. Natl. Acad. Sci. USA, vol. 95, (1998), pp. 2767-2772.
Chiu, W-L., et al., "Engineered GFP as a Vital Reporter in Plants", Current Biology, vol. 6, No. 3, (1996), pp. 325-330.
Christensen, A. H., et al., "Maize Polyubiquitin Genes: Structure, Thermal Perturbation of Expression and Transcript Splicing, and Promoter Activity Following Transfer to Protoplasts by Electroporation", Plant Molecular Biology, vol. 18, (1992), pp. 675-689.
Christensen, A. H., et al, "Ubiquitin Promoter-Based Vectors for High-Level Expression of Selectable and/or Screenable Marker Genes in Monocotyledonous Plants", Transgenic Research, vol. 5, (1996), pp. 213-218.
Cole, D.J., "Mode of Action of Glyphosate—A Literature Analysis", Chapter 5 in The Herbicide Glyphosate. Grossbard & Atkinson eds., Butterworths & Co. Ltd.: Boston, (1985), pp. 48-74.

(56) References Cited

OTHER PUBLICATIONS

Comai, L., et al., "Novel and Useful Properties of a Chimeric Plant Promoter Combining CaMV 35S and MAS Elements", Plant Molecular Biology, vol. 15, (1990), pp. 373-381.
Cummins, J., "Hazardous CaMV Promoter?", Nature Biotechnology, vol. 18, (2000), p. 363.
Cushman, J.C., et al., "Expression of a Phosphoenolpyruvate Carboxylase Promoter from *Mesembryanthemum crystallinum* is Not Salt-Inducible in Mature Transgenic Tobacco", Plant Molecular Biology, vol. 21, (1993), pp. 561-566.
Datta, N., "The Purification and Properties of a Penicillinase whose Synthesis is Mediated by an R-Factor in *Escherichia coli*", Biochem J., vol. 98, (1966), pp. 204-209.
Deak, M., et al., "Plants Ectopically Expressing the Iron-Binding Protein, Ferritin, are Tolerant to Oxidative Damage and Pathogens", Nature Biotechnology, vol. 17, (1999), pp. 192-196.
De Block, M., et al., "Engineering Herbicide Resistance in Plants by Expression of a Detoxifying Enzyme", The EMBO Journal, vol. 6, No. 9, (1987), pp. 2513-2518.
Dellaporta, S. L., et al., "Molecular Cloning of the Maize R-*nj* Allele by Transposon Tagging with Ac", In Chromosome Structure and Function: Impact of New Concepts, 18th Stadler Genetics Symposium, vol. 11, (1988), pp. 263-282.
Dunwell, J. M., "Transgenic Approaches to Crop Improvement", Journal of Experimental Botany, vol. 51, (2000), pp. 487-496.
Dunwell, J.M., "Cupins: A New Superfamily of Functionally Diverse Proteins that Include Germins and Plant Storage Proteins", Biotechnology and Genetic Engineering Reviews, vol. 15, (1998), pp. 1-32.
Ebinuma, H., et al., "Selection of Marker-Free Transgenic Plants Using the Isopentenyl Transferase Gene", Proc. Natl. Acad. Sci. USA, vol. 94, (1997), pp. 2117-2121.
Fedoroff, N. V., et al., "A Versatile System for Detecting Transposition of *Arabidopsis*", The Plant Journal, vol. 3, No. 2, (1993), pp. 273-289.
Fire, A., et al., "Potent and Specific Genetic Interference by Double-Stranded RNA in *Caenorhabditis elegans*", Nature, vol. 391, (1998), pp. 806-811.
Fischer, K., et al., "A New Class of Plastidic Phosphate Translocators: A Putative Link Between Primary and Secondary Metabolism by the Phosphoenolpyruvate/Phosphate Antiporter", The Plant Cell, vol. 9, (1997), pp. 453-462.
Forkmann, G., et al., "Metabolic Engineering and Applications of Flavonoids", Current Opinion in Biotechnology, vol. 12, (2001), pp. 155-160.
Fraley, R. T., et al., "Genetic Transformation in Higher Plants", Critical Reviews in Plant Sciences, vol. 4, No. 1, (1986), pp. 1-46.
Fromm, M., et al., "Expression of Genes Transferred into Monocot and Dicot Plant Cells by Electroporation", Proc. Natl. Acad. Sci. USA, vol. 82, (1985), pp. 5824-5828.
Gallie, D. R., et al., "A Comparison of Eukaryotic Viral 5'-leader Sequences as Enhancers of mRNA Expression in vivo", Nucleic Acids Research, vol. 15, No. 21, (1987), pp. 8693-8711.
Gautier, C., et al., "α-DNA IV: α-Anomeric and β-Anomeric Tetrathymidylates Covalently Linked to Intercalating Oxazolopyridocarbazole. Synthesis, Physicochemical Properties and Poly (rA) Binding", Nucleic Acids Research, vol. 15, No. 16, (1987), pp. 6625-6641.
Gielen, Jr., et al., "The Complete Nucleotide Sequence of the TL-DNA of the *Agrobacterium tumefaciens* Plasmid pTiAch5", The EMBO Journal, vol. 3, No. 4, (1984), pp. 835-846.
Girke, T., et al., "Identification of a Novel Δ6-acyl-group Desaturase by Targeted Gene Disruption in *Physcomitrella patens*", The Plant Journal, vol. 15, No. 1, (1998), pp. 39-48.
Gleave, A. P., et al., "Selectable Marker-Free Transgenic Plants Without Sexual Crossing: Transient Expression of *cre* Recombinase and Use of a Conditional Lethal Dominant Gene", Plant Molecular Biology, vol. 40, (1999), pp. 223-235.
Goring, D., R., et al., "Transformation of a Partial Nopaline Synthase Gene into Tobacco Suppresses the Expression of a Resident Wild-Type Gene", Proc. Natl. Acad. Sci. USA, vol. 88, (1991), pp. 1770-1774.
Hajdukiewicz, P., et al., "The Small, Versatile *pPZP* Family of *Agrobacterium* Binary Vectors for Plant Transformation", Plant Molecular Biology, vol. 25, (1994), pp. 989-994.
Hamilton, A.J., et al., "Sense and Antisense Inactivation of Fruit Ripening Genes in Tomato", Curr. Top. Microbiol. Immunol., vol. 197, (1995), pp. 77-89.
Haseloff, J., et al., "Simple RNA Enzymes with New and Highly Specific Endoribonuclease Activities", Nature, vol. 334, (1988), pp. 585-591.
Hoseloff, J., et al., "Removal of a Cryptic Intron and Subcellular Localization of Green Fluorescent Protein are Required to Mark Transgenic *Arabidopsis* Plants Brightly", Proc. Natl. Acad. Sci. USA, vol. 94, (1997), pp. 2122-2127.
Helene, C., "The Anti-Gene Strategy: Control of Gene Expression by Triplex-Forming-Oligonucleotides", Anti-Cancer Drug Design, vol. 6, (1991), pp. 569-584.
Helene, C., et al., "Control of Gene Expression by Triple Helix-Forming Oligonucleotides", Annals of the New York Academy of Sciences, vol. 660, (1992), pp. 27-36.
Higo, K., et al., "Plant cis-acting Regulatory DNA Elements (PLACE) Database: 1999", Nucleic Acids Research, vol. 27, No. 1, (1999), pp. 297-300.
Ho, M.-W., et al., "Cauliflower Mosaic Viral Promoter—A Recipe for Disaster?", Microbial Ecology in Health and Disease, vol. 11, (1999), pp. 194-197.
Heffron, F., et al., "Origin of the TEM Beta-Lactamase Gene Found on Plasmids", Journal of Bacteriology, vol. 122, No. 1, (1975), pp. 250-256.
Holsers, M., et al., "Transfection and Transformation of *Agrobacterium tumefaciens*", Molec. Gen. Genet., vol. 163, (1978), pp. 181-187.
Hood, E. E., et al., "Plant-Based Production of Xenogenic Proteins", Current Opinion in Biotechnology, vol. 10, (1999), pp. 382-386.
Hood, E. E., et al., "Molecular Farming of Industrial Proteins from Transgenic Maize", Adv. Exp. Med. Biol., vol. 464, (1999), pp. 127-147.
Horsch, R.B., et al., "A Simple and General Method for Transferring Genes into Plants", Science, vol. 227, (1985), pp. 1229-1231.
Ikuta, N., et al., "The α-Amylase Gene as a Marker for Gene Cloning: Direct Screeing of Recombinant Clones", BioTechnology, vol. 8, (1990), pp. 241-242.
Jefferson, R.A., et al., "GUS Fusions: β-Glucuronidase as a Sensitive and Versatile Gene Fusion Marker in Higher Plants", The EMBO Journal, vol. 6, No. 13, (1987), pp. 3901-3907.
Jenes, B., et al., "Techniques for Gene Transfer", Chapter 4 in Transgenic Plants, Academic Press Inc., vol. 1, (1993), pp. 125-146.
Kasuga, M., et al., "Improving Plant Drought, Salt, and Freezing Tolerance by Gene Transfer of a Single Stress-Inducible Transcription Factor", Nature Biotechnology, vol. 17, (1999), pp. 287-291.
Katz, E., et al., "Cloning and Expression of the Tyrosinase Gene from *Streptomyces antibiotucus* in *Streptomyces lividans*", Journal of General Microbiology, vol. 129, (1983), pp. 2703-2714.
Kammerer, B., et al., "Molecular Characterization of a Carbon Transporter in Plastids from Heterotrophic Tissues: The Glucose 6-Phosphate/Phosphate Antiporter", The Plant Cell., vol. 10, (1998), pp. 105-117.
Koewn, W. A., et al., "Methods for Introducing DNA into Mammalian Cells", Methods in Enzymology, vol. 185, (1990), pp. 527-537.
Klosgen, R. B., et al., "Subcellular Location and Expression Level of a Chimeric Protein Consisting of the Maize *Waxy* Transit Peptide and the β-Glucuronidase of *Escherichia coil* in Transgenic Potato Plants", Mol. Gen. Genet., vol. 225, (1991), pp. 297-304.
Koprek, T., et al., "Negative Selection Systems for Transgenic Barley (*Hordeum vulgare* L.): Comparison of Bacterial *codA*- and Cytochrome *P450* Gene-Mediated Selection", The Plant Journal. vol. 19, No. 6, (1999), pp. 719-726.
Kribii, R., et al., "Cloning and Characterization of the *Arabidopsis thaliana SQS1* Gene Encoding Squalene Synthase Involvement of the

(56) References Cited

OTHER PUBLICATIONS

C-Terminal Region of the Enzyme in the Channeling of Squalene Through the Sterol Pathway", Eur. J. Biochem., vol. 249, (1997), pp. 61-69.
Kunkel, T. A., et al., "Rapid and Efficient Site-Specific Mutagenesis Without Phenotypic Selection", Methods in Enzymology, vol. 154, (1987), pp. 367-382.
Lam, E., et al., "Tetramer of a 21-Base Pair Synthetic Element Confers Seed Expression and Transcriptional Enhancement in Response to Water Stress and Abscisic Acid", The Journal of Biological Chemistry, vol. 266, No. 26, (1991), pp. 17131-17135.
Leffel, S.M., et al., "Applications of Green Fluorescent Protein in Plants", BioTechnique, vol. 23, (1997), pp. 912-918.
Leisner, S. M., et al., "Structure of the Octopine Synthase Upstream Activator Sequence", Proc. Natl. Acad. Sci. USA, vol. 85, (1988), pp. 2553-2557.
Levin, J.G., et al., "The Enzymatic Formation and Isolation of 3-Enolpyruvylshikimate 5-Phosphate", The Journal of Biological Chemistry, vol. 239, No. 4, (1964), pp. 1142-1150.
Lohmer, S., et al., "Translation of mRNA of the Maize Transcriptional Activator *Opaque*-2 is Inhibited by Upstream Open Reading Frames Present in the Leader Sequence", The Plant Cell, vol. 5, (1993), pp. 65-73.
Lloyd, A.M., et al., "Functional Expression of the Yeast FLP/FRT Site-Specific Recombination System in *Nicotiana tabacum*", Mol. Gen. Genet., vol. 242, (1994), pp. 653-657.
Losey, J. E., et al., "Transgenic Pollen Harms Monarch Larvae", Nature, vol. 399, (1999), p. 214.
Ma, J.K.C., et al., "Plant Expression Systems for the Production of Vaccines", Curr. Top. Microbiol. Immunol., vol. 236, (1999), pp. 275-292.
Maher, L.J., "DNA Triple-Helix Formation: An Approach to Artificial Gene Repressors?" BioEssays, vol. 14, No. 12, (1992), pp. 807-815.
Matzke, M.A., et al., "Ransgene Silencing by the Host Genome Defense: Implications for the Evolution of Epigenetic Control Mechanisms in Plants and Vertebrates", Plant Molecular Biology, vol. 43, (2000), pp. 401-415.
McCormick, S., et al., "Leaf Disc Transformation of Cultivated Tomato (*L. esculentum*) Using *Agrobacterium tumefaciens*", Plant Cell Reports, vol. 5, (1986), pp. 81-84.
McElroy, D., et al., "Construction of Expression Vectors Based on the Rice Actin 1 (*Act1*) 5'Region for Use in Monocot Transformation", Mol. Gen. Genet., vol. 231, (1991), pp. 150-160.
Menard, R., et al., "Glucosinolates in Cauliflower as Biochemical Markers for Resistance Against Downy Mildew", Phytochemistry, vol. 52, (1999), pp. 29-35.
Mette, M.F., et al., "Production of Aberrant Promoter Transcripts Contributes to Methylation and Silencing of Unlinked Homologous Promoters in trans", The EMBO Journal, vol. 18, No. 1, (1999), pp. 241-248.
Michaelson, L.,V., et al., "Isolation of a $\Delta^5$-Fatty Acid Desaturase Gene from *Mortierella alpine*", The Journal of Biological Chemistry, vol. 273, No. 30, (1996), pp. 19055-19059.
Michaelson, L.V., et al., "Functional Identification of a Fatty Acid $\Delta^5$ Desaturase Gene from *Caenorhabditis elegans*", FEBS Letters, vol. 439, (1998), pp. 215-218.
Millar, A.J., et al., "Firefly Luciferase as a Reporter of Regulated Gene Expression in Higher Plants", Plant Molecular Biology Reporter, vol. 10, No. 4, (1992), pp. 324-337.
Moloney, M.M., et al., "High Efficiency Transformation of *Brassica napus* Using *Agrobacterium* Vectors", Plant Cell Reports, vol. 8, (1989), pp. 238-242.
Murashige, T., et al., "A Revised Medium for Rapid Growth and Bio Assays with Tobacco Tissue Cultures", Physiol. Plant., vol. 15, (1962), pp. 473-497.
Naested, H., et al., "A Bacterial Haloalkane Dehalogenase Gene as a Negative Selectable Marker in *Arabidopsis*", The Plant Journal, vol. 18, No. 5, (1999), pp. 571-576.
Nakamura, R., et al., "Rice Allergenic Protein and Molecular-Genetic Approach for Hypoallergenic Rice", Biosci. Biotech. Biochem., vol. 60, No. 8, (1996), pp. 1215-1221.
Napoli, C., et al., "Introduction of a Chimeric Chalcone Synthase Gene into Petunia Results in Reversible Co-Suppression of Homologous Genes in trans", The Plant Cell, vol. 2, (1990), pp. 279-289.
Nayak, P., et al., "Transgenic Elite *indica* Rice Plants Expressing CrylAc ∂-Endotoxin of *Bacillus thuringiensis* are Resistant Against Yellow Stem Borer (*Scirpophaga incertulas*)", Proc. Natl. Acad. Sci. USA, vol. 94, (1997), pp. 2111-2116.
Odell, J., et al., "Site-Directed Recombination in the Genome of Transgenic Tobacco", Mol. Gen. Genet., vol. 223, (1990), pp. 369-378.
Odell, J. T., et al., "Identification of DNA Sequences Required for Activity of the Cauliflower Mosaic Virus 35S Promoter", Nature, vol. 313, (1985), pp. 810-812.
Oelmuller, R., et al., "Characterization of the Promoter from the Single-Copy Gene Encoding Ferredoxin-$NADP^+$-Oxidoreductase from Spinach", Mol. Gen. Genet., vol. 237, (1993), pp. 261-272.
Ott, K.-H., et al., "Rational Molecular Design and Genetic Engineering of Herbicide Resistant Crops by Structure Modeling and Site-Directed Mutagenesis of Acetohydroxyacid Synthase", J. Mol. Biol., vol. 263, (1996), pp. 359-368.
Ow, D.W., et al., "Transient and Stable Expression of the Firefly Luciferase Gene in Plant Cells and Transgenic Plants", Science, vol. 234, (1986), pp. 856-859.
Padgette, S.R., et al., "Development, Indentification, and Characterization of a Glyphosate-Tolerant Soybean Line", Crop Science, vol. 35, (1995), pp. 1451-1454.
Padgette, S.R., et al., "The Composition of Glyphosate-Tolerant Soybean Seeds is Equivalent to that of Conventional Soybeans", J. Nutr., vol. 126, No. 3, (1996), pp. 702-716.
Padgette S.R., et al., "New Weed Control Opportunities: Development of Soybeans with a Roundup Ready™ Gene", Chapter 4 in Herbicide Resistant Crops. Duke SO ed. CRC Press Inc. Boca Raton, FL., (1996), pp. 53-84.
Pei, Z.-M., et al., "Role of Farnesyltransferase in ABA Regulation of Guard Cell Anion Channels and Plant Water Loss", Science, vol. 282, (1998), pp. 287-290.
Perera, R.J., et al., "Cytosine Deaminase as a Negative Selective Marker for *Arabidopsis*", Plant Molecular Biology, vol. 23, (1993), pp. 793-799.
Potrykus, I., "Gene Transfer to Plants: Assessment of Published Approaches and Results", Annu. Rev. Plant Physiol. Plant Mol. Biol., vol. 42, (1991), pp. 205-225.
Prasher, D., et al., "Cloning and Expression of the cDNA Coding for Aequorin, a Bioluminescent Calcium-Binding Protein", Biochemical and Biophysical Research Communications, vol. 126, No. 3, (1985), pp. 1259-1268.
Randez-Gil, F., et al., "$DOG^R1$ and $DOG^R2$: Two Genes from *Saccharomyces cerevisiae* and Confer 2-Deoxyglucose Resistance with OVerexpressed", Yeast, vol. 11, (1995), pp. 1233-1240.
Rao, K.V., et al., "Expression of Snowdrop Lectine (GNA) in Transgenic Rice Plants Confers Resistance to Rice Brown Planthopper", The Plant Journal, vol. 15, No. 4, (1998), pp. 469-477.
Rask, L., et al., "Myrosinase: Gene Family Evolution and Herbivore Defense in Brassicaceae", Plant Molecular Biology, vol. 42, (2000), pp. 93-113.
Rathore, K.S., et al., "Use of *bar* as a Selectable Marker Gene and for the Production of Herbicide-Resistant Rice Plants from Protoplasts", Plant Molecular Biology, vol. 21, (1993), pp. 871-884.
Reichel, C., et al., "Enhanced Green Fluorescence by the Expression of an *Aequorea victoria* Green Fluorescent Protein Mutant in Mono- and Dicotyledonous Plant Cells", Proc. Natl. Acad. Sci. USA, vol. 93, (1996), pp. 5888-5893.
Rouster, J., et al., "The Untranslated Leader Sequence of the Barley *lipoxygenase 1* (*Lox1*) Gene Confers Embryo-Specific Expression", The Plant Journal, vol. 15, No. 3, (1998), pp. 435-440.
Sakuradani, E., et al., "Δ6-Fatty Acid Desaturase from an Arachidonic Acid-Producing *Mortierella* Fungus Gene Cloning and its Heterologous Expression in a Fungus, *Aspergillus*", Gene, vol. 238, (1999), pp. 445-453.

(56) References Cited

OTHER PUBLICATIONS

Sanger, F., et al., "DNA Sequencing with Chain-Terminating Inhibitors", Proc. Natl. Acad. Sci. USA, vol. 74, No. 12, (1977), pp. 5463-5467.
Sanz, P., et al., "Molecular Characterization of a Gene that Confers 2-Deoxyglucose Resistance in Yeast", Yeast, vol. 10, (1994), pp. 1195-1202.
Saroha, M.K., et al., "Glyphosate-Tolerant Crops: Genes and Enzymes", J. Plant Biochemistry & Biotechnology, vol. 7, (1998), pp. 65-72.
Sauer, B., "Inducible Gene Targeting in Mice Using the Cre/*lox* System", Methods, vol. 14, (1988), pp. 381-392.
Schenk, P.M., et al., "A Promoter from Sugarcane Bacilliform Badnavirus Drives Transgene Expression in Banana and Other Monocot and Dicot Plants", Plant Molecular Biology, vol. 39, (1999), pp. 1221-1230.
Schoffl, F., et al., "The Function of Plant Heat Shock Promoter Elements in the Regulated Expression of Chimaeric Genes in Transgenic Tobacco", Mol. Gen. Genet., vol. 217, (1989), pp. 246-253.
Schulz, B., et al., "Expression of the Triose Phosphate Translocator Gene from Potato is Light Dependent and Restricted to Green Tissues", Mol. Gen. Genet., vol. 238, (1993), pp. 357-361.
Schwall, G.P., et al., "Production of Very-High-Amylose Potato Starch by Inhibition of SBE A and B", Nature Biotechnology, vol. 18, (2000), pp. 551-554.
Shah, D.M., et al., "Engineering Herbicide Tolerance in Transgenic Plants", Science, vol. 233, (1986), pp. 478-481.
Sheen, J., et al., "Green-Fluorescent Protein as a New Vital Marker in Plant Cells", The Plant Journal, vol. 8, No. 5, (1995), pp. 777-784.
Sathasivan, K., et al., "Nucleotide Sequence of a Mutant Acetolactate Synthase Gene from an Imidazolinone-resistant *Arabidopsis thaliana* var. Columbia", Nucleic Acids Research, vol. 18, No. 8, (1990), p. 2188.
Shaw, C.H., et al., "A Functional Map of the Nopaline Synthase Promoter", Nucleic Acids Research, vol. 12, No. 20, (1984), pp. 7831-7846.
Smith, C.J.S., et al., "Expression of a Truncated Tomato Polygalacturonase Gene Inhibits Expression of the Endogenous Gene in Transgenic Plants", Mol. Gen. Genet., vol. 224, (1990), pp. 477-481.
Steinecke, P., et al., "Ribozymes", Methods in Cell Biology, vol. 50, (1995), pp. 449-460.
Steinrucken, H.C., et al., "The Herbicide Glyphosate is a Potent Inhibitor of 5-Enolpyruvyl-Shikimic Acid-3-Phospate Synthase", Biochemical and Biophysical Research Communications, vol. 94, No. 4, (1980), pp. 1207-1212.
Stitt, M., "The Flux of Carbon Between the Chloroplast and Cytoplasm", Chapter in Plant Metabolism $2^{nd}$ Edition, Dennis eds., Longman Press, Harlow, UK. (1997), pp. 381-400.
Stougaard, J., "Substrate-Dependent Negative Selection in Plants Using a Bacterial Cytosine Deaminase Gene", The Plant Journal, vol. 3, No. 5, (1993), pp. 755-761.
Sundaresan, V et al., "Patterns of Gene Action in Plant Development Revealed by Enhancer Trap and Gene Trap Transposable Elements", Genes & Development, vol. 9, (1995), pp. 1797-1810.
Sutcliffe, J. G., "Nucleotide Sequence of the Ampicillin Resistance Gene of *Escherichia coil* Plasmid pBR322", Proc. Natl. Acad. Sci. USA, vol. 75, No. 8, (1978), pp. 3737-3741.
Tada, Y., et al., "Reduction of 14-16 kDA Allergenic Proteins in Transgenic Rice Plants by Antisense Gene", FEBS Letters, vol. 391, (1996), pp. 341-345.
Tanner, N.K., "Ribozymes: The Characteristics and Properties of Catalytic RNAs", FEMS Microbiology Reviews, vol. 23, (1999), pp. 257-275.
Thompson, C.J., et al., "Characterization of the Herbicide-Resistance Gene *bar* from *Streptomyces hygroscopicus*", The EMBO Journal, vol. 6, No. 9, (1987), pp. 2519-2523.
Tian, L., et al., "Expression of the Green Fluorescent Protein Gene in Conifer Tissues", Plant Cell Reports, vol. 16, (1997), pp. 267-271.
Tomic, M., et al., "A Rapid and Simple Method for Introducing Specific Mutations into any Position of DNA Leaving all Other Positions Unaltered", Nucleic Acids Research, vol. 18, No. 6, (1990), p. 1656.
Upender, et al., "Megaprimer Method for in Vitro Mutagenesis using Parallel Templates", BioTechniques, vol. 18, No. 1, (1995), pp. 29-30.
Vaeck, M., et al., "Transgenic Plants Protected from Insect Attack", Nature, vol. 328, (1987), pp. 33-37.
Van Breusegem, F., et al., "Processing of a Chimeric Protein in Chloroplasts is Different in Transgenic Maize and Tobacco Plants", Plant Molecular Biology, vol. 38, (1998), pp. 491-496.
Van Der Krol, A.R., et al., "Flavonoid Genes in Petunia: Addition of a Limited Number of Gene Copies May Lead to a Suppression of Gene Expression", The Plant Cell, vol. 2, (1990), pp. 291-299.
Vickers, J.E., et al., "A Protocol for the Efficient Screening of Putatively Transformed Plants for *bar*, the Selectable Marker Gene, Using the Polymerase Chain Reaction", Plant Mol. Biol. Reporter, vol. 14, (1996), pp. 363-368.
Vorst, O., et al., "Tissue-Specific Expression Directed by an *Arabidopsis thaliana* Pre-Ferredoxin Promoter in Transgenic Tobacco Plants", Plant Molecular Biology, vol. 14, (1990), pp. 491-499.
Zank, T.K., et al,, "Cloning and Functional Expression of the First Plant Fatty Acid Elongase.Specific for $\Delta^6$-Polyunsaturated Fatty Acids", Biochemical Society Transactions, vol. 28, (2000), pp. 654-657.
Zukowski, M.M., et al., "Chromogenic Identification of Genetic Regulatory Signals in *Bacillus subtilis* Based on Expression of a Cloned *Pseudomonas* Gene", Proc. Natl. Acad. Sci. USA, vol. 80, (1983), pp. 1101-1105.
Beck, E., et al., "Nucleotide Sequence and Exact Localization of the Neomycin Phosphotransferase Gene from Transposon Tn5", Gene, vol. 19, (1982), pp. 327-336.
Sambrook, Jr., "Analysis and Cloning of Eukaryotic Genomic DNA", in Molecular Cloning: A Laboratory Manual, Cold Spring Harbor Laboratory Press, NY, (1989), pp. 9.31-9.62.
Current Protocols in Molecular Biology, John Wiley & Sons, NY, (1989), pp. 6.3.1-6.3.6.
Ebinuma, H., et al., "Selection of Marker-Free Transgenic Plants Using the Oncogenes (*IPT, ROL A,B,C*) of *Agrobacterium* as Selectable Markers", in Molecular Biology of Woody Plants, vol. 2, Jain & Minocha eds., Kluwer Academic Publishers, (2000), pp. 25-46.
Ausubel, F.M., et al., "Preparation of Genomic DNA from Plant Tissue", in Current Protocols in Molecular Biology 1987-1988, Green Publishing Assoc. & Wiley Interscience, (1987), pp. 2.3.1-2.3.3.
Schenborn, E., et al., "Reporter Gene Vectors and Assays", Molecular Biotechnology, vol. 13, No. 1, (1999), pp. 29-44.
Kim, et al., Plant Molecular Biology, vol. 24, (1994), pp. 105-117.
Benfey, et al., Science, vol. 250, (1990), pp. 959-966.
Nakamura, EMBL Accession No. AB006698, Sep. 2, 1997.
GenBank Accession No. NC_001140, Chromosome VIII, *Saccharomyces cervisiae* position 194799-194056, Dec. 23, 2010.
Del Arco and Boronat (1999), "Molecular Cloning and Functional Analysis of the Promoter of the Squalene Synthase Gene of *Arabidopsis thaliana*", 4th European Symposium on Plant Isoprenoids, Apr. 21-23, 1999, Barcelona, Spain.
Bolivar, F., et al., "Construction and Characterization of New Cloning Vehicles. II. A Multipurpose Cloning System", Gene, vol. 2, (1977), pp. 95-113.

* cited by examiner

E

TPT

FNR

A

B

A
B
C

EXPRESSION CASSETTES FOR TRANSGENIC EXPRESSION OF NUCLEIC ACIDS

CROSS REFERENCE TO RELATED APPLICATIONS

This application is a divisional application of U.S. application Ser. No. 10/755,677 filed Jan. 13, 2004, issued as U.S. Pat. No. 8,022,272, which is a national stage application (under 35 U.S.C. §371) of PCT/EP2002/07527 filed Jul. 5, 2002, which claims benefit to German application 101 334 07.9 filed Jul. 13, 2001 and German application 101 594 55.0 filed Dec. 4, 2001 and German application 102 075 82.4 filed Feb. 22, 2001. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_List__12810__01171_US. The size of the text file is 470 KB, and the text file was created on Jan. 25, 2012.

FIELD OF THE INVENTION

The invention relates to expression cassettes and vectors which contain constitutive promoters of plants and to the use of said expression cassettes or vectors for transgenic expression of nucleic acid sequences, preferably selection markers, in organisms, preferably in plants. The invention further relates to transgenic plants which have been transformed with said expression cassettes or vectors, to cultures, parts or propagation material derived therefrom and also to the use of same for the production of food- and feedstuffs, seed, pharmaceuticals or fine chemicals.

DESCRIPTION OF THE BACKGROUND

The aim of biotechnological studies on plants is the preparation of plants having improved properties, for example to increase agricultural productivity. The preparation of transgenic plants is a fundamental technique in plant biotechnology and thus an indispensable prerequisite for basic research on plants in order for the preparation of plants having improved novel properties for agriculture, for improving the quality of foodstuffs or for the production of particular chemicals or pharmaceuticals (Dunwell J M, J Exp Bot. 2000; 51 Spec No: 487-96). The natural defense mechanisms of the plant, for example against pathogens, are often inadequate. The introduction of foreign genes from plants, animals or microbial sources can enhance the defense. Examples are the protection against insects feeding on tobacco by expression of the *Bacillus thuringiensis* endotoxin under the control of the 35 S CaMV promoter (Vaeck et al. (1987) Nature 328:33-37) and the protection of tobacco against fungal infection by expression of a chitinase from beans under the control of the CaMV promoter (Broglie et al. (1991) Science 254:1194-1197). It is furthermore possible to achieve resistance to herbicides by introducing foreign genes, thereby optimizing the cultivation conditions and reducing crop losses (Ott K H et al. (1996) J Mol Biol 263(2):359-368). The quality of the products may also be improved. Thus it is possible, for example, to increase the shelf life and storability of crop products by inactivating particular maturation genes. This was demonstrated, for example, by inactivating polygalacturonase in tomatoes (Hamilton A J et al. (1995) Curr Top Microbiol Immunol 197:77-89).

A basic prerequisite for transgenic expression of particular genes in plants is the provision of plant-specific promoters. Various plant promoters are known. It is possible to distinguish between constitutive promoters which enable expression in various parts of a plant, which is only slightly restricted in terms of location and time, and specific promoters which allow expression only in particular parts or cells of a plant (e.g. root, seeds, pollen, leaves, etc.) or only at particular times during development. Constitutive promoters are used, for example, for expressing "selection markers". Selection markers (e.g. antibiotic or herbicidal resistance genes) permit filtering the transformation event out of the multiplicity of untransformed but otherwise identical individual plants.

Constitutive promoters active in plants have been written relatively rarely up to now. Promoters to be mentioned are the *Agrobacterium tumefaciens*, TR double promoter, the promoters of the vacuolar ATPase subunits or the promoter of a proline-rich wheat protein (WO 91/13991) and also the Ppc1 promoter *Mesembryanthemum cryctallinum* (Cushman et al. (1993) Plant Mol Biol 21:561-566).

The constitutive promoters which are currently the predominantly used promoters in plants are almost exclusively viral promoters or promoters isolated from *Agrobacterium*. In detail, these are the nopaline synthase (nos) promoter (Shaw et al. (1984) Nucleic Acids Res. 12(20):7831-7846), the mannopine synthase (mas) promoter (Comai et al. (1990) Plant Mol Biol 15 (3):373-381) and the octopine synthase (ocs) promoter (Leisner and Gelvin (1988) Proc Natl Acad Sci USA 85(5):2553-2557) from *Agrobacterium tumefaciens* and the CaMV35S promoter from cauliflower mosaic virus. The latter is the most frequently used promoter in expression systems with ubiquitous and continuous expression (Odell et al. (1985) Nature 313:810-812; Battraw and Hall (1990) Plant Mol Biol 15:527-538; Benfey et al. (1990) EMBO J. 9(69): 1677-1684; U.S. Pat. No. 5,612,472). However, the CaMV 35S promoter which is frequently applied as constitutive promoter exhibits variations in its activity in different plants and in different tissues of the same plant (Atanassova et al. (1998) Plant Mol Biol 37:275-85; Battraw and Hall (1990) Plant Mol Biol 15:527-538; Holtorf et al. (1995) Plant Mol Biol 29:637-646; Jefferson et al. (1987) EMBO J. 6:3901-3907). A further disadvantage of the 35S promoter is a change in transgene expression in the case of an infection with cauliflower mosaic virus and its typical pathogenic variants. Thus, plants expressing the BAR gene under the control of the 35S promoter are no longer resistant after infection with the virus which typically occurs in nature (Al-Kaff et al. (2000) Nature Biotechnology 18:995-99).

From the range of viral promoters, the sugarcane bacilliform badnavirus (ScBV) which imparts an expression pattern similar to that of CamV has been described as an alternative to the CaMV 35S promoter (Schenk et al. (1999) Plant Mol Biol 39(6):1221-1230). The activity of the ScBV promoter was analyzed in transient expression analyses using various dicotyledonous plants, including *Nicotiana tabacum* and *N. benthamiana*, sunflower and oilseed rape, and monocotyledonous plants, here in the form of banana, corn and millet. In the transient analyses in corn, the ScBV promoter-mediated expression level was comparable to that of the ubiquitin promoter from corn (see below). Furthermore, the ScBV promoter-mediated rate of expression was assayed in transgenic banana and tobacco plants and displayed in both plant species essentially constitutive expression.

Common promoters for expressing selection markers in plants are especially the nos promoter, or else the mas promoter and ocs promoter, all of which have been isolated from *Agrobacterium* strains.

The use of viral sequences is often met with great reservations on the part of the consumer. These doubts are fed not least by studies which question the safety of the 35S CaMV promoter, owing to a possible horizontal gene transfer due to a recombination hot spot (Ho M W et al. (1999) Microbial Ecology in Health and Disease 11:194-197; Cummins J et al. (2000) Nature Biotechnology 18:363). It is therefore an aim of future biotechnological studies on plants to replace viral genetic elements by plant regulatory elements in order to keep as closely as possible to the plant system.

Owing to the prevailing doubts with regard to viral promoters, there are extensive efforts to replace said promoters by plant promoters. However, a promoter of plant origin, which is comparable to the viral elements, has not been described as yet.

What has been described, is a plant ubiquitin promoter from *Arabidopsis thaliana* (Callis et al. (1990) J Biol Chem 265:12486-12493; Holtorf S et al. (1995) Plant Mol Biol 29:637-747). Contrary to the findings in the articles mentioned, some studies revealed that the *Arabidopsis* ubiquitin promoter is unsuitable for expressing selection marker genes and that, for this reason, its general applicability must be called into question (see comparative examples 1 and 3).

The expression pattern mediated by the corn ubiquitin promoter has been described for the Ubi-1 and Ubi-2 promoters from corn (Christensen et al. (1992) Plant Mol Biol 18(4): 675-689). While the Ubi-1 promoter has good expression activity in corn and other monocotyledonous plants, it exhibits in dicotyledonous tobacco plants only 10% of the activity which had been achieved in comparable experiments using the viral 35S promoter. It was furthermore shown that the corn Ubi-1 promoter is suitable for over expression of genes in monocotyledonous plant systems and, in addition, is sufficiently strong in order to mediate a herbicidal resistance via the expression of selection markers (Christensen and Quail (1996) Transgenic Res 5(3):213-218). The Ubi-1 promoter proved unsuitable for dicotyledonous expression systems.

A comparison of the organ specificity and strength of various constitutive promoters was carried out by Holtorf (Holtorf et al. (1995) Plant Mol Biol 29(4):637-646) on the basis of stably transformed *Arabidopsis* plants. The study comprised, inter alia, the CaMV35S promoter, the leaf-specific thionine promoter from barley and the *Arabidopsis* ubiquitin promoter (UBQ1). The CaMV35S promoter exhibited the highest rate of expression. On the basis of using an additional translational enhancer (TMV omega element), it was possible to increase the rate of expression of the promoter by a factor of two to three with unchanged organ specificity. The leaf-specific thionine promoter from barley was inactive in the majority of transformed lines, while the UBQ1 promoter from *Arabidopsis* resulted in medium rates of expression.

McElroy and colleagues reported a construct for transforming monocotyledonous plants, which is based on the rice actin 1 (Act1) promoter (McElroy et al. (1991) Mol Gen Genet. 231:150-160). Overall, it was concluded from the afore-described studies that the Act1 promoter-based expression vectors are suitable for controlling a sufficiently strong and constitutive expression of foreign DNA in transformed cells of monocotyledonous plants.

Another constitutive promoter which has been described is the promoter of an S-adenosyl-L-methionine synthetase (WO 00/37662). A disadvantage here is especially a dependence of the strength of expression on the methionine concentration (see WO 00/37662; FIG. 7).

WO 99/31258 describes chimeric constitutive plant promoters which are composed of various elements of various promoters with complementary expression patterns so that combination of individual tissue specificities additively results in a constitutive expression pattern.

Ferredoxin NADPH oxidoreductase (FNR) is a protein of the electron transport chain and reduces NADP+ to NADPH. Experiments in spinach using the spinach FNR promoter fused to the GUS gene hint at a light-inducible element in the FNR promoter (Oelmüller et al. (1993) Mol. Gen. Genet. 237:261-72). Owing to its function, a strictly leaf-specific expression pattern would have been expected for the promoter. Owing to the tissue-dependent expression pattern, the promoter would be poorly suited to expressing selection markers. Here, a selection in all tissue parts, if possible, is required in order to ensure efficient selection.

Owing to its function during photosynthesis, the promoter of the triose phosphate translocator (TPT) should be mainly leaf-specific. The cDNAs from potato (Schulz et al. (1993) Mol Gen Genet. 238:357-61), cauliflower (Fischer et al. (1997) Plant Cell 9:453-62), oilseed rape (WO 97/25346) and corn Kammerer B (1998) The Plant Cell 10:105-117) have been described. Kammerer et al. demonstrate that TPT mRNA expression in corn is strong in the leaves and the stamen. In contrast, no expression was observed in the stem or in the roots. Owing to the tissue-dependent expression pattern, the promoter would be poorly suited to expressing selection markers. Here, a selection in all tissue parts, if possible, is required in order to ensure efficient selection.

The "constitutive" promoters described in the prior art have one or more of the following disadvantages:

1. Inadequate homogeneity of expression:

The known "constitutive" promoters frequently display a different level of expression, depending on the type of tissue or cell. Moreover, the expression property is often highly dependent on the site of insertion into the host genome. As a consequence of this, the effects to be obtained by heterologous expression cannot be achieved to the same extent homogeneously in the plant. Under or over dosages may occur. This may have an adverse effect on plant growth or plant value.

2. Inadequate time profile:

The "constitutive" promoters known in the prior art often exhibit a nonconsistent activity during the development of a tissue. As a result, it is not possible, for example, to achieve desirable effects (such as selection) in the early phase of somatic embryogenesis which would be advantageous, especially here, due to the sensitivity of the embryo to in vitro conditions and stress factors.

3. Inadequate applicability to many plant species:

The "constitutive" promoters described in the prior art are often not active in the same way in all species.

4. If a plurality of expression cassettes with in each case the same "constitutive" promoter are present in an organism, interactions between said expression cassettes and even switching-off (gene silencing) of individual expression cassettes may occur (Mette et al. (1999) EMBO J. 18:241-248).

5. Promoters of viral origin may be influenced by virus infections of the transgenic plant and may then no longer express the desired property (Al-Kaff et al. (2000) Nature Biotechnology 18:995-99).

6. The public acceptance toward the use of promoters and elements from plant systems is higher than for viral systems.

7. The number of promoters suitable for expressing selection markers in plants is low and said promoters are usually of viral or bacterial origin.

8. Pollen/anther expression: The promoters mentioned (such as, for example, 35S CaMV) exhibit strong activity in the pollen or in the anthers. This may have disadvantageous effects on the environment. Thus, unspecific expression of *Bacillus thuringiensis* endotoxins resulted not only in the desired effect on feeding insects due to expression in the root but also, due to expression in the pollen, in considerable damage in the population of the Monarch butterfly which feeds predominantly on the pollen (Losey J E et al. (1999) Nature 399, 214).

An ideal constitutive promoter should have as many of the following properties as possible: (a) a gene expression which is as homogeneous as possible with regard to location and time, i.e. an expression in as many cell types or tissues of an organism as possible during the various phases of the developmental cycle. Furthermore, an efficient selection in differentiated cells (various callus phases) from a tissue culture and other developmental stages suitable for tissue culture is desired, (b) an applicability to various plant species, which is as broad as possible, and applicability to species in which it is not possible to achieve any expression using the "constitutive" promoters known to date, (c) to combine a plurality of transgenes in one plant, it is desirable to carry out a plurality of transformations in succession or to use constructs with a plurality of promoter cassettes, but without generating silencing effects due to the multiple use of identical regulatory sequences, (d) a plant origin in order to avoid problems of acceptance by the consumer and possible problems of future approval, and (e) secondary activities of a promoter in the anthers/pollen are undesirable, for example in order to avoid environmental damage, as discussed herein.

SUMMARY OF THE INVENTION

The present invention overcomes the problems and disadvantages associated with current strategies and designs and provides new tools and methods for the expression of nucleic acids.

One embodiment of the invention is directed to expression cassettes for transgenic expression of nucleic acids, comprising a promoter containing the sequence of SEQ ID NO: 1, 2 or 3 which possesses a promoter activity, or a fragment, functional equivalent or equivalent fragment thereof which possesses said promoter activity, wherein said promoter or said fragment is functionally linked to a nucleic acid sequence to be expressed transgenically. The equivalent fragment may comprise a sequence that contains the sequence of SEQ ID NO: 4 or SEQ ID NO: 27. The nucleic acid sequence to be expressed may be functionally linked to one or more further genetic control sequences, or the expression cassette contains one or more additional functional elements. Transgenic expression with cassettes of the invention enables expression of a protein encoded by said nucleic acid sequence, or expression of a sense or antisense RNA encoded by said nucleic acid sequence. Preferred nucleic acid sequences to be expressed transgenically include, but are not limited to nucleic acids coding for selection markers, reporter genes, cellulases, chitinases, glucanases, ribosome-inactivating proteins, lysozymes, *Bacillus thuringiensis* endotoxin, α-amylase inhibitor, protease inhibitors, lectins, RNAases, ribozymes, acetyl-CoA carboxylases, phytases, 2S albumin from *Bertholletia excelsa*, antifreeze proteins, trehalose phosphate synthase, trehalose phosphate phosphatase, trehalase, DREB1A factor, farnesyl transferases, ferritin, oxalate oxidase, calcium-dependent protein kinases, calcineurins, glutamate dehydrogenases, N-hydroxylating multifunctional cytochrome P450, transcriptional activator CBF1, phytoene desaturases, polygalacturonases, flavonoid 3'-hydroxylases, dihydroflavanol 4-reductases, chalcone isomerases, chalcone synthases, flavanone 3-beta-hydroxylases, flavone synthase II, branching enzyme Q, starch branching enzyme or combinations thereof. In addition, nucleic acid sequences to be expressed transgenically may also include the nucleic acid sequences with GenBank accession numbers U77378, AF306348, A19451, L25042, S78423, U32624, X78815, AJO02399, AFO078796, ABO44391, AJ222980, X14074, AB045593, AFO17451, AF276302, ABO61022, X72592, AB045592, or AR123356.

Preferably, the nucleic acid sequence to be expressed transgenically is a positive selection marker, a negative selection marker, a factor that gives a growth advantage, or a combinations thereof. Preferred positive or negative selection marker include proteins that impart a resistance to antibiotics, metabolism inhibitors, herbicides, biocides, proteins that impart a resistance to phosphinothricin, glyphosate, bromoxynil, dalapon, 2-deoxyglucose 6-phosphate, tetracyclines, ampicillin, kanamycin, G418, neomycin, paromomycin, bleomycin, zeocin, hygromycin, chloramphenicol, sulfonyl urea herbicides, imidazolinone herbicides, or combinations thereof.

Preferred selection markers include phosphinothricin acetyltransferases, 5-enolpyruvylshikimate 3-phosphate synthases, glyphosate oxidoreductases, dehalogenases, nitrilases, neomycin phosphotransferases, $DOG^R1$ genes, acetolactate synthases, hygromycin phosphotransferases, chloramphenicol acetyltransferases, streptomycin adenylyltransferases, β-lactamases, tetA genes, tetR genes, isopentenyl transferases, thymidine kinases, diphtheria toxin A, cytosine deaminase (codA), cytochrome P450, haloalkanedehalogenases, iaaH gene, tms2 gene, β-glucuronidases, mannose 6-phosphate isomerases, UDP-galactose 4-epimerases and combinations thereof.

Positive or negative selection markers may be encoded by a nucleic acid that contains the sequence of SEQ ID NO: 5 or 6; or the sequence of GenBank Acc. No.: X17220, X05822, M22827, X65195, AJ028212, X17220, X05822, M22827, X65195, AJ028212, X63374, M10947, AX022822, AX022820, E01313, J03196, AF080390, AF234316, AF080389, AF234315, AF234314, U00004, NC001140, X51514, AB049823, AF094326, X07645, X07644, A19547, A19546, A19545, 105376, 105373, X74325, AF294981, AF234301, AF234300, AF234299, AF234298, AF354046, AF354045, X65876, X51366, AJ278607, L36849, AB025109, or AL133315.

The nucleic acid sequence to be expressed from the expression cassette may be functionally linked to one or more further genetic control sequences, and/or one or more additional functional elements.

Another embodiment of the invention is directed to vectors comprising the expression cassette of the invention.

Another embodiment of the invention is directed to transgenic organisms transformed with vectors of the invention. Preferred transgenic organisms include bacteria, yeasts, fungi, animal and plant organisms. Preferred plant organisms include *Arabidopsis*, tomato, tobacco, potatoes, corn, oilseed rape, wheat, barley, sunflowers, millet, beet, rye, oats, sugarbeet, bean plants and soyabean.

Another embodiment of the invention is directed to a cell culture, plant or transgenic propagation material, derived from a transgenic organism of the invention.

Another embodiment of the invention is directed to methods for transgenic expression of nucleic acids comprising transgenically expressing a nucleic acid sequence which is functionally linked to a promoter containing the sequence of SEQ ID NO: 1, 2 or 3 and has a promoter activity; or a fragment, functional equivalent or equivalent fragment thereof which possesses the promoter activity. Functionally equivalent fragments may contain a sequence such as, but not limited to the sequences of SEQ ID NO: 4 and 27. Preferably, the nucleic acid sequence to be expressed is functionally linked to one or more further genetic control sequences, and one or more additional functional elements, and transgenically enables the expression of a protein encoded by said nucleic acid sequence, or the expression of a sense or antisense RNA encoded by said nucleic acid sequence.

Another embodiment of the invention is directed to methods for selecting transformed organisms comprising introducing a nucleic acid sequence coding for a selection marker to said organisms, wherein said nucleic acid sequence is functionally and transgenically linked to a promoter according to SEQ ID NO: 1, 2 or 3, which possesses a promoter activity; or a fragment, functional equivalent or equivalent fragment thereof which possesses said promoter activity; selecting organisms expressing said selection marker; and isolating selected organisms. Preferred selection markers include nucleic acid sequences with GenBank accession numbers U77378, AF306348, A19451, L25042, S78423, U32624, X78815, AJO02399, AFO78796, ABO44391, AJ222980, X14074, AB045593, AFO17451, AF276302, ABO61022, X72592, AB045592, or AR123356, positive selection markers, negative selection markers, factors which give a growth advantage, proteins which impart a resistance to antibiotics, metabolism inhibitors, herbicides, biocides, phosphinothricin acetyltransferases, 5-enolpyruvylshikimate 3-phosphate synthases, glyphosate oxidoreductases, dehalogenases, nitrilases, neomycin phosphotransferases, $DOG^R1$ genes, acetolactate synthases, hygromycin phosphotransferases, chloramphenicol acetyltransferases, streptomycin adenylyltransferases, β-lactamases, tetA genes, tetR genes, isopentenyl transferases, thymidine kinases, diphtheria toxin A, cytosine deaminase (codA), cytochrome P450, haloalkanedehalogenases, iaaH gene, tms2 gene, β-glucuronidases, mannose 6-phosphate isomerases, UDP-galactose 4-epimerases and combinations thereof.

Another embodiment of the invention is directed to methods for the production of a foodstuff, a feedstuff, a seed, a pharmaceutical or a fine chemical comprising propagating the transgenic organism of the invention or cell cultures, parts or transgenic propagation material derived therefrom. Optionally, methods further comprise growing the transgenic organism and isolating the foodstuff, feedstuff, seed, pharmaceutical or fine chemical. Preferred fine chemicals include, but are not limited to enzymes, vitamins, amino acids, sugars, saturated or unsaturated fatty acids, natural or synthetic flavorings, aromatizing substances and colorants. Preferred pharmaceuticals include, but are not limited to an antibody, enzyme or pharmaceutically active protein.

Other embodiments and advantages of the invention are set forth in part in the description, which follows, and in part, may be obvious from this description, or may be learned from the practice of the invention.

DESCRIPTION OF THE INVENTION

Figure 1A:
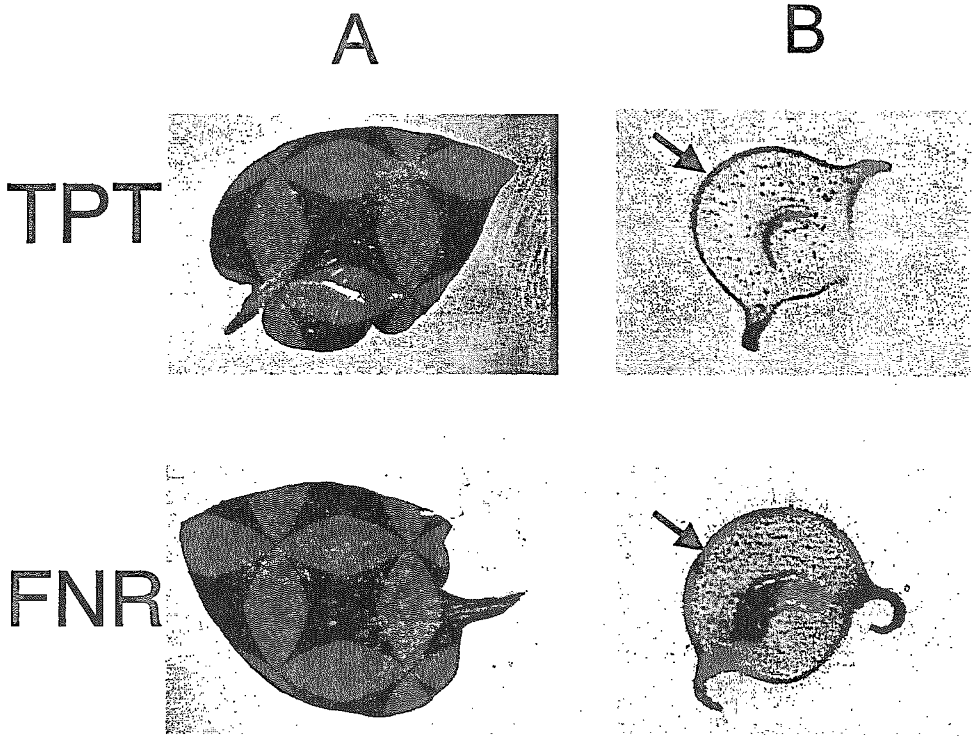
FIG. 1. The TPT and the FNR promoters show a comparable expression pattern in green tissue and in flowers of tobacco and potato. (a) A: Potato leaves. B: Tobacco petioles. (b) C: Tobacco stems. D: Tobacco internodia. (c) E: Tobacco flower.

The present invention is directed to providing regulatory sequences of plants, which fulfill as many of the herein mentioned properties as possible and which mediate especially a ubiquitous and development-independent (constitutive) expression of a nucleic acid sequence to be expressed which preferably codes for a selection marker. Despite various plant promoters for which a constitutive expression at least in individual species is claimed, no promoter having the desired properties listed herein has been described up to now. The invention is further directed to the identification of appropriate promoters.

We found that this is achieved by providing expression cassettes based on the promoters of a putative ferredoxin gene (pFD "putative ferredoxin" herein) from *Arabidopsis thaliana*, of the ferredoxin NADPH oxidoreductase (FNR herein) gene from *Arabidopsis thaliana* and of the triose phosphate translocator (TPT) gene from *Arabidopsis thaliana:*

Promoter of a Putative Ferredoxin (pFD) from *Arabidopsis thaliana:*

During analysis of the *Arabidopsis* genome, the ORF of a putative ferredoxin gene was identified. The isolated 836 bp 5'-flanking sequence fused to the *Glucuronidase* gene surprisingly exhibited a constitutive expression pattern in transgenic tobacco. The sequence corresponds to a sequence section on *Arabidopsis thaliana* chromosome 4, as it has been deposited at GenBank under Acc. No. Z97337 (Version Z97337.2; base pair 85117 to 85952; the gene starting from bp 85953 is annotated "strong similarity to ferredoxin [2Fe-2S]I, Nostoc muscorum"). (The gene is not to be confused with the *A. thaliana* gene for preferredoxin annotated under GenBank Acc.—NoAcc. No: X51370; Vorst O et al. (1990) Plant Mol Biol 14(4):491-499).

Only a weak activity was detected in the anthers/pollen of the closed flower buds and no activity whatsoever was detected in mature flowers. Contrary to the reservations, derived from the findings in the literature, toward a suitability of the promoter for effective expression of selection markers (for example, owing to the suspected leaf specificity or function in the photosynthetic electron transport), it was possible to demonstrate a highly efficient selection by combination with, for example, the homolog resistance gene (nptII).

2.) Ferredoxin NADPH Oxidoreductase (FNR) Promoter from *Arabidopsis thaliana:*

Starting from the information on FNR-encoding cDNA from *N. tabacum* (GenBank Acc. No.: Y14032) the *Arabidopsis* data base was screened for a homologous gene. Primers were synthesized according to said sequence information. The promoter amplified via PCR from *Arabidopsis thaliana* genomic DNA (635 bp), of which a leaf-specific expression was expected, exhibited in transgenic tobacco plants a surprisingly ubiquitous and insertion site-independent expression.

The promoter sequence partly corresponds to a sequence section on *Arabidopsis thaliana* chromosome 5, as it is deposited at GenBank under Acc. No. AB011474 (Version AB011474.1 from Dec. 27, 2000; base pair 70127 to 69493; the gene starting at by 69492 is annotated with "ferredoxin-NADP+reductase").

No activity was detected in the pollen. Contrary to the reservations, derived from the findings in the literature, toward a suitability of the promoter for effective expression of selection markers (for example, owing to the suspected leaf specificity or function in the photosynthetic electron transport), it was possible to demonstrate a highly efficient selection by combination with, for example, the phosphinothricin resistance gene (bar/pat).

The nondetectable activity of the FNR promoter in seeds allows a use for the expression of genes whose gene products are desired in other parts of the plant and are unwanted in the seeds. For example, pests can be repelled by expressing appropriate toxins such as, for example, *Bacillus thuringiensis* crystal proteins. Thus it is possible to achieve in potatoes expression in the plant organs above the ground (and thus, for example, a repulsion of pests such as the potato beetle) without simultaneous expression in the tuber which is used as food or animal feed, and this could increase the suitability and acceptance.

3.) Triose Phosphate Translocator (TPT) Promoter from *Arabidopsis thaliana:*

A 2038 bp PCR fragment was amplified, starting from *Arabidopsis* GenBank data of chromosome V, clone MCL19. The promoter sequence partly corresponds to a sequence section on *Arabidopsis thaliana* chromosome 5, as it is deposited with GenBank under Ace. No. AB006698 (Version AB006698.1 from Dec. 27, 2000; base pair 53242 to 55281; the gene starting at by 55282 is annotated with "phosphate/triose-phosphate translocator").

Surprisingly, transgenic tobacco plants exhibited not only a high activity in numerous parts of the plant. No activity was detected in the pollen. Contrary to the reservations, derived from the findings in the literature, toward a suitability of the promoter for effective expression of selection markers (for example, owing to the suspected leaf specificity), it was possible to demonstrate a highly efficient selection by combination with, for example, the phosphinothricin resistance gene (bar/pat).

The ubiquitous expression pattern, but especially also the ability of the TPT promoter regarding the expression of selection markers, comes as a great surprise for the skilled worker, since the triosephosphate translocator is responsible for the exchange of C3 sugar phosphates between the cytosol and the plastids in photosynthetic leaves. The TPT is located in the inner chloroplast membrane. Colorless plastids typically contain a hexose transporter via which C6-sugar phosphates are exchanged. It is not to be expected that such genes are active in the early callus and embryogenesis stages (Stitt (1997) Plant Metabolism, 2nd ed., Dennis eds. Longman Press, Harlow, U K, 382-400).

The pFD, FNR and TPT promoters proved to be sufficiently strong in order to express nucleic acid sequences, in particular selection marker genes, successfully. Furthermore, various deletion variants of the abovementioned promoters, in particular a truncated variant of the pFD promoter (699 bp) and of the TPT promoter (1318 bp), proved suitable for ensuring the expression of, for example, selection markers such as the homolog resistance (nptII).

Furthermore, the *Arabidopsis thaliana* ubiquitin promoter (Holtorf et al. (1995) Plant Mol Biol 29:637-646) and the squalene synthase promoter (Kribii et al. (1997) Eur J Biochem 249:61-69) were studied within the framework of the studies mentioned, both of which, however, were surprisingly unsuitable for mediating selection marker gene expression although the literature data of the ubiquitin promoters from monocotyledons (see above) had led to the assumption that in particular the ubiquitin promoter of a dicotyledonous plant should have worked as a promoter of a selection marker system (see comparative examples 1 and 3). A similar statement applies to the squalene synthase promoter whose characterization had led to the expectation that it would be possible to achieve sufficiently high rates of expression for the successful control of a selection marker gene (Del Arco and Boronat (1999) 4th European Symposium on Plant Isoprenoids, 21.—Dec. 23, 1999, Barcelona, Spain) (see comparative examples 2 and 3).

The present invention therefore relates firstly to expression cassettes for transgenic expression of nucleic acids, comprising: a) a promoter according to SEQ ID No: 1, 2 or 3, b) a functional equivalent or equivalent fragment of a), which essentially possesses the same promoter activity as a), a) or b) being functionally linked to a nucleic acid sequence to be expressed transgenically.

The invention further relates to methods for transgenic expression of nucleic acids, wherein a nucleic acid sequence which is functionally linked to a) a promoter according to SEQ ID NO: 1, 2 or 3 or b) a functional equivalent or equivalent fragment of a) which essentially possesses the same promoter activities as a), is expressed transgenically.

Expression comprises transcription of the nucleic acid sequence to be expressed transgenically but may also include, in the case of an open reading frame in sense orientation, translation of the transcribed RNA of the nucleic acid sequence to be expressed transgenically into a corresponding polypeptide.

An expression cassette for transgenic expression of nucleic acids or a method for transgenic expression of nucleic acids comprises all those constructions produced by genetic methods or methods in which either a) a promoter according to SEQ ID No: 1, 2 or 3 or a functional equivalent or equivalent fragment thereof, or b) the nucleic acid sequence to be expressed, or c) (a) and (b) are not present in their natural genetic environment (i.e. at their natural chromosomal locus) or have been modified by genetic methods, and said modification may be, by way of example, a substitution, addition, deletion, inversion or insertion of one or more nucleotide residues.

The expression cassettes of the invention, vectors derived from them or the methods of the invention may comprise functional equivalents of the promoter sequences described under SEQ ID No: 1, 2 or 3. Functionally equivalent sequences also comprise all those sequences which are derived from the complementary counter strand of the sequences defined by SEQ ID NO: 1, 2 or 3 and which have essentially the same promoter activity.

Functional equivalents with respect to the promoters of the invention means in particular natural or artificial mutations of the promoter sequences described under SEQ ID No: 1, 2 or 3 and of the homologs thereof from other plant genera and species, which furthermore have essentially the same promoter activity.

A promoter activity is essentially referred to as identical, if the transcription of a particular gene to be expressed under the control of a particular promoter derived from SEQ ID NO: 1, 2 or 3 under otherwise unchanged conditions has a location within the plant, which is at least 50%, preferably at least 70%, particularly preferably at least 90%, very particularly preferably at least 95%, congruent with that of a comparative expression obtained using a promoter described by SEQ ID NO: 1, 2 or 3. In this connection, the expression level may deviate both downward and upward in comparison to a comparative value. In this connection, preference is given to those sequences whose expression level, measured on the basis of the transcribed mRNA or the subsequently translated protein, differs quantitatively by not more than 50%, preferably 25%, particularly preferably 10%, from a comparative value obtained using a promoter described by SEQ ID NO: 1, 2 or 3, under otherwise unchanged conditions. Particular preference is given to those sequences whose expression level, measured on the basis of the transcribed mRNA or of the subsequently translated protein, is quantitatively more than 50%, preferably 100%, particularly preferably 500%, very particularly preferably 1000%, higher than a comparative value obtained with the promoter described by SEQ ID NO: 1, 2 or 3, under otherwise unchanged conditions. The comparative value is preferably the expression level of the natural mRNA of the particular gene or of the natural gene product. A further preferred comparative value is the expression level obtained using a random but particular nucleic acid sequence, preferably those nucleic acid sequences which code for readily quantifiable proteins. In this connection, very particular preference is given to reporter proteins (Schenborn E, Groskreutz D. Mol. Biotechnol. 1999; 13(1):29-44) such as the green fluorescence protein (GFP) (Chui W L et al., Curr Biol 1996, 6:325-330; Leffel S M et al., Biotechniques. 23(5): 912-8, 1997), chloramphenicol transferase, a luciferase (Millar et al., Plant Mol Biol Rep 1992 10:324-414) or β-galactosidase, and very particular preference is given to .beta.-glucuronidase (Jefferson et al. (1987) EMBO J. 6:3901-3907).

Otherwise unchanged conditions means the expression initiated by one of the expression cassettes to be compared is not modified by a combination with additional genetic control sequences, for example enhancer sequences. Unchanged conditions further means that all basic conditions such as, for example, plant species, developmental stage of the plants, growing conditions, assay conditions (such as buffer, temperature, substrates, etc.) are kept identical between the expressions to be compared.

Mutations comprise substitutions, additions, deletions, inversions or insertions of one or more nucleotide residues. Thus, for example, the present invention also includes those nucleotide sequences which are obtained by modification of a promoter of SEQ ID NO: 1, 2 or 3. The aim of such a modification may be the further narrowing down of the sequence comprised therein or else, for example, the introduction of further restriction enzyme cleavage sites, the removal of excess DNA or the addition of further sequences, for example of further regulatory sequences.

Where insertions, deletions or substitutions such as, for example, transitions and transversions are suitable, techniques known per se, such as in vitro mutagenesis, "primer repair", restriction or ligation, may be used. Manipulations such as, for example, restriction, chewing-back or filling-in of protruding ends to give blunt ends can provide complementary fragment ends for ligation. Similar results can be obtained using the polymerase chain reaction (PCR) using specific oligonucleotide primers.

Homology between two nucleic acids means the identity of the nucleic acid sequence over the in each case entire length of the sequence, which is calculated by comparison with the aid of the GAP program algorithm (Wisconsin Package Version 10.0, University of Wisconsin, Genetics Computer Group (GCG), Madison, USA), with the parameters set as follows:

| | |
|---|---|
| Gap Weight: 12 | Length Weight: 4 Average |
| Match: 2.912 | Average Mismatch: −2.003 |

By way of example, a sequence which is at least 50% homologous at the nucleic acid level with the sequence SEQ ID NO: 1, 2 or 3 means a sequence which is at least 50% homologous when compared to the sequence SEQ ID NO. 1, 2 or 3 according to the above program algorithm using the above set of parameters.

Functional homologs to the abovementioned promoters for use in the expression cassettes of the invention preferably include those sequences which, are at least 50%, preferably 70%, preferentially at least 80%, particularly preferably at least 90%, very particularly preferably at least 95%, most preferably 99%, homologous over a length of at least 100 base pairs, preferably at least 200 base pairs, particularly preferably at least 300 base pairs, very particularly preferably at least 400 base pairs and most preferably of at least 500 base pairs.

Further examples of the promoter sequences employed in the expression cassettes or vectors of the invention can readily be found, for example, in various organisms whose genomic sequence is known, such as, for example, *Arabidopsis thaliana, Brassica napus, Nicotiana tabacum, Solanum tuberosum, Helianthium anuus, Linum sativum* by comparing homologies in databases.

Functional equivalents further means DNA sequences which hybridize under standard conditions with the nucleic acid sequence coding for a promoter according to SEQ ID NO:1, 2 or 3 or with the nucleic acid sequences complementary to it and which have essentially the same properties. Standard hybridization conditions has a broad meaning and means both stringent and less stringent hybridization conditions. Such hybridization conditions are described, inter alia, in Sambrook J, Fritsch E F, Maniatis T et al., in Molecular Cloning—A Laboratory Manual, 2nd Edition, Cold Spring Harbor Laboratory Press, 1989, pp. 9.31-9.57) or in Current Protocols in Molecular Biology, John Wiley & Sons, N.Y. (1989), 6.3.1-6.3.6.

The conditions during the washing step may be selected by way of example from the range of conditions limited by those of low stringency (with approximately 2.times.SSC at 50° C.) and those with high stringency (with approximately 0.2×SSC at 50° C., preferably at 65° C.) (20×SSC: 0.3 M sodium citrate, 3 M NaCl, pH 7.0). In addition, the temperature may be raised during the washing step from low stringency conditions at room temperature, approximately 22° C., to higher stringency conditions at approximately 65° C. Both parameters, salt concentration and temperature, may be varied simultaneously, and it is also possible to keep one of the two parameters constant and to vary only the other one. Denaturing agents such as, for example, formamide or SDS may also be employed during hybridization. In the presence of 50% formamide, hybridization is preferably carried out at 42° C.

Some exemplary conditions for hybridization and washing are listed below:

(1) Hybridization conditions with, for example, a) 4×SSC at 65° C., or b) 6×SSC, 0.5% SDS, 10.mu.g/ml denatured, fragmented salmon sperm DNA at 65° C., or c) 4×SSC, 50% formamide, at 42° C., or d) 6×SSC, 0.5% SDS, 10.mu.g/ml denatured, fragmented salmon sperm-DNA, 50% formamide at 42° C., or e) 2× or 4×SSC at 50° C. (low stringency condition), or f) 2× or 4×SSC, 30 to 40% formamide at 42° C. (low stringency condition).

g) 6×SSC at 45° C., or, h) 50% formamide, 4×SSC at 42° C., or i) 50% (vol/vol) formamide, 0.1% bovine serum albumin, 0.1% Ficoll, 0.1% polyvinylpyrrolidone, 50 mM sodium phosphate buffer pH 6.5, 75 mM NaCl, 75 mM sodium citrate at 42° C., or j) 0.05 M sodium phosphate buffer pH 7.0, 2 mM EDTA, 1% BSA and 7% SDS.

(2) Washing steps with, for example:

a) 0.1 C SSC at 65° C., or b) 0.1×SSC, 0.5% SDS at 68° C., or c) 0.1×SSC, 0.5% SDS, 50% formamide at 42° C., or d) 0.2×SSC, 0.1% SDS at 42° C., or e) 2×SSC at 65° C. (low stringency condition), or f) 40 mM sodium phosphate buffer pH 7.0, 1% SDS, 2 mM EDTA.

Methods for preparing functional equivalents of the invention preferably comprise introducing mutations into a promoter of SEQ ID NO: 1, 2 or 3. A mutagenesis may be random and the mutagenized sequences are subsequently screened with respect to their properties according to a trial-by-error procedure. Examples of particularly advantageous selection criteria are an increased resistance to a selection marker and the level of the resulting expression of the introduced nucleic acid sequence.

As an alternative, it is possible to delete non-essential sequences of a promoter of the invention without substantially impairing said properties. Such deletion variants are functionally equivalent fragments of the promoters described by SEQ ID NO: 1, 2 or 3. Examples of such deletion mutants or functionally equivalent fragments, which may be mentioned, are the truncated pFD promoter sequence (pFDs) according to SEQ ID NO: 4 and the truncated TPT promoter sequence according to SEQ ID NO: 27 which, as functionally equivalent parts of their respective source promoters, are expressly included.

The narrowing-down of the promoter sequence to particular essential regulatory regions may also be carried out with the aid of search routines for searching for promoter elements. Particular promoter elements are often present in increased numbers in the regions relevant for promoter activity. Said analysis may be carried out, for example, by computer programs such as the program PLACE ("Plant Cis-acting Regulatory DNA Elements") (K. Higo et al., (1999) Nucleic Acids Research 27:1, 297-300) or the BIOBASE data bank "Transfac" (Biologische Datenbanken GmbH, Brunswick).

Methods for mutagenizing nucleic acid sequences are known to the skilled worker and include, by way of example, the use of oligonucleotides having one or more mutations in comparison with the region to be mutated (for example, within the framework of a site-specific mutagenesis). Typically, primers with from approximately 15 to approximately 75 nucleotides or more are employed, preferably from approx. 10 to approx. 25 or more nucleotide residues being located on both sites of the sequence to be modified. Details and the procedure of said mutagenesis methods are familiar to the skilled worker (Kunkel et al., Methods Enzymol, 154: 367-382, 1987; Tomic et al. (1990) Nucl Acids Res 12:1656; Upender, Raj, Weir (1995) Biotechniques 18(1):29-30; U.S. Pat. No. 4,237,224). A mutagenesis may also be carried out by treating, for example, vectors comprising one of the nucleic acid sequences of the invention with mutagenizing agents such as hydroxylamine.

The nucleic acid sequences which are comprised in the expression cassettes of the invention and which are to be expressed transgenically may be functionally linked to further genetic control sequences, in addition to one of the promoters of the invention.

A functional linkage means, for example, the sequential arrangement of a promoter, of the nucleic acid sequence to be expressed transgenically and, where appropriate, of further regulatory elements such as, for example, a terminator in such a way that each of the regulatory elements can carry out its function in the transgenic expression of said nucleic acid sequence, depending on the arrangement of the nucleic acid sequences with respect to sense or antisense RNA. This does not absolutely necessitate a direct linkage in the chemical sense. Genetic control sequences such as, for example, enhancer sequences may exert their function on the target sequence also from relatively distant positions or even from other DNA molecules. Preference is given to arrangements in which the nucleic acid sequence to be expressed transgenically is positioned downstream of the sequence functioning as promoter so that both sequences are covalently linked to one another. The distance between the promoter sequence and the nucleic acid sequence to be expressed transgenically is preferably less than 200 base pairs, particularly preferably less than 100 base pairs and very particularly preferably less than 50 base pairs.

A functional linkage may be prepared by means of common recombination and cloning techniques, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987). It is also possible to position further sequences between said two sequences, which have, for example, the function of a linker with particular restriction enzyme cleavage sites or of a signal peptide. Likewise, the insertion of sequences may lead to the expression of fusion proteins.

The term "genetic control sequences" has a broad meaning and means all those sequences which influence the generation or function of the expression cassette of the invention. For example, genetic control sequences modify transcription and translation in prokaryotic or eukaryotic organisms. The expression cassettes of the invention preferably comprise 5'-upstream of the particular nucleic acid sequence to be expressed transgenically one of the promoters of the invention and 3'-downstream a terminator sequence as an additional genetic control sequence and also, where appropriate, further common regulatory elements which are in each case functionally linked to the nucleic acid sequence to be expressed transgenically.

Genetic control sequences also include further promoters, promoter elements or minimal promoters which may modify the expression-controlling properties. Thus, for example, genetic control sequences can effect tissue-specific expression additionally depending on particular stress factors. Corresponding elements have been described, for example, for water stress, abscisic acid (Lam E and Chua N H (1991) J Biol Chem 266(26): 17131-17135) and heat stress (Schoffl F et al., (1989) Molecular & General Genetics 217(2-3):246-53).

Further promoters which make possible expression in further plant tissues or in other organisms such as, for example, in *E. coli* bacteria may furthermore be functionally linked to the nucleic acid sequence to be expressed. Suitable plant promoters are in principle all of the above-described promoters. It is conceivable, for example, that a particular nucleic acid sequence is transcribed as sense RNA via one promoter (for example one of the promoters of the invention) in one plant tissue and is translated into the corresponding protein, while the same nucleic acid sequence is transcribed to antisense RNA via another promoter having a different specificity in another tissue and the corresponding protein is down-regulated. This may be carried out via an expression cassette of the invention by positioning the one promoter upstream of the nucleic acid sequence to be expressed transgenically and the other promoter downstream of said sequence.

Genetic control sequences furthermore also include the 5'-untranslated region, introns or the noncoding 3'-region of genes, preferably of the pFD, FNR or TPT-genes. It has been demonstrated that these genes may have a substantial function in the regulation of gene expression. Thus it was shown that 5'-untranslated sequences can enhance transient expression of heterologous genes. They may furthermore promote tissue specificity (Rouster J et al. (1998) Plant J. 15:435-440). Conversely, the 5'-untranslated region of the opaque-2 gene suppresses expression. A deletion of the corresponding region leads to an increase in gene activity (Lohmer S et al. (1993) Plant Cell 5:65-73). The nucleic acid sequence indicated under SEQ ID NO:1, 2 or 3 contains the pFD, FNR or TPT-gene section which represents the promoter and the 5'-untranslated region up to the ATG start codon of the respective protein.

McElroy and colleagues (McElroy et al. (1991) Mol Gen Genet 231(1):150-160) reported a construct for transforming monocotyledonous plants, which is based on the rice actin 1 (Act1) promoter. The use of the Act1 intron in combination with the 35S promoter leads in transgenic rice cells to a ten times higher rate of expression compared to the isolated 35S promoter. Optimization of the sequence surrounding the translation initiation site of the reporter gene (GUS) resulted in a four-fold increase of GUS expression in transformed rice cells. A combination of optimized translation initiation site and Act1 intron resulted in a 40-fold increase in GUS expression via the CaMV35S promoter in transformed rice cells; similar results were achieved on the basis of transformed corn cells. Overall, it was concluded from the above-described studies that the expression vectors based on the Act1 promoter are suitable for controlling a sufficiently strong and constitutive expression of foreign DNA in transformed cells of monocotyledonous plants.

The expression cassette may advantageously contain one or more "enhancer sequences" which are functionally linked to the promoter and which enable an increased transgenic expression of the nucleic acid sequence. It is possible to insert additional advantageous sequences such as further regulatory elements or terminators at the 3'-end of the nucleic acid sequences to be expressed transgenically, too. Any of the expression cassettes of the invention may contain one or more copies of the nucleic acid sequences to be expressed transgenically.

Control sequences furthermore means those which enable homologous recombination or insertion into the genome of a host organism or which allow the removal from the genome. In homologous recombination, for example, the natural promoter of a particular gene may be replaced with one of the promoters of the invention. Methods such as the cre/lox technology allow tissue-specific, specifically inducible removal of the expression cassette from the genome of the host organism (Sauer B. (1998) Methods. 14(4):381-92). In this case, particular flanking sequences are attached to the target gene (lox sequences), which later enable a removal by means of the cre recombinase.

The promoter to be introduced may be placed upstream of the target gene to be expressed transgenically by means of homologous recombination by linking the promoter to DNA sequences which are, for example, homologous to endogenous sequences upstream of the reading frame of the target gene. Such sequences are to be understood as genetic control sequences. After a cell has been transformed with the appropriate DNA construct, the two homologous sequences can interact and thus place the promoter sequence at the desired position upstream of the target gene so that said promoter sequence is now functionally linked to the target gene and forms an expression cassette of the invention. The selection of the homologous sequences determines the insertion point of the promoter. In this case, the expression cassette can be generated by homologous recombination by means of a simple or a doubly-reciprocal recombination. In the case of the singly-reciprocal recombination, only a single recombination sequence is used and the entire introduced DNA is inserted. In the case of the doubly-reciprocal recombination, the DNA to be introduced is flanked by two homologous sequences and the flanked region is inserted. The latter method is suitable for replacing, as described above, the natural promoter of a particular gene with one of the promoters of the invention and thus modifying the location and time of expression of this gene. This functional linkage represents an expression cassette of the invention.

The selection of successfully homologously recombined or else transformed cells normally requires the additional introduction of a selectable marker which imparts to the successfully recombined cells a resistance to a biocide (for example a herbicide), a metabolism inhibitor such as 2-desoxyglucose 6-phosphate (WO 98/45456) or to an antibiotic. The selection marker permits selection of the transformed cells from the untransformed cells (McCormick et al., Plant Cell Reports 5 (1986), 81-84).

Homologous recombination is a relatively rare event in higher eukaryotes, especially in plants. Random integrations into the host genome predominate. One possibility of removing the randomly integrated sequences and thus accumulating cell clones having a correct homologous recombination is the use of a sequence-specific recombination system as described in U.S. Pat. No. 6,110,736. This system consists of three elements: two pairs of specific recombination sequences and a sequence-specific recombinase. This recombinase catalyzes a recombination merely between the two pairs of specific recombination sequences. One pair of these specific DNA sequences is placed outside the DNA sequence to integrated, i.e. outside the two homologous DNA sequences. In the case of a correct homologous recombination, these sequences are not cotransferred into the genome. In the case of a random integration, they normally insert together with the rest of the construct. Using a specific recombinase and a construct comprising a second pair of said specific sequences, the randomly inserted sequences can be excised or inactivated by inversion, while the sequences inserted correctly via homologous recombination remain in the genome. It is possible to use a multiplicity of sequence-specific recombination systems and the Cre/lox system of bacteriophage P1, the FLP/FRT system of yeast, the Gin recombinase of phase Mu, the *E. coli* Pin recombinase and the R/RS system of the plasmid pSR1 are mentioned by way of example. Preference is given to the bacteriophage P1 Cre/10.times. and the yeast FLP/FRT system. Here the recombinase (Cre or FLP) interacts specifically with its respective recombination sequences (34 bp lox sequence or 47 bp FRT sequence) in order to delete or invert the transiently stored sequences. The FLP/FRT and cre/lox recombinase systems have already been applied to plant systems (Odell et al. (1990) Mol. Gen. Genet., 223:369-378).

Polyadenylation signals suitable as control sequences are plant polyadenylation signals and, preferably, those which correspond essentially to *Agrobacterium tumefaciens* T-DNA polyadenylation signals, in particular of the T-DNA gene 3 (octopene synthase) of the Ti plasmid pTiACHS (Gielen et al., (1984) EMBO J. 3:(1984), 835 ff) or functional equivalents thereof.

In a particularly preferred embodiment, the expression cassette contains a terminator sequence functional in plants. Terminator sequences functional in plants means in general those sequences which are capable of causing the termination of transcription of a DNA sequence in plants. Examples of suitable terminator sequences are the OCS (octopene synthase) terminator and the NOS (nopaline synthase) terminator. However, particular preference is given to terminator sequences of plants. Terminator sequences of plants means in general those sequences which are part of a natural plant gene. In this connection, particular preference is given to the terminator of the potato cathepsin D inhibitor gene (GenBank Acc. No.: X74985; terminator: SEQ ID NO: 28) or of the terminator of the field bean storage protein gene VfLEIB3 (GenBank Ace. No.: Z26489; terminator: SEQ ID NO: 29). These terminators are at least equivalent to the viral or T-DNA terminators described in the prior art. The plasmid pSUN5NPTIICat (SEQ ID NO: 24) contains the plant terminator of the potato cathepsin D inhibitor gene.

The skilled worker knows a multiplicity of nucleic acids or proteins whose recombinant expression which is controlled by the expression cassettes or methods of the invention is advantageous. The skilled worker further knows a multiplicity of genes whose repression or elimination by means of expression of a corresponding antisense RNA can likewise achieve advantageous effects. Advantageous effects which may be mentioned by way of example and not by way of limitation are:

- easier preparation of a transgenic organism, for example by expression of selection markers:
- achieving a resistance to abiotic stress factors (heat, cold, drought, increased humidity, environmental toxins, UV radiation);
- achieving a resistance to biotic stress factors (pathogens, viruses, insects and diseases);
- improvement of the properties of food- or feedstuffs;
- improvement of growth rate or yield.

Some specific examples of nucleic acids whose expression provides the desired advantageous effects are mentioned below:

1. Selection Markers.

Selection markers includes both positive selection markers which impart a resistance to an antibiotic, herbicide or biocide and negative selection markers which impart a sensitivity to exactly these substances and also markers which give a growth advantage to the transformed organism (for example by expressing key genes of cytokine biosynthesis; Ebinuma H et al. (2000) Proc Natl Acad Sci USA 94:2117-2121). In the case of positive selection, only those organisms which express the appropriate selection marker grow, while the same organisms die in the case of negative selection. The preparation of transgenic plants prefers the use of a positive selection marker. Furthermore, preference is given to using selection markers which impart growth advantages. Negative selection markers may be used advantageously if particular genes or genome sections are to be removed from an organism (for example in a crossing process).

The selectable marker introduced with the expression cassette imparts to the successfully recombined or transformed cells a resistance to a biocide (for example a herbicide such as phosphinothricin, glyphosate or bromoxynil), a metabolism inhibitor such as 2-desoxyglucose 6-phosphate (WO 98/45456) or to an antibiotic such as, for example, kanamycin, G 418, bleomycin, hygromycin. The selection marker permits selection of the transformed cells from the untransformed cells (McCormick et al., Plant Cell Reports 5 (1986), 81-84). Particularly preferred selection markers are those which impart a resistance to herbicides. A large number of such selection markers and the sequences coding therefor are known to the skilled worker. Examples which may be mentioned by way of example but not by way of limitation are the following:

i) Positive Selection Markers.

The selectable marker introduced with the expression cassette imparts to the successfully recombined or transformed cells a resistance to a biocide (for example a herbicide such as phosphinothricin, glyphosate or bromoxynil), a metabolism inhibitor such as 2-desoxyglucose 6-phosphate (WO 98/45456) or to an antibiotic such as, for example, tetracyclines, ampicillin, kanamycin, G418, neomycin, bleomycin or hygromycin. The selection marker permits selection of the transformed cells from the untransformed cells (McCormick et al., Plant Cell Reports 5 (1986), 81-84). Particularly preferred selection markers are those which impart a resistance to herbicides. Examples of selection markers which may be mentioned are:

- DNA sequences coding for phosphinothricin acetyltransferases (PAT) which acetylate the free amino group of the glutamine synthase inhibitor phosphinothricin (PPT) and thus detoxify PPT (de Block et al. 1987, EMBO J. 6, 2513-2518) (also referred to as Bialaphos®-Resistance gene (bar)). The bar gene coding for a phosphinothricin acetyltransferase (PAT) may be isolated, for example, from *Streptomyces hygroscopicus* or *S. viridochromogenes*. Corresponding sequences are known to the skilled worker (from *Streptomyces hygroscopicus* GenBank Acc. No.: X17220 and X05822, from *Streptomyces viridochromogenes* GenBank Acc. No.: M 22827 and X65195; U.S. Pat. No. 5,489,520). Furthermore, synthetic genes, for example for expression in plastids, have been described AJ028212. A synthetic Pat gene is described in Becker et al. (1994), The Plant J. 5:299-307. Very particular preference is likewise given to the expression of the polypeptide according to SEQ ID NO: 5, for example encoded by a nucleic acid sequence according to SEQ ID NO: 4. The genes impart a resistance to the herbicide Bialaphos® or glufosinate and are frequently used markers in transgenic plants (Vickers, J E et al. (1996). Plant Mol. Biol. Reporter 14:363-368; Thompson C J et al. (1987) EMBO Journal 6:2519-2523).
- 5-Enolpyruvylshikimate 3-phosphate synthase genes (EPSP synthasegenes) which impart a resistance to Glyphosat® (N-(phosphonomethyl)glycin). The molecular target of the unselective herbicide glyphosate is 5-enolpyruvyl-3-phosphoshikimate synthase (EPSPS). This enzyme has a key function in the biosynthesis of aromatic amino acids in microbes and plants but not in mammals (Steinrucken H C et al. (1980) Biochem. Biophys. Res. Commun. 94:1207-1212; Levin J G and Sprinson D B (1964) J. Biol. Chem. 239: 1142-1150; Cole D J (1985) Mode of action of glyphosate; A literature analysis, p. 48-74. In: Grossbard E and Atkinson D (eds.). The herbicide glyphosate. Buttersworths, Boston). Preference is given to using glyphosate-tolerant EPSPS variants as selection markers (Padgette S R et al. (1996). New weed control opportunities: development of soybeans with a Roundup Ready™ gene. In: Herbicide Resistant Crops (Duke, S. O., ed.), pp. 53-84. CRC Press, Boca Raton, Fla.; Saroha M K and Malik V S (1998) J Plant Biochemistry and Biotechnology 7:65-72). The EPSPS gene of *Agrobacterium* sp. strain CP4 has a natural tolerance for glyphosate, which can be transferred to appropriate transgenic plants. The CP4 EPSPS gene was cloned from *Agrobacterium* sp. strain CP4 (Padgette S R et al. (1995) Crop Science 35(5): 1451-1461). 5-Enolpyruvylshikimate 3-phosphate synthases, which are glyphosate-tolerant, as described, for example, in U.S. Pat. No. 5,510,471; U.S. Pat. No. 5,776,760; U.S. Pat. No. 5,864,425; U.S. Pat. No. 5,633,435; U.S. Pat. No. 5,627,061; U.S. Pat. No. 5,463,175; EP 0 218 571, are preferred and the sequences described in each case in the patents have also been deposited with GenBank. Further sequences are described under GenBank Accession X63374. The aroA gene is also preferred (M10947 *S. typhimurium* aroA locus 5-enolpyruvylshikimate-3-phosphate synthase (aroA protein) gene).

the gox (glyphosate oxidoreductase) gene coding for the Glyphosat®-degrading enzyme. GOX (for example *Achromobacter* sp. glyphosate oxidoreductase) catalyzes the cleavage of a C—N bond in glyphosate which is thus converted to aminomethylphosphonic acid (AMPA) and glyoxylate. GOX can thereby mediate a resistance to glyphosate (Padgette S R et al. (1996) J. Nutr. 1996 March; 126(3):702-16; Shah D et al. (1986) Science 233: 478-481).

the deh gene (coding for a dehalogenase which inactivates Dalaponr), (GenBank Acc. No.: AX022822, AX022820 and WO99/27116).

bxn genes which code for Bromoxynil®-degrading nitrilase enzyme. For example the *Klebsiella ozanenae* nitrilase. Sequences can be found at GenBank, for example under Acc. No: EO 1313 (DNA encoding bromoxynil-specific nitrilase) and J03196 (K. pneumoniae bromoxynil-specific nitrilase (bxn) gene, complete cds).

Neomycin phosphotransferases impart a resistance to antibiotics (aminoglycosides) such as neomycin, G418, hygromycin, paromomycin or kanamycin by reducing the inhibiting action thereof by a phosphorylation reaction. Particular preference is given to the nptII gene. Sequences can be obtained from GenBank (AF080390 minitransposon mTn5-GNm; AF080389 minitransposon mTn5-Nm, complete sequence). Moreover, the gene is already part of numerous expression vectors and can be isolated therefrom by using methods familiar to the skilled worker (such as, for example, polymerase chain reaction) (AF234316 pCAMBIA-2301; AF234315 pCAMBIA-2300, AF234314 pCAMBIA-2201). The NPTII gene codes for an aminoglycoside 3'-O-phosphotransferase from *E. coli*, Tn5 (GenBank Acc. No: U00004 position 1401-2300; Beck et al. (1982) Gene 19 327-336).

the DOG®1-gene. The DOG®1 gene was isolated from the yeast *Saccharomyces cerevisiae* (EP 0 807 836). It codes for a 2-desoxyglucose 6-phosphate phosphatase which imparts resistance to 2-DOG (Randez-Gil et al. 1995, Yeast 11, 1233-1240; Sanz et al. (1994) Yeast 10:1195-1202, Sequence: GenBank Ace. No.: NC001140 chromosome VIII, *Saccharomyces cervisiae* position 194799-194056).

Sulfonylurea- and imidazolinone-inactivating acetolactate synthases which impart a resistance to imidazolinone/sulfonylurea herbicides. Examples of imidazolinone herbicides which may be mentioned are the active substances imazamethabenz-methyl, imazamox, imazapyr, imazaquin, imazethapyr. Examples of sulfonylurea herbicides which may be mentioned are amidosulfuron, azimsulfuron, chlorimuronethyl, chlorsulfuron, cinosulfuron, imazosulfuron, oxasulfuron, prosulfuron, rimsulfuron, sulfosulfuron. Numerous further active substances of said classes are known to the skilled worker. An example of a suitable sequence is the sequence of *Arabidopsis thaliana* Csr 1.2 gene deposited under the GenBank Acc-No.: X51514 (EC 4.1.3.18) (Sathasivan K et al. (1990) Nucleic Acids Res. 18(8):2188). Acetolactate synthases which impart a resistance to imidazolinon herbicides are furthermore described under GenBank Ace. Nos.:

a) AB049823 *Oryza sativa* ALS mRNA for acetolactate synthase, complete cds, herbicide resistant biotype;

b) AF094326 *Bassia scoparia* herbicide resistant acetolactate synthase precursor (ALS) gene, complete cds;

c) X07645 Tobacco acetolactate synthase gene, ALS SuRB (EC 4.1.3.18);

d) X07644 Tobacco acetolactate synthase gene, ALS SuRA (EC 4.1.3.18);

e) A19547 Synthetic nucleotide mutant acetolactate synthase;

f) A19546 Synthetic nucleotide mutant acetolactate synthase;

g) A19545 Synthetic nucleotide mutant acetolactate synthase;

h) 105376 Sequence 5 from Patent EP 0257993;

i) Sequence 2 from Patent EP 0257993;

j) AL133315.

Preference is given to expressing an acetolactate synthase according to SEQ ID NO: 7, for example encoded by a nucleic acid sequence according to SEQ ID NO: 6.

Hygromycin phosphotransferases (X74325 *P. pseudomallei* gene for hygromycin phosphotransferase) which impart a resistance to the antibiotic hygromycin. The gene is part of numerous expression vectors and can be isolated therefrom by using methods familiar to the skilled worker (such as, for example, polymerase chain reaction) (AF294981 pINDEX4; AF234301 pCAMBIA-1380; AF234300 pCAMBIA-1304; AF234299 pCAMBIA-1303; AF234298 pCAMBIA-1302; AF354046 pCAMBIA-1305; AF354045 pCAMBIA-1305.1).

Genes for resistance to:

a) chloramphenicol (chloramphenicol acetyltransferase);

tetracycline, various resistance genes have been described, for example X65876 *S. ordonez* genes class D tetA and tetR for tetracycline resistance and repressor proteins X51366 *Bacillus cereus* plasmid pBC16 tetracycline resistance gene.

The gene is also already part of numerous expression vectors and can be isolated therefrom by using methods familiar to the skilled worker (such as, for example, polymerase chain reaction);

c) streptomycin, various resistance genes have been described, for example under GenBank Acc. No.: AJ278607 *Corynebacterium acetoacidophilum* ant gene for streptomycin adenylyltransferase;

d) zeocin, the corresponding resistance gene is part of numerous cloning vectors (e.g. L36849 cloning vector pZEO) and can be isolated therefrom by using methods familiar to the skilled worker (such as, for example, polymerase chain reaction);

e) ampicillin (β-lactamase gene; Datta N, Richmond M H. (1966) Biochem J. 98(1):204-9; Heffron F et al (1975) J. Bacteriol 122: 250-256; the amp gene was initially cloned for preparing the *E. coli* vectors pBR322; Bolivar F et al. (1977) Gene 2:95-114). The sequence is part of numerous cloning vectors and can be isolated therefrom by using methods familiar to the skilled worker (such as, for example, polymerase chain reaction).

Genes such as the isopentenyl transferase from *Agrobacterium tumefaciens* (strain:PO22) (GenBank Acc. No.: AB025109). The ipt gene is [lacuna] a key enzyme of cytokine biosynthesis. Its overexpression facilitates the regeneration of plants (e.g. selection of cytokine-free medium). The method for using the ipt gene has been described (Ebinuma H et al. (2000) Proc Natl Acad Sci USA 94:2117-2121; Ebinuma, H et al. (2000) Selection of Marker-free transgenic plants using the oncogenes (ipt, rol A, B, C) of *Agrobacterium* as selectable markers, In Molecular Biology of Woody Plants. Kluwer Academic Publishers).

Various other positive selection markers which impart to the transformed plants a growth advantage over untransformed plants and methods of their use are described, inter alia, in EP-A 0 601 092. Examples which may be mentioned are β-glucuronidase (in connection with, for example, cytokinine glucuronide), mannose 6-phosphate isomerase (in connection with mannose), UDP-galactose 4-epimerase (in connection with, for example, galactose), mannose 6-phosphate isomerase in connection with mannose being particularly preferred.

ii) Negative Selection Markers.

Negative selection markers make possible, for example, the selection of organisms in which sequences comprising the marker gene have been successfully deleted (Koprek T et al. (1999) The Plant Journal 19(6):719-726). In negative selection, for example, a compound which otherwise has no disadvantageous effect on the plant is converted to a compound having a disadvantageous effect, due to the negative selection marker introduced into the plant. Genes which have a disadvantageous effect per se, such as, for example, TK thymidine kinase (TK), and diphtheria toxin A fragment (DT-A), the codA gene product coding for a cytosine deaminase (Gleave A P et al. (1999) Plant Mol. Biol. 40(2):223-35; Perera R J et al. (1993) Plant Mol. Biol. 23(4): 793-799; Stougaard J; (1993) Plant J 3:755-761), the cytochrom P450 gene (Koprek et al. (1999) Plant J. 16:719-726), genes coding for a haloalkane dehalogenase (Naested H (1999) Plant J. 18:571-576), the iaaH gene (Sundaresan V et al. (1995) Genes & Development 9:1797-1810) and the tms2 gene (Fedoroff N V & Smith D L 1993, Plant J 3: 273-289) are also suitable.

The concentrations of the antibiotics, herbicides, biocides or toxins, used in each case for selection, have to be adapted to the particular assay conditions or organisms. Examples which may be mentioned for plants are kanamycin (Km) 50 mg/l, hygromycin B 40 mg/l, phosphinothricin (Ppt) 6 mg/l.

It is furthermore possible to express functional analogs of said nucleic acids coding for selection markers. Functional analogs here means all those sequences which have essentially the same function, i.e. which are capable of selection of transformed organisms. In this connection, the functional analog may quite possibly differ in other features. It may have, for example, a higher or lower activity or else further functionalities.

2. Improved protection of the plant against abiotic stress factors such as drought, heat or cold, for example by overexpression of antifreeze-polypeptides from *Myoxocephalus Scorpius* (WO 00/00512), *Myoxocephalus octodecemspinosus*, of *Arabidopsis thaliana* transcription activator CBF1, of glutamate dehydrogenases (WO 97/12983, WO 98/11240), calcium-dependent protein kinase genes (WO 98/26045), calcineurins (WO 99/05902), farnesyl transferases (WO 99/06580, Pei Z M et al., Science 1998, 282: 287-290), ferritin (Deak M et al., Nature Biotechnology 1999, 17:192-196), oxalate oxidase (WO 99/04013; Dunwell J M Biotechnology and Genetic Engineering Reviews 1998, 15:1-32), DREB1A-Factor (dehydration response element B 1A; Kasuga M et al., Nature Biotechnology 1999, 17:276-286), of genes of mannitol or trehalose synthesis, such as trehalose phosphate synthase or trehalose phosphate phosphatase (WO 97/42326), or by inhibition of genes such as trehalose (WO 98/50561). Particular preference is given to nucleic acids which code for the *Arabidopsis thaliana* transcription activator CBF1 (GenBank Acc. No.: U77378) or for the *Myoxocephalus octodecemspinosus* antifreeze protein (GenBank Acc. No.: AF306348) or functional equivalents of the same.

3. Expression of metabolic enzymes for use in the feed and food sectors, for example expression of phytase and cellulases. Particular preference is given to nucleic acids such as the artificial cDNA coding for a microbial phytase (GenBank Acc. No.: A119451) or functional equivalents thereof.

4. Achieving a resistance, for example to fungi, insects, nematodes and diseases, by specific isolation or accumulation of particular metabolites or proteins in the embryonic epidermis. Examples which may be mentioned are glucosinolates (repulsion of herbivores), chitinases or glucanases and other enzymes which destroy the cell wall of parasites, ribosome-inactivating proteins (RIPs) and other proteins of resistance and stress reactions of the plant, such as those induced by injury or microbial infection of plants or chemically by, for example, salicylic acid, jasmonic acid or ethylene, lysozymes from sources other than plants, such as, for example, T4 lysozyme or lysozyme from various mammals, insecticidal proteins such as *Bacillus thuringiensis* endotoxin, α-amylase inhibitor or protease inhibitors (cowpea trypsine inhibitor), glucanases, lectins such as phytohemagglutinin, snowdrop lectin, wheat germ agglutinine, RNases and ribozymes. Particular preference is given to nucleic acids coding for chit42 endochitinase from *Trichoderma harzianum* (GenBank Acc. No.: S78423) or for the N-hydroxylating, multifunctional cytochrome P-450 (CYP79) protein from *Sorghum bicolor* (GenBank Am. No.: U32624) or functional equivalents thereof.

What is known is the accumulation of glucosinolates in plants of the genus of *Cardales*, in particular of oilseeds, for protection against pests (Rask L et al. (2000) Plant Mol Biol 42:93-113; Menard R et al. (1999) Phytochemistry 52:29-35), the expression of the *Bacillus thuringiensis* endotoxin under the control of the 35 S CaMV promoter (Vaeck et al. (1987) Nature 328:33-37) or the protection of tobacco against fungal infection by expression of a bean chitinase under the control of the CaMV promoter (Broglie et al. (1991) Science 254:1194-1197).

The expression of the snowdrop (*Galanthus nivalis*) lectin agglutinine can achieve a resistance to pests such as the rice pest *Nilaparvata lugens*, for example in transgenic rice plants (Rao et al. (1998) Plant J. 15(4):469-77.). *Nilaparvata lugens* belongs to the phloem-sucking pests and, in addition, acts as a transmitter of important virus-based plant diseases.

The expression of synthetic cryIA(b) and cryIA(c) genes which code for lepidoptera-specific delta-entotoxins from *Bacillus thuringiensis*, can cause a resistance to insect pests in various plants. Thus it is possible to achieve a resistance in rice to two of the most important rice insect pests, the striped stem borer (*Chilo suppressalis*) and the yellow stem borer (*Scirpophaga incertulas*), (Cheng X et al. (1998) Proc Natl Acad Sci USA 95(6):2767-2772; Nayak P et al. (1997) Proc Natl Acad Sci USA 94(6):2111-2116).

5. Expression of genes which cause accumulation of fine chemicals such as tocopherols, tocotrienols or carotenoids. Phytoene desaturase may be mentioned as an example. Preference is given to nucleic acids which code for *Narcissus pseudonarcissus* phytoene desaturase (GenBank Acc. No.: X78815) or functional equivalents thereof.

6. Production of nutraceuticals such as, for example, polyunsaturated fatty acids such as, for example, arachidonic acid or EP (eicosapentenoic acid) or DHA (docosahexaenoic acid) by expressing fatty-acid elongases and/or desaturases or by producing proteins having an improved nutritional value such as, for example, a high proportion of essential amino acids (e.g. the methionine-rich brazil nut albumingen). Preference is given to nucleic acids coding for the methionine-rich *Bertholletia excelsa* 2S albumin (GenBank Acc. No.: AB044391), the *Physcomitrella patens* Δ6-acyllipid desaturase (GenBank Acc. No.: AJ222980; Girke et al 1998, The Plant Journal 15:39-48), the *Mortierella alpina* Δ6-desaturase (Sakuradani et al 1999 Gene 238:445-453), the *Caenorhabditis elegans* Δ5-desaturase (Michaelson et al. 1998, FEBS Letters 439:215-218), the *Caenorhabditis elegans* Δ5-fatty-acid desaturase (des-5) (GenBank Acc. No.: AF078796), the *Mortierella alpina* Δ5-desaturase (Michaelson et al. JBC 273:19055-19059), the *Caenorhabditis elegans* Δ6-elongase (Beaudoin et al. 2000, PNAS 97:6421-6426), the *Physcomitrella patens* Δ6-elongase (Zank et al. 2000, Biochemical Society Transactions 28:654-657) or functional equivalents thereof.

7. Production of fine chemicals (such as, for example, enzymes) and pharmaceuticals (such as, for example, antibodies or vaccines, as described in Hood E E, Jilka J M. (1999) Curr Opin Biotechnol. 10(4):382-6; Ma J K, Vine N D (1999) Curr Top Microbiol Immunol 236:275-92). For example, it was possible to produce on a large scale recombinant avidin from egg white and bacterial .beta.-glucuronidase (GUS) in transgenic corn plants (Hood et al. (1999) Adv Exp Med Biol 464:127-47. Review). These recombinant proteins from corn plants are sold by Sigma (Sigma Chemicals Co.) as high-purity biochemicals.

8. Achieving an increased storage capability in cells which usually contain relatively few storage proteins or storage lipids, with the aim of increasing the yield of said substances, for example by expressing an acetyl-CoA carboxylase. Preference is given to nucleic acids coding for *Medicago sativa* acetyl-CoA carboxylase (accase) (GenBank Acc. No.: L25042) or functional equivalents thereof Further examples of advantageous genes are mentioned, for example, in Dunwell J M, Transgenic approaches to crop improvement, J Exp Bot. 2000; 51 Spec No; pages 487-96. It is furthermore possible to express functional analogs of the nucleic acids and proteins mentioned. Functional analogs here means all those sequences which have essentially the same function, i.e. which are capable of the same function (for example substrate conversion or signal transduction) as the protein mentioned by way of example. The functional analog may quite possibly differ in other features. It may have, for example, a higher or lower activity or else have further functionalities. Functional analogs further means sequences which code for fusion proteins comprising one of the preferred proteins and other proteins, for example another preferred protein, or else a signal peptide sequence.

The nucleic acids may be expressed under the control of the promoters of the invention in any desired cell compartment such as, for example, the endomembrane system, the vacuole and the chloroplasts. Desired glycosylation reactions, particular foldings, and the like are possible by utilizing the secretory pathway. Secretion of the target protein to the cell surface or secretion into the culture medium, for example when using suspension-cultured cells or protoplasts, is also possible. The required target sequences may both be taken into account in individual vector variations and be introduced into the vector together with the target gene to be cloned by using a suitable cloning strategy. Target sequences which may be used are both endogenous, if present, and heterologous sequences. Additional heterologous sequences which are preferred for functional linkage but not limited thereto are further targeting sequences for ensuring subcellular localization in the apoplast, in the vacuole, in plastids, in mitochondria, in the endoplasmic reticulum (ER), in the nucleus, in elaioplasts or other compartments; and also translation enhancers such as the 5'-leader sequence from tobacco mosaic virus (Gallie et al., Nucl. Acids Res. 15 (1987), 8693-8711) and the like. The method of transporting proteins which are per se not located in the plastids specifically into said plastids has been described, (Klosgen R B and Weil J H (1991) Mol Gen Genet. 225(2):297-304; Van Breusegem F et al. (1998) Plant Mol. Biol. 38(3):491-496).

Preferred Sequences are:

a) small subunit (SSU) of ribulose bisphosphate carboxylase (Rubisco ssu) from pea, corn, sunflower;

b) transit peptides derived from genes of fatty-acid biosynthesis in plants, such as the transit peptide of the plastid acyl carrier protein (ACP), stearyl-ACP desaturase, β-ketoacyl-ACP synthase or acyl-ACP thioesterase;

c) the transit peptide for GBSSI ("granule bound starch synthase I"); and d) LHCP II genes.

The target sequences may be linked to other targeting sequences which differ from the transit peptide-encoding sequences, in order to ensure subcellular localization in the apoplast, in the vacuole, in plastids, in the mitochondrion, in the endoplastic reticulum (ER), in the nucleus, in elaioplasts or in other compartments. It is also possible to use translation enhancers such as the 5'-leader sequence from tobacco mosaic virus (Gallie et al. (1987), Nucl. Acids Res. 15: 8693-8711) and the like.

The skilled worker further knows that there is no need for him to express the above-described genes directly by using the nucleic acid sequences coding for said genes or to repress them by antisense, for example. He may also use, for example, artificial transcription factors of the zinc finger protein type (Beerli R R et al. (2000) Proc Natl Acad Sci USA 97(4):1495-500). These factors attach to the regulatory regions of the endogenous genes to be expressed or repressed and cause expression or repression of the endogenous gene, depending on the design of the factor. Thus it is also possible to achieve the desired effects by expressing an appropriate zinc finger transcription factor under the control of one of the promoters of the invention.

It is likewise possible to use the expression cassettes of the invention for suppressing or reducing the replication or/and translation of target genes by gene silencing.

The expression cassettes of the invention may also be employed for expressing nucleic acids which mediate "antisense" effects and thus are capable of reducing the expression of a target protein, for example.

Preferred genes and proteins whose suppression results in an advantageous phenotype include by way of example but not by way of limitation:

a) polygalacturonase for preventing cell degradation and preventing plants and fruits, for example tomatoes, from becoming "mushy". Preference is given to using for this nucleic acid sequences such as that of the tomato polygalacturonase gene (GenBank Acc. No.: X14074) or its homologs from other genera and species.

reducing the expression of allergenic proteins, as described, for example, in Tada Y et al. (1996) FEBS Lett 391(3):341-345 or Nakamura R (1996) Biosci Biotechnol Biochem 60(8):1215-1221.

c) modifying the color of flowers by suppressing the expression of enzymes of anthocyane biosynthesis. Appropriate procedures have been described (for example in Forkmann G, Martens S. (2001) Curr Opin Biotechnol 12(2):155-160). Preference is given to using for this nucleic acid sequences such as those of flavonoid 3'-hydroxylase (GenBank Acc. No.: AB045593), dihydroflavanol 4-reductase (GenBank Acc. No.: AF017451), chalcone isomerase (GenBank Acc. No.: AF276302), chalcone synthase (GenBank Acc. No.: AB061022), flavanone 3-beta-hydroxylase (GenBank Acc. No.: X72592) and flavone synthase II (GenBank Acc. No.: AB045592) and the homologs thereof from other genera and species.

d) altering the amylose/amylopectin content in starch by suppressing the branching enzyme Q which is responsible for the α-1,6-glycosidic linkage. Appropriate procedures have been described (for example in Schwall G P et al. (2000) Nat Biotechnol 18(5):551-554). Preference is given to using for this nucleic acid sequences such as that of the potato starch branching enzyme II (GenBank Ace. No.: AR123356; U.S. Pat. No. 6,169,226) or its homologs from other genera and species.

An antisense nucleic acid first means a nucleic acid sequence which is completely or partially complementary to at least a part of the sense strand of said target protein. The skilled worker knows that it is possible to use, as an alternative, the cDNA or the corresponding gene as starting template for corresponding antisense constructs. Preferably, the antisense nucleic acid is complementary to the coding region of the target protein or to a part thereof. However, the antisense nucleic acid may also be complementary to the noncoding region or to a part thereof. Starting from the sequence information for a target protein, it is possible to design an antisense nucleic acid in the manner familiar to the skilled worker by taking into account the Watson and Crick base pairing rules. An antisense nucleic acid may be complementary to the entire or to a part of the nucleic acid sequence of a target protein. In a preferred embodiment, the antisense nucleic acid is an oligonucleotide of, for example, 15, 20, 25, 30, 35, 40, 45 or 50 nucleotides in length.

In a preferred embodiment, the antisense nucleic acid comprises α-anomeric nucleic acid molecules. α-anomeric nucleic acid molecules form particular double-stranded hybrids with complementary RNA, in which, in contrast to the normal β-units, the strands run parallel to one another (Gautier et al. (1987) Nucleic Acids. Res. 15:6625-6641).

Likewise included is the use of the above-described sequences in sense orientation, which may lead to cosuppression, as is familiar to the skilled worker. It has been demonstrated in tobacco, tomato and petunia that expression of sense RNA of an endogenous gene can reduce or eliminate expression of said gene, in a similar manner to what has been described for antisense approaches (Goring et al. (1991) Proc. Natl. Acad Sci USA, 88:1770-1774; Smith et al. (1990) Mol Gen Genet. 224:447-481; Napoli et al. (1990) Plant Cell 2:279-289; Van der Krol et al. (1990) Plant Cell 2:291-299). The introduced construct may represent the gene to be reduced completely or only partially. The possibility of translation is not required.

Very particular preference is also given to the use of methods such as gene regulation by means of double-stranded RNA (double-stranded RNA interference). Relevant methods are known to the skilled worker and have been described in detail (e.g. Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). The processes and methods described in the references listed are hereby expressly incorporated by reference. The simultaneous introduction of strand and complementary strand causes here a highly efficient suppression of native genes.

Advantageously, the antisense strategy may be coupled with a ribozyme method. Ribozymes are catalytically active RNA sequences which, coupled to the antisense sequences, catalytically cleave the target sequences (Tanner N K. FEMS Microbiol Rev. 1999; 23 (3):257-75). This can increase the efficiency of an antisense strategy. The expression of ribozymes in order to reduce particular proteins is known to the skilled worker and is described, for example, in EP-A1 0 291 533, EP-A1 0 321 201 and EP-A1 0 360 257. Suitable target sequences and ribozymes may be determined, for example, as described in Steinecke (Ribozymes, Methods in Cell Biology 50, Galbraith et al eds Academic Press, Inc. (1995), 449-460), by calculations of the secondary structure of ribozyme RNA and target RNA and by the interaction thereof (Bayley C C et al., Plant Mol. Biol. 1992; 18(2):353-361; Lloyd A M and Davis R W et al., Mol Gen Genet. 1994 March; 242(6):653-657). An example which may be mentioned is hammerhead ribozymes (Haselhoff and Gerlach (1988) Nature 334:585-591). Preferred ribozymes are based on derivatives of Tetrahymena L-19 IVS RNA (U.S. Pat. No. 4,987,071; U.S. Pat. No. 5,116,742). Further ribozymes with selectivity for an L119 mRNA may be selected (Bartel D and Szostak J W (1993) Science 261:1411-1418).

In another embodiment, target protein expression may be reduced using nucleic acid sequences which are complementary to regulatory elements of the target protein genes and which form together with said genes a triple-helical structure and thus prevent gene transcription (Helene C (1991) Anticancer Drug Des. 6(6):569-84; Helene C et al. (1992) Ann NY Acad Sci 660:27-36; Maher L J (1992) Bioassays 14(12): 807-815).

The expression cassette of the invention and the vectors derived therefrom may contain further functional elements.

The term functional element has a broad meaning and means all those elements which influence preparation, propagation or function of the expression cassettes of the invention or of vectors or organisms derived therefrom. Examples which may be mentioned but which are not limiting are:

reporter genes which code for readily quantifiable proteins and which ensure, via intrinsic color or enzyme activity, an evaluation of the transformation efficiency and of the location or time of expression. In this connection, very particular preference is given to genes coding for reporter proteins (see also Schenborn E, Groskreutz D. Mol. Biotechnol. 1999; 13(1):29-44) such as:

green fluorescence protein (GFP) (Chui W L et al., Curr Biol 1996, 6:325-330; Leffel S M et al., Biotechniques. 23(5): 912-8, 1997; Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12): 5888-5893; Tian et al. (1997) Plant Cell Rep 16:267-271; WO 97/41228);

chloramphenicol transferase (Fromm et al. (1985) Proc. Natl. Acad. Sci. USA 82:5824-5828);

Luciferase (Millar et al., Plant Mol Biol Rep 1992 10:324-414; Ow et al. (1986) Science, 234:856-859); allows bioluminescence detection;

β-galactosidase, coding for an enzyme for which various chromogenic substrates are available;

β-glucuronidase (GUS) (Jefferson et al., EMBO J. 1987, 6, 3901-3907) or the uidA gene which encodes an enzyme for various chromogenic substrates;

R-locus gene product: protein which regulates production of anthocyanine pigments (red color) in plant tissue and thus makes possible a direct analysis of the promoter activity without the addition of additional auxiliary substances or chromogenic substrates (Dellaporta et al., In: Chromosome Structure and Function: Impact of New Concepts, 18th Stadler Genetics Symposium, 11:263-282, 1988);

β-lactamase (Sutcliffe (1978) Proc Natl Acad Sci USA 75:3737-3741), enzyme for various chromogenic substrates (e.g. PADAC, a chromogenic cephalosporin);

xylE gene product (Zukowsky et al. (1983) Proc Natl Acad Sci USA 80:1101-1105), catechol dioxygenase which can convert chromogenic catechols;

alpha-amylase (Ikuta et al. (1990) Bio/technol. 8:241-242);

tyrosinase (Katz et al. (1983) J Gen Microbiol 129:2703-2714), enzyme which oxidizes tyrosine to give DOPA and dopaquinone which consequently form the readily detectable melanine;

aequorin (Prasher et al. (1985) Biochem Biophys Res Commun 126(3):1259-1268), may be used in calcium-sensitive bioluminescence detection.

replication origins which ensure a propagation of the expression cassettes or vectors of the invention, for example in *E. coli*. Examples which may be mentioned are ORI (origin of DNA replication), the pBR322 ori or the P15A ori (Sambrook et al.: Molecular Cloning. A Laboratory Manual, 2$^{nd}$ ed. Cold Spring Harbor Laboratory Press, Cold Spring Harbor, N.Y., 1989).

elements, for example border sequences, which enable agrobacteria-mediated transfer into plant cells for transfer and integration into the plant genome, such as, for example, the right or left border of T-DNA or the vir region.

multiple cloning regions (MCS) allow and facilitate the insertion of one or more nucleic acid sequences.

Various ways to achieve an expression cassette of the invention are known to the skilled worker. An expression cassette of the invention is prepared, for example, by fusing one of the promoters of the invention (or a functional equivalent or functionally equivalent part according to SEQ ID NO: 1, 2 or 3) or a functional equivalent to a nucleotide sequence to be expressed, where appropriate to a sequence coding for a transit peptide, preferably a chloroplast-specific transit peptide, which is preferably located between the promoter and the particular nucleotide sequence, and also with a terminator or polyadenylation signal. For this purpose, common recombination and cloning techniques as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., (1987) Current Protocols in Molecular Biology, Greene Publishing Assoc. and Wiley Interscience are used.

However, an expression cassette means also those constructs in which the promoter without having been functionally linked beforehand to a nucleic acid sequence to be expressed, is introduced into a host genome, for example, via specific homologous recombination or random insertion and takes over there regulatory control over nucleic acid sequences then functionally linked to it and controls transgenic expression of said nucleic acid sequences. Insertion of the promoter, for example by homologous recombination, upstream of a nucleic acid coding for a particular polypeptide results in an expression cassette of the invention, which controls expression of the particular polypeptide in the plant. Furthermore, the promoter may also be inserted such that antisense RNA of the nucleic acid coding for a particular polypeptide is expressed. As a result, the expression of said particular polypeptide in plants is down-regulated or eliminated.

Analogously, it is also possible to place a nucleic acid sequence to be expressed transgenically downstream of the endogenous natural promoter, for example by homologous recombination, resulting in an expression cassette of the invention, which controls expression of the nucleic acid sequence to be expressed transgenically in the cotyledons of the plant embryo.

The invention further relates to vectors which contain the above-described expression cassettes. Vectors may be, by way of example, plasmids, cosmids, phages, viruses or else agrobacteria.

The invention also relates to transgenic organisms transformed with at least one expression cassette of the invention or one vector of the invention and also to cells, cell cultures, tissue, parts, such as, for example in the case of plant organisms, leaves, roots, etc., or propagation material derived from such organisms.

Organisms, starting or host organisms mean prokaryotic or eukaryotic organisms such as, for example, microorganisms or plant organisms. Preferred microorganisms are bacteria, yeasts, algae or fungi. Preferred bacteria are bacteria of the genus *Escherichia, Erwinia, Agrobacterium, Flavobacterium, Alcaligenes* or cyanobacteria for example of the genus *Synechocystis*. Preference is given especially to microorganisms which are capable of infecting plants and thus transferring the cassettes of the invention. Preferred microorganisms are those of the genus *Agrobacterium* and, in particular of the species *Agrobacterium tumefaciens*. Preferred yeasts are *Candida, Saccharomyces, Hansenula* and *Pichia*. Preferred fungi are *Aspergillus, Trichoderma, Ashbya, Neurospora, Fusarium, Beauveria* or other fungi described in Indian Chem. Engr. Section B. Vol 37, No 1,2 (1995) on page 15, Table 6.

Host or starting organisms preferred as transgenic organisms are especially plants. Included within the scope of the invention are all genera and species of the higher and lower plants of the plant kingdom. The mature plants, seeds, shoots and seedlings and also parts, propagation material and cultures, for example cell cultures, derived therefrom are also included. Mature plants means plants at any development stage beyond the seedling. Seedling means a young immature plant in an early development stage.

Annual, perennial, monocotyledonous and dicotyledonous plants are preferred host organisms for preparing transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); pteridophytes such as ferns, horsetail and club mosses; gymnosperms such as conifers, cycades, ginkgo and Gnetalae; algae such as Chlorophyceae, Phaeophpyceae, Rhodophyceae, Myxophyceae, Xanthophyceae, Bacillariophyceae (diatoms) and Euglenophyceae.

Preference is given to plants of the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanacea, Sterculiaceae, Tetragoniacea, Theaceae, Umbelliferae. Preferred monocotyledonous plants are in particular selected from the monocotyledonous crop plants, for example of the Gramineae family, such as rice, corn, wheat, or other cereal species such as barley, malt, rye, triticale or oats, and also sugar cane and all grass species. Preferred dicotyledonous plants are in particular selected from the dicotyledonous crop plants, for example: Asteraceae such as sunflower, Tagetes or Calendula and others, Compositae, particularly the genus *Lactuca*, in particular the species *sativa* (lettuce), and others, Cruciferae, particularly the genus *Brassica*, very particularly the species *napus* (oilseed rape), *campestris* (beet), *oleracea* cv *Tastie* (cabbage), *oleracea* cv Snowball Y (cauliflower) and *oleracea* cv Emperor (broccoli), and further cabbage species; and the genus *Arabidopsis*, very particularly the species *thaliana*, and also cress or canola, and others, Cucurbitaceae such as melon, pumpkin or zucchini, and others, Leguminosae particularly the genus *Glycine*, very particularly the species max (soyabean), soya and also alfalfa, pea, bean plants or peanut, and others, Rubiaceae, preferably of the subclass Lamidae, such as, for example, *Coffea arabica* or *Coffea liberica* (coffee bush), and others, Solanaceae, in particular the genus *Lycopersicon*, very particularly the species *esculentum* (tomato), and the genus *Solanum*, very particularly the species *tuberosum* (potato) and *melongena* (aubergine) and also tobacco or paprika, and others, Sterculiaceae, preferably of the subclass Dilleniidae, such as, for example, *Theobroma cacao* (cacao bush) and others, Theaceae, preferably of the subclass Dilleniidae, such as, for example, *Camellia sinensis* or *Thea sinensis* (tea shrub) and others, Umbelliferae, preferably the genus *Daucus*, very particularly the species *carota* (carrot), and *Apium* (very particularly the species *graveolens dulce* (celery), and others; and the genus *Capsicum*, very particularly the species *annum* (pepper), and others, and also linseed, soya, cotton, hemp, flax, cucumber, spinach, carrot, sugarbeet and the various tree, nut and vine species, in particular banana and kiwi fruit.

Also included are ornamental plants, useful and ornamental trees, flowers, cut flowers, shrubs and lawns. Plants which may be mentioned by way of example but not by limitation are angiosperms, bryophytes such as, for example, Hepaticae (liverworts) and Musci (mosses); pteridophytes such as ferns, horsetail and club mosses; gymnosperms such as conifers, cycades, ginkgo and Gnetalae, the Rosaceae families, such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as catch-me-not, Orchidaceae such as orchids, Iridaceae such as gladioli, iris, freesia and crocus, Compositae such as marigold, Geraniaceae such as gerania, Liliaceae such as dracaena, Moraceae such as ficus, Araceae such as sweetheart plant, and others.

Most preference is given to *Arabidopsis thaliana, Nicotiana tabacum, Tagetes erecta, Calendula officinalis* and *Brassica napus* and to all genera and species which are used as food- or feedstuffs, such as the cereal species described, or which are suitable for preparing oils, such as oilseeds (e.g. oilseed rape), nut species, soya, sunflower, pumpkin and peanut.

Plant organisms for the purposes of this invention are furthermore other organisms capable of photosynthetic activity, such as, for example, algae or cyanobacteria, and also mosses. Preferred algae are green algae such as, for example, algae of the genus *Haematococcus, Phaedactylum tricornatum, Volvox* or *Dunaliella*.

The preparation of a transformed organism or of a transformed cell requires introducing the appropriate DNA into the appropriate host cell. A multiplicity of methods is available for this process which is referred to as transformation (see also Keown et al. 1990 Methods in Enzymology 185: 527-537). Thus, by way of example, the DNA may be introduced directly by microinjection or by bombardment with DNA-coated microparticles. The cell may also be permeabilized chemically, for example using polyethylene glycol, so that the DNA can enter the cell via diffusion. The DNA may also be formed via protoplast fusion with other DNA-comprising units such as minicells, cells, lysosomes or liposomes. Another suitable method for introducing DNA is electroporation in which the cells are reversibly permeabilized by an electric impulse.

In the case of plants, the methods described for transforming and regenerating plants from plant tissues or plant cells are utilized for transient or stable transformation. Suitable methods are especially protoplast transformation by polyethylene glycol-induced DNA uptake, the biolistic method using the gene gun, the "particle bombardment" method, electroporation, the incubation of dry embryos in DNA-comprising solution and microinjection.

Apart from these "direct" transformation techniques, a transformation may also be carried out by bacterial infection by means of *Agrobacterium tumefaciens* or *Agrobacterium rhizogenes*. These strains contain a plasmid (Ti or R1 plasmid) which is transferred to the plant after *Agrobacteria* infection. A part of this plasmid, denoted T-DNA (transferred DNA) is integrated into the genome of the plant cell.

The *Agrobacterium*-mediated transformation is best suited to dicotyledonous diploid plant cells, whereas the direct transformation techniques are suitable for any cell type.

An expression cassette of the invention may be introduced advantageously into cells, preferably into plant cells, by using vectors.

In an advantageous embodiment, the expression cassette is introduced by means of plasmid vectors. Preference is given to those vectors which enable a stable integration of the expression cassette into the host genome.

In the case of injection or electroporation of DNA into plant cells, no particular demands on the plasmid used are made. It is possible to use simple plasmids such as those of the pUC series. If complete plants are to be regenerated from the transformed cells, it is necessary for an additional selectable marker gene to be present on the plasmid.

Transformation techniques have been described for various monocotyledonous and dicotyledonous plant organisms. Furthermore, various possible plasmid vectors which normally contain an origin of replication for propagation in *E. coli* and a marker gene for selection of transformed bacteria are available for introducing foreign genes into plants. Examples are pBR322, pUC series, M13 mp series, pACYC184 etc.

The expression cassette may be introduced into the vector via a suitable restriction cleavage site. The resultant plasmid is first introduced into *E. coli*. Correctly transformed *E. coli* cells are selected, cultivated and the recombinant plasmid is obtained using methods familiar to the skilled worker. Restriction analysis and sequencing may be used in order to check the cloning step.

Transformed cells, i.e. those which contain the introduced DNA integrated into the DNA of the host cell may be selected from untransformed cells, if a selectable marker is part of the introduced DNA. A marker may be, by way of example, any gene which is capable of imparting a resistance to antibiotics or herbicides. Transformed cells which express such a marker gene are capable of surviving in the presence of concentrations of an appropriate antibiotic or herbicide, which kill an untransformed wild type. Examples are the bar gene which imparts resistance to the herbicide phosphinothricin (Rathore K S et al., Plant Mol. Biol. 1993 March; 21(5):871-884), the nptII gene which imparts resistance to kanamycin, the hpt gene which imparts resistance to hygromycin and the EPSP gene which imparts resistance to the herbicide glyphosate.

Depending on the method of DNA introduction, further genes may be required on the vector plasmid. If *agrobacteria* are used, the expression cassette is to be integrated into specific plasmids, either into an intermediate vector (shuttle vector) or a binary vector. If, for example, a Ti or Ri plasmid is to be used for transformation, at least the right border, in most cases, however, the right and the left border, of the Ti or Ri plasmid T-DNA is connected as flanking region with the expression cassette to be introduced. Preference is given to using binary vectors. Binary vectors can replicate both in *E. coli* and in *Agrobacterium*. They normally contain a selection marker gene and a linker or polylinker flanked by the right and left T-DNA border sequences. They may be transformed directly into *Agrobacterium* (Holsters et al., Mol. Gen. Genet. 163 (1978), 181-187). The selection marker gene permits selection of transformed *Agrobacteria*; an example is the nptII gene which imparts a resistance to kanamycin. The *Agrobacterium* which in this case acts as the host organism should already contain a plasmid with the vir region. This region is required for the transfer of T-DNA into the plant cell. An *Agrobacterium* transformed in this way may be used for transformation of plant cells.

The use of T-DNA for transformation of plant cells has been intensely studied and described (EP 120516; Hoekema, In: The Binary Plant Vector System, Offsetdrukkerij Kanters B. V., Alblasserdam, Chapter V; Fraley et al., Crit. Rev. Plant. Sci., 4:1-46 and An et al., EMBO J. 4 (1985), 277-287). Various binary vectors are known and partly commercially available, such as, for example, pBIN19 (Clontech Laboratories, Inc. U.S.A.).

The DNA is transferred into the plant cell by coculturing plant explants with *Agrobacterium tumefaciens* or *Agrobacterium rhizogenes*. Starting from infected plant material (e.g. leaf, root or stem parts, but also protoplasts or plant cell suspensions), it is possible to regenerate whole plants by using a suitable medium which may contain, for example, antibiotics or biocides for selection of transformed cells. The plants obtained may then be screened for the presence of the introduced DNA, in this case the expression cassette of the invention. As soon as the DNA has integrated into the host genome, the corresponding genotype is normally stable and the corresponding insertion is also found again in subsequent generations. Normally, the integrated expression cassette contains a selection marker which imparts to the transformed plant a resistance to a biocide (for example a herbicide), a metabolism inhibitor such as 2-DOG or an antibiotic such as kanamycin, G 418, bleomycin, hygromycin or phosphinothricin etc. The selection marker allows the selection of transformed cells from untransformed cells (McCormick et al., (1986) Plant Cell Reports 5: 81-84). The plants obtained may be cultivated and crossed in the common manner. Two or more generations should be cultured in order to ensure that the genomic integration is stable and heritable.

The abovementioned methods are described, for example, in B. Jenes et al., Techniques for Gene Transfer, in: Transgenic Plants, Vol. 1, Engineering and Utilization, edited by S. D. Kung and R. Wu, Academic Press (1993), pp. 128-143 and in Potrykus, (1991) Annu Rev. Plant Physiol. Plant Molec. Biol. 42: 205-225). The construct to be expressed is preferably cloned into a vector which is suitable for transforming *Agrobacterium tumefaciens*, for example pBin19 (Bevan et al., (1984) Nucl. Acids Res. 12: 871 f.).

As soon as a transformed plant cell has been prepared, it is possible to obtain a complete plant by using methods known to the skilled worker. To this end, callus cultures are used as starting point, by way of example. From these still undifferentiated cell masses, it is possible to induce formation of shoot and root in the known manner. The shoots obtained can be planted out and cultivated.

The efficacy of expression of the nucleic acids to be expressed transgenically can be determined, for example, in vitro by shoot meristem propagation using one of the above-described selection methods.

The invention further relates to cells, cell cultures, parts, such as, for example, roots, leaves, etc. in the case of transgenic plant organisms, and transgenic propagation material such as seeds or fruits derived from the above-described transgenic organisms.

Genetically modified plants of the invention, which can be consumed by humans and animals, may also be used, for example directly or after preparation known per se, as foodstuffs or feedstuffs.

The invention further relates to the use of the above-described transgenic organisms of the invention and of the cells, cell cultures, parts, such as, for example, roots, leaves, etc., in the case of transgenic plant organisms, and transgenic propagation material such as seeds or fruits for the production of food- or feedstuffs, pharmaceuticals or fine chemicals.

Preference is further given to a method for the recombinant production of pharmaceuticals or fine chemicals in host organisms, in which a host organism is transformed with one of the above-described expression cassettes or vectors and said expression cassette contains one or more structural genes which code for the fine chemical of interest or catalyze the biosynthesis of the fine chemical of interest, and the transformed host organism is cultivated and the fine chemical of interest is isolated from the cultivation medium. This method is broadly applicable for fine chemicals such as enzymes, vitamins, amino acids, sugars, fatty acids, natural and synthetic flavorings, aromatizing substances and colorants. Particular preference is given to the production of tocopherols and tocotrienols and also carotenoids. Cultivation of the transformed host organisms and isolation from said host organisms or from the cultivation medium are carried out by means of the methods known to the skilled worker. The production of pharmaceuticals such as, for example, antibodies or vaccines is described in Hood E E, Jilka J M (1999). Curr Opin Biotechnol. 10(4):382-6; Ma J K, Vine N D (1999) Curr Top Microbiol Immunol. 236:275-92.

Sequences:

SEQ ID NO: 1
Promoter and 5'-untranslated region of the *Arabidopsis thaliana* pFD promoter.

SEQ ID NO: 2
Promoter and 5'-untranslated region of the *Arabidopsis thaliana* FNR promoter.

SEQ ID NO: 3
Promoter and 5'-untranslated region of the *Arabidopsis thaliana* TPT promoter (2038 bp).

SEQ ID NO: 4
Promoter and 5'-untranslated region of the truncated *Arabidopsis thaliana* pFDs promoter.

SEQ ID NO: 5
Nucleic acids coding for a phosphinothricin acetyltransferase.

SEQ ID NO: 6
Amino acid sequence coding for a phosphinothricin acetyltransferase.

SEQ ID NO: 7
Nucleic acid coding for an acetolactate synthase.

SEQ ID NO: 8
Amino acid sequence coding for an acetolacate synthase.

SEQ ID NO: 9-oligonucleotide primer pWL35
5'-GTC GAC GAA TTC GAG AGA CAG AGA GAC GG-3'

SEQ ID NO: 10-oligonucleotide primer pWL36
5'-GTC GAC GGT ACC GAT TCA AGC TTC ACT GC-3'

SEQ ID NO: 11-oligonucleotide primer pFD1
5'-GAG AAT TCG ATT CAA GCT TCA CTG C-3'

SEQ ID NO: 12-oligonucleotide primer pFD2
5'-CCA TGG GAG AGA CAG AGA GAC G-3'

SEQ ID NO: 13-oligonucleotide primer pFD3
5'-acggatccgagagacagagagacggagacaaaa-3'

SEQ ID NO: 14-oligonucleotide primer pFD5
5'-gcggatccaacactcttaacaccaaatcaaca-3'

SEQ ID NO: 15-oligonucleotide primer L-FNR ara
5'-GTCGACGGATCCGGTTGATCAGAAGAAGAAGAAGAAG ATGAACT-3'

SEQ ID NO: 16-oligonucleotide primer R-FNR ara
5'-GTCGACTCTAGATTCATTATTTCGATTTTGATTTCGT GACC-3'

SEQ ID NO: 17-oligonucleotide primer L-TPT ara
5'-AGTCGACGGATCCATAACCAAAAGAACTCTGATCATGT ACGTACCCATT-3'

SEQ ID NO: 18-oligonucleotide primer R-TPT ara
5'-AGACGTCGACTCTAGATGAAATCGAAATTCAGAGT TTTGA TAGTGAGAGC-3'

SEQ ID NO: 19-oligonucleotide primer ubi5
5'-CCAAACCATGGTAAGTTTGTCTAAAGCTTA-3'

SEQ ID NO: 20-oligonucleotide primer ubi3
5'-CGGATCCTTTTGTGTTTCGTCTTCTCTCA-CG-3'

SEQ ID NO: 21-oligonucleotide primer sqs5
5'-GTCTAGAGGCAAACCACCGAGTGTT-3'

-continued

SEQ ID NO: 22. oligonucleotide primer sqs3
5'-CGGTACCTGTTTCCAGAAAATTTTGATTCAG-3'

SEQ ID NO: 23
binary plasmid pSUN3 (Sungene GmbH & Co KGaA)

SEQ ID NO: 24
binary plasmid pSUN5NPTIICat (Sungene GmbH & Co KGaA)

SEQ ID NO: 25
binary plasmid pSUN3PatNos (Sungene GmbH & Co KGaA)

SEQ ID NO: 26-oligonucleotide primer 5-TPTara
5'-AAG TCG ACG GAT CCT GAT AGC TTA TAC TCA AAT TCA ACA AGT TAT-3'

SEQ ID NO: 27
truncated promoter and 5'-untranslated region of the *Arabidopsis thaliana* and TPT-Promoters (1318 bp)

SEQ ID NO: 28
nucleic acid sequence of the terminator of the potato cathepsin D inhibitor gene (GenBank Acc. No. X74985)

SEQ ID NO: 29
nucleic acid sequence of the terminator of the field bean storage protein gene VfLE1B3 (GenBank Acc. No. Z26489).

DESCRIPTION OF THE FIGURES

Figure 1B:
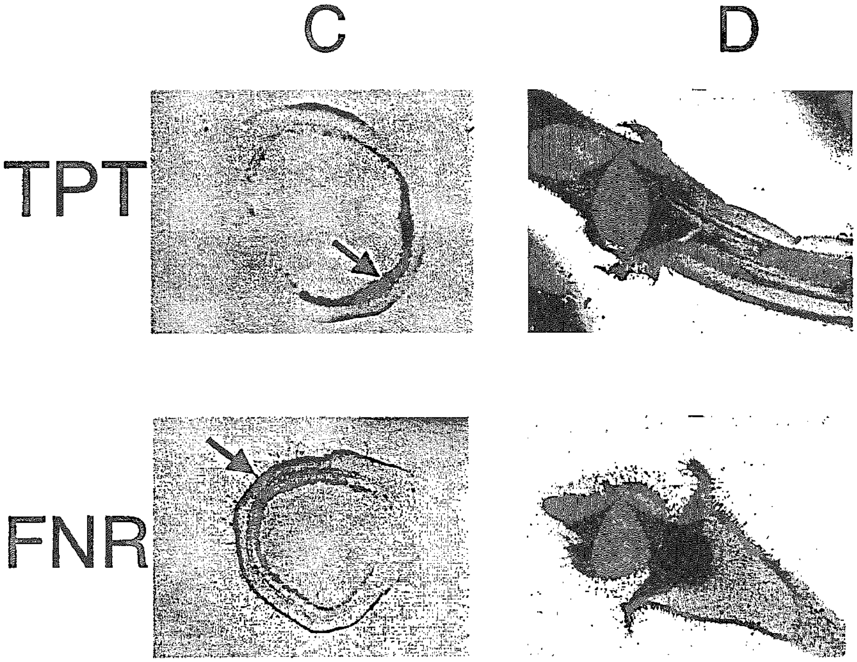
Figure 1C:
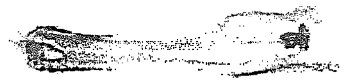
Figure 1C:
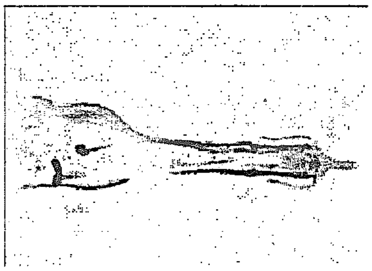

FIG. 1*a-c*: The TPT and the FNR promoters show a comparable expression pattern in green tissue and in flowers of tobacco and potato. GUS-histochemical stains are formed. The intensity of the GUS blue stain corresponds to the shades of gray displayed. The figures show:

In FIG. 1*a:*

A: Potato leaves with a homogeneous intensity stain over the entire leaf region.

B: Tobacco petioles, intensive blue stain, especially on the edges and in the vascular regions (see arrow).

In FIG. 1*b:*

C: Tobacco stems, intensive blue stains, especially on the edges (see arrow). D: Tobacco internodia.

In FIG. 1*c:*

E: Tobacco flower; blue stain, especially in sepals and petals.

Figure 2A:
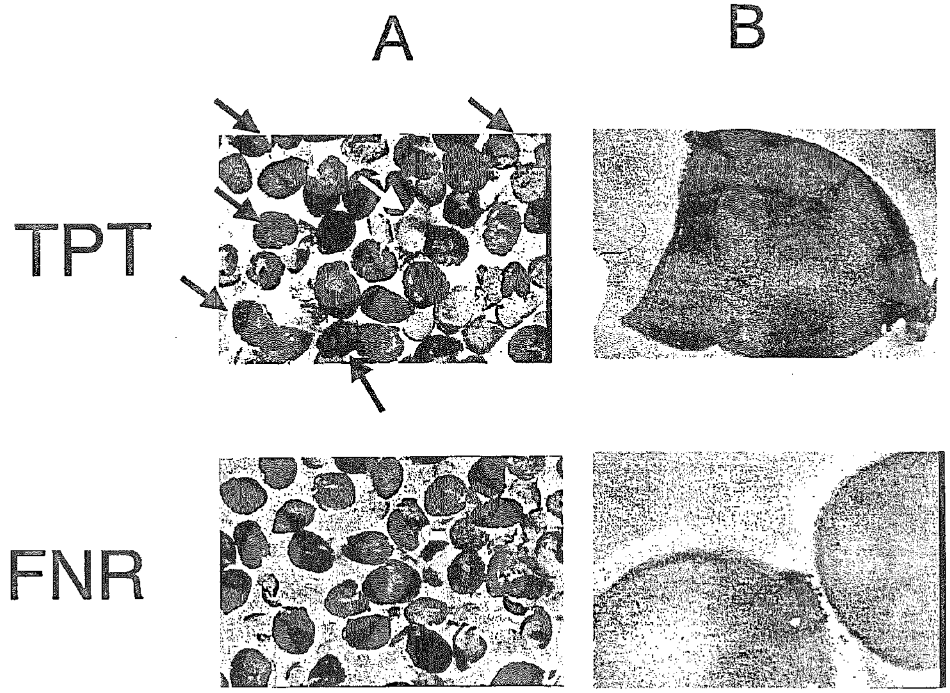
FIG. 2. The TPT promoter and the FNR promoter show a different expression pattern in vegetative and germinative storage tissue of tobacco and potato. (a) A: Tobacco seeds. B: Potato tubers. (b) C: Tobacco seedlings.
Figure 2B:
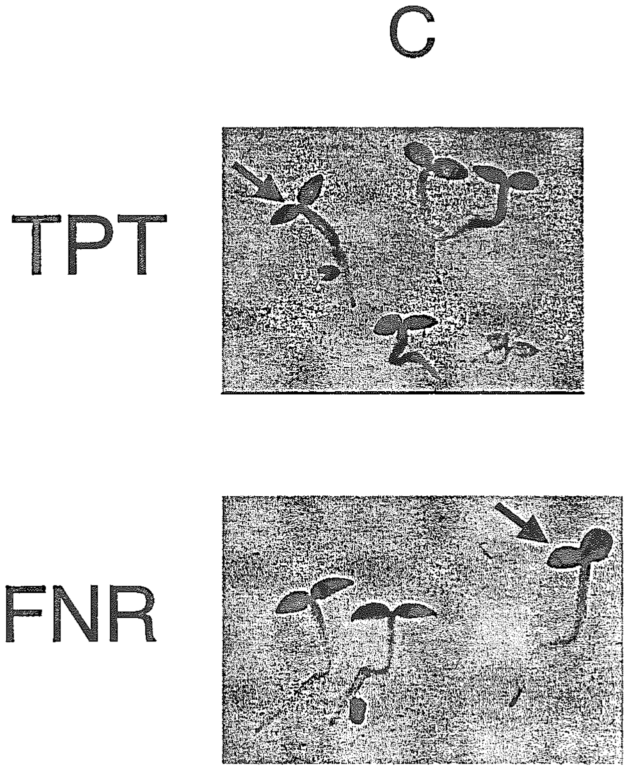
Figure 3:
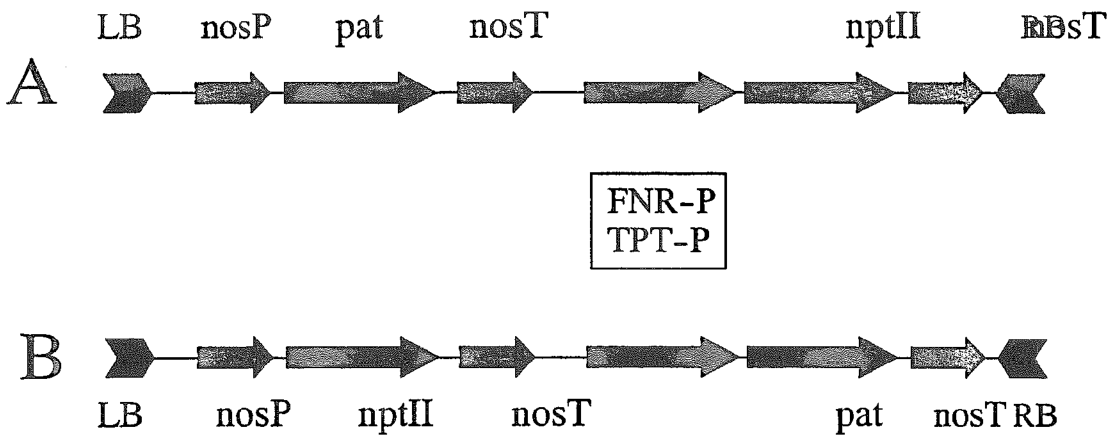
FIG. 3. Expression cassettes for the expression of kanamycin-resistance (nptII) and phosphinothricin-resistance (pat) markers.
Figure 4:
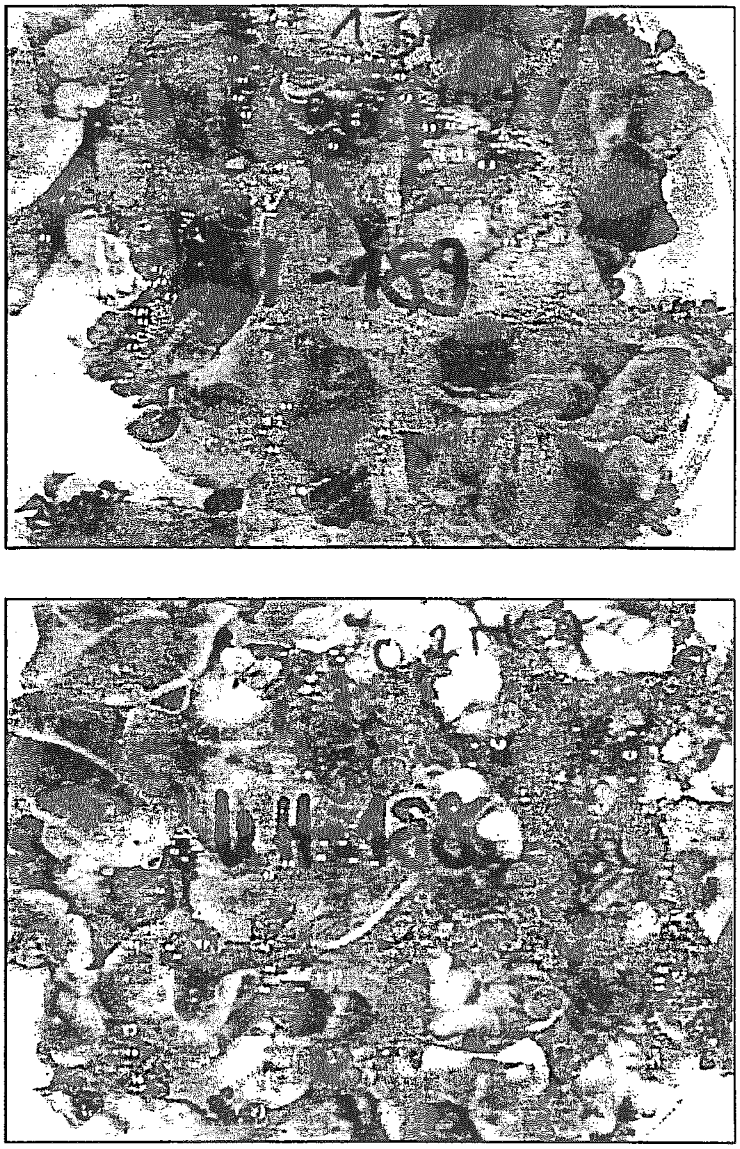
FIG. 4. Regeneration of transformed tobacco plumulae under kanamycin selection pressure. A: transformation with an FNR promoter-nptII construct. B; transformation with a TPT promoter-nptII construct.
Figure 5:
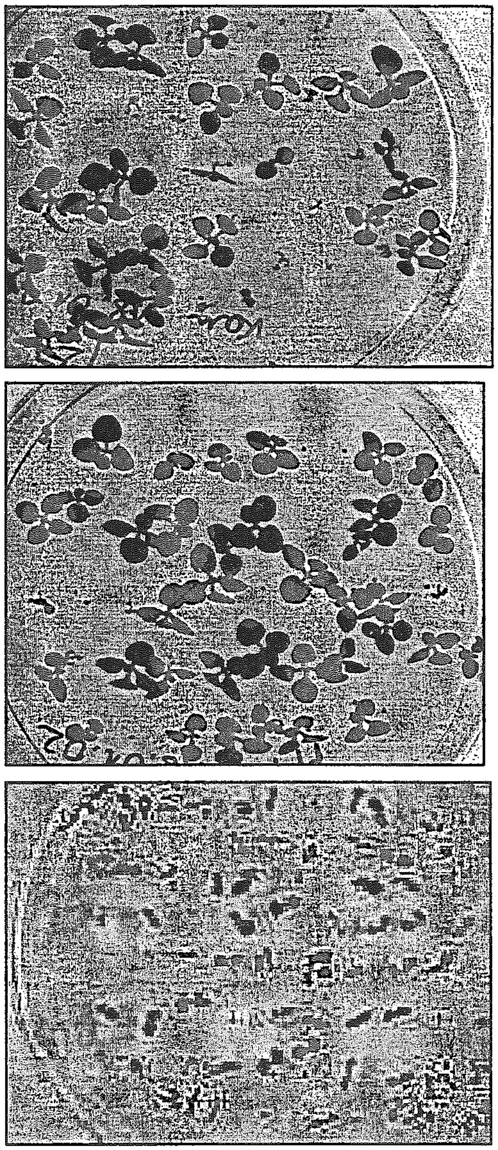
FIG. 5. Germination of transformed tobacco plants from transgenic tobacco seeds under phosphinothricin selection pressure. A: transformed with an FNR promoter-pat construct. B: transformed with a TPT promoter-pat construct. C: control with untransformed tobacco seeds.

FIG. 2*a-b*: The TPT promoter and the FNR promoter show a different expression pattern in vegetative and germinative storage tissue of tobacco and potato. While the TPT promoter is active here, the FNR promoter shows no expression. GUS histochemical stains of tobacco seeds and tobacco seedlings and also of potato tubers are shown. However, both promoters exhibit again a comparable activity in seedlings. The intensity of the GUS blue stain corresponds to the shades of gray displayed. The figures show:

In FIG. 2*a:*

A: Tobacco seeds. In the case of the TPT promoter, individual blue stained seeds are visible (see arrow). In the case of the FNR promoter, no stains are detectable.

B: Potato tubers. In the case of the TPT promoter, a homogenous strong blue stain of the potato tuber is visible. In the case of the FNR promoter, only a very weak stain is detectable, if at all.

In FIG. 2*b:*

C: Tobacco seedlings (10 days old). Both promoters show a comparable blue stain (see arrow).

Expression cassettes for the expression of kanamycin-resistance (nptII) and phosphinothricin-resistance (pat) markers. Cassette A permits expression of kanamycin resistance under the TPT or FNR promoter, in addition to a phosphinothricin resistance under the NOS promoter. Cassette B permits expression of phosphinothricin resistance under the TPT or FNR promoter, in addition to kanamycin resistance under the NOS promoter.

LB, RB: left and right border, respectively, of *Agrobacterium* T-DNA nosP: NOS promoter pat: nucleic acid sequence coding for phosphinothricin acetyltransferase (pat)

nptII: kanamycin resistance gene (Neomycin phosphotransferase)

nosT: NOS terminator

FNR-P: FNR promoter

TPT-P: TPT promoter

Regeneration of transformed tobacco plumulae under kanamycin selection pressure (100 mg/l kanamycin). A: transformation with an FNR promoter-nptII construct. B: transformation with a TPT promoter-nptII construct. A comparable efficient regeneration of transformed tobacco plants was observed.

Germination of transformed tobacco plants from transgenic tobacco seeds under phosphinothricin selection pressure (10 mg/l phosphinotricin).

A: transformed with an FNR promoter-pat construct.

B: transformed with a TPT promoter-pat construct.

C: control with untransformed tobacco seeds.

A comparably efficient germination of tobacco plants transformed with the FNR promoter-pat construct and the TPT promoter-pat construct was observed, while untransformed tobacco plants treated in a corresponding manner had no resistance.

The following examples illustrate embodiments of the invention, but should not be viewed as limiting the scope of the invention.

EXAMPLES

General Methods

The chemical synthesis of oligonucleotides may be carried out in a manner known per se, for example according to the phosphoramidite method (Voet, $2^{nd}$ edition, Wiley Press New York, pages 896-897). The cloning steps carried out within the framework of the present invention, such as, for example, restriction cleavages, agarose gel electrophoreses, purification of DNA fragments, transfer of nucleic acids to nitrocellulose and nylon membranes, ligation of DNA fragments, transformation of *E. coli* cells, cultivation of bacteria, propagation of phages and sequence analysis of recombinant DNA, are carried out as described in Sambrook et al. (1989) Cold Spring Harbor Laboratory Press; ISBN 0-87969-309-6. Recombinant DNA molecules are sequenced according to the method of Sanger (Sanger et al. (1977) Proc Natl Acad Sci USA 74:5463-5467), using a laser fluorescence DNA sequencer from ABI.

Example 1

Isolation of Genomic DNA from *Arabidopsis thaliana* (CTAB Method)

Genomic DNA is isolated from *Arabidopsis thaliana* by grinding approx. 0.25 g of leaf material of young plants in the vegetative state in liquid nitrogen to give a fine powder. The pulverulent plant material is introduced together with 1 ml of 65° C. CTAB I buffer (CTAB: hexadecyltrimethylammonium bromide, also called cetyltrimethylammonium bromide; Sigma Cat.-No.: H6269) and 20 µl of β-mercaptoethanol into a prewarmed second mortar and, after complete homogenization, the extract is transferred to a 2 ml Eppendorf vessel and incubated with careful regular mixing at 65° C. for 1 h. After cooling to room temperature, the mixture is extracted with 1 ml of chloroform/octanol (24:1, equilibrated by shaking with 1 M Tris/HCl, pH8.0) by slowly inverting the vessel and the phases are separated by centrifugation at 8,500 rpm (7,500×g) and room temperature for 5 min. Subsequently, the aqueous phase is extracted again with 1 ml of chloroform/octanol, centrifuged and carefully mixed with {fraction (1/10)} volume of CTAB II buffer prewarmed to 65° C. by inverting the vessel. One ml of chloroform/octanol mixture (see above) is then added with careful agitation to the reaction mixture and the phases are again separated by centrifugation at 8,500 rpm (7,500×g) and room temperature for 5 min. The aqueous lower phase is transferred to a fresh Eppendorf vessel and the upper organic phase is again centrifuged in a fresh Eppendorf vessel at 8,500 rpm (7,500×g) and room temperature for 15 min. The aqueous phase resulting herefrom is combined with the aqueous phase of the previous centrifugation step and the entire reaction mixture is then mixed with exactly the same volume of prewarmed CTAB III buffer. This is followed by an incubation at 65° C. until the DNA precipitates in flakes. This may continue for up to 1 h or be affected by incubation at 37° C. overnight. The sediment resulting from the subsequent centrifugation step (5 min, 2000 rpm (500×g), 4.degree° is admixed with 250 µl of CTAB IV buffer prewarmed to 65.degree. C., and the mixture is incubated at 65° C. for at least 30 min or until the sediment has completely dissolved. The DNA is then precipitated by mixing the solution with 2.5 volumes of ice-cold ethanol and incubating at −20° C. for 1 h. As an alternative, the reaction mixture is mixed with 0.6 volumes of isopropanol and, without further incubation, immediately centrifuged at 8,500 rpm (7,500×g) and 4° C. for 15 min. The sedimented DNA is washed twice with in each case 1 ml of 80% strength ice-cold ethanol by inverting the Eppendorf vessel, each washing step being followed by another centrifugation (5 min, 8,500 rpm (7,500×g), 4° C.) and the DNA pellet is then dried in air for approx. 15 min Finally, the DNA is resuspended in 100 µl of TE comprising 100 µg/ml RNase and the mixture is incubated at room temperature for 30 min. After another incubation phase at 4° C. overnight, the DNA solution is homogeneous and can be used for subsequent experiments.

Solution for CTAB:

Solution I (for 200 ml):

100 mM Tris/HCl pH 8.0 (2.42 g)

1.4 M NaCl (16.36 g)

20 mM EDTA (8.0 ml of 0.5 M stock solution)

2% (w/v) CTAB (4.0 g)

The following is added in each case prior to use: 2% β-mercaptoethanol (20 µl for 1 ml of solution I).

Solution II (for 200 ml):

0.7 MNaCl (8.18 g)

10% (w/v) CTAB (20 g)

Solution III (for 200 ml):
50 mM Tris/HCl pH 8.0 (1.21 g)
10 mM EDTA (4 ml 0.5 M of 0.5 M stock solution)
1% (w/v) CTAB (2.0 g)
Solution IV (High-Salt TE) (for 200 ml):
10 mM Tris/HCl pH 8.0 (0.242 g)
0.1 mM EDTA (40 μl of 0.5 M stock solution)
1 M NaCl (11.69 g)
Chloroform/Octanol (24:1) (for 200 ml):
192 ml of chloroform
8 ml of octanol The mixture is equilibrated by shaking 2× with 1 M Tris/HCl pH 8.0 and stored protected from light.

Example 2

Transformation of Tobacco, Oilseed Rape and Potato

Tobacco was transformed via infection with *Agrobacterium tumefaciens*. According to the method developed by Horsch (Horsch et al. (1985) Science 227: 1229-1231). All constructs used for transformation were transformed into *Agrobacterium tumefaciens* by using the freeze/thaw method (repeated thawing and freezing). The *Agrobacterium* colonies comprising the desired construct were selected on mannitol/glutamate medium comprising 50 μg/ml kanamycin, 50 μg/ml ampicillin and 25 μg/ml rifampicin.

Tobacco plants (*Nicotiana tabacum* L. cv. Samsun N N) were transformed by centrifuging 10 ml of an *Agrobacterium tumefaciens* overnight culture grown under selection, discarding the supernatant and resuspending the bacteria in the same volume of antibiotics-free medium. Leaf disks of sterile plants (approx. 1 cm in diameter) were bathed in this bacteria solution in a sterile Petri dish. The leaf disks were then laid out in Petri dishes on MS medium (Murashige and Skoog (1962) Physiol Plant 15:473ff.) comprising 2% sucrose and 0.8% Bacto agar. After incubation in the dark at 25° C. for 2 days, they were transferred to MS medium comprising 100 mg/l kanamycin, 500 mg/i Claforan, 1 mg/l benzylaminopurine (BAP), 0.2 mg/l naphthylacetic acid (NAA), 1.6% glucose and 0.8% Bacto agar and cultivation was continued (16 hours light/8 hours dark). Growing shoots were transferred to hormone-free MS medium comprising 2% sucrose, 250 mg/l Claforan and 0.8% Bacto agar.

Oilseed rape was transformed by means of petiole transformation according to Moloney et al. (Moloney M M, Walker J M & Sharma K K (1989) Plant Cell Reports 8:238-242).

Potatoes (*Solanum tuberosum*) were transformed by infecting leaf disks and internodia of in vitro plants with *Agrobacterium tumefaciens* in liquid Murashige Skoog Medium for 20 minutes and then coculturing them in the dark for 2 d. After coculturing, the explants were cultured on solid MS medium which contains instead of sucrose 1.6% glucose (MG) and which has been supplemented with 5 mg/l NAA, 0.1 mg/l BAP, 250 mg/l Timentin and 30 to 40 mg/l kanamycin (KIM), at 21° C. in a 16 h light/8 h dark rhythm. After this callus phase, the explants were placed on shoot induction medium (SIM). SIM was composed as follows: MG+2 mg/l Zeatinriboside, 0.02 mg/l NAA, 0.02 mg/l GA3, 250 mg/l Timentin, 30 to 40 mg/l kanamycin. Every two weeks, the explants were transferred to fresh SIM. The developing shoots were rooted on MS medium comprising 2% sucrose and 250 mg/l Timentin and 30 to 40 mg/l kanamycin.

Example 3

Studies on the Suitability of the Putative Ferredoxin (pFD) Promoter

Cloning of the pFD Promoters from *Arabidopsis thaliana*

The putative ferredoxin promoter was amplified from genomic *Arabidopsis thaliana* DNA by means of PCR using the primers pWL35 and pWL36. The primer pWL35 starts with the SalI and EcoRI restriction cleavage sites which are located immediately upstream of the coding region of the pFD gene and are highlighted in bold type. The primer pWL36 starts with the SalI and Asp718 restriction cleavage sites highlighted in bold type.

```
Primer pWL35
                                        (SEQ ID NO: 9)
5' GTC GAC GAA TTC GAG AGA CAG AGA GAC GG 3'

Primer pWL36
                                       (SEQ ID NO: 10)
5' GTC GAC GGT ACC GAT TCA AGC TTC ACT GC 3'
```

Reaction Mixture:
1 μl Genomic *Arabidopsis* DNA (approx. 250 ng)
0.5 μl Tth polymerase (2 U/.mu.l)
3 μl $Mg(OAc)_2$ (25 mM, final conc. 1.5 mM $Mg^{2+}$)
15.2 μl 3.3× buffer
4 μl dNTPs (2.5 mM each, Takara, final concentration: 200 μM each)
24.3 μl $H_2O$ PCR Conditions:
1 cycle at 95° C. for 3 min
10 cycles at 94° C. for 10 s, 50° C. for 20 s and 72° C. for 1 min
20 cycles at 94° C. for 10 s, 65° C. for 20 s and 72° C. for 1 min
1 cycle at 72° C. for 5 min.—followed by cooling to 4° C. until further use.

b) Construction of the pFD Promoter-GUS Expression Cassette.

The PCR product of the pFD promoter was cloned into the pCRII vector (Invitrogen) and subsequently isolated by means of the SalI restriction cleavage sites introduced by the pair of primers and purified by gel electrophoresis. For fusion with the GUS gene, the approx. 850 bp pFD promoter fragment was cloned into the Sail-cut binary vector pBI101.2 (Clontech Inc.) and the orientation of the fragment was subsequently verified on the basis of restriction analyses using the endonucleases BglII and BamHI. The resulting plasmid pFD::GUS was transformed into tobacco. The tobacco plants generated were denoted pFD:GUS.

c) Construction of the pFD Promoter-NptII Expression Cassette.

The putative ferredoxin promoter was amplified from genomic *Arabidopsis thaliana* DNA by means of PCR. The primers were used to add the restriction sites EcoRI and NcoI.

```
Primer pFD1
                                   (SEQ ID NO: 11)
5' GAG AAT TCG ATT CAA GCT TCA CTG C

Primer pFD2
                                   (SEQ ID NO: 12)
5' CCA TGG GAG AGA CAG AGA GAC G
```

Reaction Mixture:

37.5 μl $H_2O$ 5.0 μl 10× reaction buffer (final concentration $Mg^{2+}$ 1.5 mM)

4.0 μl dNTP mix (2.5 mM each)

1.0 μl Primer pFD1 (10 μM)

1.0 μl Primer pFD2 (10 μM)

0.5 μl Taq polymerase (Takara, 2 U/μl)

1.0 μl genomic *Arabidopsis* DNA (approx. 250 ng)

PCR Conditions:

cycle at 94° C. for 3 min cycles at 94° C. for 10 s, 48° C. for 20 s and 72° C. for 1 min.

cycles at 94° C. for 10 s, 65° C. for 20 s and 72° C. for 1 min.

cycle at 72° C. for 5 min.

The PCR product was subcloned into the pCRII plasmid (Invitrogen). The plasmid pCAMBIA 2300 (CAMBIA, GPO Box 3200, Canberra ACT 2601, Australia; GenBank Acc. No: AF234315; Binary vector pCAMBIA-2300, complete sequence; Hajdukiewicz P et al. (1994) Plant Mol Biol 25(6): 989-994) was cut with EcoRI/NcoI and the pFD promoter fragment was cloned as EcoRI/NcoI fragment from the pCRII plasmid into this vector. In the process, the 35S promoter was removed from the Cambia vector. The resulting plasmid was referred to as pFD promoter:NPTII and transformed into tobacco.

Results of GUS Analysis of the Transgenic Tobacco Plants.

In the context of histochemical investigations, transgenic pFD::GUS tobacco plants showed strong GUS staining in source leaves and weak GUS staining in the tissues of all flower organs. Strong staining in root tissue was only observed in in vitro plants whose roots had been exposed to the illumination. Callus growth was induced on the basis of leaf disks which had been punched out of plants identified as pFD::GUS-positive. The callus tissue and also the plant shoots developing therefrom showed GUS staining whose intensity was comparable to that of the GUS staining of CaMV35S::GUS (in pCambia 1304; CAMBIA, GPO Box 3200, Canberra ACT 2601, Australia; GenBank Acc. No.: AF234300, Binary vector pCAMBIA-1304, complete sequence, Hajdukiewicz P et al. (1994) Plant Mol. Biol. 25(6):989-994) (1994)) transgenic plants. The table listed below (Table 3) summarizes the data of quantifying the GUS activity in the anthers and source leaves of selected transgenic pFD::GUS tobacco plants.

TABLE 3

Quantification of GUS activity in anthers and source leaves of selected transgenic pFD::GUS tobacco plants.

| | GUS-Activity (pmol [4 MU]/mg[protein]/min) | |
|---|---|---|
| pFD::GUS Plant no. | Anthers | 'Source' leaves |
| pFD5 | 275 | 3785 |
| pFD11 | 174 | 6202 |
| pFD14 | 362 | 2898 |
| pFD15 | 57 | 2678 |

The anthers of the mature flowers display no promoter activity. Said activity is weak in closed flowers.

e) Results of the Analysis of Kanamycin Resistance of the Transgenic Tobacco Plants.

In order to study the pFD promoter-assisted imparting of resistance to kanamycin, the pFD promoter:NPTII plasmid was transformed into tobacco. The tobacco plants were selectively regenerated on kanamycin (100 mg/l). The plants regenerated from the developing plumulae comprised kanamycin, demonstrating that the pFD promoter had expressed the NPTII gene and thus made selection possible. The results demonstrate that the isolated nucleic acid sequence has the desired advantageous promoter properties, i.e. it exhibits a promoter activity which is suitable for expressing selection markers effectively and its activity in the pollen is low. The activity in the anthers is normally less than 10% of the activity in the source leaves.

f) Results of GUS Analysis of the Transgenic Potato Plants.

The pFD:GUS plasmid (cf. Example 3b) is transformed into potatoes according to the method described in Example 2.

Result of functional studies: The pFD promoter is strongly expressed in the leaves of the transgenic potato plants analyzed. GUS staining was found to be stronger in the leaves of the potato plants than in the leaves of the tobacco plants described. Weak staining of the flowers and no staining of the tubers indicated low expression in the flowers and no expression in the tubers, respectively.

The data demonstrate that this promoter has no activity in the tubers of potato plants and is suitable for the expression of genes, for example of insecticides, in the leaves and other organs above the ground of plants, whose gene products are unwanted in the storage organs.

Preparation of Deletion Variants of the pFD Promoter.

A further pFD promoter variant is the deletion pFD-short (pFds). For this purpose, the pFD promoter section from base pairs 137 to 837 was amplified using the following primers:

```
pFD3 (SEQ ID NO: 13):
5'-acggatccgagagacagagagacggagacaa-aa-3':

pFD5 (SEQ ID NO: 14):
5'gcggatccaacactataacaccaaatcaaca-3':
```

Reaction Mixture:

37.5 μl $H_2O$ 5.0 μl 10× reaction buffer ("genomic PCR")

4.0 μl dNTP mix (2.5 mM each)

2.2 μl 25 mM Mg(OAc).sub.2 (final concentration 1.1 mM)

1.0 μl Primer pFD3 (10 μM)

1.0 μl Primer pFD5 (10 μM)

0.5 μl Pfu-turbo polymerase mix 1.0 μl Genomic *Arabidopsis* DNA (approx. 250 ng)

PCR Conditions:

cycle at 95° C. for 5 min 25 cycles at 94° C. for 30 s, 50° C. for 60 s and 72° C. for 1 min.

cycle at 50° C. for 60 s, 72° C. for 10 min, followed by cooling to 4° C. until further use.

The primers comprised recognition sequences for the restriction enzyme BamHI. After BamHI cleavage, the PCR product was ligated into the plasmid pGUSINT37 (see above) which had likewise been cut with BamHI and had been dephosphorylated. Tobacco leaves were bombarded with the resulting construct pFDsGUSINT by means of Biolistics (BioRad). In this connection, microcarriers (25 μg of Gold, Heraeus 0.3 to 3 μm) were treated with 10 μg of plasmid DNA, 2.5 M $CaCl_2$, and 0.1 M spermidine, washed with alcohol and fired at the leaves which were lying on MS medium under a vacuum of 26 inches and a pressure of 1100 psi. The explants were then incubated in MS medium comprising 2% sucrose for 24 h and then histochemically stained with X-gluc. Blue spots indicated the activity of the promoter.

Fusing the pFDs Promoter to the NPTII Gene.

The pFDs promoter is excised as BamHI fragment from pFDsGUSINT and its ends are rendered blunt by means of Klenow-"Fill-In." The fragment obtained is cloned upstream of the NPTII gene of the EcoRV-cut and dephosphorylated plasmid pSUN5NPTIICat (SEQ ID NO: 24). The plasmid pSUN5NPTII is a derivative of plasmid pSUN3 (SEQ ID NO: 23), which contains, apart from nosP/Pat cassette, also a promoterless NPTII gene. This construct makes it possible to assay promoters on their ability to express NPTII. Selection on phosphinothricin-comprising medium may be carried out in parallel.

The resulting plasmid pSun5FdsNPTII is transformed into tobacco. Regenerated and selected shoots showed that the pFDs promoter allows selection for NPTII.

Example 4

Studies on the Suitability of the Ferredoxin NADPH Oxidoreductase (FNR) Promoter Cloning of the FNR Promoter from *Arabidopsis thaliana.*

The putative promoter region of the FNR gene was amplified from genomic DNA by using the oligonucleotide primers L-FNRara and R-FNRara, bypassing the ATG start codon of the FNR gene and retaining four putative stop codons of the open reading frame located upstream. Using the primers L-FNRara and R-FNRara, the FNR promoter was amplified as a 635 bp fragment corresponding to the section of the clone K2A18.15 from position 69493 to position 70127 (including these two nucleotides) from genomic *Arabidopsis thaliana* DNA by means of PCR. The primer L-FNRara starts with the restriction cleavage sites SalI and BamHI highlighted in bold type and is located upstream of the four stop codons of the gene located upstream of the FNR promoter. The primer R-FNRara starts with the SalI and XbaI restriction cleavage sites which are located immediately upstream of the ATG start codon of the FNR gene and are highlighted in bold type.

```
Primer L-FNR ara (44 mer) (SEQ ID NO: 15):
5' GTC GAC GGA TCC GGT TGA TCA GAA GAA GAA GAA GAA
GAT GAA CT 3'

Primer R-FNR ara (41 mer) (SEQ ID NO: 16):
5' GTC GAC TCT AGA TTC ATT ATT TCG ATT TTG ATT TCG
TGA CC 3'
```

The FNR promoter was amplified using a "touchdown" PCR protocol with the use of the 'Advantage Genomic Polymerase Mix' (Clontech Laboratories, Inc; Catalogue No. #8418-1). The above-mentioned polymerase mix contains a thermostable DNA polymerase from *Thermus thermophilus* (Tth DNA polymerase), mixed with a smaller proportion of Vent proofreading 3'-5' polymerase, and the Tth start antibody which makes hot-start PCR possible.

Reaction Mixture:

36.8 μl $H_2O$

5 μl 10× reaction buffer ("genomic PCR")

1 μl dNTP mix (10 mM each)

2.2 μl 25 mM $Mg(OAc)^2$ (final concentration 1.1 mM)

1 μl Primer L-FNR ara (10 μM)

1 μl Primer R-FNR ara (10 μM)

1 μl 50× polymerase mix

2 μl Genomic *Arabidopsis* DNA (approx. 500 ng)

PCR Conditions:

1 cycle at 94° C. for 1 min 10 cycles at 94° C. for 30 s and 70° C. for 3 min.

32 cycles at 94° C. for 30 s and 65° C. for 3 min.

1 cycle at 65° C. for 4 min.—followed by cooling to 4° C. until further use.

Construction of the FNR Promoter-GUS Expression Cassette.

After gel-electrophoretic fractionation and purification from the gel using the Quiagen PCR purification kit, the PCR product of the FNR promoter was cloned into the pCRII vector (Invitrogen) via TA cloning The promoter fragment was then isolated from the resulting plasmid pATFNR1 bp digestion with XbaI/BamHI by means of the XbaI and BamHI restriction cleavage sites introduced by the pair of primers and purified by gel electrophoresis. For fusion with the GUS gene, the approx. 600 bp FNR promoter fragment was cloned into the XbaI/BamHI-digested binary vector pBI101. The correct insertion of the correct fragment in the resulting plasmid pATFNR-Bi was then verified on the basis of a restriction analysis using the endonuclease EcoRV. The plasmid pATFNR-Bi was used for transformation of tobacco.

For transformation in oilseed rape, the FNR promoter was cloned as SalI fragment of plasmid pCR_ATFNR into the vector pS3NitGUS cut with SalI and XhoI, thereby replacing the nitrilase promoter.

Construction of the FNR Promoter-PAT Expression Cassette.

In order to study the FNR promoter-assisted imparting of resistance to phosphinothricin, the FNR promoter was cloned as SalI fragment from plasmid pATFNR1 into the SalI-cut plasmid pSUN3 PatNos (SEQ ID NO: 25) upstream of the phosphinothricin resistance gene.

Construction of the FNR Promoter-NptII Expression Cassette.

In order to impart resistance to kanamycin, the FNR promoter was cloned as SalI fragment into the Xha-cut dephosphorylated plasmid pSUN5NptIICat (Sungene GmbH & Co KGaA, SEQ ID NO: 24) upstream of the NPTII resistance gene. The resulting plasmid is referred to as pS5FNRNptII and was transformed into tobacco and oilseed rape.

Results of GUS Analysis of the Transgenic Tobacco Plants.

Qualitative data: Transgenic FNR::GUS-Tobacco plants displayed strong GUS expression in all green tissues, especially in source leaves, leaf stalks and internodia, and also in all flower organs of fully developed flowers, (ovary, stigma, sepals and petals) with the exception of pollen which showed no GUS activity; a low staining intensity was detected in anthers. In the first analysis of leaf disks of 80 in vitro plants, 70 plants displayed strong GUS staining with low variation in staining intensity between the individual plants. This was regarded as an indication that the FNR promoter contains an element which provides limited positional effects. In the tissue culture plants, the GUS activity of the FNR::GUS plants was markedly lower than the activity of TPT::GUS plants. Transgenic oilseed rape plants displayed the same staining pattern.

Seed material (F1) of the lines FNR 13, FNR 45 and FNR 28 was analyzed with respect to its GUS activity. It turned out that GUS activity was detected neither in resting seeds nor in growing seedlings (3.5 days after sowing).

In later seedlings stages (6 and 10 days after sowing), strong GUS activity was detected in the cotyledons and in the upper region of the seedling axis, whereas no GUS staining was detected in the roots. In seedlings which had been cultivated in the dark, GUS activity was limited to the cotyledons and was overall lower than in the light-germinated seedlings.

Quantitative analysis of the GUS activity in FNR::GUS transgenic tobacco plants (transformed with plasmid pATFNR-Bi) was analyzed on the first fully developed leaves of tobacco plants 21 days after transfer from the tissue culture to the greenhouse. The data corresponds to the average of four independent measurements.

TABLE 4

Quantification of GUS activity in leaf material of selected transgenic FNR::GUS tobacco plants (transformed with plasmid pATFNR-Bi).

| FNR::GUS Plant No. | Rank (x-strongest GUS activity among 50 plants) | GUS Activity (pmol 4-MU/mg Protein/min) | Standard deviation |
|---|---|---|---|
| 13 | 1 | 86491 | 2974 |
| 45 | 2 | 41726 | 1829 |
| 14 | 7 | 23951 | 2443 |
| 28 | 9 | 22148 | 401 |
| 17 | 10 | 21557 | 1157 |
| 30 | 20 | 13444 | 744 |
| 40 | 26 | 11972 | 1144 |
| 25 | 35 | 7662 | 519 |
| 35 | 39 | 5643 | 96 |
| 21 | 43 | 2858 | 194 |
| C2-(WT) | 49 | 28 | 4 |

f) Result of Analysis of Phosphinothricin Resistance of the Transgenic Tobacco Plants.

The plasmid pSUN3FNRPat was used for transformation of tobacco by using the *Agrobacterium tumefaciens* strain EHA101, as described under 3. The tobacco plants are selectively regenerated either on phosphinothricin (5 mg/l) or, as a control, on kanamycin (100 mg/l). 97% of explants selected under kanamycin pressure (nosP:NPTII) and 40% of explants selected under phosphinothricin pressure (FNR:Bar) developed plumulae. The plants regenerated under phosphinothricin pressure comprised both the kanamycin and the phosphinothricin gene, demonstrating that the FNR promoter had expressed the phosphinothricin acetyltransferase gene and thus made selection possible. Seeds of the transgenic tobacco plants were laid out on MS medium comprising 10 mg/l phosphinothricin and the rate of germination was determined. In contrast to the control of untransformed tobacco seeds, the seedlings developed normally. The gene of phosphinothricin acetyltransferase, which had been transferred and expressed via the FNR promoter, was detected in the progeny of said lines by means of PCR. The results demonstrated that the isolated nucleic acid sequence has the desired advantageous promoter properties, i.e. it shows a promoter activity which is suitable for expressing selection markers effectively and has no activity in pollen.

g) Results of the Analysis of Kanamycin Resistance of the Transgenic Tobacco and Oilseed Rape Plants.

In order to study the FNR promoter-assisted imparting of resistance to kanamycin, the FNR promoter was combined with the NptII gene. The resulting construct pS5FNRNptII was transformed into the *Agrobacterium tumefaciens* strain GV3101 [mp 90] for transformation in tobacco and oilseed rape.

Seeds of the transgenic tobacco plants were laid out on MS medium comprising 100 mg/l kanamycin and the rate of germination was determined. In contrast to the control of untransformed tobacco seeds, the seedlings developed normally. The gene of neomycin phosphotransferase (nptII), which had been transferred and expressed via the FNR promoter, was detected in the progeny of said lines by means of PCR.

The resulting strains have been used for transformation, as described under Example 2. Selective regeneration was achieved in the presence of 100 mg/l (or 18 mg/l in the case of oilseed rape) kanamycin. The plants regenerated under kanamycin pressure comprised both the kanamycin and the phosphinothricin gene, demonstrating that the FNR promoter had expressed the NptII gene and thus made selection of the plants possible.

The results demonstrated that the isolated nucleic acid sequence has the desired advantageous promoter properties, i.e. it shows a promoter activity which is suitable for expressing selection markers effectively and has no activity in pollen.

Results of GUS Analysis of the Transgenic Potato Plants.

The analysis of putatively transgenic potato plants showed in 20 lines a strong GUS staining in the leaves, comparable to the expression pattern of tobacco plants. With the exception of 5 plants which showed a very weak staining in the potato tubers, no FNR promoter expression was detected in the remaining plants.

The data demonstrate that this promoter has very weak, if any, activity in the storage organs of potato plants and is suitable for the expression of genes, for example of insecticides, in the leaves and other organs above the ground of plants, whose gene products are unwanted in the storage organs.

Example 5

Studies on the Suitability of the Triose Phosphate Translocator (TPT) Promoter Cloning of the TPT Promoter from *Arabidopsis thaliana.*

The putative promoter region of the TPT gene from *Arabidopsis thaliana* was isolated by amplification using the oligonucleotide primers L-TPTara and R-TPTara, the ATG start codon of the TPT gene being bypassed. Using the primers L-TPTara and R-TPTara, the TPT promoter was amplified as a 2038 bp fragment from genomic *Arabidopsis thaliana* DNA by means of PCR (SEQ ID NO: 3). The primer L-TPTara starts with the SalI and BamHI restriction cleavage sites highlighted in bold type. The primer R-TPTara starts with the AatII, SalI and XbaI restriction cleavage sites which are located immediately upstream of the ATG start codon of the TPT gene and are highlighted in bold type.

```
Primer L-TPTara (SEQ ID NO: 17):
5' AAG TCG ACG GAT CCA TAA CCA AAA GAA CTC TGA TCA
TGT ACG TAC CCA TT 3'

Primer R-TPTara (SEQ ID NO: 18):
5' AGA CGT CGA CTC TAG ATG AAA TCG AAA TTC AGA GTT
TTG ATA GTG AGA GC 3'
```

The TPT promoter was amplified using a "touchdown" PCR protocol with the use of the Advantage Genomic Polymerase Mix (Clontech Laboratories, Inc; Catalogue No. #8418-1). The above-mentioned polymerase mix contains a thermostable DNA polymerase from *Thermus thermophilus* (Tth DNA polymerase), mixed with a smaller proportion of Vent proofreading 3'-5' polymerase, and the Tth start antibody which makes hot-start PCR possible.

Reaction Mixture:

36.8 µl $H_2O$

5 µl 10× reaction buffer ("genomic PCR")

1 µl dNTP mix (10 mM each)

2.2 µl. 25 mM Mg(OAc).sub.2 (final concentration 1.1 mM)

1 µl Primer L-FNR ara (10 µM)

1 µl Primer R-FNR ara (10 µM)

1 µl 50× polymerase mix

2 µl Genomic *Arabidopsis* DNA (approx. 500 ng)

PCR Conditions:

1 cycle at 94° C. for 1 min.

10 cycles at 94° C. for 30 s and 70° C. for 3 min.

32 cycles at 94° C. for 30 s and 65° C. for 3 min.

1 cycle at 65° C. for 4 min.—followed by cooling to 4° C. until further use.

b) Construction of the TPT Promoter-GUS Expression Cassette.

After gel-electrophoretic fractionation and purification from the gel using the Quiagen PCR purification kit, the PCR product of the TPT promoter was cloned into the pCRII vector (Invitrogen) via TA cloning. The promoter fragment was then isolated from the resulting plasmid pATTPT by means of the SalI and XbaI restriction cleavage sites introduced by the pair of primers and purified by gel electrophoresis. For fusion with the GUS gene, the approx. 2.0 kb TPT promoter fragment was cloned into the SalI/XbaI-digested binary vector pBI101. The correct insertion of the correct fragment in the resulting plasmid pATTPT-Bi was then verified on the basis of a restriction analysis using the endonuclease HindIII. The plasmid pATTPT-Bi was used for transformation of tobacco.

For transformation in oilseed rape, the TPT promoter was cloned as SalI fragment of plasmid pATTPT into the vector pS3NitGUS cut with SalI and XhoI, thereby replacing the nitrilase promoter.

c) Construction of the TPT Promoter-PAT Expression Cassette.

In order to study the TPT promoter-assisted imparting of resistance to phosphinothricin, the TPT promoter was cloned as SalI fragment from plasmid pATTPT into the SalI-cut plasmid pSUN3 PatNos upstream of the phosphinothricin resistance gene. The resulting plasmid pSUN3TPTPat was used for transformation of tobacco using the *Agrobacterium tumefaciens* strain EHA101. The tobacco plants were selectively regenerated either on phosphinothricin (5 mg/l) or, as a control, on kanamycin (100 mg/l).

d) Construction of the TPT Promoter-NptII Expression Cassette.

In order to impart resistance to kanamycin, the TPT promoter was cloned as SalI fragment into the Xha-cut dephosphorylated plasmid pSUN5NptIICat (Sungene GmbH & Co KGaA, SEQ ID NO: 24) upstream of the NPTII resistance gene. The resulting plasmid is referred to as pS5TPTNptII and was transformed into tobacco and oilseed rape.

e) Results of GUS Analysis of the Transgenic Tobacco Plants.

Qualitative Data

Transgenic TPT::GUS-tobacco plants displayed strong GUS expression in all green tissues, especially in source leaves, here in particular in the trichomes and the flower organs of young and fully developed flowers. GUS activity in the flower region was strongest in the ovaries and in the stigma; staining of the sepals and petals was somewhat weaker. The GUS activity was lowest in the anthers. No GUS activity was detected in the pollen. Transgenic oilseed rape plants showed the same staining pattern.

In the first analysis of leaf disks of 80 in vitro-plants, 22 plants showed no staining whatsoever and 22 plants showed strong GUS staining after staining for only 3 hours. The remaining plants displayed a good variety of GUS stainings of various intensities in the individual plants. In the tissue culture plants, the GUS activity of the TPT::GUS plants was markedly stronger than that of the FNR::GUS plants. Seed material (F1) of the lines TPT 55 and TPT 60 were analyzed with respect to their GUS activity. It turned out that strong, GUS activity was detected both in resting seeds and in growing seedlings (3.5 days after sowing). In later seedling stages (6 and 10 days after sowing), the strongest GUS activity was detected in cotyledons and in the upper region of the seedling axis and a weaker GUS staining in the roots. Seedlings which had been cultivated in the dark displayed an unchanged GUS staining pattern.

Quantitative Data

Quantitative analysis of the GUS activity in TPT::GUS transgenic tobacco plants (transformed with plasmid pAT-TPT-Bi) was carried out on the first fully developed leaves of tobacco plants 19 days after transfer from the tissue culture to the greenhouse. The data correspond to the average of four independent measurements.

TABLE 5

Quantification of GUS activity in leaf tissue of selected transgenic TPT::GUS tobacco plants (transformed with plasmid pAT-TPT-Bi). WT2: controls from untransformed wild-type plants.

| TPT::GUS Plant no. | Rank (x-strongest GUS activity among 50 plants) | GUS Activity (pmol 4-MU/mg Protein/min) | Standard deviation |
|---|---|---|---|
| 55 | 1st | 62910 | 3576 |
| 15 | 2nd | 58251 | 2533 |
| 10 | 5th | 36759 | 1008 |
| 60 | 10th | 19536 | 1783 |
| 56 | 11th | 18876 | 1177 |
| 43 | 12th | 18858 | 1404 |
| 27 | 35th | 7390 | 233 |
| 44 | 59th | 311 | 24 |
| 80-WT2 | 80th | 5 | 13 |

Results of GUS Analysis of the Transgenic Potato Plants.

The analysis of putatively transgenic potato plants showed in 28 lines strong GUS staining in the leaves, comparable to the expression pattern of tobacco plants. A strong staining was likewise detected in the potato tubers of the transgenic plants. This demonstrates that the TPT promoter is expressed strongly and ubiquitously in potatoes, too.

g) Results of the Analysis of Phosphinothricin Resistance of the Transgenic Tobacco Plants.

The plasmid pSUN3TPTPat was used for transformation of tobacco by using the *Agrobacterium tumefaciens* strain EHA101, as described under 3. The tobacco plants are selectively regenerated either on phosphinothricin (5 mg/l) or, as a control, on kanamycin (100 mg/l). 97% of explants selected under kanamycin pressure and 70% of explants selected under phosphinothricin pressure developed plumulae. The plants regenerated under phosphinothricin pressure comprised both the kanamycin and the phosphinothricin gene, demonstrating that the TPT promoter had expressed the phosphinothricin acetyltransferase gene and thus made selection possible. Seeds of the transgenic tobacco plants were laid out on MS medium comprising 10 mg/l phosphinothricin and the rate of germination was determined. In contrast to the control of untransformed tobacco seeds, the seedlings developed normally. The gene of phosphinothricin acetyltransferase, which had been transferred and expressed via the TPT promoter, was detected in the progeny of said lines by means of PCR. The results demonstrate that the isolated nucleic acid sequence has the desired advantageous promoter properties, i.e. it shows a promoter activity which is suitable for expressing selection markers effectively and has no activity in pollen.

h) Results of the Analysis of Kanamycin Resistance of the Transgenic Tobacco and Oilseed Rape Plants.

In order to study the TPT promoter-assisted imparting of resistance to kanamycin, the TPT promoter was combined with the NptII gene. The resulting construct pS5TPTNptII was transformed into the *Agrobacterium tumefaciens* strain GV3101 [mp 90] for transformation in tobacco and oilseed rape.

The resulting strains have been used for transformation, as described under Example 2. Selective regeneration was achieved in the presence of 100 mg/l (or 18 mg/l in the case of oilseed rape) kanamycin. The plants regenerated under kanamycin pressure comprised both the kanamycin and the phosphinothricin gene, demonstrating that the TPT promoter had expressed the NptII gene and thus made selection of the plants possible.

Seeds of the transgenic tobacco plants were laid out on MS medium comprising 100 mg/l kanamycin and the rate of germination was determined. In contrast to the control of untransformed tobacco seeds, the seedlings developed normally. The gene of neomycin phosphotransferase (nptII), which had been transferred and expressed via the TPT promoter, was detected in the progeny of said lines by means of PCR.

The results demonstrate that the isolated nucleic acid sequence has the desired advantageous promoter properties, i.e. it shows a promoter activity which is suitable for expressing selection markers effectively and has no activity in pollen.

i) Cloning of the Truncated TPT Promoter (STPT).

The truncated putative promoter region of the *Arabidopsis thaliana* TPT gene (STPT) was isolated from the plasmid pATTPT (SEQ ID NO: 27) by amplification by means of PCR using the primer 5-TPTara (SEQ-ID NO: 26) and R-TPTara (see above SEQ ID NO: 18).

Reaction Mixture:

37.8 µl $H_2O$

5 µl 10× Reaction buffer (“genomic PCR”)

1 µl dNTP mix (2.5 mM each)

2.2 µl 25 mM Mg(OAc).sub.2 (final concentration 1.1 mM)

1 µl Primer 5-TPTara (10 µM)

1 µl Primer R-TPTara (10 µM)

1 µl 50× polymerase mix (“Advantage Genomic Polymerase Mix”; Clontech Lab., Inc.; Cat.-No.: #8418-1)

1 µpATTPT plasmid DNA (1 ng)

PCR Conditions:

1 cycle at 94° C. for 5 min 25 cycles at 94° C. for 30 s and 52° C. for 1 min.

1 cycle at 52° C. for 4 min., followed by cooling to 4° C. until further use.

```
Promoter Primer 5-TPTara
                                        (SEQ ID NO: 26)
5'-AAG TCG ACG GAT CCT-GAT-AGC-TTA-TAC-TCA-AAT-

TCA-ACA-AGT-TAT-3'
```

The 1.3 kb PCR product of the truncated TPT promoter was cloned, after gel-electrophoretic fractionation and purification from the gel, into the SmaI-cut and dephosphorylated vector pUC18, using the SureClone Ligation Kit (Amersham Pharmacia Biotech; Code-No.: 27-9300-01). The resulting plasmid is referred to as pATSTPT. The sequence was checked by means of sequencing.

j) Construction of the STPT Promoter-NptII Expression Cassette.

In order to impart resistance to kanamycin, the STPT promoter (SEQ ID NO: 27) was cloned as SalI fragment into the XhoI-cut dephosphorylated plasmid pSUN5NptIICat (Sungene GmbH & Co KGaA, SEQ ID NO: 24) upstream of the NptII resistance gene. The resulting plasmid is referred to as pS5STPTNptII and was transformed into tobacco and oilseed rape.

k) Results of the Analysis of Kanamycin Resistance of the Transgenic Tobacco and Oilseed Rape Plants.

In order to study the STPT promoter-assisted imparting of resistance to kanamycin, the plasmid pS5STPTNptII was transformed into the *Agrobacterium tumefaciens* strain GV3101 [mp 90] for transformation into tobacco and oilseed rape. The resulting strain has been used for transformation, as described under Example 2. Selective regeneration was achieved in the presence of 100 mg/l (or 18 mg/l for oilseed rape) kanamycin.

The results demonstrate that the isolated nucleic acid sequence has the desired advantageous promoter properties, i.e. it shows a promoter activity which is suitable for expressing selection markers effectively.

Example 6

Comparison of the Transformation Efficiencies of the FNR and TPT Promoters and of the NOS Promoter In a comparative experiment, the efficiency of the transformation of tobacco was determined using the FNR promoter (FNR-P), the TPT promoter (TPT-P) and the Nos promoter (Nos-P). The promoters were, as described, fused in each case to the NptII gene. After the plumulae had formed and, respectively, the shoot had roots on kanamycin-comprising medium, the resistant transformants were counted and their numbers were compared. A PCR which was used to detect the NptII gene showed the high proportion of transgenic plants.

TABLE 6

| Transformation efficiency | | | |
|---|---|---|---|
| | NOS-P | FNR-P | TPT-P |
| Shoot formation | 100% | 68% | 76% |
| Rooted plants | 80% | 81% | 80% |
| Transgenic plants | 92% | 100% | 100% |

Comparative Example 1

Studies of the Suitability of the Ubiquitin Promoter a) Cloning of the Ubiquitin Promoter from *Arabidopsis thaliana.*

The ubiquitin promoter was amplified from genomic *Arabidopsis thaliana* DNA by means of PCR using the primers ubi5 and ubi3.

```
ubi5 (SEQ ID NO: 19):
5'-CCAAACCATGGTAAGTTTGTCTAAAGCTTA-3-'

ubi3 (SEQ ID NO: 20):
5'-CGGATCCTTTTGTGTTTCGTCT-TCTCTCACG-3'
```

Reaction Mixture:

37.5 µl $H_2O$

5 µl 10× reaction buffer (“genomic PCR”)

4 µl dNTP mix (2.5 mM each)

2.2 µl 25 mM $Mg(OAc)_2$ (final concentration 1.1 mM)

1 µl Primer ubi3 (10 µM)

1 μl Primer ubi5 (10 μM)

0.5 μl Pfu-turbo polymerase mix

1 μl Genomic *Arabidopsis* DNA (ca. 250 ng)

PCR Conditions:

1 cycle at 94° C. for 5 min.

25 cycles at 94° C. for 30 s, 52° C. for 1 min. and 72° C. for 1 min.

1 cycle at 52° C. for 1 min. and 72° C. for 10 min, followed by cooling to 4° C. until further use.

The resultant PCR fragment was cooled as HindIII/BamHI fragment into the HindIII/BamHI-cut plasmid pGUSINT37 (pUBI42GUS) and verified by means of sequence analysis.

b) Cloning of the Ubiquitin Promoter Upstream of the PAT Gene.

In order to study the ubiquitin promoter-assisted imparting of resistance to phosphinothricin, the ubiquitin promoter was cloned as BamHIII/HindIII fragment into the BamHI/HindIII-cut plasmid pSUN3 PatNos upstream of the phosphinothricin resistance gene. The resulting plasmid pSUN3UBIPat was used for transformation of tobacco using the *Agrobacterium tumefaciens* strain EHA101. The tobacco plants were selectively regenerated either on phosphinothricin (5 mg/l) or, as a control, on kanamycin (100 mg/l).

c) Results of the Analysis of Phosphinothricin Resistance of the Transgenic Tobacco Plants.

In contrast to selection on kanamycin, which was normal, no calli or shoots were obtained under selection on phosphinothricin. Thus, the ubiquitin promoter is unsuitable for expression of a selective marker for the *Agrobacterium tumefaciens*-mediated gene transfer with subsequent regeneration of tissues.

Comparative Example 2

Studies on the Suitability of the Squalene Synthase (SQS) Promoter a) Cloning of the Squalene Synthase (SQS) Promoter from *Arabidopsis thaliana*

The squalene synthase promoter was amplified from genomic *Arabidopsis thaliana* DNA by means of PCR using the primers sqs5 and sqs3.

```
sqs5 (SEQ ID NO: 21):
5'-GTCTAGAGGCAAACCACCGAGTGTT-3'

sqs3 (SEQ ID NO: 22):
5'-CGGTACCTGTTTCCAGAAAAT-TTTGATTCAG-3'
```

Reaction Mixture:

37.5 μl $H_2O$

5 μl 10× Reaction buffer (“genomic PCR”)

4 μl dNTP mix (2.5 mM each)

2.2 ml 25 mM $Mg(OAc)_2$ (final concentration 1.1 mM)

1 μl Primer sqs3 (10 μM) (10 μM)

1 μl Primer sqs5 (10 μM)

0.5 μl Pfu-turbo polymerase mix

1 μl Genomic *Arabidopsis* DNA (approx. 250 ng)

PCR Conditions:

1 cycle at 94° C. for 5 min.

25 cycles at 94° C. for 30 s, 52° C. for 1 min. and 72° C. for 1 min.

1 cycle at 52° C. for 1 min. and 72° C. for 10 min., followed by cooling to 4° C. until further use.

The resultant PCR fragment was cloned as XbaII/BamHI fragment into the XbaII/BamHI-cut plasmid pGUSINT37 (PSQSPGUS) and verified by means of sequence analysis.

b) Cloning of the Squalene Synthase Promoter Upstream of the PAT Gene.

In order to study the squalene synthase promoter-assisted imparting of resistance to phosphinothricin, the squalene synthase promoter was cloned as BamHI/SalI fragment into the BamHI/SaliI-cut plasmid pSUN3 PatNos upstream of the phosphinothricin resistance gene. The resulting plasmid pSUN3SQSPat was used for transformation of tobacco using the *Agrobacterium tumefaciens* strain EHA101. The tobacco plants were selectively regenerated either on phosphinothricin (5 mg/l) or, as a control, on kanamycin (100 mg/l).

c) Results of the Analysis of Phosphinothricin Resistance of the Transgenic Tobacco Plants.

In contrast to selection on kanamycin, which was normal, no calli or shoots were obtained under selection on phosphinothricin. Thus, the ubiquitin promoter is unsuitable for expression of a selective marker for the *Agrobacterium tumefaciens*-mediated gene transfer with subsequent regeneration of tissues.

Comparative Example 3

Promoter Activity Assay of the Ubiquitin and Squalene Synthase-Promoter by Means of a Particle Gun In order to assay the activity of the ubiquitin promoter and the squalene synthase promoter, sterile tobacco leaves were bombarded with plasmid DNA of plasmids pUBI42GUS, pSQSPGUS and pGUSINT37 by means of the BioRad Biolistics particle gun. In this connection, microcarriers (25 μg of Gold, Heraeus 0.3 to 3 μm) were treated with 10 μg of plasmid DNA, 2.5 M $CaCl_2$, and 0.1 M spermidine, washed with alcohol and fired at the leaves which were lying on MS agar medium under a vacuum of 26 inches and a pressure of 1100 psi. The explants were then incubated in MS medium comprising 2% sucrose for 24 h and then histochemically stained with X-gluc.

In contrast to the comparative construct pGUSINT37 in which the GUS gene was expressed under the control of the 35S promoter, the ubiquitin promoter and the squalene synthase promoter showed only very few and very weak GUS-stained dots. This indicates that the ubiquitin and squalene synthase promoter activities are distinctly weaker than the CaMV35S promoter activity.

Other embodiments and uses of the invention will be apparent to those skilled in the art from consideration of the specification and practice of the invention disclosed herein. All references cited herein, including all U.S. and foreign patents and patent applications, and all publications or other documentary materials, are specifically and entirely hereby incorporated herein by reference. It is intended that the specification and examples be considered exemplary only, with the true scope and spirit of the invention indicated by the following claims.

We claim:

1. An expression cassette for transgenic expression of nucleic acids, comprising:

i) a promoter; and ii) a nucleic acid sequence to be expressed transgenically which is operably linked to and heterologous in relation to said promoter;

wherein the promoter comprises the sequence of SEQ ID NO: 1, or a fragment thereof, or a sequence having at least 99% identity to the sequence of SEQ ID NO: 1 or 4, wherein said promoter or fragment thereof has constitutive promoter activity.

2. The expression cassette of claim 1, wherein the fragment comprises the sequence of SEQ ID NO: 4.

3. The expression cassette of claim 1, wherein: the nucleic acid sequence to be expressed is further operably linked to one or more genetic control sequences, or the expression cassette comprises one or more additional functional elements.

4. The expression cassette of claim 1, wherein the nucleic acid sequence to be expressed transgenically enables: expression of a protein encoded by said nucleic acid sequence, or expression of a sense RNA, antisense RNA, or ribozyme encoded by said nucleic acid sequence.

5. The expression cassette of claim 1, wherein the nucleic acid sequence to be expressed transgenically is selected from the group consisting of nucleic acids coding for selection markers, reporter genes, cellulases, chitinases, glucanases, ribosome-inactivating proteins, lysozymes, *Bacillus thuringiensis* endotoxin, α-amylase inhibitor, protease inhibitors, lectins, RNAases, ribozymes, acetyl-CoA carboxylases, phytases, 2S albumin from *Bertholletia excelsa*, antifreeze proteins, trehalose phosphate synthase, trehalose phosphate phosphatase, trehalase, DREB 1A factor, farnesyl transferases, ferritin, oxalate oxidase, calcium-dependent protein kinases, calcineurins, glutamate dehydrogenases, N-hydroxylating multifunctional cytochrome P450, transcriptional activator CBF1, phytoene desaturases, polygalacturonases, flavonoid 3'-hydroxylases, dihydroflavanol 4-reductases, chalcone isomerases, chalcone synthases, flavanone 3-beta-hydroxylases, flavone synthase II, branching enzyme Q, starch branching enzyme, and combinations thereof.

6. The expression cassette of claim 1, wherein the nucleic acid sequence to be expressed transgenically comprises a nucleic acid sequence selected from the group consisting of the nucleic acid sequence of SEQ ID NO: 30, 32, 34, 36, 38, 40, 42, 44, 46, 48, 50, 52, 54, 56, 58, 60, 62, and 64; or a nucleic acid sequence encoding a polypeptide comprising an amino acid sequence selected from the group consisting of the amino acid sequence of SEQ ID NO: 31, 33, 35, 37, 39, 41, 43, 45, 47, 49, 51, 53, 55, 57, 59, 61, and 63.

7. The expression cassette of claim 1, wherein the nucleic acid sequence to be expressed transgenically is selected from the group consisting of positive selection markers, negative selection markers, factors that provide a growth advantage and combinations thereof.

8. The expression cassette of claim 7, wherein the positive or negative selection marker is selected from the group consisting of proteins that impart a resistance to antibiotics, metabolism inhibitors, herbicides, biocides and combinations thereof.

9. The expression cassette of claim 7, wherein the positive or negative selection marker is selected from the group consisting of proteins that impart a resistance to phosphinothricin, glyphosate, bromoxynil, dalapon, 2-deoxyglucose 6-phosphate, tetracyclines, ampicillin, kanamycin, G418, neomycin, paromomycin, bleomycin, zeocin, hygromycin, chloramphenicol, sulfonyl urea herbicides, imidazolinone herbicides and combinations thereof.

10. The transgenic expression cassette of claim 7, wherein the selection marker is selected from the group consisting of phosphinothricin acetyltransferases, 5-enolpyruvylshikimate 3-phosphate synthases, glyphosate oxidoreductases, dehalogenases, nitrilases, neomycin phosphotransferases, 2-desoxyglucose 6-phosphate phosphatases, acetolactate synthases, hygromycin phosphotransferases, chloramphenicol acetyltransferases, streptomycin adenylyltransferases, β-lactamases, tetA genes, tetR genes, isopentenyl transferases, thymidine kinases, diphtheria toxin A, cytosine deaminase (codA), cytochrome P450, haloalkanedehalogenases, indole acetic acid hydrolases, indole acetimide hydrolases, β-glucuronidases, mannose 6-phosphate isomerases, uridine diphosphate-galactose 4-epimerases and combinations thereof.

11. The transgenic expression cassette of claim 7, wherein the positive or negative selection marker is encoded by a nucleic acid comprising the nucleic acid sequence of SEQ ID NO: 5, 65, 67, 69, 70, 72, 74, 75, 76, 78, 79, 80, 82, 84, 86, 88, 90, 92, 93, 94, 95, 96, 97, 98, 99, 101, 103, or 105; or a nucleic acid sequence encoding a polypeptide comprising the amino acid sequence of SEQ ID NO: 6, 66, 68, 71, 73, 77, 81, 83, 85, 87, 89, 91, 100, 102, 104, or 106.

12. A vector comprising the expression cassette of claim 1.

13. A transgenic organism transformed with a vector comprising the expression cassette of claim 1.

14. The transgenic organism of claim 13, which is selected from the group of organisms consisting of bacteria, yeasts, fungi, animal, and plant organisms.

15. The transgenic organism of claim 13, which is selected from the group of organisms consisting of *Arabidopsis*, tomato, tobacco, potatoes, corn, oilseed rape, wheat, barley, sunflowers, millet, beet, rye, oats, sugarbeet, bean plants and soybean.

16. A cell culture, plant or transgenic propagation material, obtained from the transgenic organism of claim 13, wherein the cell culture, plant and transgenic propagation material comprise the expression cassette.

17. A method for transgenic expression of a nucleic acid in an organism comprising:

transgenically expressing a nucleic acid sequence in an organism, wherein said nucleic acid sequence is operably linked and heterologous to:

(i) a promoter comprising the sequence of SEQ ID NO: 1 or a fragment thereof; or (ii) a promoter having at least 99% identity to the sequence of SEQ ID NO: 1 or 4, wherein said promoter or said fragment thereof of part (i) and the promoter of part (ii) have constitutive promoter activity.

18. The method of claim 17, wherein the fragment contains the sequence of SEQ ID NO: 4.

19. The method of claim 17, wherein the nucleic acid sequence to be expressed is further operably linked to one or more genetic control sequences, and one or more additional functional elements.

20. The method of claim 17, wherein the nucleic acid sequence to be expressed is further operably linked to one or more genetic control sequences; or one or more additional functional elements.

21. The method of claim 17, wherein the nucleic acid sequence to be expressed transgenically enables:

expression of a protein encoded by said nucleic acid sequence, or expression of a sense RNA, antisense RNA, or ribozyme encoded by said nucleic acid sequence.

22. The method of claim 17, wherein the nucleic acid sequence to be expressed transgenically is selected from the group consisting of nucleic acids coding for selection markers, reporter genes, cellulases, chitinases, glucanases, ribosome-inactivating proteins, lysozymes, *Bacillus thuringiensis* endotoxin, α-amylase inhibitor, protease inhibitors, lectins, RNAases, ribozymes, acetyl-CoA carboxylases, phytases, 2S albumin from *Bertholletia excelsa*, antifreeze proteins, trehalose phosphate synthase, trehalose phosphate phosphatase, trehalase, DREB1A factor, farnesyl transferases, ferritin, oxalate oxidase, calcium-dependent protein kinases, calcineurins, glutamate dehydrogenases, N-hydroxylating multifunctional cytochrome P450, transcriptional activator CBF1, phytoene desaturases, polygalacturonases, flavonoid 3'-hydroxylases, dihydroflavanol 4-reductases, chalcone isomerases, chalcone synthases, flavanone 3-beta-hydroxylases, flavone synthase II, branching enzyme Q, starch branching enzyme, and combinations thereof.

23. The method of claim 17, wherein the nucleic acid sequence to be expressed transgenically comprises a nucleic acid sequence selected from the group consisting of the nucleic acid sequence of SEQ ID NO: 30, 32, 34, 36, 38, 40, 42, 44, 46, 48, 50, 52, 54, 56, 58, 60, 62, and 64; or a nucleic acid sequence encoding a polypeptide comprising an amino acid sequence selected from the group consisting of the amino acid sequence of SEQ ID NO: 31, 33, 35, 37, 39, 41, 43, 45, 47, 49, 51, 53, 55, 57, 59, 61, and 63.

24. A method for selecting a transformed organism comprising:

introducing a nucleic acid sequence coding for a selection marker to an organism, wherein said nucleic acid sequence is operably and transgenically linked to:

(i) a promoter comprising the sequence of SEQ ID NO: 1 or a fragment thereof; or (ii) a promoter having at least 99% identity to the sequence of SEQ ID NO: 1 or 4, wherein said promoter or said fragment thereof of part (i) and the promoter of part (ii) have constitutive promoter activity;

selecting a transformed organism expressing said selection marker; and isolating said selected transformed organism, and wherein said selected organism comprises said promoter of part (i) or part (ii).

25. The method of claim 24, wherein the selection marker comprises a nucleic acid sequence selected from the group consisting of the nucleic acid sequence of SEQ ID NO: 30, 32, 34, 36, 38, 40, 42, 44, 46, 48, 50, 52, 54, 56, 58, 60, 62, and 64; or a nucleic acid sequence encoding a polypeptide comprising an amino acid sequence selected from the group consisting of the amino acid sequence of SEQ ID NO: 31, 33, 35, 37, 39, 41, 43, 45, 47, 49, 51, 53, 55, 57, 59, 61, and 63.

26. The method of claim 24, wherein the selection marker is selected from the group consisting of positive selection markers, negative selection markers, factors that provide a growth advantage, proteins that impart a resistance to antibiotics, metabolism inhibitors, herbicides, biocides, phosphinothricin acetyltransferases, 5-enolpyruvylshikimate 3-phosphate synthases, glyphosate oxidoreductases, dehalogenases, nitrilases, neomycin phosphotransferases, 2-desoxyglucose 6-phosphate phosphatases, acetolactate synthases, hygromycin phosphotransferases, chloramphenicol acetyltransferases, streptomycin adenylyltransferases, β-lactamases, tetA genes, tetR genes, isopentenyl transferases, thymidine kinases, diphtheria toxin A, cytosine deaminase (codA), cytochrome P450, haloalkanedehalogenases, indole acetic acid hydrolases, indole acetimide hydrolases, β-glucuronidases, mannose 6-phosphate isomerases, uridine diphosphate-galactose 4-epimerases and combinations thereof.

27. The expression cassette of claim 1, wherein the promoter is of a plant origin.

28. A method for the production of a foodstuff, a feedstuff, or a seed comprising:

providing a transgenic organism comprising an expression cassette for transgenic expression of nucleic acids wherein said nucleic acid is operably linked and heterologous to:

(i) a promoter comprising the sequence of SEQ ID NO: 1 or a fragment thereof; or (ii) a promoter having at least 99% identity to the sequence of SEQ ID NO: 1 or 4, wherein said promoter or fragment thereof of part (i) and the promoter of part (ii) have constitutive promoter activity;

propagating said transgenic organism or cell culture, part or transgenic propagation material obtained from said transgenic organism; and producing a foodstuff, a feedstuff, or a seed from said transgenic organism or cell culture, part or transgenic propagation material obtained from said transgenic organism, wherein said foodstuff, feedstuff, or seed from said transgenic organism, or cell culture, part or transgenic propagation material obtained from said transgenic organism comprise said expression cassette.

29. A plant cell, plant or part thereof, or propagation material obtained therefrom, which plant cell, plant or part thereof, or propagation material derived therefrom comprises the expression cassette of claim 1.

* * * * *

SEQUENCE LISTING

<160> NUMBER OF SEQ ID NOS: 106

<210> SEQ ID NO 1
<211> LENGTH: 836
<212> TYPE: DNA
<213> ORGANISM: Arabidopsis thaliana
<220> FEATURE:
<221> NAME/KEY: promoter
<222> LOCATION: (1)..(836)
<223> OTHER INFORMATION: pFD promoter

<400> SEQUENCE: 1

```
gattcaagct tcactgctta aattcacaaa aagagaaaag taagaccaaa ggaataaatc     60

atcctcaaac caaaaacaca tcatacaaaa tcatcaaaca taaatctcca gatgtatgag    120

caccaatcca gttatacaac actcttaaca ccaaatcaac agatttaaca gcgaaataag    180

cttaagccca tacaattatc cgatccaaac aaatataatc gaaaccggca gaggaataag    240

caagtgaatc aaaaagtatg ggacgaggaa gaagatgata cctgaatgag aaagtcaata    300

accttgaccc gaatcgtttt gaagaaaatg gagaaaatcg gttgtatgga ataaaatctt    360

cgaatgatga gatatatgat ctctttggtg tcagtcacat ggcacacgct atcaatttag    420

aaaaacgcgg tggttggtca ccagaattac tacttctcgg tctgatttgg tcatatccgt    480

attaagtccg gttaatattt tccataactg gggtttgaac attcggtttc tttttttcag    540

ttagtccgat ttggagtttt gagtatggaa aaataatact gaatttattt gttcaaactg    600

ttttggaaaa aatatttccc ttaattacga atataattaa aattttaaaa ttcattttat    660

tagatcttgg ttaattcggt ttaatgcatt aatgaatttc ggtttaagtc ggttttcggt    720

ttttatgtcc caccactatc tacaaccgat gatcaacctt atctccgtat tcaccacaaa    780

cagtcatcac tctcacttga cacaaaaact cttttgtctc cgtctctctg tctctc        836
```

<210> SEQ ID NO 2
<211> LENGTH: 635
<212> TYPE: DNA
<213> ORGANISM: Arabidopsis thaliana
<220> FEATURE:
<221> NAME/KEY: promoter
<222> LOCATION: (1)..(635)
<223> OTHER INFORMATION: FNR promoter

<400> SEQUENCE: 2

```
ttcattattt cgattttgat ttcgtgacca gcgaacgcag aataccttgt tgtgtaatac     60

tttacccgtg taaatcaaaa acaaaaaggc ttttgagctt tttgtagttg aatttctctg    120

gctgatcttt tctgtacaga ttcatatatc tgcagagacg atatcattga ttatttgagc    180

ttcttttgaa ctatttcgtg taatttggga tgagagctct atgtatgtgt gtaaactttg    240

aagacaacaa gaaaggtaac aagtgaggga gggatgactc catgtcaaaa tagatgtcat    300

aagaggccca tcaataagtg cttgagccca ttagctagcc cagtaactac cagattgtga    360

gatggatgtg tgaacagttt ttttttgat gtaggactga aatgtgaaca acaggcgcat     420

gaaaggctaa attaggacaa tgataagcag aaataactta tcctctctaa cacttggcct    480

cacattgccc ttcacacaat ccacacacat ccaatcacaa cctcatcata tatctcccgc    540

taatcttttt ttctttgatc tttttttttt tgcttattat tttttgact ttgatctccc     600

atcagttcat cttcttcttc ttcttctgat caacc                               635
```

<210> SEQ ID NO 3

<211> LENGTH: 2038
<212> TYPE: DNA
<213> ORGANISM: Arabidopsis thaliana
<220> FEATURE:
<221> NAME/KEY: promoter
<222> LOCATION: (1)..(2038)
<223> OTHER INFORMATION: TPT promoter

<400> SEQUENCE: 3

```
ataaccaaaa gaactctgat catgtacgta cccatttgcg tattccgccg ttgcggaatc      60

aaaaactgcc atagacttct ccacatcttt ttcagctcgc atcagtttga taacctgtga     120

aggcgtgatg ttctttgacc acttgaacat catcactttg ttacccatta ctaaacaatg     180

ataccttcca acaatagcaa agaatacacc tttttataga gaagaatctc agctacgcac     240

tacgtcgaac aggttgtgtg cataaacgat ttcgataggc ccaaaccaaa tgaaagaaac     300

acagaccaga aaaatcattt gatcttcaaa acatacgagt tccaaaagtg aaggaagcaa     360

caatgaaact cgttacgaac tagaaggtta atcaaattgc cggagaagaa tcgctcacca     420

gttttggcta gggtttatga aatgggagac tttagctgca aagagaagag tctctggacg     480

atttagaggg tgtctctcta ataggcaaca aagtacatat tattacagta ttaaccaaat     540

ttaaacgaat taagtgtcaa caaaagctta tataaaaaat ttaaagttta aaaattataa     600

aatatgtcaa caatatttta gtacttaaaa ttattatgcg aaatatttag atcaatggac     660

tactcatcta atatatttgc acctaatttt aaagtataaa ttcaaccaat aattagaaaa     720

tgatagctta tactcaaatt caacaagtta tatataaatg tatagatact acaatatcat     780

taacaaaagt caccttaaat aaatacacat atcttttatg ttctctattg ttttgcgtac     840

gctaacacaa tttctcatat gcaaaaggat gaatgagtaa caaattacct cataagaaca     900

atcatctttg cttacatact aatacaataa tcactcaatc aaccaataac atcaatcaca     960

taggtttaca tacaataatc actcaatcaa cttcataaga agaatcatgt ttacttaatt    1020

catcaattat ccccaaaaac accactatta agtataaact ataacatatt tgtagtgatg    1080

ggtcaacatt tttatcatat ttaaactcgg gttccctcaa atcgagaaat agtgaacatg    1140

taatattaat tttaaatcgc aattacagaa attaattgaa tttggtcaaa tggacagaat    1200

tttatagatt gggtggaact agaaaaaaaa aaaaaaagag tatagggtga attgagtaca    1260

tgaaagtaca tggtaatcct agttaaacgc ataatacatg tgggttcatt tgtatttttt    1320

tgtaacttac gagtaaactg gctacaacaa aaaaaattag aagatttttt tgttttgtag    1380

aaaaccctaa ttttagttat agttgtataa ctttgataaa attataaaat tgtattacga    1440

aaaaagtaat aagatattca aaaaagccta gaataacgta tatgactatg agcatgaaac    1500

tgcaagtcaa atgctgacag acaaccataa acaaaagaaa ttaaatagag atacctttaa    1560

aataagtaaa atttcattta taaaaaatct actttcttgt gaatctgtca cgttcaataa    1620

tttgaagacc actcaacata caaggtaaat aatgaaaaat aaaatctacc aaaatttcaa    1680

tcattattat cttccaaaaa aacaaaatta tacagatgat gatggtgata tggaacttcg    1740

attggctaat attcactgtg tctctaaaaa ccatccactt atcaagataa gatggaccct    1800

acactcatcc aatctaaacc agtatctcaa gattcttatc taattacatc attctctacc    1860

gttagatgaa attgaccatt aaccctacca taactccata caccgcgaga tactggatta    1920

accaaatcga gatcatcgta gccgtccgat caacaagtac catctcttga aatactcgaa    1980

atcctcataa gtccgtccct ctttgctctc actatcaaaa ctctgaattt cgatttca      2038
```

<210> SEQ ID NO 4

<211> LENGTH: 699
<212> TYPE: DNA
<213> ORGANISM: Arabidopsis thaliana
<220> FEATURE:
<221> NAME/KEY: promoter
<222> LOCATION: (1)..(699)
<223> OTHER INFORMATION: FDS promoter

<400> SEQUENCE: 4

```
aacactctta acaccaaatc aacagattta acagcgaaat aagcttaagc ccatacaatt     60

atccgatcca aacaaatata atcgaaaccg gcagaggaat aagcaagtga atcaaaaagt    120

atgggacgag gaagaagatg atacctgaat gagaaagtca ataaccttga cccgaatcgt    180

tttgaagaaa atggagaaaa tcggttgtat ggaataaaat cttcgaatga tgagatatat    240

gatctctttg gtgtcagtca catggcacac gctatcaatt tagaaaaacg cggtggttgg    300

tcaccagaat tactacttct cggtctgatt tggtcatatc cgtattaagt ccggttaata    360

ttttccataa ctggggtttg aacattcggt ttcttttttt cagttagtcc gatttggagt    420

tttgagtatg gaaaaataat actgaattta tttgttcaaa ctgttttgga aaaaatattt    480

cccttaatta cgaatataat taaaatttta aaattcattt tattagatct tggttaattc    540

ggtttaatgc attaatgaat ttcggtttaa gtcggttttc ggtttttatg tcccaccact    600

atctacaacc gatgatcaac cttatctccg tattcaccac aaacagtcat cactctcact    660

tgacacaaaa actcttttgt ctccgtctct ctgtctctc                           699
```

<210> SEQ ID NO 5
<211> LENGTH: 552
<212> TYPE: DNA
<213> ORGANISM: Artificial sequence
<220> FEATURE:
<223> OTHER INFORMATION: Description of the artificial sequence: codon
      adapted sequence for phosphinotricin-N-acetyltransferase
<220> FEATURE:
<221> NAME/KEY: CDS
<222> LOCATION: (1)..(549)
<223> OTHER INFORMATION: phosphinotricin-N-acetyltransferase (PAT)

<400> SEQUENCE: 5

```
atg tct ccg gag agg aga cca gtt gag att agg cca gct aca gca gcc       48
Met Ser Pro Glu Arg Arg Pro Val Glu Ile Arg Pro Ala Thr Ala Ala
1               5                   10                  15

gat atg gcc gcg gtt tgt gac atc gtt aac cat tac att gag acg tct       96
Asp Met Ala Ala Val Cys Asp Ile Val Asn His Tyr Ile Glu Thr Ser
            20                  25                  30

aca gtg aac ttt agg aca gag cca caa aca cca caa gag tgg att gat      144
Thr Val Asn Phe Arg Thr Glu Pro Gln Thr Pro Gln Glu Trp Ile Asp
        35                  40                  45

gac cta gag agg ttg caa gat aga tac cct tgg ttg gtt gct gag gtt      192
Asp Leu Glu Arg Leu Gln Asp Arg Tyr Pro Trp Leu Val Ala Glu Val
    50                  55                  60

gag ggt gtt gtg gct ggt att gct tac gct ggg ccc tgg aag gct agg      240
Glu Gly Val Val Ala Gly Ile Ala Tyr Ala Gly Pro Trp Lys Ala Arg
65                  70                  75                  80

aac gct tac gat tgg aca gtt gag agt act gtt tac gtg tca cat agg      288
Asn Ala Tyr Asp Trp Thr Val Glu Ser Thr Val Tyr Val Ser His Arg
                85                  90                  95

cat caa agg ttg ggc cta gga tct aca ttg tac aca cat ttg ctt aag      336
His Gln Arg Leu Gly Leu Gly Ser Thr Leu Tyr Thr His Leu Leu Lys
            100                 105                 110

tct atg gag gcg caa ggt ttt aag tct gtg gtt gct gtt ata ggc ctt      384
Ser Met Glu Ala Gln Gly Phe Lys Ser Val Val Ala Val Ile Gly Leu
        115                 120                 125
```

```
cca aac gat cca tct gtt agg ttg cat gag gct ttg gga tac aca gcg      432
Pro Asn Asp Pro Ser Val Arg Leu His Glu Ala Leu Gly Tyr Thr Ala
    130                 135                 140

cgg ggt aca ttg cgc gcg gct gga tac aag cat ggt gga tgg cat gat      480
Arg Gly Thr Leu Arg Ala Ala Gly Tyr Lys His Gly Gly Trp His Asp
145                 150                 155                 160

gtt ggt ttt tgg caa agg gat ttt gag ttg cca gct cct cca agg cca      528
Val Gly Phe Trp Gln Arg Asp Phe Glu Leu Pro Ala Pro Pro Arg Pro
                165                 170                 175

gtt agg cca gtt acc cag atc tga                                      552
Val Arg Pro Val Thr Gln Ile
            180


<210> SEQ ID NO 6
<211> LENGTH: 183
<212> TYPE: PRT
<213> ORGANISM: Artificial sequence
<220> FEATURE:
<223> OTHER INFORMATION: Synthetic Construct

<400> SEQUENCE: 6

Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
            20                  25                  30

Thr Val Asn Phe Arg Thr Glu Pro Gln Thr Pro Gln Glu Trp Ile Asp
        35                  40                  45

Asp Leu Glu Arg Leu Gln Asp Arg Tyr Pro Trp Leu Val Ala Glu Val
    50                  55                  60

Glu Gly Val Val Ala Gly Ile Ala Tyr Ala Gly Pro Trp Lys Ala Arg
65                  70                  75                  80

Asn Ala Tyr Asp Trp Thr Val Glu Ser Thr Val Tyr Val Ser His Arg
                85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
        115                 120                 125

Pro Asn Asp Pro Ser Val Arg Leu His Glu Ala Leu Gly Tyr Thr Ala
    130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
            180


<210> SEQ ID NO 7
<211> LENGTH: 2013
<212> TYPE: DNA
<213> ORGANISM: Arabidopsis thaliana
<220> FEATURE:
<221> NAME/KEY: CDS
<222> LOCATION: (1)..(2010)
<223> OTHER INFORMATION: acetolactate synthase

<400> SEQUENCE: 7

atg gcg gcg gca aca aca aca aca aca aca tct tct tcg atc tcc ttc       48
Met Ala Ala Ala Thr Thr Thr Thr Thr Thr Ser Ser Ser Ile Ser Phe
1               5                   10                  15

tcc acc aaa cca tct cct tcc tcc tcc aaa tca cca tta cca atc tcc       96
```

-continued

```
Ser Thr Lys Pro Ser Pro Ser Ser Ser Lys Ser Pro Leu Pro Ile Ser
            20                  25                  30

aga ttc tcc ctc cca ttc tcc cta aac ccc aac aaa tca tcc tcc tcc      144
Arg Phe Ser Leu Pro Phe Ser Leu Asn Pro Asn Lys Ser Ser Ser Ser
        35                  40                  45

tcc cgc cgc cgc ggt atc aaa tcc agc tct ccc tcc tcc atc tcc gcc      192
Ser Arg Arg Arg Gly Ile Lys Ser Ser Ser Pro Ser Ser Ile Ser Ala
    50                  55                  60

gtg ctc aac aca acc acc aat gtc aca acc act ccc tct cca acc aaa      240
Val Leu Asn Thr Thr Thr Asn Val Thr Thr Thr Pro Ser Pro Thr Lys
65                  70                  75                  80

cct acc aaa ccc gaa aca ttc atc tcc cga ttc gct cca gat caa ccc      288
Pro Thr Lys Pro Glu Thr Phe Ile Ser Arg Phe Ala Pro Asp Gln Pro
                85                  90                  95

cgc aaa ggc gct gat atc ctc gtc gaa gct tta gaa cgt caa ggc gta      336
Arg Lys Gly Ala Asp Ile Leu Val Glu Ala Leu Glu Arg Gln Gly Val
            100                 105                 110

gaa acc gta ttc gct tac cct gga ggt gca tca atg gag att cac caa      384
Glu Thr Val Phe Ala Tyr Pro Gly Gly Ala Ser Met Glu Ile His Gln
        115                 120                 125

gcc tta acc cgc tct tcc tca atc cgt aac gtc ctt cct cgt cac gaa      432
Ala Leu Thr Arg Ser Ser Ser Ile Arg Asn Val Leu Pro Arg His Glu
    130                 135                 140

caa gga ggt gta ttc gca gca gaa gga tac gct cga tcc tca ggt aaa      480
Gln Gly Gly Val Phe Ala Ala Glu Gly Tyr Ala Arg Ser Ser Gly Lys
145                 150                 155                 160

cca ggt atc tgt ata gcc act tca ggt ccc gga gct aca aat ctc gtt      528
Pro Gly Ile Cys Ile Ala Thr Ser Gly Pro Gly Ala Thr Asn Leu Val
                165                 170                 175

agc gga tta gcc gat gcg ttg tta gat agt gtt cct ctt gta gca atc      576
Ser Gly Leu Ala Asp Ala Leu Leu Asp Ser Val Pro Leu Val Ala Ile
            180                 185                 190

aca gga caa gtc cct cgt cgt atg att ggt aca gat gcg ttt caa gag      624
Thr Gly Gln Val Pro Arg Arg Met Ile Gly Thr Asp Ala Phe Gln Glu
        195                 200                 205

act ccg att gtt gag gta acg cgt tcg att acg aag cat aac tat ctt      672
Thr Pro Ile Val Glu Val Thr Arg Ser Ile Thr Lys His Asn Tyr Leu
    210                 215                 220

gtg atg gat gtt gaa gat atc cct agg att att gag gaa gct ttc ttt      720
Val Met Asp Val Glu Asp Ile Pro Arg Ile Ile Glu Glu Ala Phe Phe
225                 230                 235                 240

tta gct act tct ggt aga cct gga cct gtt ttg gtt gat gtt cct aaa      768
Leu Ala Thr Ser Gly Arg Pro Gly Pro Val Leu Val Asp Val Pro Lys
                245                 250                 255

gat att caa caa cag ctt gcg att cct aat tgg gaa cag gct atg aga      816
Asp Ile Gln Gln Gln Leu Ala Ile Pro Asn Trp Glu Gln Ala Met Arg
            260                 265                 270

tta cct ggt tat atg tct agg atg cct aaa cct ccg gaa gat tct cat      864
Leu Pro Gly Tyr Met Ser Arg Met Pro Lys Pro Pro Glu Asp Ser His
        275                 280                 285

ttg gag cag att gtt agg ttg att tct gag tct aag aag cct gtg ttg      912
Leu Glu Gln Ile Val Arg Leu Ile Ser Glu Ser Lys Lys Pro Val Leu
    290                 295                 300

tat gtt ggt ggt ggt tgt ttg aat tct agc gat gaa ttg ggt agg ttt      960
Tyr Val Gly Gly Gly Cys Leu Asn Ser Ser Asp Glu Leu Gly Arg Phe
305                 310                 315                 320

gtt gag ctt acg ggg atc cct gtt gcg agt acg ttg atg ggg ctg gga     1008
Val Glu Leu Thr Gly Ile Pro Val Ala Ser Thr Leu Met Gly Leu Gly
                325                 330                 335

tct tat cct tgt gat gat gag ttg tcg tta cat atg ctt gga atg cat     1056
```

-continued

```
Ser Tyr Pro Cys Asp Asp Glu Leu Ser Leu His Met Leu Gly Met His
            340                 345                 350

ggg act gtg tat gca aat tac gct gtg gag cat agt gat ttg ttg ttg     1104
Gly Thr Val Tyr Ala Asn Tyr Ala Val Glu His Ser Asp Leu Leu Leu
        355                 360                 365

gcg ttt ggg gta agg ttt gat gat cgt gtc acg ggt aag ctt gag gct     1152
Ala Phe Gly Val Arg Phe Asp Asp Arg Val Thr Gly Lys Leu Glu Ala
    370                 375                 380

ttt gct agt agg gct aag att gtt cat att gat att gac tcg gct gag     1200
Phe Ala Ser Arg Ala Lys Ile Val His Ile Asp Ile Asp Ser Ala Glu
385                 390                 395                 400

att ggg aag aat aag act cct cat gtg tct gtg tgt ggt gat gtt aag     1248
Ile Gly Lys Asn Lys Thr Pro His Val Ser Val Cys Gly Asp Val Lys
            405                 410                 415

ctg gct ttg caa ggg atg aat aag gtt ctt gag aac cga gcg gag gag     1296
Leu Ala Leu Gln Gly Met Asn Lys Val Leu Glu Asn Arg Ala Glu Glu
            420                 425                 430

ctt aag ctt gat ttt gga gtt tgg agg aat gag ttg aac gta cag aaa     1344
Leu Lys Leu Asp Phe Gly Val Trp Arg Asn Glu Leu Asn Val Gln Lys
        435                 440                 445

cag aag ttt ccg ttg agc ttt aag acg ttt ggg gaa gct att cct cca     1392
Gln Lys Phe Pro Leu Ser Phe Lys Thr Phe Gly Glu Ala Ile Pro Pro
    450                 455                 460

cag tat gcg att aag gtc ctt gat gag ttg act gat gga aaa gcc ata     1440
Gln Tyr Ala Ile Lys Val Leu Asp Glu Leu Thr Asp Gly Lys Ala Ile
465                 470                 475                 480

ata agt act ggt gtc ggg caa cat caa atg tgg gcg gcg cag ttc tac     1488
Ile Ser Thr Gly Val Gly Gln His Gln Met Trp Ala Ala Gln Phe Tyr
            485                 490                 495

aat tac aag aaa cca agg cag tgg cta tca tca gga ggc ctt gga gct     1536
Asn Tyr Lys Lys Pro Arg Gln Trp Leu Ser Ser Gly Gly Leu Gly Ala
            500                 505                 510

atg gga ttt gga ctt cct gct gcg att gga gcg tct gtt gct aac cct     1584
Met Gly Phe Gly Leu Pro Ala Ala Ile Gly Ala Ser Val Ala Asn Pro
        515                 520                 525

gat gcg ata gtt gtg gat att gac gga gat gga agc ttt ata atg aat     1632
Asp Ala Ile Val Val Asp Ile Asp Gly Asp Gly Ser Phe Ile Met Asn
    530                 535                 540

gtg caa gag cta gcc act att cgt gta gag aat ctt cca gtg aag gta     1680
Val Gln Glu Leu Ala Thr Ile Arg Val Glu Asn Leu Pro Val Lys Val
545                 550                 555                 560

ctt tta tta aac aac cag cat ctt ggc atg gtt atg caa tgg gaa gat     1728
Leu Leu Leu Asn Asn Gln His Leu Gly Met Val Met Gln Trp Glu Asp
            565                 570                 575

cgg ttc tac aaa gct aac cga gct cac aca ttt ctc ggg gat ccg gct     1776
Arg Phe Tyr Lys Ala Asn Arg Ala His Thr Phe Leu Gly Asp Pro Ala
            580                 585                 590

cag gag gac gag ata ttc ccg aac atg ttg ctg ttt gca gca gct tgc     1824
Gln Glu Asp Glu Ile Phe Pro Asn Met Leu Leu Phe Ala Ala Ala Cys
        595                 600                 605

ggg att cca gcg gcg agg gtg aca aag aaa gca gat ctc cga gaa gct     1872
Gly Ile Pro Ala Ala Arg Val Thr Lys Lys Ala Asp Leu Arg Glu Ala
    610                 615                 620

att cag aca atg ctg gat aca cca gga cct tac ctg ttg gat gtg att     1920
Ile Gln Thr Met Leu Asp Thr Pro Gly Pro Tyr Leu Leu Asp Val Ile
625                 630                 635                 640

tgt ccg cac caa gaa cat gtg ttg ccg atg atc ccg aat ggt ggc act     1968
Cys Pro His Gln Glu His Val Leu Pro Met Ile Pro Asn Gly Gly Thr
            645                 650                 655

ttc aac gat gtc ata acg gaa gga gat ggc cgg att aaa tac tga         2013
```

```
Phe Asn Asp Val Ile Thr Glu Gly Asp Gly Arg Ile Lys Tyr
            660                 665                 670


<210> SEQ ID NO 8
<211> LENGTH: 670
<212> TYPE: PRT
<213> ORGANISM: Arabidopsis thaliana

<400> SEQUENCE: 8

Met Ala Ala Ala Thr Thr Thr Thr Thr Thr Ser Ser Ser Ile Ser Phe
1               5                   10                  15

Ser Thr Lys Pro Ser Pro Ser Ser Ser Lys Ser Pro Leu Pro Ile Ser
            20                  25                  30

Arg Phe Ser Leu Pro Phe Ser Leu Asn Pro Asn Lys Ser Ser Ser Ser
        35                  40                  45

Ser Arg Arg Arg Gly Ile Lys Ser Ser Ser Pro Ser Ser Ile Ser Ala
    50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
        115                 120                 125

Ala Leu Thr Arg Ser Ser Ser Ile Arg Asn Val Leu Pro Arg His Glu
    130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
            180                 185                 190

Thr Gly Gln Val Pro Arg Arg Met Ile Gly Thr Asp Ala Phe Gln Glu
        195                 200                 205

Thr Pro Ile Val Glu Val Thr Arg Ser Ile Thr Lys His Asn Tyr Leu
    210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
            260                 265                 270

Leu Pro Gly Tyr Met Ser Arg Met Pro Lys Pro Pro Glu Asp Ser His
        275                 280                 285

Leu Glu Gln Ile Val Arg Leu Ile Ser Glu Ser Lys Lys Pro Val Leu
    290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
                325                 330                 335

Ser Tyr Pro Cys Asp Asp Glu Leu Ser Leu His Met Leu Gly Met His
            340                 345                 350

Gly Thr Val Tyr Ala Asn Tyr Ala Val Glu His Ser Asp Leu Leu Leu
        355                 360                 365
```

-continued

```
Ala Phe Gly Val Arg Phe Asp Asp Arg Val Thr Gly Lys Leu Glu Ala
    370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
                405                 410                 415

Leu Ala Leu Gln Gly Met Asn Lys Val Leu Glu Asn Arg Ala Glu Glu
            420                 425                 430

Leu Lys Leu Asp Phe Gly Val Trp Arg Asn Glu Leu Asn Val Gln Lys
        435                 440                 445

Gln Lys Phe Pro Leu Ser Phe Lys Thr Phe Gly Glu Ala Ile Pro Pro
    450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Ser Gly Gly Leu Gly Ala
            500                 505                 510

Met Gly Phe Gly Leu Pro Ala Ala Ile Gly Ala Ser Val Ala Asn Pro
        515                 520                 525

Asp Ala Ile Val Val Asp Ile Asp Gly Asp Gly Ser Phe Ile Met Asn
    530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Glu Asp
                565                 570                 575

Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
        595                 600                 605

Gly Ile Pro Ala Ala Arg Val Thr Lys Lys Ala Asp Leu Arg Glu Ala
    610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Asn Gly Gly Thr
                645                 650                 655

Phe Asn Asp Val Ile Thr Glu Gly Asp Gly Arg Ile Lys Tyr
            660                 665                 670


<210> SEQ ID NO 9
<211> LENGTH: 29
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 9

gtcgacgaat tcgagagaca gagagacgg                                         29


<210> SEQ ID NO 10
<211> LENGTH: 29
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 10
```

gtcgacggta ccgattcaag cttcactgc 29

<210> SEQ ID NO 11
<211> LENGTH: 25
<212> TYPE: DNA
<213> ORGANISM: Artificial sequence
<220> FEATURE:
<223> OTHER INFORMATION: Description of the artificial sequence: oligonucleotide primer

<400> SEQUENCE: 11
gagaattcga ttcaagcttc actgc 25

<210> SEQ ID NO 12
<211> LENGTH: 22
<212> TYPE: DNA
<213> ORGANISM: Artificial sequence
<220> FEATURE:
<223> OTHER INFORMATION: Description of the artificial sequence: oligonucleotide primer

<400> SEQUENCE: 12
ccatgggaga gacagagaga cg 22

<210> SEQ ID NO 13
<211> LENGTH: 33
<212> TYPE: DNA
<213> ORGANISM: Artificial sequence
<220> FEATURE:
<223> OTHER INFORMATION: Description of the artificial sequence: oligonucleotide primer

<400> SEQUENCE: 13
acggatccga gagacagaga gacggagaca aaa 33

<210> SEQ ID NO 14
<211> LENGTH: 32
<212> TYPE: DNA
<213> ORGANISM: Artificial sequence
<220> FEATURE:
<223> OTHER INFORMATION: Description of the artificial sequence: oligonucleotide primer

<400> SEQUENCE: 14
gcggatccaa cactcttaac accaaatcaa ca 32

<210> SEQ ID NO 15
<211> LENGTH: 44
<212> TYPE: DNA
<213> ORGANISM: Artificial sequence
<220> FEATURE:
<223> OTHER INFORMATION: Description of the artificial sequence: oligonucleotide primer

<400> SEQUENCE: 15
gtcgacggat ccggttgatc agaagaagaa gaagaagatg aact 44

<210> SEQ ID NO 16
<211> LENGTH: 41
<212> TYPE: DNA
<213> ORGANISM: Artificial sequence
<220> FEATURE:
<223> OTHER INFORMATION: Description of the artificial sequence: oligonucleotide primer

<400> SEQUENCE: 16
gtcgactcta gattcattat ttcgattttg atttcgtgac c 41

-continued

<210> SEQ ID NO 17
<211> LENGTH: 50
<212> TYPE: DNA
<213> ORGANISM: Artificial sequence
<220> FEATURE:
<223> OTHER INFORMATION: Description of the artificial sequence: oligonucleotide primer

<400> SEQUENCE: 17
aagtcgacgg atccataacc aaaagaactc tgatcatgta cgtacccatt 50

<210> SEQ ID NO 18
<211> LENGTH: 50
<212> TYPE: DNA
<213> ORGANISM: Artificial sequence
<220> FEATURE:
<223> OTHER INFORMATION: Description of the artificial sequence: oligonucleotide primer

<400> SEQUENCE: 18
agacgtcgac tctagatgaa atcgaaattc agagttttga tagtgagagc 50

<210> SEQ ID NO 19
<211> LENGTH: 30
<212> TYPE: DNA
<213> ORGANISM: Artificial sequence
<220> FEATURE:
<223> OTHER INFORMATION: Description of the artificial sequence: oligonucleotide primer

<400> SEQUENCE: 19
ccaaaccatg gtaagtttgt ctaaagctta 30

<210> SEQ ID NO 20
<211> LENGTH: 31
<212> TYPE: DNA
<213> ORGANISM: Artificial sequence
<220> FEATURE:
<223> OTHER INFORMATION: Description of the artificial sequence: oligonucleotide primer

<400> SEQUENCE: 20
cggatccttt tgtgtttcgt cttctctcac g 31

<210> SEQ ID NO 21
<211> LENGTH: 25
<212> TYPE: DNA
<213> ORGANISM: Artificial sequence
<220> FEATURE:
<223> OTHER INFORMATION: Description of the artificial sequence: oligonucleotide primer

<400> SEQUENCE: 21
gtctagaggc aaaccaccga gtgtt 25

<210> SEQ ID NO 22
<211> LENGTH: 31
<212> TYPE: DNA
<213> ORGANISM: Artificial sequence
<220> FEATURE:
<223> OTHER INFORMATION: Description of the artificial sequence: oligonucleotide primer

<400> SEQUENCE: 22
cggtacctgt ttccagaaaa ttttgattca g 31

<210> SEQ ID NO 23
<211> LENGTH: 7554
<212> TYPE: DNA
<213> ORGANISM: Artificial sequence
<220> FEATURE:
<223> OTHER INFORMATION: Description of the artificial sequence: binary plant expression vector

<400> SEQUENCE: 23
ttccatggac atacaaatgg acgaacggat aaaccttttc acgccctttt aaatatccga 60
ttattctaat aaacgctctt ttctcttagg tttacccgcc aatatatcct gtcaaacact 120
gatagtttaa actgaaggcg ggaaacgaca atcagatcta gtaggaaaca gctatgacca 180
tgattacgcc aagcttgcat gcctgcaggt cgactctaga ctagtggatc cgatatcgcc 240
cgggctcgag gtaccgagct cgaattcact ggccgtcgtt ttacaacgac tcagagcttg 300
acaggaggcc cgatctagta acatagatga caccgcgcgc gataatttat cctagtttgc 360
gcgctatatt ttgttttcta tcgcgtatta aatgtataat tgcgggactc taatcataaa 420
aacccatctc ataaataacg tcatgcatta catgttaatt attacatgct taacgtaatt 480
caacagaaat tatatgataa tcatcgcaag accggcaaca ggattcaatc ttaagaaact 540
ttattgccaa atgtttgaac gatcggggat catccgggtc tgtggcggga actccacgaa 600
aatatccgaa cgcagcaaga tctaagcttg ggtcccgctc agaagaactc gtcaagaagg 660
cgatagaagg cgatgcgctg cgaatcggga gcggcgatac cgtaaagcac gaggaagcgg 720
tcagcccatt cgccgccaag ctcttcagca atatcacggg tagccaacgc tatgtcctga 780
tagcggtccg ccacacccag ccggccacag tcgatgaatc cagaaaagcg gccattttcc 840
accatgatat tcggcaagca ggcatcgcca tgggtcacga cgagatcctc gccgtcgggc 900
atgcgcgcct tgagcctggc gaacagttcg gctggcgcga gcccctgatg ctcttcgtcc 960
agatcatcct gatcgacaag accggcttcc atccgagtac gtgctcgctc gatgcgatgt 1020
ttcgcttggt ggtcgaatgg gcaggtagcc ggatcaagcg tatgcagccg ccgcattgca 1080
tcagccatga tggatacttt ctcggcagga gcaaggtgag atgacaggag atcctgcccc 1140
ggcacttcgc ccaatagcag ccagtccctt cccgcttcag tgacaacgtc gagcacagct 1200
gcgcaaggaa cgcccgtcgt ggccagccac gatagccgcg ctgcctcgtc ctgcagttca 1260
ttcagggcac cggacaggtc ggtcttgaca aaaagaaccg ggcgcccctg cgctgacagc 1320
cggaacacgg cggcatcaga gcagccgatt gtctgttgtg cccagtcata gccgaatagc 1380
ctctccaccc aagcggccgg agaacctgcg tgcaatccat cttgttcaat catgcgaaac 1440
gatccagatc cggtgcagat tatttggatt gagagtgaat atgagactct aattggatac 1500
cgaggggaat ttatggaacg tcagtggagc atttttgaca agaaatattt gctagctgat 1560
agtgacctta ggcgactttt gaacgcgcaa taatggtttc tgacgtatgt gcttagctca 1620
ttaaactcca gaaacccgcg gctgagtggc tccttcaacg ttgcggttct gtcagttcca 1680
aacgtaaaac ggcttgtccc gcgtcatcgg cgggggtcat aacgtgactc ccttaattct 1740
ccgctcatga tcagattgtc gtttcccgcc ttcagtttaa actatcagtg tttgacagga 1800
tcctgcttgg taataattgt cattagattg tttttatgca tagatgcact cgaaatcagc 1860
caattttaga caagtatcaa acggatgtta attcagtaca ttaaagacgt ccgcaatgtg 1920
ttattaagtt gtctaagcgt caatttgttt acaccacaat atatcctgcc accagccagc 1980
caacagctcc ccgaccggca gctcggcaca aaatcaccac gcgttaccac cacgccggcc 2040
ggccgcatgg tgttgaccgt gttcgccggc attgccgagt tcgagcgttc cctaatcatc 2100

-continued gaccgcaccc ggagcgggcg cgaggccgcc aaggcccgag gcgtgaagtt tggccccccgc 2160 cctaccctca ccccggcaca gatcgcgcac gcccgcgagc tgatcgacca ggaaggccgc 2220
accgtgaaag aggcggctgc actgcttggc gtgcatcgct cgaccctgta ccgcgcactt 2280
gagcgcagcg aggaagtgac gcccaccgag gccaggcggc gcggtgcctt ccgtgaggac 2340
gcattgaccg aggccgacgc cctggcggcc gccgagaatg aacgccaaga ggaacaagca 2400
tgaaaccgca ccaggacggc caggacgaac cgtttttcat taccgaagag atcgaggcgg 2460
agatgatcgc ggccgggtac gtgttcgagc cgcccgcgca cgtctcaacc gtgcggctgc 2520
atgaaatcct ggccggtttg tctgatgcca agctggcggc ctggccggcc agcttggccg 2580
ctgaagaaac cgagcgccgc cgtctaaaaa ggtgatgtgt atttgagtaa aacagcttgc 2640
gtcatgcggt cgctgcgtat atgatgcgat gagtaaataa acaaatacgc aaggggaacg 2700
catgaaggtt atcgctgtac ttaaccagaa aggcgggtca ggcaagacga ccatcgcaac 2760
ccatctagcc cgcgccctgc aactcgccgg ggccgatgtt ctgttagtcg attccgatcc 2820
ccagggcagt gcccgcgatt gggcggccgt gcgggaagat caaccgctaa ccgttgtcgg 2880
catcgaccgc ccgacgattg accgcgacgt gaaggccatc ggccggcgcg acttcgtagt 2940
gatcgacgga gcgccccagg cggcggactt ggctgtgtcc gcgatcaagg cagccgactt 3000
cgtgctgatt ccggtgcagc caagccctta cgacatatgg gccaccgccg acctggtgga 3060
gctggttaag cagcgcattg aggtcacgga tggaaggcta caagcggcct ttgtcgtgtc 3120
gcgggcgatc aaaggcacgc gcatcggcgg tgaggttgcc gaggcgctgg ccgggtacga 3180
gctgcccatt cttgagtccc gtatcacgca gcgcgtgagc tacccaggca ctgccgccgc 3240
cggcacaacc gttcttgaat cagaacccga gggcgacgct gcccgcgagg tccaggcgct 3300
ggccgctgaa attaaatcaa aactcatttg agttaatgag gtaaagagaa aatgagcaaa 3360
agcacaaaca cgctaagtgc cggccgtccg agcgcacgca gcagcaaggc tgcaacgttg 3420
gccagcctgg cagacacgcc agccatgaag cgggtcaact ttcagttgcc ggcggaggat 3480
cacaccaagc tgaagatgta cgcggtacgc caaggcaaga ccattaccga gctgctatct 3540
gaatacatcg cgcagctacc agagtaaatg agcaaatgaa taaatgagta gatgaatttt 3600
agcggctaaa ggaggcggca tggaaaatca agaacaacca ggcaccgacg ccgtggaatg 3660
ccccatgtgt ggaggaacgg gcggttggcc aggcgtaagc ggctgggttg tctgccggcc 3720
ctgcaatggc actggaaccc ccaagcccga ggaatcggcg tgagcggtcg caaaccatcc 3780
ggcccggtac aaatcggcgc ggcgctgggt gatgacctgg tggagaagtt gaaggccgcg 3840
caggccgccc agcggcaacg catcgaggca gaagcacgcc ccggtgaatc gtggcaagcg 3900
gccgctgatc gaatccgcaa agaatcccgg caaccgccgg cagccggtgc gccgtcgatt 3960
aggaagccgc ccaagggcga cgagcaacca gatttttcg ttccgatgct ctatgacgtg 4020
ggcacccgcg atagtcgcag catcatggac gtggccgttt tccgtctgtc gaagcgtgac 4080
cgacgagctg gcgaggtgat ccgctacgag cttccagacg ggcacgtaga ggtttccgca 4140
gggccggccg gcatggccag tgtgtgggat tacgacctgg tactgatggc ggtttcccat 4200
ctaaccgaat ccatgaaccg ataccgggaa gggaagggag acaagcccgg ccgcgtgttc 4260
cgtccacacg ttgcggacgt actcaagttc tgccggcgag ccgatggcgg aaagcagaaa 4320
gacgacctgg tagaaacctg cattcggtta aacaccacgc acgttgccat gcagcgtacg 4380
aagaaggcca agaacggccg cctggtgacg gtatccgagg gtgaagcctt gattagccgc 4440
tacaagatcg taaagagcga aaccgggcgg ccggagtaca tcgagatcga gctagctgat 4500

-continued

```
tggatgtacc gcgagatcac agaaggcaag aacccggacg tgctgacggt tcaccccgat   4560
tactttttga tcgatcccgg catcggccgt tttctctacc gcctggcacg ccgcgccgca   4620
ggcaaggcag aagccagatg gttgttcaag acgatctacg aacgcagtgg cagcgccgga   4680
gagttcaaga agttctgttt caccgtgcgc aagctgatcg ggtcaaatga cctgccggag   4740
tacgatttga aggaggaggc ggggcaggct ggcccgatcc tagtcatgcg ctaccgcaac   4800
ctgatcgagg gcgaagcatc cgccggttcc taatgtacgg agcagatgct agggcaaatt   4860
gccctagcag gggaaaaagg tcgaaaaggt ctctttcctg tggatagcac gtacattggg   4920
aacccaaagc cgtacattgg gaaccggaac ccgtacattg ggaacccaaa gccgtacatt   4980
gggaaccggt cacacatgta agtgactgat ataaaagaga aaaaaggcga tttttccgcc   5040
taaaactctt taaaacttat taaaactctt aaaacccgcc tggcctgtgc ataactgtct   5100
ggccagcgca cagccgaaga gctgcaaaaa gcgcctaccc ttcggtcgct gcgctcccta   5160
cgccccgccg cttcgcgtcg gcctatcgcg gccgctggcc gctcaaaaat ggctggccta   5220
cggccaggca atctaccagg gcgcggacaa gccgcgccgt cgccactcga ccgccggcgc   5280
ccacatcaag gcaccctgcc tcgcgcgttt cggtgatgac ggtgaaaacc tctgacacat   5340
gcagctcccg gagacggtca cagcttgtct gtaagcggat gccgggagca gacaagcccg   5400
tcagggcgcg tcagcgggtg ttggcgggtg tcggggcgca gccatgaccc agtcacgtag   5460
cgatagcgga gtgtatactg gcttaactat gcggcatcag agcagattgt actgagagtg   5520
caccatatgc ggtgtgaaat accgcacaga tgcgtaagga gaaaataccg catcaggcgc   5580
tcttccgctt cctcgctcac tgactcgctg cgctcggtcg ttcggctgcg gcgagcggta   5640
tcagctcact caaaggcggt aatacggtta tccacagaat caggggataa cgcaggaaag   5700
aacatgtgag caaaaggcca gcaaaaggcc aggaaccgta aaaaggccgc gttgctggcg   5760
tttttccata ggctccgccc ccctgacgag catcacaaaa atcgacgctc aagtcagagg   5820
tggcgaaacc cgacaggact ataaagatac caggcgtttc cccctggaag ctccctcgtg   5880
cgctctcctg ttccgaccct gccgcttacc ggatacctgt ccgcctttct cccttcggga   5940
agcgtggcgc tttctcatag ctcacgctgt aggtatctca gttcggtgta ggtcgttcgc   6000
tccaagctgg gctgtgtgca cgaacccccc gttcagcccg accgctgcgc cttatccggt   6060
aactatcgtc ttgagtccaa cccggtaaga cacgacttat cgccactggc agcagccact   6120
ggtaacagga ttagcagagc gaggtatgta ggcggtgcta cagagttctt gaagtggtgg   6180
cctaactacg gctacactag aaggacagta tttggtatct gcgctctgct gaagccagtt   6240
accttcggaa aaagagttgg tagctcttga tccggcaaac aaaccaccgc tggtagcggt   6300
ggtttttttg tttgcaagca gcagattacg cgcagaaaaa aaggatctca agaagatcct   6360
ttgatctttt ctacggggtc tgacgctcag tggaacgaaa actcacgtta agggattttg   6420
gtcatgcatg atatatctcc caatttgtgt agggcttatt atgcacgctt aaaaataata   6480
aaagcagact tgacctgata gtttggctgt gagcaattat gtgcttagtg catctaacgc   6540
ttgagttaag ccgcgccgcg aagcggcgtc ggcttgaacg aatttctagc tagacattat   6600
ttgccgacta ccttggtgat ctcgcctttc acgtagtgga caaattcttc caactgatct   6660
gcgcgcgagg ccaagcgatc ttcttcttgt ccaagataag cctgtctagc ttcaagtatg   6720
acgggctgat actgggccgg caggcgctcc attgcccagt cggcagcgac atccttcggc   6780
gcgattttgc cggttactgc gctgtaccaa atgcgggaca acgtaagcac tacatttcgc   6840
tcatcgccag cccagtcggg cggcgagttc catagcgtta aggtttcatt tagcgcctca   6900
```

```
aatagatcct gttcaggaac cggatcaaag agttcctccg ccgctggacc taccaaggca   6960

acgctatgtt ctcttgcttt tgtcagcaag atagccagat caatgtcgat cgtggctggc   7020

tcgaagatac ctgcaagaat gtcattgcgc tgccattctc caaattgcag ttcgcgctta   7080

gctggataac gccacggaat gatgtcgtcg tgcacaacaa tggtgacttc tacagcgcgg   7140

agaatctcgc tctctccagg ggaagccgaa gtttccaaaa ggtcgttgat caaagctcgc   7200

cgcgttgttt catcaagcct tacggtcacc gtaaccagca aatcaatatc actgtgtggc   7260

ttcaggccgc catccactgc ggagccgtac aaatgtacgg ccagcaacgt cggttcgaga   7320

tggcgctcga tgacgccaac tacctctgat agttgagtcg atacttcggc gatcaccgct   7380

tcccccatga tgtttaactt tgttttaggg cgactgccct gctgcgtaac atcgttgctg   7440

ctccataaca tcaaacatcg acccacggcg taacgcgctt gctgcttgga tgcccgaggc   7500

atagactgta ccccaaaaaa acagtcataa caagccatga aaaccgccac tgcg         7554


<210> SEQ ID NO 24
<211> LENGTH: 8327
<212> TYPE: DNA
<213> ORGANISM: Artificial sequence
<220> FEATURE:
<223> OTHER INFORMATION: Description of the artificial sequence:  binary
      plant expression vector
<220> FEATURE:
<221> NAME/KEY: misc_feature
<222> LOCATION: (476)..(478)
<223> OTHER INFORMATION: n is a, c, g, or t
<220> FEATURE:
<221> NAME/KEY: misc_feature
<222> LOCATION: (1261)..(1263)
<223> OTHER INFORMATION: n is a, c, g, or t

<400> SEQUENCE: 24

ttccatggac atacaaatgg acgaacggat aaaccttttc acgccctttt aaatatccga     60

ttattctaat aaacgctctt ttctcttagg tttacccgcc aatatatcct gtcaaacact    120

gatagtttaa actgaaggcg ggaaacgaca atcagatcta gtaggaaaca gctatgacca    180

tgattacgcc aagcttgcat gccgatcccc cctgcagata gactatacta tgttttagcc    240

tgcctgctgg ctagctacta tgttatgtta tgttgtaaaa taaacacctg ctaaggtata    300

tctatctata ttttagcatg gctttctcaa taaattgtct ttccttatcg tttactatct    360

tatacctaat aatgaaataa taatatcaca tatgaggaac ggggcaggtt taggcatata    420

tatacgagtg tagggcggag tgggggggta cggtcgactc tagactagtg gatccnnntc    480

aagaaggcga tagaaggcga tgcgctgcga atcgggagcg gcgataccgt aaagcacgag    540

gaagcggtca gcccattcgc cgccaagctc ttcagcaata tcacgggtag ccaacgctat    600

gtcctgatag cggtccgcca cacccagccg gccacagtcg atgaatccag aaaagcggcc    660

attttccacc atgatattcg gcaagcaggc atcgccatgg gtcacgacga gatcctcgcc    720

gtcgggcatg cgcgccttga gcctggcgaa cagttcggct ggcgcgagcc cctgatgctc    780

ttcgtccaga tcatcctgat cgacaagacc ggcttccatc cgagtacgtg ctcgctcgat    840

gcgatgtttc gcttggtggt cgaatgggca ggtagccgga tcaagcgtat gcagccgccg    900

cattgcatca gccatgatgg atactttctc ggcaggagca aggtgagatg acaggagatc    960

ctgccccggc acttcgccca atagcagcca gtcccttccc gcttcagtga caacgtcgag   1020

cacagctgcg caaggaacgc ccgtcgtggc cagccacgat agccgcgctg cctcgtcctg   1080

cagttcattc agggcaccgg acaggtcggt cttgacaaaa agaaccgggc gcccctgcgc   1140
```

-continued

```
tgacagccgg aacacggcgg catcagagca gccgattgtc tgttgtgccc agtcatagcc   1200
gaatagcctc tccacccaag cggccggaga acctgcgtgc aatccatctt gttcaatcat   1260
nnnagatccg atatcgcccg ggctcgaggt accgagctcg aattcactgg ccgtcgtttt   1320
acaacgactc agccagcttg acaggaggcc cgatctagta acatagatga caccgcgcgc   1380
gataatttat cctagtttgc gcgctatatt ttgttttcta tcgcgtatta aatgtataat   1440
tgcgggactc taatcataaa aacccatctc ataaataacg tcatgcatta catgttaatt   1500
attacatgct taacgtaatt caacagaaat tatatgataa tcatcgcaag accggcaaca   1560
ggattcaatc ttaagaaact ttattgccaa atgtttgaac gatcggggat catccgggtc   1620
tgtggcggga actccacgaa aatatccgaa cgcagcaaga tcggtcgatc gactcagatc   1680
tgggtaactg gcctaactgg ccttggagga gctggcaact caaaatccct ttgccaaaaa   1740
ccaacatcat gccatccacc atgcttgtat ccagccgcgc gcaatgtacc ccgcgctgtg   1800
tatcccaaag cctcatgcaa cctaacagat ggatcgtttg gaaggcctat aacagcaacc   1860
acagacttaa aaccttgcgc ctccatagac ttaagcaaat gtgtgtacaa tgtagatcct   1920
aggcccaacc tttgatgcct atgtgacacg taaacagtac tctcaactgt ccaatcgtaa   1980
gcgttcctag ccttccaggg cccagcgtaa gcaataccag ccacaacacc ctcaacctca   2040
gcaaccaacc aagggtatct atcttgcaac ctctctaggt catcaatcca ctcttgtggt   2100
gtttgtggct ctgtcctaaa gttcactgta gacgtctcaa tgtaatggtt aacgatgtca   2160
caaaccgcgg ccatatcggc tgctgtagct ggcctaatct caactggtct cctctccgga   2220
gacatgtcga gattatttgg attgagagtg aatatgagac tctaattgga taccgagggg   2280
aatttatgga acgtcagtgg agcatttttg acaagaaata tttgctagct gatagtgacc   2340
ttaggcgact tttgaacgcg caataatggt ttctgacgta tgtgcttagc tcattaaact   2400
ccagaaaccc gcggctgagt ggctccttca acgttgcggt tctgtcagtt ccaaacgtaa   2460
aacggcttgt cccgcgtcat cggcgggggt cataacgtga ctcccttaat tctccgctca   2520
tgatcagatt gtcgtttccc gccttcagtt taaactatca gtgtttgaca ggatcctgct   2580
tggtaataat tgtcattaga ttgtttttat gcatagatgc actcgaaatc agccaatttt   2640
agacaagtat caaacggatg ttaattcagt acattaaaga cgtccgcaat gtgttattaa   2700
gttgtctaag cgtcaatttg tttacaccac aatatatcct gccaccagcc agccaacagc   2760
tccccgaccg gcagctcggc acaaaatcac cacgcgttac caccacgccg gccggccgca   2820
tggtgttgac cgtgttcgcc ggcattgccg agttcgagcg ttccctaatc atcgaccgca   2880
cccggagcgg gcgcgaggcc gccaaggccc gaggcgtgaa gtttggcccc cgccctaccc   2940
tcaccccggc acagatcgcg cacgcccgcg agctgatcga ccaggaaggc cgcaccgtga   3000
aagaggcggc tgcactgctt ggcgtgcatc gctcgaccct gtaccgcgca cttgagcgca   3060
gcgaggaagt gacgcccacc gaggccaggc ggcgcggtgc cttccgtgag gacgcattga   3120
ccgaggccga cgccctggcg gccgccgaga atgaacgcca agaggaacaa gcatgaaacc   3180
gcaccaggac ggccaggacg aaccgttttt cattaccgaa gagatcgagg cggagatgat   3240
cgcggccggg tacgtgttcg agccgcccgc gcacgtctca accgtgcggc tgcatgaaat   3300
cctggccggt ttgtctgatg ccaagctggc ggcctggccg gccagcttgg ccgctgaaga   3360
aaccgagcgc cgccgtctaa aaaggtgatg tgtatttgag taaaacagct tgcgtcatgc   3420
ggtcgctgcg tatatgatgc gatgagtaaa taaacaaata cgcaagggga acgcatgaag   3480
gttatcgctg tacttaacca gaaaggcggg tcaggcaaga cgaccatcgc aacccatcta   3540
```

-continued

```
gcccgcgccc tgcaactcgc cggggccgat gttctgttag tcgattccga tccccagggc   3600
agtgcccgcg attgggcggc cgtgcgggaa gatcaaccgc taaccgttgt cggcatcgac   3660
cgcccgacga ttgaccgcga cgtgaaggcc atcggccggc gcgacttcgt agtgatcgac   3720
ggagcgcccc aggcggcgga cttggctgtg tccgcgatca aggcagccga cttcgtgctg   3780
attccggtgc agccaagccc ttacgacata tgggccaccg ccgacctggt ggagctggtt   3840
aagcagcgca ttgaggtcac ggatggaagg ctacaagcgg cctttgtcgt gtcgcgggcg   3900
atcaaaggca cgcgcatcgg cggtgaggtt gccgaggcgc tggccgggta cgagctgccc   3960
attcttgagt cccgtatcac gcagcgcgtg agctacccag gcactgccgc cgccggcaca   4020
accgttcttg aatcagaacc cgagggcgac gctgcccgcg aggtccaggc gctggccgct   4080
gaaattaaat caaaactcat ttgagttaat gaggtaaaga gaaaatgagc aaaagcacaa   4140
acacgctaag tgccggccgt ccgagcgcac gcagcagcaa ggctgcaacg ttggccagcc   4200
tggcagacac gccagccatg aagcgggtca actttcagtt gccggcggag gatcacacca   4260
agctgaagat gtacgcggta cgccaaggca agaccattac cgagctgcta tctgaataca   4320
tcgcgcagct accagagtaa atgagcaaat gaataaatga gtagatgaat tttagcggct   4380
aaaggaggcg gcatggaaaa tcaagaacaa ccaggcaccg acgccgtgga atgccccatg   4440
tgtggaggaa cgggcggttg gccaggcgta agcggctggg ttgtctgccg gccctgcaat   4500
ggcactggaa cccccaagcc cgaggaatcg gcgtgagcgg tcgcaaacca tccggcccgg   4560
tacaaatcgg cgcggcgctg ggtgatgacc tggtggagaa gttgaaggcc gcgcaggccg   4620
cccagcggca acgcatcgag gcagaagcac gccccggtga atcgtggcaa gcggccgctg   4680
atcgaatccg caaagaatcc cggcaaccgc cggcagccgg tgcgccgtcg attaggaagc   4740
cgcccaaggg cgacgagcaa ccagattttt tcgttccgat gctctatgac gtgggcaccc   4800
gcgatagtcg cagcatcatg gacgtggccg ttttccgtct gtcgaagcgt gaccgacgag   4860
ctggcgaggt gatccgctac gagcttccag acgggcacgt agaggtttcc gcagggccgg   4920
ccggcatggc cagtgtgtgg gattacgacc tggtactgat ggcggtttcc catctaaccg   4980
aatccatgaa ccgataccgg gaagggaagg gagacaagcc cggccgcgtg ttccgtccac   5040
acgttgcgga cgtactcaag ttctgccggc gagccgatgg cggaaagcag aaagacgacc   5100
tggtagaaac ctgcattcgg ttaaacacca cgcacgttgc catgcagcgt acgaagaagg   5160
ccaagaacgg ccgcctggtg acggtatccg agggtgaagc cttgattagc cgctacaaga   5220
tcgtaaagag cgaaaccggg cggccggagt acatcgagat cgagctagct gattggatgt   5280
accgcgagat cacagaaggc aagaacccgg acgtgctgac ggttcacccc gattactttt   5340
tgatcgatcc cggcatcggc cgttttctct accgcctggc acgccgcgcc gcaggcaagg   5400
cagaagccag atggttgttc aagacgatct acgaacgcag tggcagcgcc ggagagttca   5460
agaagttctg tttcaccgtg cgcaagctga tcgggtcaaa tgacctgccg gagtacgatt   5520
tgaaggagga ggcggggcag gctggcccga tcctagtcat gcgctaccgc aacctgatcg   5580
agggcgaagc atccgccggt tcctaatgta cggagcagat gctagggcaa attgccctag   5640
caggggaaaa aggtcgaaaa ggtctctttc ctgtggatag cacgtacatt gggaacccaa   5700
agccgtacat tgggaaccgg aacccgtaca ttgggaaccc aaagccgtac attgggaacc   5760
ggtcacacat gtaagtgact gatataaaag agaaaaaagg cgatttttcc gcctaaaact   5820
ctttaaaact tattaaaact cttaaaaccc gcctggcctg tgcataactg tctggccagc   5880
gcacagccga agagctgcaa aaagcgccta cccttcggtc gctgcgctcc ctacgccccg   5940
```

-continued

```
ccgcttcgcg tcggcctatc gcggccgctg gccgctcaaa aatggctggc ctacggccag   6000
gcaatctacc agggcgcgga caagccgcgc cgtcgccact cgaccgccgg cgcccacatc   6060
aaggcaccct gcctcgcgcg tttcggtgat gacggtgaaa acctctgaca catgcagctc   6120
ccggagacgg tcacagcttg tctgtaagcg gatgccggga gcagacaagc ccgtcagggc   6180
gcgtcagcgg gtgttggcgg gtgtcggggc gcagccatga cccagtcacg tagcgatagc   6240
ggagtgtata ctggcttaac tatgcggcat cagagcagat tgtactgaga gtgcaccata   6300
tgcggtgtga aataccgcac agatgcgtaa ggagaaaata ccgcatcagg cgctcttccg   6360
cttcctcgct cactgactcg ctgcgctcgg tcgttcggct gcggcgagcg gtatcagctc   6420
actcaaaggc ggtaatacgg ttatccacag aatcagggga taacgcagga aagaacatgt   6480
gagcaaaagg ccagcaaaag gccaggaacc gtaaaaaggc cgcgttgctg gcgtttttcc   6540
ataggctccg cccccctgac gagcatcaca aaaatcgacg ctcaagtcag aggtggcgaa   6600
acccgacagg actataaaga taccaggcgt ttccccctgg aagctccctc gtgcgctctc   6660
ctgttccgac cctgccgctt accggatacc tgtccgcctt tctcccttcg ggaagcgtgg   6720
cgctttctca tagctcacgc tgtaggtatc tcagttcggt gtaggtcgtt cgctccaagc   6780
tgggctgtgt gcacgaaccc cccgttcagc ccgaccgctg cgccttatcc ggtaactatc   6840
gtcttgagtc caacccggta agacacgact tatcgccact ggcagcagcc actggtaaca   6900
ggattagcag agcgaggtat gtaggcggtg ctacagagtt cttgaagtgg tggcctaact   6960
acggctacac tagaaggaca gtatttggta tctgcgctct gctgaagcca gttaccttcg   7020
gaaaaagagt tggtagctct tgatccggca aacaaaccac cgctggtagc ggtggttttt   7080
ttgtttgcaa gcagcagatt acgcgcagaa aaaaaggatc tcaagaagat cctttgatct   7140
tttctacggg gtctgacgct cagtggaacg aaaactcacg ttaagggatt ttggtcatgc   7200
atgatatatc tcccaatttg tgtagggctt attatgcacg cttaaaaata ataaaagcag   7260
acttgacctg atagtttggc tgtgagcaat tatgtgctta gtgcatctaa cgcttgagtt   7320
aagccgcgcc gcgaagcggc gtcggcttga acgaatttct agctagacat tatttgccga   7380
ctaccttggt gatctcgcct ttcacgtagt ggacaaattc ttccaactga tctgcgcgcg   7440
aggccaagcg atcttcttct tgtccaagat aagcctgtct agcttcaagt atgacgggct   7500
gatactgggc cggcaggcgc tccattgccc agtcggcagc gacatccttc ggcgcgattt   7560
tgccggttac tgcgctgtac caaatgcggg acaacgtaag cactacattt cgctcatcgc   7620
cagcccagtc gggcggcgag ttccatagcg ttaaggtttc atttagcgcc tcaaatagat   7680
cctgttcagg aaccggatca aagagttcct ccgccgctgg acctaccaag gcaacgctat   7740
gttctcttgc ttttgtcagc aagatagcca gatcaatgtc gatcgtggct ggctcgaaga   7800
tacctgcaag aatgtcattg cgctgccatt ctccaaattg cagttcgcgc ttagctggat   7860
aacgccacgg aatgatgtcg tcgtgcacaa caatggtgac ttctacagcg cggagaatct   7920
cgctctctcc aggggaagcc gaagtttcca aaaggtcgtt gatcaaagct cgccgcgttg   7980
tttcatcaag ccttacggtc accgtaacca gcaaatcaat atcactgtgt ggcttcaggc   8040
cgccatccac tgcggagccg tacaaatgta cggccagcaa cgtcggttcg agatggcgct   8100
cgatgacgcc aactacctct gatagttgag tcgatacttc ggcgatcacc gcttccccca   8160
tgatgtttaa ctttgtttta gggcgactgc cctgctgcgt aacatcgttg ctgctccata   8220
acatcaaaca tcgacccacg gcgtaacgcg cttgctgctt ggatgcccga ggcatagact   8280
gtaccccaaa aaaacagtca taacaagcca tgaaaaccgc cactgcg                 8327
```

<210> SEQ ID NO 25
<211> LENGTH: 8441
<212> TYPE: DNA
<213> ORGANISM: Artificial sequence
<220> FEATURE:
<223> OTHER INFORMATION: Description of the artificial sequence: binary plant expression vector

<400> SEQUENCE: 25
ttccatggac atacaaatgg acgaacggat aaacctttc acgcccttt aaatatccga 60 ttattctaat aaacgctctt ttctcttagg tttacccgcc aatatatcct gtcaaacact 120
gatagtttaa actgaaggcg ggaaacgaca atcagatcta gtaggaaaca gctatgacca 180
tgattacgcc aagcttgcat gccagcttga caggaggccc gatctagtaa catagatgac 240
accgcgcgcg ataatttatc ctagtttgcg cgctatattt tgttttctat cgcgtattaa 300
atgtataatt gcgggactct aatcataaaa acccatctca taaataacgt catgcattac 360
atgttaatta ttacatgctt aacgtaattc aacagaaatt atatgataat catcgcaaga 420
ccggcaacag gattcaatct taagaaactt tattgccaaa tgtttgaacg atcggggatc 480
atccgggtct gtggcgggaa ctccacgaaa atatccgaac gcagcaagat cggtcgatcg 540
actcagatct gggtaactgg cctaactggc cttggaggag ctggcaactc aaaatccctt 600
tgccaaaaac caacatcatg ccatccacca tgcttgtatc cagccgcgcg caatgtaccc 660
cgcgctgtgt atcccaaagc ctcatgcaac ctaacagatg gatcgtttgg aaggcctata 720
acagcaacca cagacttaaa accttgcgcc tccatagact taagcaaatg tgtgtacaat 780
gtagatccta ggcccaacct ttgatgccta tgtgacacgt aaacagtact ctcaactgtc 840
caatcgtaag cgttcctagc cttccagggc ccagcgtaag caataccagc cacaacaccc 900
tcaacctcag caaccaacca agggtatcta tcttgcaacc tctctaggtc atcaatccac 960
tcttgtggtg tttgtggctc tgtcctaaag ttcactgtag acgtctcaat gtaatggtta 1020
acgatgtcac aaaccgcggc catatcggct gctgtagctg gcctaatctc aactggtctc 1080
ctctccggag acatgtcgac tctagactag tggatccgat atcgcccggg ctcgaggtac 1140
cgagctcgaa ttcactggcc gtcgttttac aacgactcag agcttgacag gaggcccgat 1200
ctagtaacat agatgacacc gcgcgcgata atttatccta gtttgcgcgc tatattttgt 1260
tttctatcgc gtattaaatg tataattgcg ggactctaat cataaaaacc catctcataa 1320
ataacgtcat gcattacatg ttaattatta catgcttaac gtaattcaac agaaattata 1380
tgataatcat cgcaagaccg gcaacaggat tcaatcttaa gaaactttat tgccaaatgt 1440
ttgaacgatc ggggatcatc cgggtctgtg gcgggaactc cacgaaaata tccgaacgca 1500
gcaagatcta gagcttgggt cccgctcaga agaactcgtc aagaaggcga tagaaggcga 1560
tgcgctgcga atcgggagcg gcgataccgt aaagcacgag gaagcggtca gcccattcgc 1620
cgccaagctc ttcagcaata tcacgggtag ccaacgctat gtcctgatag cggtccgcca 1680
cacccagccg gccacagtcg atgaatccag aaaagcggcc attttccacc atgatattcg 1740
gcaagcaggc atcgccatgg gtcacgacga gatcctcgcc gtcgggcatg cgcgccttga 1800
gcctggcgaa cagttcggct ggcgcgagcc cctgatgctc ttcgtccaga tcatcctgat 1860
cgacaagacc ggcttccatc cgagtacgtg ctcgctcgat gcgatgtttc gcttggtggt 1920
cgaatgggca ggtagccgga tcaagcgtat gcagccgccg cattgcatca gccatgatgg 1980
atactttctc ggcaggagca aggtgagatg acaggagatc ctgccccggc acttcgccca 2040
atagcagcca gtcccttccc gcttcagtga caacgtcgag cacagctgcg caaggaacgc 2100

-continued

```
ccgtcgtggc cagccacgat agccgcgctg cctcgtcctg cagttcattc agggcaccgg   2160
acaggtcggt cttgacaaaa agaaccgggc gcccctgcgc tgacagccgg aacacggcgg   2220
catcagagca gccgattgtc tgttgtgccc agtcatagcc gaatagcctc tccacccaag   2280
cggccggaga acctgcgtgc aatccatctt gttcaatcat gcgaaacgat ccagatccgg   2340
tgcagattat ttggattgag agtgaatatg agactctaat tggataccga ggggaattta   2400
tggaacgtca gtggagcatt tttgacaaga aatatttgct agctgatagt gaccttaggc   2460
gacttttgaa cgcgcaataa tggtttctga cgtatgtgct tagctcatta aactccagaa   2520
acccgcggct gagtggctcc ttcaacgttg cggttctgtc agttccaaac gtaaaacggc   2580
ttgtcccgcg tcatcggcgg gggtcataac gtgactccct taattctccg ctcatgatca   2640
gattgtcgtt tcccgccttc agtttaaact atcagtgttt gacaggatcc tgcttggtaa   2700
taattgtcat tagattgttt ttatgcatag atgcactcga aatcagccaa ttttagacaa   2760
gtatcaaacg gatgttaatt cagtacatta aagacgtccg caatgtgtta ttaagttgtc   2820
taagcgtcaa tttgtttaca ccacaatata tcctgccacc agccagccaa cagctccccg   2880
accggcagct cggcacaaaa tcaccacgcg ttaccaccac gccggccggc cgcatggtgt   2940
tgaccgtgtt cgccggcatt gccgagttcg agcgttccct aatcatcgac cgcacccgga   3000
gcgggcgcga ggccgccaag gcccgaggcg tgaagtttgg cccccgccct accctcaccc   3060
cggcacagat cgcgcacgcc cgcgagctga tcgaccagga aggccgcacc gtgaaagagg   3120
cggctgcact gcttggcgtg catcgctcga ccctgtaccg cgcacttgag cgcagcgagg   3180
aagtgacgcc caccgaggcc aggcggcgcg gtgccttccg tgaggacgca ttgaccgagg   3240
ccgacgccct ggcggccgcc gagaatgaac gccaagagga acaagcatga aaccgcacca   3300
ggacggccag gacgaaccgt ttttcattac cgaagagatc gaggcggaga tgatcgcggc   3360
cgggtacgtg ttcgagccgc ccgcgcacgt ctcaaccgtg cggctgcatg aaatcctggc   3420
cggtttgtct gatgccaagc tggcggcctg gccggccagc ttggccgctg aagaaaccga   3480
gcgccgccgt ctaaaaaggt gatgtgtatt tgagtaaaac agcttgcgtc atgcggtcgc   3540
tgcgtatatg atgcgatgag taaataaaca aatacgcaag gggaacgcat gaaggttatc   3600
gctgtactta accagaaagg cgggtcaggc aagacgacca tcgcaaccca tctagcccgc   3660
gccctgcaac tcgccggggc cgatgttctg ttagtcgatt ccgatcccca gggcagtgcc   3720
cgcgattggg cggccgtgcg ggaagatcaa ccgctaaccg ttgtcggcat cgaccgcccg   3780
acgattgacc gcgacgtgaa ggccatcggc cggcgcgact tcgtagtgat cgacggagcg   3840
ccccaggcgg cggacttggc tgtgtccgcg atcaaggcag ccgacttcgt gctgattccg   3900
gtgcagccaa gcccttacga catatgggcc accgccgacc tggtggagct ggttaagcag   3960
cgcattgagg tcacggatgg aaggctacaa gcggcctttg tcgtgtcgcg ggcgatcaaa   4020
ggcacgcgca tcggcggtga ggttgccgag gcgctggccg ggtacgagct gcccattctt   4080
gagtcccgta tcacgcagcg cgtgagctac ccaggcactg ccgccgccgg cacaaccgtt   4140
cttgaatcag aacccgaggg cgacgctgcc cgcgaggtcc aggcgctggc cgctgaaatt   4200
aaatcaaaac tcatttgagt taatgaggta aagagaaaat gagcaaaagc acaaacacgc   4260
taagtgccgg ccgtccgagc gcacgcagca gcaaggctgc aacgttggcc agcctggcag   4320
acacgccagc catgaagcgg gtcaactttc agttgccggc ggaggatcac accaagctga   4380
agatgtacgc ggtacgccaa ggcaagacca ttaccgagct gctatctgaa tacatcgcgc   4440
agctaccaga gtaaatgagc aaatgaataa atgagtagat gaattttagc ggctaaagga   4500
```

ggcggcatgg aaaatcaaga acaaccaggc accgacgccg tggaatgccc catgtgtgga 4560
ggaacgggcg gttggccagg cgtaagcggc tgggttgtct gccggccctg caatggcact 4620
ggaaccccca agcccgagga atcggcgtga gcggtcgcaa accatccggc ccggtacaaa 4680
tcggcgcggc gctgggtgat gacctggtgg agaagttgaa ggccgcgcag gccgcccagc 4740
ggcaacgcat cgaggcagaa gcacgccccg gtgaatcgtg gcaagcggcc gctgatcgaa 4800
tccgcaaaga atcccggcaa ccgccggcag ccggtgcgcc gtcgattagg aagccgccca 4860
agggcgacga gcaaccagat tttttcgttc cgatgctcta tgacgtgggc acccgcgata 4920
gtcgcagcat catggacgtg gccgttttcc gtctgtcgaa gcgtgaccga cgagctggcg 4980
aggtgatccg ctacgagctt ccagacgggc acgtagaggt ttccgcaggg ccggccggca 5040
tggccagtgt gtgggattac gacctggtac tgatggcggt ttcccatcta accgaatcca 5100
tgaaccgata ccgggaaggg aagggagaca agcccggccg cgtgttccgt ccacacgttg 5160
cggacgtact caagttctgc cggcgagccg atggcggaaa gcagaaagac gacctggtag 5220
aaacctgcat tcggttaaac accacgcacg ttgccatgca gcgtacgaag aaggccaaga 5280
acggccgcct ggtgacggta tccgagggtg aagccttgat tagccgctac aagatcgtaa 5340
agagcgaaac cgggcggccg gagtacatcg agatcgagct agctgattgg atgtaccgcg 5400
agatcacaga aggcaagaac ccggacgtgc tgacggttca ccccgattac tttttgatcg 5460
atcccggcat cggccgtttt ctctaccgcc tggcacgccg cgccgcaggc aaggcagaag 5520
ccagatggtt gttcaagacg atctacgaac gcagtggcag cgccggagag ttcaagaagt 5580
tctgtttcac cgtgcgcaag ctgatcgggt caaatgacct gccggagtac gatttgaagg 5640
aggaggcggg gcaggctggc ccgatcctag tcatgcgcta ccgcaacctg atcgagggcg 5700
aagcatccgc cggttcctaa tgtacggagc agatgctagg gcaaattgcc ctagcagggg 5760
aaaaaggtcg aaaaggtctc tttcctgtgg atagcacgta cattgggaac ccaaagccgt 5820
acattgggaa ccggaacccg tacattggga acccaaagcc gtacattggg aaccggtcac 5880
acatgtaagt gactgatata aaagagaaaa aaggcgattt ttccgcctaa aactctttaa 5940
aacttattaa aactcttaaa acccgcctgg cctgtgcata actgtctggc cagcgcacag 6000
ccgaagagct gcaaaaagcg cctacccttc ggtcgctgcg ctccctacgc cccgccgctt 6060
cgcgtcggcc tatcgcggcc gctggccgct caaaaatggc tggcctacgg ccaggcaatc 6120
taccagggcg cggacaagcc gcgccgtcgc cactcgaccg ccggcgccca catcaaggca 6180
ccctgcctcg cgcgtttcgg tgatgacggt gaaaacctct gacacatgca gctcccggag 6240
acggtcacag cttgtctgta agcggatgcc gggagcagac aagcccgtca gggcgcgtca 6300
gcgggtgttg gcgggtgtcg gggcgcagcc atgacccagt cacgtagcga tagcggagtg 6360
tatactggct taactatgcg gcatcagagc agattgtact gagagtgcac catatgcggt 6420
gtgaaatacc gcacagatgc gtaaggagaa aataccgcat caggcgctct tccgcttcct 6480
cgctcactga ctcgctgcgc tcggtcgttc ggctgcggcg agcggtatca gctcactcaa 6540
aggcggtaat acggttatcc acagaatcag gggataacgc aggaaagaac atgtgagcaa 6600
aaggccagca aaaggccagg aaccgtaaaa aggccgcgtt gctggcgttt ttccataggc 6660
tccgcccccc tgacgagcat cacaaaaatc gacgctcaag tcagaggtgg cgaaacccga 6720
caggactata aagataccag gcgtttcccc ctggaagctc cctcgtgcgc tctcctgttc 6780
cgaccctgcc gcttaccgga tacctgtccg cctttctccc ttcgggaagc gtggcgcttt 6840
ctcatagctc acgctgtagg tatctcagtt cggtgtaggt cgttcgctcc aagctgggct 6900
gtgtgcacga accccccgtt cagcccgacc gctgcgcctt atccggtaac tatcgtcttg 6960
agtccaaccc ggtaagacac gacttatcgc cactggcagc agccactggt aacaggatta 7020
gcagagcgag gtatgtaggc ggtgctacag agttcttgaa gtggtggcct aactacggct 7080
acactagaag gacagtattt ggtatctgcg ctctgctgaa gccagttacc ttcggaaaaa 7140
gagttggtag ctcttgatcc ggcaaacaaa ccaccgctgg tagcggtggt ttttttgttt 7200
gcaagcagca gattacgcgc agaaaaaaag gatctcaaga agatcctttg atcttttcta 7260
cggggtctga cgctcagtgg aacgaaaact cacgttaagg gattttggtc atgcatgata 7320
tatctcccaa tttgtgtagg gcttattatg cacgcttaaa aataataaaa gcagacttga 7380
cctgatagtt tggctgtgag caattatgtg cttagtgcat ctaacgcttg agttaagccg 7440
cgccgcgaag cggcgtcggc ttgaacgaat ttctagctag acattatttg ccgactacct 7500
tggtgatctc gcctttcacg tagtggacaa attcttccaa ctgatctgcg cgcgaggcca 7560
agcgatcttc ttcttgtcca agataagcct gtctagcttc aagtatgacg ggctgatact 7620
gggccggcag gcgctccatt gcccagtcgg cagcgacatc cttcggcgcg attttgccgg 7680
ttactgcgct gtaccaaatg cgggacaacg taagcactac atttcgctca tcgccagccc 7740
agtcgggcgg cgagttccat agcgttaagg tttcatttag cgcctcaaat agatcctgtt 7800
caggaaccgg atcaaagagt tcctccgccg ctggacctac caaggcaacg ctatgttctc 7860
ttgcttttgt cagcaagata gccagatcaa tgtcgatcgt ggctggctcg aagatacctg 7920
caagaatgtc attgcgctgc cattctccaa attgcagttc gcgcttagct ggataacgcc 7980
acggaatgat gtcgtcgtgc acaacaatgg tgacttctac agcgcggaga atctcgctct 8040
ctccagggga agccgaagtt tccaaaaggt cgttgatcaa agctcgccgc gttgtttcat 8100
caagccttac ggtcaccgta accagcaaat caatatcact gtgtggcttc aggccgccat 8160
ccactgcgga gccgtacaaa tgtacggcca gcaacgtcgg ttcgagatgg cgctcgatga 8220
cgccaactac ctctgatagt tgagtcgata cttcggcgat caccgcttcc cccatgatgt 8280
ttaactttgt tttagggcga ctgccctgct gcgtaacatc gttgctgctc cataacatca 8340
aacatcgacc cacggcgtaa cgcgcttgct gcttggatgc ccgaggcata gactgtaccc 8400
caaaaaaaca gtcataacaa gccatgaaaa ccgccactgc g 8441

<210> SEQ ID NO 26
<211> LENGTH: 45
<212> TYPE: DNA
<213> ORGANISM: Artificial sequence
<220> FEATURE:
<223> OTHER INFORMATION: Description of the artificial sequence: oligonucleotide primer

<400> SEQUENCE: 26
aagtcgacgg atcctgatag cttatactca aattcaacaa gttat 45

<210> SEQ ID NO 27
<211> LENGTH: 1318
<212> TYPE: DNA
<213> ORGANISM: Arabidopsis thaliana
<220> FEATURE:
<221> NAME/KEY: promoter
<222> LOCATION: (1)..(1318)
<223> OTHER INFORMATION: TPT truncated promoter

<400> SEQUENCE: 27
tgatagctta tactcaaatt caacaagtta tatataaatg tatagatact acaatatcat 60

-continued

```
taacaaaagt caccttaaat aaatacacat atcttttatg ttctctattg ttttgcgtac    120

gctaacacaa tttctcatat gcaaaaggat gaatgagtaa caaattacct cataagaaca    180

atcatctttg cttacatact aatacaataa tcactcaatc aaccaataac atcaatcaca    240

taggtttaca tacaataatc actcaatcaa cttcataaga agaatcatgt ttacttaatt    300

catcaattat ccccaaaaac accactatta agtataaact ataacatatt tgtagtgatg    360

ggtcaacatt tttatcatat ttaaactcgg gttccctcaa atcgagaaat agtgaacatg    420

taatattaat tttaaatcgc aattacagaa attaattgaa tttggtcaaa tggacagaat    480

tttatagatt gggtggaact agaaaaaaaa aaaaaaagag tatagggtga attgagtaca    540

tgaaagtaca tggtaatcct agttaaacgc ataatacatg tgggttcatt tgtatttttt    600

tgtaacttac gagtaaactg gctacaacaa aaaaaattag aagatttttt tgttttgtag    660

aaaaccctaa ttttagttat agttgtataa ctttgataaa attataaaat tgtattacga    720

aaaaagtaat aagatattca aaaaagccta gaataacgta tatgactatg agcatgaaac    780

tgcaagtcaa atgctgacag acaaccataa acaaaagaaa ttaaatagag ataccttttaa   840

aataagtaaa atttcattta taaaaaatct actttcttgt gaatctgtca cgttcaataa    900

tttgaagacc actcaacata caaggtaaat aatgaaaaat aaaatctacc aaaatttcaa    960

tcattattat cttccaaaaa aacaaaatta tacagatgat gatggtgata tggaacttcg   1020

attggctaat attcactgtg tctctaaaaa ccatccactt atcaagataa gatggaccct   1080

acactcatcc aatctaaacc agtatctcaa gattcttatc taattacatc attctctacc   1140

gttagatgaa attgaccatt aaccctacca taactccata caccgcgaga tactggatta   1200

accaaatcga gatcatcgta gccgtccgat caacaagtac catctcttga aatactcgaa   1260

atcctcataa gtccgtccct ctttgctctc actatcaaaa ctctgaattt cgatttca     1318


<210> SEQ ID NO 28
<211> LENGTH: 234
<212> TYPE: DNA
<213> ORGANISM: Solanum tuberosum
<220> FEATURE:
<221> NAME/KEY: terminator
<222> LOCATION: (1)..(234)
<223> OTHER INFORMATION: terminator sequence of  the  Cathepsin D
      Inhibitor gene from potato

<400> SEQUENCE: 28

cctgcagata gactatacta tgttttagcc tgcctgctgg ctagctacta tgttatgtta     60

tgttgtaaaa taaacacctg ctaaggtata tctatctata ttttagcatg gctttctcaa    120

taaattgtct ttccttatcg tttactatct tatacctaat aatgaaataa taatatcaca    180

tatgaggaac ggggcaggtt taggcatata tatacgagtg tagggcggag tggg          234


<210> SEQ ID NO 29
<211> LENGTH: 298
<212> TYPE: DNA
<213> ORGANISM: Vicia faba
<220> FEATURE:
<221> NAME/KEY: terminator
<222> LOCATION: (1)..(298)
<223> OTHER INFORMATION: terminator of storage protein gene VflElB3 from
      Vicia faba

<400> SEQUENCE: 29

gatcctgcaa tagaatgttg aggtgaccac tttctgtaat aaaataatta taaaataaat     60

ttagaattgc tgtagtcaag aacatcagtt ctaaaatatt aataaagtta tggccttttg    120
```

-continued

```
acatatgtgt ttcgataaaa aaatcaaaat aaattgagat ttattcgaaa tacaatgaaa      180

gtttgcagat atgagatatg tttctacaaa ataataactt aaaactcaac tatatgctaa      240

tgttttctt ggtgtgtttc atagaaaatt gtatccgttt cttagaaaat gctcgtaa        298
```

<210> SEQ ID NO 30
<211> LENGTH: 905
<212> TYPE: DNA
<213> ORGANISM: Arabidopsis thaliana
<220> FEATURE:
<221> NAME/KEY: CDS
<222> LOCATION: (159)..(800)
<223> OTHER INFORMATION: transcriptional activator CBF1contains AP2
    domain

<400> SEQUENCE: 30

```
aaaaagaatc tacctgaaaa gaaaaaaaag agagagagat ataaatagct taccaagaca       60

gatatactat cttttattaa tccaaaaaga ctgagaactc tagtaactac gtactactta      120

aaccttatcc agtttcttga aacagagtac tctgatca atg aac tca ttt tca gct      176
                                            Met Asn Ser Phe Ser Ala
                                              1               5

ttt tct gaa atg ttt ggc tcc gat tac gag cct caa ggc gga gat tat        224
Phe Ser Glu Met Phe Gly Ser Asp Tyr Glu Pro Gln Gly Gly Asp Tyr
         10                  15                  20

tgt ccg acg ttg gcc acg agt tgt ccg aag aaa ccg gcg ggc cgt aag        272
Cys Pro Thr Leu Ala Thr Ser Cys Pro Lys Lys Pro Ala Gly Arg Lys
     25                  30                  35

aag ttt cgt gag act cgt cac cca att tac aga gga gtt cgt caa aga        320
Lys Phe Arg Glu Thr Arg His Pro Ile Tyr Arg Gly Val Arg Gln Arg
 40                  45                  50

aac tcc ggt aag tgg gtt tct gaa gtg aga gag cca aac aag aaa acc        368
Asn Ser Gly Lys Trp Val Ser Glu Val Arg Glu Pro Asn Lys Lys Thr
55                  60                  65                  70

agg att tgg ctc ggg act ttc caa acc gct gag atg gca gct cgt gct        416
Arg Ile Trp Leu Gly Thr Phe Gln Thr Ala Glu Met Ala Ala Arg Ala
                 75                  80                  85

cac gac gtc gct gca tta gcc ctc cgt ggc cga tca gca tgt ctc aac        464
His Asp Val Ala Ala Leu Ala Leu Arg Gly Arg Ser Ala Cys Leu Asn
         90                  95                 100

ttc gct gac tcg gct tgg cgg cta cga atc ccg gag tca aca tgc gcc        512
Phe Ala Asp Ser Ala Trp Arg Leu Arg Ile Pro Glu Ser Thr Cys Ala
    105                 110                 115

aag gat atc caa aaa gcg gct gct gaa gcg gcg ttg gct ttt caa gat        560
Lys Asp Ile Gln Lys Ala Ala Ala Glu Ala Ala Leu Ala Phe Gln Asp
120                 125                 130

gag acg tgt gat acg acg acc acg gat cat ggc ctg gac atg gag gag        608
Glu Thr Cys Asp Thr Thr Thr Thr Asp His Gly Leu Asp Met Glu Glu
135                 140                 145                 150

acg atg gtg gaa gct att tat aca ccg gaa cag agc gaa ggt gcg ttt        656
Thr Met Val Glu Ala Ile Tyr Thr Pro Glu Gln Ser Glu Gly Ala Phe
                155                 160                 165

tat atg gat gag gag aca atg ttt ggg atg ccg act ttg ttg gat aat        704
Tyr Met Asp Glu Glu Thr Met Phe Gly Met Pro Thr Leu Leu Asp Asn
        170                 175                 180

atg gct gaa ggc atg ctt tta ccg ccg ccg tct gtt caa tgg aat cat        752
Met Ala Glu Gly Met Leu Leu Pro Pro Pro Ser Val Gln Trp Asn His
    185                 190                 195

aat tat gac ggc gaa gga gat ggt gac gtg tcg ctt tgg agt tac taa        800
Asn Tyr Asp Gly Glu Gly Asp Gly Asp Val Ser Leu Trp Ser Tyr
200                 205                 210

tattcgatag tcgtttccat ttttgtacta tagtttgaaa atattctagt tcctttttta     860
```

```
gaatggttcc ttcattttat tttattttat tgttgtagaa acgag                    905


<210> SEQ ID NO 31
<211> LENGTH: 213
<212> TYPE: PRT
<213> ORGANISM: Arabidopsis thaliana

<400> SEQUENCE: 31

Met Asn Ser Phe Ser Ala Phe Ser Glu Met Phe Gly Ser Asp Tyr Glu
1               5                   10                  15

Pro Gln Gly Gly Asp Tyr Cys Pro Thr Leu Ala Thr Ser Cys Pro Lys
            20                  25                  30

Lys Pro Ala Gly Arg Lys Lys Phe Arg Glu Thr Arg His Pro Ile Tyr
        35                  40                  45

Arg Gly Val Arg Gln Arg Asn Ser Gly Lys Trp Val Ser Glu Val Arg
    50                  55                  60

Glu Pro Asn Lys Lys Thr Arg Ile Trp Leu Gly Thr Phe Gln Thr Ala
65                  70                  75                  80

Glu Met Ala Ala Arg Ala His Asp Val Ala Ala Leu Ala Leu Arg Gly
                85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
        115                 120                 125

Ala Leu Ala Phe Gln Asp Glu Thr Cys Asp Thr Thr Thr Thr Asp His
    130                 135                 140

Gly Leu Asp Met Glu Glu Thr Met Val Glu Ala Ile Tyr Thr Pro Glu
145                 150                 155                 160

Gln Ser Glu Gly Ala Phe Tyr Met Asp Glu Glu Thr Met Phe Gly Met
                165                 170                 175

Pro Thr Leu Leu Asp Asn Met Ala Glu Gly Met Leu Leu Pro Pro Pro
            180                 185                 190

Ser Val Gln Trp Asn His Asn Tyr Asp Gly Glu Gly Asp Gly Asp Val
        195                 200                 205

Ser Leu Trp Ser Tyr
    210


<210> SEQ ID NO 32
<211> LENGTH: 779
<212> TYPE: DNA
<213> ORGANISM: Myoxocephalus octodecemspinosus
<220> FEATURE:
<221> NAME/KEY: CDS
<222> LOCATION: (138)..(266)
<223> OTHER INFORMATION: longhorn sculpin skin-type antifreeze protein

<400> SEQUENCE: 32

ggcatcttct tctaacaccc tggaagagac agacctcgag tttatcatca tcctttattg     60

agagaaacag ttgtgactca tcacgaagtt gttgatcttt ctcttttccg aacgcaccga    120

gctaaacaaa agtgaga atg gac gca cca gca aaa gca gcg gca aag acg       170
                   Met Asp Ala Pro Ala Lys Ala Ala Ala Lys Thr
                   1               5                   10

gca gcg gac gcg aag gct gcg gcg gcc aag acg gca gcg gac gcg ttg      218
Ala Ala Asp Ala Lys Ala Ala Ala Ala Lys Thr Ala Ala Asp Ala Leu
            15                  20                  25

gct gcg gcg aac aag acg gcg gcg gcg gcc aag gcg gct gct aaa taa      266
Ala Ala Ala Asn Lys Thr Ala Ala Ala Ala Lys Ala Ala Ala Lys
        30                  35                  40
```

```
ttggcaaaca tagttaattt gttcagtaat gcataaatta cactataagg ttcttttagg    326

gtgtgtgtgt gtaggggggg tgggggtatg gtttgtctat gcttaattct taatccctga    386

tgttgctgac ccaactcagt gtggtgcttg tcaaacaaaa agcatcttga gacgctcctg    446

ttgtgaatca gtttaatcaa tttaaatgtg tggttaaaaa cccgctgctt agatctcata    506

accaagaaat gtttttacag cccgggaaaa gtgaacctcc acaaagatct ttctttagag    566

ctaatgtagt agcttaaaga tctcatcagt gttgatgagc aaagtcgttg gtgaacaaac    626

tgtacctctt taaaaacttt ttgaaggtca gaccggagct aaaactccca atttatctcc    686

atctggttat tgagaaatgt tgtgatttgg gtgatttgga tgaattaaaa gaacctctat    746

aaacaaaaaa aaaaaaaaaa aaaaaaaaaa aaa                                  779
```

<210> SEQ ID NO 33
<211> LENGTH: 42
<212> TYPE: PRT
<213> ORGANISM: Myoxocephalus octodecemspinosus

<400> SEQUENCE: 33

```
Met Asp Ala Pro Ala Lys Ala Ala Ala Lys Thr Ala Ala Asp Ala Lys
1               5                   10                  15

Ala Ala Ala Ala Lys Thr Ala Ala Asp Ala Leu Ala Ala Ala Asn Lys
            20                  25                  30

Thr Ala Ala Ala Ala Lys Ala Ala Ala Lys
        35                  40
```

<210> SEQ ID NO 34
<211> LENGTH: 6756
<212> TYPE: DNA
<213> ORGANISM: Artificial Sequence
<220> FEATURE:
<223> OTHER INFORMATION: phytase gene locus of plasmids pAF 2-3, pAF 2-6, pAF 2-7
<220> FEATURE:
<221> NAME/KEY: CDS
<222> LOCATION: (210)..(254)
<220> FEATURE:
<221> NAME/KEY: CDS
<222> LOCATION: (357)..(1712)
<220> FEATURE:
<221> NAME/KEY: misc_feature
<222> LOCATION: (4156)..(4157)
<223> OTHER INFORMATION: n is a, c, g, or t
<220> FEATURE:
<221> NAME/KEY: misc_feature
<222> LOCATION: (6316)..(6316)
<223> OTHER INFORMATION: n is a, c, g, or t

<400> SEQUENCE: 34

```
gtcgacttcc cgtcctattc ggcctcgtcc gctgaagatc catcccacca ttgcacgtgg     60

gccacctttg tgagcttcta acctgaactg gtagagtatc acacaccatg ccaaggtggg    120

atgaaggggt tatatgagac cgtccggtcc ggcgcgatgg ccgtagctgc cactcgctgc    180

tgtgcaagaa attacttctc ataggcatc atg ggc gtc tct gct gtt cta ctt      233
                                Met Gly Val Ser Ala Val Leu Leu
                                1               5

cct ttg tat ctc ctg tct ggg tatgctaagc accacaatca aagtctaata         284
Pro Leu Tyr Leu Leu Ser Gly
    10                  15

aggaccctcc cttccgaggg cccctgaagc tcggactgtg tgggactact gatcgctgac    344

tatctgtgca ga gtc acc tcc gga ctg gca gtc ccc gcc tcg aga aat caa    395
              Val Thr Ser Gly Leu Ala Val Pro Ala Ser Arg Asn Gln
              20                  25
```

```
tcc agt tgc gat acg gtc gat cag ggg tat caa tgc ttc tcc gag act      443
Ser Ser Cys Asp Thr Val Asp Gln Gly Tyr Gln Cys Phe Ser Glu Thr
    30                  35                  40

tcg cat ctt tgg ggt caa tac gca ccg ttc ttc tct ctg gca aac gaa      491
Ser His Leu Trp Gly Gln Tyr Ala Pro Phe Phe Ser Leu Ala Asn Glu
45                  50                  55                  60

tcg gtc atc tcc cct gag gtg ccc gcc gga tgc aga gtc act ttc gct      539
Ser Val Ile Ser Pro Glu Val Pro Ala Gly Cys Arg Val Thr Phe Ala
                65                  70                  75

cag gtc ctc tcc cgt cat gga gcg cgg tat ccg acc gac tcc aag ggc      587
Gln Val Leu Ser Arg His Gly Ala Arg Tyr Pro Thr Asp Ser Lys Gly
            80                  85                  90

aag aaa tac tcc gct ctc att gag gag atc cag cag aac gcg acc acc      635
Lys Lys Tyr Ser Ala Leu Ile Glu Glu Ile Gln Gln Asn Ala Thr Thr
        95                  100                 105

ttt gac gga aaa tat gcc ttc ctg aag aca tac aac tac agc ttg ggt      683
Phe Asp Gly Lys Tyr Ala Phe Leu Lys Thr Tyr Asn Tyr Ser Leu Gly
    110                 115                 120

gca gat gac ctg act ccc ttc gga gaa cag gag cta gtc aac tcc ggc      731
Ala Asp Asp Leu Thr Pro Phe Gly Glu Gln Glu Leu Val Asn Ser Gly
125                 130                 135                 140

atc aag ttc tac cag cgg tac gaa tcg ctc aca agg aac atc gtt cca      779
Ile Lys Phe Tyr Gln Arg Tyr Glu Ser Leu Thr Arg Asn Ile Val Pro
                145                 150                 155

ttc atc cga tcc tct ggc tcc agc cgc gtg atc gcc tcc ggc aag aaa      827
Phe Ile Arg Ser Ser Gly Ser Ser Arg Val Ile Ala Ser Gly Lys Lys
            160                 165                 170

ttc atc gag ggc ttc cag agc acc aag ctg aag gat cct cgt gcc cag      875
Phe Ile Glu Gly Phe Gln Ser Thr Lys Leu Lys Asp Pro Arg Ala Gln
        175                 180                 185

ccc ggc caa tcg tcg ccc aag atc gac gtg gtc att tcc gag gcc agc      923
Pro Gly Gln Ser Ser Pro Lys Ile Asp Val Val Ile Ser Glu Ala Ser
    190                 195                 200

tca tcc aac aac act ctc gac cca ggc acc tgc act gtc ttc gaa gac      971
Ser Ser Asn Asn Thr Leu Asp Pro Gly Thr Cys Thr Val Phe Glu Asp
205                 210                 215                 220

agc gaa ttg gcc gat acc gtc gaa gcc aat ttc acc gcc acg ttc gtc     1019
Ser Glu Leu Ala Asp Thr Val Glu Ala Asn Phe Thr Ala Thr Phe Val
                225                 230                 235

ccc tcc att cgt caa cgt ctg gag aac gac ctg tcc ggt gtg act ctc     1067
Pro Ser Ile Arg Gln Arg Leu Glu Asn Asp Leu Ser Gly Val Thr Leu
            240                 245                 250

aca gac aca gaa gtg acc tac ctc atg gac atg tgc tcc ttc gac acc     1115
Thr Asp Thr Glu Val Thr Tyr Leu Met Asp Met Cys Ser Phe Asp Thr
        255                 260                 265

atc tcc acc agc acc gtc gac acc aag ctg tcc ccc ttc tgt gac ctg     1163
Ile Ser Thr Ser Thr Val Asp Thr Lys Leu Ser Pro Phe Cys Asp Leu
    270                 275                 280

ttc acc cat gac gaa tgg atc aac tac gac tac ctc cag tcc ttg aaa     1211
Phe Thr His Asp Glu Trp Ile Asn Tyr Asp Tyr Leu Gln Ser Leu Lys
285                 290                 295                 300

aag tat tac ggc cat ggt gca ggt aac ccg ctc ggc ccg acc cag ggc     1259
Lys Tyr Tyr Gly His Gly Ala Gly Asn Pro Leu Gly Pro Thr Gln Gly
                305                 310                 315

gtc ggc tac gct aac gag ctc atc gcc cgt ctg acc cac tcg cct gtc     1307
Val Gly Tyr Ala Asn Glu Leu Ile Ala Arg Leu Thr His Ser Pro Val
            320                 325                 330

cac gat gac acc agt tcc aac cac act ttg gac tcg agc ccg gct acc     1355
His Asp Asp Thr Ser Ser Asn His Thr Leu Asp Ser Ser Pro Ala Thr
        335                 340                 345
```

-continued

```
ttt ccg ctc aac tct act ctc tac gcg gac ttt tcg cat gac aac ggc     1403
Phe Pro Leu Asn Ser Thr Leu Tyr Ala Asp Phe Ser His Asp Asn Gly
    350                 355                 360

atc atc tcc att ctc ttt gct tta ggt ctg tac aac ggc act aag ccg     1451
Ile Ile Ser Ile Leu Phe Ala Leu Gly Leu Tyr Asn Gly Thr Lys Pro
365                 370                 375                 380

cta tct acc acg acc gtg gag aat atc acc cag aca gat gga ttc tcg     1499
Leu Ser Thr Thr Thr Val Glu Asn Ile Thr Gln Thr Asp Gly Phe Ser
                385                 390                 395

tct gct tgg acg gtt ccg ttt gct tcg cgt ttg tac gtc gag atg atg     1547
Ser Ala Trp Thr Val Pro Phe Ala Ser Arg Leu Tyr Val Glu Met Met
            400                 405                 410

cag tgt cag gcg gag cag gag ccg ctg gtc cgt gtc ttg gtt aat gat     1595
Gln Cys Gln Ala Glu Gln Glu Pro Leu Val Arg Val Leu Val Asn Asp
        415                 420                 425

cgc gtt gtc ccg ctg cat ggg tgt ccg gtt gat gct ttg ggg aga tgt     1643
Arg Val Val Pro Leu His Gly Cys Pro Val Asp Ala Leu Gly Arg Cys
    430                 435                 440

acc cgg gat agc ttt gtg agg ggg ttg agc ttt gct aga tct ggg ggt     1691
Thr Arg Asp Ser Phe Val Arg Gly Leu Ser Phe Ala Arg Ser Gly Gly
445                 450                 455                 460

gat tgg gcg gag tgt ttt gct tagctgaatt accttgatga atggtatgta        1742
Asp Trp Ala Glu Cys Phe Ala
                465

tcacattgca tatcattagc acttcaggta tgtattatcg aagatgtata tcgaaaggat   1802

caatggtgac tgtcactggt tatctgaata tccctctata cctcgtccca caaccaatca   1862

tcaccottta aacaatcaca ctcaacgcac agcgtacaaa cgaacaaacg cacaaagaat   1922

attttacact cctccccaac gcaataccaa ccgcaattca tcatacctca tataaataca   1982

atacaataca atacatccat ccctaccctc aagtccaccc atcctataat caatccctac   2042

ttacttactt ctccccctcc ccctcaccct tcccagaact cacccccgaa gtagtaatag   2102

tagtagtaga agaagcagac gacctctcca ccaatctctt cggcctctta tccccatacg   2162

ctacacaaaa cccccacccc gttagcatgc actcagaaaa taatcaaaaa taactaagaa   2222

ggaaaaaaaa gaagaagaaa ggttacatac tcctctcata caaactccaa gacgtataca   2282

tcaagatggg caatcccacc attactgata tccatctatg aacccattcc catcccacgt   2342

tagttgatta ctttacttag aagaagaaaa agggaaggga agggaaagaa gtggatggga   2402

ttgagttagt gctcaccgtc tcgcagcaag tttatattct tttgtttggc ggatatcttt   2462

cactgctcct gctggacgtt gtcacggggt ggtagtggtt ggcggtggtg agggtccatg   2522

atcactcttg gtttgggggg ttgttgttgt cgttgttgtt gttgttgggt gggcattttc   2582

ttttcttcac ttggggatta ttatttggaa ttggttagtt tgagtgagtg ggtaatattg   2642

aatgggtgat tattgggaat gaagtagatt tggctatgaa tggttgatgg gatggaatga   2702

atggatggat gaatagatgg aggcggaaaa gtcaggtggt ttgaggttcg gattattatc   2762

tttgtgcctg aggcatcact ctccatctat gttgttcttt ctataccgat ctaccagagc   2822

taagttgact gattctacca cagtgcacaa taagtatgta cttatttcat ttagagtatt   2882

tagattaacc cgctgtgcta tttgccgtag ctttccaccc aatttcgaag ttcgaagaat   2942

taaaactcat cctacagtac agaatagaag taaaaggaga agagaaaaac aagataatac   3002

aaccagtcca ggtccattct agatctcgaa tgaccaccaa ataagaaagc aacaagcaag   3062

taagcaaagc ataagtctaa atgaacgcca ataacttcat cgcctgcctt tgaaactgaa   3122

cgctatgcac gaatggctcg aaatgattcc cttaactccg tagtattgag agtgagagga   3182
```

-continued aaagaaaaaa agagacagaa aagctgacca tgggaaagaa gcatgatcag tcgggaatgg 3242 atctgcgggt tgagatagat atgagttgcc tcgcagatcc ggtgacaaga taagagaatt 3302 gggagatgtg atcagccact gtaacttcat caagcatcga cattcaacgg tcgggtctgc 3362 gggttgagat gcaagttgag atgccacgca gacccgaaca gagtgagaga tgtgagactt 3422 ttgaaccact gtgacttcat caagcatcaa aacacactcc atggtcaatc ggttagggtg 3482 tgagggttga tatgccaggt tcgatgccac gcagacccga accgactgag aaatatgaaa 3542 agttggacag ccacttcatc ttcatcaagc gtaaaacccc aatcaatggt aaatcgaaaa 3602 cgaatctgcg ggctgatgtg gaaatgagac gaatgcctcg cagattcgaa gacacgtaaa 3662 tcgagatgaa caatcacttt aacttcatca aagccttaaa tcacccaatg gccagtctat 3722 tcgggtctgc gggttgaggt tcctgttgag atgccacgca gactgcgaac atgcgatgca 3782 ttataagttg gacgagtgta gactgaccat tgataaccga gataaacaat cacttcaact 3842 tcatcaaagc cttaaatcac tcaatggcca gtctgtttgc ggtctgcggg ctgataccca 3902 agttgcgatg ccacgcagac tgcaaacatt gatcgagaga cgagaaaaac aacgcacttt 3962 aacttcaaca aaagcctttc aatcagtcaa tggccagtct gttcgcggtc tgcgggctga 4022 tatgcgagtt gaggtgcctc gcagaccgcg aacatgcgat gtaatttctt agttagacga 4082 gtgcctggcc attgagaaac gagagaaaca accactttaa cttcatgaaa gccttgaact 4142 actcaatgac ccgnntgttg gcggtctgcg ggctgatatt cgagttgaga tgccacgcag 4202 accgccaaca tgcgatgtat catgtaagtt agatgagtga ctggccattg agaaacgaga 4262 gaaacaacca cacttcatga gagccttaaa ttattcaatg accagtctgt tcacggtctg 4322 cgggttggta tgcgagtcga ggtgcctcgc agaccgcgaa catgcgatgt tttcgatgga 4382 cgagtgaagc ctgacgatcg agaactatct cagttgggtt ggccattcgg ctggccgttg 4442 ggtttagtat taggatcgtc aggtttgtcc gatggaacgt tccgtttgcg tgcgttggcg 4502 cgacgagccc tctcctcggc gtgattctga aattctgcaa tcagggcagc cgcagcacgg 4562 cgacgggacg tcctccagga gctgtgttga agtttcgggg tggcggtcca gaagggggag 4622 ttacattaaa agcctcatag atgtctttgg gtggttccgg ggggcccatc gcaagatctt 4682 ctggagttgt gcgtctgatc atctcttgag tgtaattgcg acgcagaccg agcttcagga 4742 ttttggaagg gctggatcgc tcctgctgac tctttccctc agcgggcttc gtctcggcag 4802 tcttcatttc ggcgggctga tcttccatct cagaatggga tcgctttctg gtcgctgcac 4862 ccgctcctcc cttcaaggtc agcttgatgc gcagcgtctt gggcggctca gctggtggag 4922 ttggttccgg ctctggctcc ctccggcgtc gcttgggcac ttgagtagtc tctgaggctt 4982 cgccgcggcg ccgtttgcga gtcggctcct tggtctcttt ggcctctttc acttcacctg 5042 gaccgtcttt cggggcggtt tcatcgtgct gagcgatcaa ggtttggatg taggcagccg 5102 gcatcattcg atcaacggca attcctctct tgcgggcctc ctcccgagcc ttgattgtcg 5162 ccttgacctc gtccacgttt tcgaagaaga aaggcatctt gttatcctga ggcaagttgc 5222 gctctcccat gcgtggggat atccgaagat gcggtccttc tcgaactgtt catgagactt 5282 cagacgaatt ggaggctggg ggagcaattt gtctccgtag gtgttgttag ggcggaacca 5342 agaatagcct tcgcctacaa cgacaagctc ttcgccaaat ttattttttt ggcctgtaaa 5402 aacgaaccca tcctcgtcag tccaccggtg cgtctcggac gtagagattg gcttacttat 5462 tccctcaacg ccgatctctg cctggggctg cgcttcggat gcggcctcgg tcacggctcc 5522 gcctcggact gcaccgctgg agtttcggtc ttcttctcct gcttctccag gtactccttg 5582

```
cgtaactctt cgatcagcct cggcttccga tgactgctca aattctggag caacagctgc   5642

cgcggccagg tcaagcaggc ggtttgctaa aactgcccat tttccatcga cacctgcctc   5702

cgacgcctgt gcaaaaccag ctgttttcgc attggcctgt ttgttggcac gcgtcttctt   5762

gactgctgcc ttgcccttta cttccttgag agcagactct ggcttagatg atggtgcacg   5822

gtttctgcgg aagcgccgct cagattccaa agattccata gctttaatgg taggctttct   5882

ggttcttcca gaagtgcgcg cagctgacgt agtggttgag tagctggcag ttggggatcc   5942

tgggccctca ttggaaccat caagaccaaa tttgtttcca tacatatcag catggtattc   6002

aaaaggaaaa ctttcgccgt acggagtact gcgttcgatt ccgggtgtat ccaagtcgta   6062

tccagacatg gtgtcgaatt cagccttgct gtcaagagca ggggtacttt caatgctgtc   6122

agcaaccacg cggccaaagg gcgtcttcgg gaaagaaggt gtttcaagag aagcgtcatc   6182

cacggcctgg cttgcggcgt tgattgcaga ctttcgagta gatcgctgag gtcgcgaact   6242

ggttcgagta gcaacctgtg aattggcagc cttgtgactg cttcgattca ctgcagagac   6302

ggagtagact gcantgattt ggaattctga gtcgcagcca ttctggattt gcgttcggcg   6362

cgacgagatc tcgcagtcgt ggtacgagga gtagagcgag gctgcgtagc agtgttgcaa   6422

gcttggtgct agcctcctgg gcttcagcag cttcagcagt ggtggcagac gcagcagaat   6482

tagcggagct ttatcggctt tgccgctctg agcgttggga gtagaagtga gagaagaggt   6542

agagtccacg gaagaagtct tctcgctgtt ctcaaagccg ttcagctttg ctggcataga   6602

cttacgcgtc ttgcggctgt tggaagcgga agagttcatg gcgggagagg agacgttaga   6662

agtagacatg gtggggtttg ttgacgggtt ttgagtaaca agagacttgc gtcgatcttt   6722

gagtgttctt gacagaaagt tatgcaacgt cgac                               6756
```

```
<210> SEQ ID NO 35
<211> LENGTH: 467
<212> TYPE: PRT
<213> ORGANISM: Artificial Sequence
<220> FEATURE:
<223> OTHER INFORMATION: Synthetic Construct

<400> SEQUENCE: 35

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160
```

```
Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 36
<211> LENGTH: 7175
<212> TYPE: DNA
<213> ORGANISM: Medicago sativa
<220> FEATURE:
<221> NAME/KEY: CDS
<222> LOCATION: (70)..(6843)
<223> OTHER INFORMATION: Medicago sativa acetyl-CoA carboxylase

<400> SEQUENCE: 36

agcaaagaat aaaaatactg acttcatttt tttttatgta tattggaaat aactagaagg      60

agaacaata atg gct agc gtg ggc cgt gga aat gga tat tta aac agt gtg     111
          Met Ala Ser Val Gly Arg Gly Asn Gly Tyr Leu Asn Ser Val
          1               5                   10

cta ccg agt agg cac cct gct act aca acc gaa gta gat gaa tac tgc      159
```

-continued

```
Leu Pro Ser Arg His Pro Ala Thr Thr Thr Glu Val Asp Glu Tyr Cys
15                  20                  25                  30

aat gcc ctt gga gga aac aag ccg att cat agc ata ttg att gca aac      207
Asn Ala Leu Gly Gly Asn Lys Pro Ile His Ser Ile Leu Ile Ala Asn
                35                  40                  45

aat gga atg gca gca gtc aag ttt ata cgt agt gtt agg agt tgg gct      255
Asn Gly Met Ala Ala Val Lys Phe Ile Arg Ser Val Arg Ser Trp Ala
            50                  55                  60

tac gag aca ttt ggc acg gaa aaa gct atc ttg ttg gtt gcc atg gca      303
Tyr Glu Thr Phe Gly Thr Glu Lys Ala Ile Leu Leu Val Ala Met Ala
        65                  70                  75

act cca gag gat atg aga atc aat gca gaa cat atc aga ata gcc gat      351
Thr Pro Glu Asp Met Arg Ile Asn Ala Glu His Ile Arg Ile Ala Asp
    80                  85                  90

caa ttt gtg gaa gta cct ggt ggg acc aat aac aat aac tac gcc aat      399
Gln Phe Val Glu Val Pro Gly Gly Thr Asn Asn Asn Asn Tyr Ala Asn
95                  100                 105                 110

gtg cag ctt att cta gag att gct gag ata act cac gtt gat gcg gtg      447
Val Gln Leu Ile Leu Glu Ile Ala Glu Ile Thr His Val Asp Ala Val
                115                 120                 125

tgg cct ggt tgg ggt cat gca tca gaa aat cct gag ctt cca gat gca      495
Trp Pro Gly Trp Gly His Ala Ser Glu Asn Pro Glu Leu Pro Asp Ala
            130                 135                 140

tta aaa gca aag gga att gta ttc ctt gga cct cct gct ata tct atg      543
Leu Lys Ala Lys Gly Ile Val Phe Leu Gly Pro Pro Ala Ile Ser Met
        145                 150                 155

gca gca ttg gga gac aaa att ggt tcc tcg ttg att gct cag gca gca      591
Ala Ala Leu Gly Asp Lys Ile Gly Ser Ser Leu Ile Ala Gln Ala Ala
    160                 165                 170

gaa gtt cca acc ctt cca tgg agt ggt tct cat gtg aaa att cct cca      639
Glu Val Pro Thr Leu Pro Trp Ser Gly Ser His Val Lys Ile Pro Pro
175                 180                 185                 190

gaa agt gac ttg att act att cct gat gaa att tac cgt gca gca tgt      687
Glu Ser Asp Leu Ile Thr Ile Pro Asp Glu Ile Tyr Arg Ala Ala Cys
                195                 200                 205

gtt tat aca aca gaa gaa gca att gca agt tgt caa gta gta ggt tac      735
Val Tyr Thr Thr Glu Glu Ala Ile Ala Ser Cys Gln Val Val Gly Tyr
            210                 215                 220

cct gca atg att aag gca tct tgg ggt ggt ggc ggc aaa ggc ata aga      783
Pro Ala Met Ile Lys Ala Ser Trp Gly Gly Gly Gly Lys Gly Ile Arg
        225                 230                 235

aag gtt cat aat gat gat gag gtt agg gca ttg ttc aag caa gtt caa      831
Lys Val His Asn Asp Asp Glu Val Arg Ala Leu Phe Lys Gln Val Gln
    240                 245                 250

ggt gaa gta cca ggc tca cct ata ttt ata atg aaa gtt gct tcc cag      879
Gly Glu Val Pro Gly Ser Pro Ile Phe Ile Met Lys Val Ala Ser Gln
255                 260                 265                 270

agc cga cat ctt gaa gtc caa ttg att tgc gat cag cac gga aat ttt      927
Ser Arg His Leu Glu Val Gln Leu Ile Cys Asp Gln His Gly Asn Phe
                275                 280                 285

gca gca ttg cac agc cgt gat tgt agt gtt caa aga agg cat caa aag      975
Ala Ala Leu His Ser Arg Asp Cys Ser Val Gln Arg Arg His Gln Lys
            290                 295                 300

att att gaa gag ggt ccc att act gta gca cct cca gaa acg gtg aaa     1023
Ile Ile Glu Glu Gly Pro Ile Thr Val Ala Pro Pro Glu Thr Val Lys
        305                 310                 315

gaa ctt gaa cag gcg gct aga aga tta gct aaa tct gta aat tat gtg     1071
Glu Leu Glu Gln Ala Ala Arg Arg Leu Ala Lys Ser Val Asn Tyr Val
    320                 325                 330

ggg gca gct acc gtt gag tat ctt tat agc atg gaa act ggc gag tac     1119
```

-continued

```
Gly Ala Ala Thr Val Glu Tyr Leu Tyr Ser Met Glu Thr Gly Glu Tyr
335                 340                 345                 350

tac ttt tta gag ttg aac ccc cga cta cag gtt gag cat cct gtt act      1167
Tyr Phe Leu Glu Leu Asn Pro Arg Leu Gln Val Glu His Pro Val Thr
                355                 360                 365

gaa tgg ata gct gag ata aat ctg cca gca gca caa gtt gca gtt ggg      1215
Glu Trp Ile Ala Glu Ile Asn Leu Pro Ala Ala Gln Val Ala Val Gly
            370                 375                 380

atg ggc atc cca ctc tgg caa att cct gag att agg cgt ttc tat ggg      1263
Met Gly Ile Pro Leu Trp Gln Ile Pro Glu Ile Arg Arg Phe Tyr Gly
        385                 390                 395

atg gaa cat ggt ggg gga aat gat ggt tgg aag aaa aca tca gtg tta      1311
Met Glu His Gly Gly Gly Asn Asp Gly Trp Lys Lys Thr Ser Val Leu
    400                 405                 410

gct acc cct ttt gat ttt gac gaa gca caa tct aca aag ccg aaa ggt      1359
Ala Thr Pro Phe Asp Phe Asp Glu Ala Gln Ser Thr Lys Pro Lys Gly
415                 420                 425                 430

cat tgt gtg gct gta cga gtc acc agt gag gac ccc gat gat ggt ttt      1407
His Cys Val Ala Val Arg Val Thr Ser Glu Asp Pro Asp Asp Gly Phe
                435                 440                 445

acg cct aca gga gga aaa gtg cag gag ctc agc ttt aaa agc aag cca      1455
Thr Pro Thr Gly Gly Lys Val Gln Glu Leu Ser Phe Lys Ser Lys Pro
            450                 455                 460

aat gtg tgg gct tat ttc tct gtt aag tcc gga gga gga att cat gaa      1503
Asn Val Trp Ala Tyr Phe Ser Val Lys Ser Gly Gly Gly Ile His Glu
        465                 470                 475

ttc tca gat tct caa ttt gga cat gtt ttt gcg ttt gga gaa tct aga      1551
Phe Ser Asp Ser Gln Phe Gly His Val Phe Ala Phe Gly Glu Ser Arg
    480                 485                 490

gct tta gca att gca aat atg gta ctg ggg ttg aag gaa att caa att      1599
Ala Leu Ala Ile Ala Asn Met Val Leu Gly Leu Lys Glu Ile Gln Ile
495                 500                 505                 510

cga gga gaa att cgt acc aac gtt gat tac aca att gat ctt ctg aat      1647
Arg Gly Glu Ile Arg Thr Asn Val Asp Tyr Thr Ile Asp Leu Leu Asn
                515                 520                 525

gct tca gac tac aga gac aac aaa att cac aca gga tgg cta gac agt      1695
Ala Ser Asp Tyr Arg Asp Asn Lys Ile His Thr Gly Trp Leu Asp Ser
            530                 535                 540

aga att gca atg cgg gtt aga gca gag agg cct ccc tgg tat ctg tct      1743
Arg Ile Ala Met Arg Val Arg Ala Glu Arg Pro Pro Trp Tyr Leu Ser
        545                 550                 555

gtt gtt ggt ggg gca ctc tat aaa gct tct gcc agc agt gca gct tta      1791
Val Val Gly Gly Ala Leu Tyr Lys Ala Ser Ala Ser Ser Ala Ala Leu
    560                 565                 570

gtt tcg gac tat gtt ggc tat ctt gaa aag ggg caa atc cct ccc aag      1839
Val Ser Asp Tyr Val Gly Tyr Leu Glu Lys Gly Gln Ile Pro Pro Lys
575                 580                 585                 590

cac att tct ctt gtc cat tct caa gtt tct ttg agc att gaa gga agc      1887
His Ile Ser Leu Val His Ser Gln Val Ser Leu Ser Ile Glu Gly Ser
                595                 600                 605

aaa tac acg att gac atg gta cga gga gga cct gga agt tac aaa ttg      1935
Lys Tyr Thr Ile Asp Met Val Arg Gly Gly Pro Gly Ser Tyr Lys Leu
            610                 615                 620

aaa ttg aat caa tcg gag ata gaa gcg gag ata cac act tta cgt gat      1983
Lys Leu Asn Gln Ser Glu Ile Glu Ala Glu Ile His Thr Leu Arg Asp
        625                 630                 635

gga ggt ttg cta atg cag ttg gat gga aac agt cat gta ata tat gca      2031
Gly Gly Leu Leu Met Gln Leu Asp Gly Asn Ser His Val Ile Tyr Ala
    640                 645                 650

gag gaa gaa gca gct gga act cgg ctt tta ata gat gga agg act tgc      2079
```

-continued

```
Glu Glu Glu Ala Ala Gly Thr Arg Leu Leu Ile Asp Gly Arg Thr Cys
655                 660                 665                 670

ttg ctt cag aat gat gac gat cca tca aag tta att gga gag aca ccg      2127
Leu Leu Gln Asn Asp Asp Asp Pro Ser Lys Leu Ile Gly Glu Thr Pro
                675                 680                 685

tgc aag ctt ctg aga tat ttg gtt gcg gat gat agt cag att gat gca      2175
Cys Lys Leu Leu Arg Tyr Leu Val Ala Asp Asp Ser Gln Ile Asp Ala
            690                 695                 700

gac aca cca tat gct gaa gtt gag gtc atg aag atg tgc atg cct ctt      2223
Asp Thr Pro Tyr Ala Glu Val Glu Val Met Lys Met Cys Met Pro Leu
        705                 710                 715

ctt tcc cct gct tct gga att att cat ttc aga atg gct gaa ggt caa      2271
Leu Ser Pro Ala Ser Gly Ile Ile His Phe Arg Met Ala Glu Gly Gln
    720                 725                 730

gcc atg cag gct ggt gaa ctt ata gca aag ctt gat cta gat gat ggt      2319
Ala Met Gln Ala Gly Glu Leu Ile Ala Lys Leu Asp Leu Asp Asp Gly
735                 740                 745                 750

tct gca gta agg aag gca gaa ccc ttc act ggg agc ttc cct atc ctg      2367
Ser Ala Val Arg Lys Ala Glu Pro Phe Thr Gly Ser Phe Pro Ile Leu
                755                 760                 765

ggc cct cct act gca att tca ggt aaa gtt cat cag aaa tgt gca gca      2415
Gly Pro Pro Thr Ala Ile Ser Gly Lys Val His Gln Lys Cys Ala Ala
            770                 775                 780

agc tta aac gct gca cgg atg att ctt gct ggc tat gag cac aac att      2463
Ser Leu Asn Ala Ala Arg Met Ile Leu Ala Gly Tyr Glu His Asn Ile
        785                 790                 795

gat gaa gtt gtg gtc aaa agt ttg ctc aat tgc ctt gac agc cct gaa      2511
Asp Glu Val Val Val Lys Ser Leu Leu Asn Cys Leu Asp Ser Pro Glu
    800                 805                 810

ctg cct ttc ctt caa tgg caa gag tgc ttt gca gtt ttg gca acc cgt      2559
Leu Pro Phe Leu Gln Trp Gln Glu Cys Phe Ala Val Leu Ala Thr Arg
815                 820                 825                 830

ctt ccc aaa gat ctt aga aac gag ttg gaa gct aaa tat aag gag ttc      2607
Leu Pro Lys Asp Leu Arg Asn Glu Leu Glu Ala Lys Tyr Lys Glu Phe
                835                 840                 845

gaa att att tca agc tcc caa act att gat ttc cct gcc aaa tta ttg      2655
Glu Ile Ile Ser Ser Ser Gln Thr Ile Asp Phe Pro Ala Lys Leu Leu
            850                 855                 860

aag gca atc ctt gaa gct cat ctt tcc tcc tgt cct gaa aac gaa aaa      2703
Lys Ala Ile Leu Glu Ala His Leu Ser Ser Cys Pro Glu Asn Glu Lys
        865                 870                 875

gga gcc tta gaa aga cta gtt gaa ccg ctg aca agt ctt gta aag tct      2751
Gly Ala Leu Glu Arg Leu Val Glu Pro Leu Thr Ser Leu Val Lys Ser
    880                 885                 890

tat gag ggt gga aga gag agc cat gct cat aaa att gtt caa tct cta      2799
Tyr Glu Gly Gly Arg Glu Ser His Ala His Lys Ile Val Gln Ser Leu
895                 900                 905                 910

ttt gaa gag tat ctt tca gtt gaa gaa cta ttc agt gat aat ata cag      2847
Phe Glu Glu Tyr Leu Ser Val Glu Glu Leu Phe Ser Asp Asn Ile Gln
                915                 920                 925

gct gat gta att gaa cga ctc cgt ctt caa tac aag aaa gat ttg ttg      2895
Ala Asp Val Ile Glu Arg Leu Arg Leu Gln Tyr Lys Lys Asp Leu Leu
            930                 935                 940

aag att gta gat att gtg ctc tct cat cag ggt gtc aag agc aaa aac      2943
Lys Ile Val Asp Ile Val Leu Ser His Gln Gly Val Lys Ser Lys Asn
        945                 950                 955

aag ctg ata ctg cga cta atg gat aaa ctg gtt tac cct aat cct gct      2991
Lys Leu Ile Leu Arg Leu Met Asp Lys Leu Val Tyr Pro Asn Pro Ala
    960                 965                 970

gcc tat agg gat caa tta atc cga ttc tcc caa ctc aac cat ata gtt      3039
```

-continued

```
Ala Tyr Arg Asp Gln Leu Ile Arg Phe Ser Gln Leu Asn His Ile Val
975                 980                 985                 990

tat tct gag ttg gct ctt aag gca agt caa  ctg ttg gag caa act  aaa    3087
Tyr Ser Glu Leu Ala Leu Lys Ala Ser Gln  Leu Leu Glu Gln Thr  Lys
                995                 1000                1005

ctc agt gaa ctt  cga tcc agc att gct  aga agt ctt tct gaa  cta     3132
Leu Ser Glu Leu  Arg Ser Ser Ile Ala  Arg Ser Leu Ser Glu  Leu
            1010                 1015                 1020

gaa atg ttt acc  gag gat ggt gaa aat  att gat act ccg aag  agg     3177
Glu Met Phe Thr  Glu Asp Gly Glu Asn  Ile Asp Thr Pro Lys  Arg
            1025                 1030                 1035

aag agt gcc att  aat gac aga atg gag  gac ctt gtg agc gct  cct     3222
Lys Ser Ala Ile  Asn Asp Arg Met Glu  Asp Leu Val Ser Ala  Pro
            1040                 1045                 1050

ttg gct gtt gaa  gat gcc ctt gtt ggt  tta ttt gat cac agc  gat     3267
Leu Ala Val Glu  Asp Ala Leu Val Gly  Leu Phe Asp His Ser  Asp
            1055                 1060                 1065

cac acc ctt caa  agg aga gtt gtt gaa  act tat atc cgt agg  ctc     3312
His Thr Leu Gln  Arg Arg Val Val Glu  Thr Tyr Ile Arg Arg  Leu
            1070                 1075                 1080

tat cag cca tat  ctt gtc aaa gat agc  atc agg atg cag tgg  cac     3357
Tyr Gln Pro Tyr  Leu Val Lys Asp Ser  Ile Arg Met Gln Trp  His
            1085                 1090                 1095

aga tct ggc ctt  att gct aca tgg gaa  ttc tta gaa gaa tac  gtt     3402
Arg Ser Gly Leu  Ile Ala Thr Trp Glu  Phe Leu Glu Glu Tyr  Val
            1100                 1105                 1110

gaa cgg aag aat  ggg gtt gaa gac aaa  aca ctg gtg gag aaa  cat     3447
Glu Arg Lys Asn  Gly Val Glu Asp Lys  Thr Leu Val Glu Lys  His
            1115                 1120                 1125

agt gag aag aaa  tgg gga gtg atg gtt  gta att aaa tct ctt  cag     3492
Ser Glu Lys Lys  Trp Gly Val Met Val  Val Ile Lys Ser Leu  Gln
            1130                 1135                 1140

ttt ttg cca gca  att atc agt gct gca  tta aga gaa gca acc  aat     3537
Phe Leu Pro Ala  Ile Ile Ser Ala Ala  Leu Arg Glu Ala Thr  Asn
            1145                 1150                 1155

aac ttt cac gat  cct ctt aaa agt ggt  tct ggt gac tca agt  aac     3582
Asn Phe His Asp  Pro Leu Lys Ser Gly  Ser Gly Asp Ser Ser  Asn
            1160                 1165                 1170

cat ggt aat atg  atg cat att gga tta  gtg ggg atc aac aac  caa     3627
His Gly Asn Met  Met His Ile Gly Leu  Val Gly Ile Asn Asn  Gln
            1175                 1180                 1185

atg agt tta ctt  caa gac agt ggt gat  gag gat cag gct caa  gaa     3672
Met Ser Leu Leu  Gln Asp Ser Gly Asp  Glu Asp Gln Ala Gln  Glu
            1190                 1195                 1200

aga att gat aag  ttg gcc aaa ata ctc  aga gag cag gaa ata  ggg     3717
Arg Ile Asp Lys  Leu Ala Lys Ile Leu  Arg Glu Gln Glu Ile  Gly
            1205                 1210                 1215

tcc ata ata cat  gct gca ggt gtt gga  gat att agc tgt atc  ata     3762
Ser Ile Ile His  Ala Ala Gly Val Gly  Asp Ile Ser Cys Ile  Ile
            1220                 1225                 1230

cag agg gat gaa  ggg cgt gct cca atg  agg cat tcc ttt cac  tgg     3807
Gln Arg Asp Glu  Gly Arg Ala Pro Met  Arg His Ser Phe His  Trp
            1235                 1240                 1245

tca tct gaa aag  cta tat tat gta gag  gaa cca ttg ttg ctc  cat     3852
Ser Ser Glu Lys  Leu Tyr Tyr Val Glu  Glu Pro Leu Leu Leu  His
            1250                 1255                 1260

ctt gaa cct ccc  cta tcc att tat ctt  gaa ctg gac aag ctt  aag     3897
Leu Glu Pro Pro  Leu Ser Ile Tyr Leu  Glu Leu Asp Lys Leu  Lys
            1265                 1270                 1275

tgc tat gaa aat  att cgc tat aca cca  tcc cga gat cgt caa  tgg     3942
```

-continued

```
Cys Tyr Glu Asn Ile Arg Tyr Thr Pro Ser Arg Asp Arg Gln Trp
            1280                1285                1290

cac ctc tac aca gtt gtg gat acc aag cca caa cca att caa aga      3987
His Leu Tyr Thr Val Val Asp Thr Lys Pro Gln Pro Ile Gln Arg
            1295                1300                1305

atg ttt ctt cga aca ctt atc aga cag cca acc aca aat gaa gga      4032
Met Phe Leu Arg Thr Leu Ile Arg Gln Pro Thr Thr Asn Glu Gly
            1310                1315                1320

tac tct tct tat caa aga ctg gat gca gaa acg tcc cgt acc caa      4077
Tyr Ser Ser Tyr Gln Arg Leu Asp Ala Glu Thr Ser Arg Thr Gln
            1325                1330                1335

ttg gct atg tct tat act tca agg agc att ttt agg tcc cta atg      4122
Leu Ala Met Ser Tyr Thr Ser Arg Ser Ile Phe Arg Ser Leu Met
            1340                1345                1350

ggc gca atg gag gag ttg gaa ctt aac tca cac aat acc acc atc      4167
Gly Ala Met Glu Glu Leu Glu Leu Asn Ser His Asn Thr Thr Ile
            1355                1360                1365

aaa tct gaa cat gct cat atg tac ctc tat atc ata cgc gag cag      4212
Lys Ser Glu His Ala His Met Tyr Leu Tyr Ile Ile Arg Glu Gln
            1370                1375                1380

caa ata gat gat ctt gtg cct tat tcc aag aaa att aac ata gaa      4257
Gln Ile Asp Asp Leu Val Pro Tyr Ser Lys Lys Ile Asn Ile Glu
            1385                1390                1395

gct ggc caa gaa gaa aca aca gtt gag gca atc ttg gaa gaa ctg      4302
Ala Gly Gln Glu Glu Thr Thr Val Glu Ala Ile Leu Glu Glu Leu
            1400                1405                1410

gca cag gaa atc cat tcc tct gtt ggt gta aga atg cac aga tta      4347
Ala Gln Glu Ile His Ser Ser Val Gly Val Arg Met His Arg Leu
            1415                1420                1425

ggc gtt ttc gtg tgg gaa atc aag ctc tgg att aca gca tgt gga      4392
Gly Val Phe Val Trp Glu Ile Lys Leu Trp Ile Thr Ala Cys Gly
            1430                1435                1440

cag gca aat ggt gct tgg agg gtc att gta aac aat gtg act ggt      4437
Gln Ala Asn Gly Ala Trp Arg Val Ile Val Asn Asn Val Thr Gly
            1445                1450                1455

cat aca tgc act gta cat ata tat cga gag atg gag gat gcc acc      4482
His Thr Cys Thr Val His Ile Tyr Arg Glu Met Glu Asp Ala Thr
            1460                1465                1470

act cat aaa gtg gtc tac agt tca gtc act gta aag ggt ccg ttg      4527
Thr His Lys Val Val Tyr Ser Ser Val Thr Val Lys Gly Pro Leu
            1475                1480                1485

cat ggt gta ccg gtg aat gaa aac tat caa cct ttg gga ggt att      4572
His Gly Val Pro Val Asn Glu Asn Tyr Gln Pro Leu Gly Gly Ile
            1490                1495                1500

gac cga aaa cgt ctt gca gcg aga aag aac agc acc aca tac tgc      4617
Asp Arg Lys Arg Leu Ala Ala Arg Lys Asn Ser Thr Thr Tyr Cys
            1505                1510                1515

tat gat ttc ccc ctt gca ttt caa aca tcc ttg gaa cag tcc tgg      4662
Tyr Asp Phe Pro Leu Ala Phe Gln Thr Ser Leu Glu Gln Ser Trp
            1520                1525                1530

tca ata cag cag aca gga att caa aga gct aat gat aag gat ctc      4707
Ser Ile Gln Gln Thr Gly Ile Gln Arg Ala Asn Asp Lys Asp Leu
            1535                1540                1545

cta aaa gta aca gag ctt aaa ttt tcc gaa aaa gct ggt agt tgg      4752
Leu Lys Val Thr Glu Leu Lys Phe Ser Glu Lys Ala Gly Ser Trp
            1550                1555                1560

ggt act tct ctt gtt cct gca gag cgt ctt cct gga ctc aat gat      4797
Gly Thr Ser Leu Val Pro Ala Glu Arg Leu Pro Gly Leu Asn Asp
            1565                1570                1575

gtt ggc atg gta gcc tgg ttg atg gaa atg tgt acg cct aaa ttc      4842
```

-continued

```
Val Gly Met Val  Ala Trp Leu Met Glu  Met Cys Thr Pro Lys  Phe
            1580                1585                1590

cca tct gga agg  aca ata ttg gtt gtt  tca aac gat gtg acc  ttc      4887
Pro Ser Gly Arg  Thr Ile Leu Val Val  Ser Asn Asp Val Thr  Phe
            1595                1600                1605

aag gcc ggg tct  ttt ggc cca aga gag  gat gca ttc ttt aga  gca      4932
Lys Ala Gly Ser  Phe Gly Pro Arg Glu  Asp Ala Phe Phe Arg  Ala
            1610                1615                1620

gta act gat ctt  gcc tgt gca aag aaa  ata cct tta att tac  ttg      4977
Val Thr Asp Leu  Ala Cys Ala Lys Lys  Ile Pro Leu Ile Tyr  Leu
            1625                1630                1635

gca gca aat tct  ggt gcc cgt tta ggt  gtt gcc gag gaa gtc  aaa      5022
Ala Ala Asn Ser  Gly Ala Arg Leu Gly  Val Ala Glu Glu Val  Lys
            1640                1645                1650

gct tgt ttc aaa  gtt ggt tgg tct gag  gaa tct aaa cct gaa  cat      5067
Ala Cys Phe Lys  Val Gly Trp Ser Glu  Glu Ser Lys Pro Glu  His
            1655                1660                1665

ggt ttt cag tat  gta tat tta aca cct  gag gat tat gct cga  atc      5112
Gly Phe Gln Tyr  Val Tyr Leu Thr Pro  Glu Asp Tyr Ala Arg  Ile
            1670                1675                1680

gga tca tca gtg  atg gca cat gaa tta  aag ctt gaa agt gga  gaa      5157
Gly Ser Ser Val  Met Ala His Glu Leu  Lys Leu Glu Ser Gly  Glu
            1685                1690                1695

acc aga tgg gtt  ata gat acc att gtt  ggc aaa gaa gat gga  ctg      5202
Thr Arg Trp Val  Ile Asp Thr Ile Val  Gly Lys Glu Asp Gly  Leu
            1700                1705                1710

gga gtt gaa aac  ttg agt ggt agt ggg  gcc att gcc ggt gcc  tat      5247
Gly Val Glu Asn  Leu Ser Gly Ser Gly  Ala Ile Ala Gly Ala  Tyr
            1715                1720                1725

tca agg gca tac  aag gaa acc ttt aca  ttg aca tat gtt acc  ggt      5292
Ser Arg Ala Tyr  Lys Glu Thr Phe Thr  Leu Thr Tyr Val Thr  Gly
            1730                1735                1740

agg act gtt gga  att ggt gct tat ctt  gct agg ctt ggg atg  agg      5337
Arg Thr Val Gly  Ile Gly Ala Tyr Leu  Ala Arg Leu Gly Met  Arg
            1745                1750                1755

tgc ata cag agg  ctt gat caa cct ata  att ctt acc ggg ttt  tca      5382
Cys Ile Gln Arg  Leu Asp Gln Pro Ile  Ile Leu Thr Gly Phe  Ser
            1760                1765                1770

gca tta aac aaa  ctt ctt ggt agg gag  gtg tac agc tct cac  atg      5427
Ala Leu Asn Lys  Leu Leu Gly Arg Glu  Val Tyr Ser Ser His  Met
            1775                1780                1785

caa ctt ggt gga  ccg aaa atc atg gca  aca aat gga gtc gtt  cat      5472
Gln Leu Gly Gly  Pro Lys Ile Met Ala  Thr Asn Gly Val Val  His
            1790                1795                1800

ctc aca gtt tcg  gac gac ctt gaa ggc  gtt tct tct att ttg  aag      5517
Leu Thr Val Ser  Asp Asp Leu Glu Gly  Val Ser Ser Ile Leu  Lys
            1805                1810                1815

tgg ctt agc tac  gtt cct tct cat gta  ggt ggt gca ctt ccc  att      5562
Trp Leu Ser Tyr  Val Pro Ser His Val  Gly Gly Ala Leu Pro  Ile
            1820                1825                1830

gta aag ccc ctt  gat ccc cca gag agg  gaa gtg gag tat tta  ccg      5607
Val Lys Pro Leu  Asp Pro Pro Glu Arg  Glu Val Glu Tyr Leu  Pro
            1835                1840                1845

gaa aat tca tgc  gat cct cgt gct gcc  att tcc gga act ctg  gat      5652
Glu Asn Ser Cys  Asp Pro Arg Ala Ala  Ile Ser Gly Thr Leu  Asp
            1850                1855                1860

gtt aat gga aag  tgg ctg gga ggc att  ttt gac aag gac agc  ttt      5697
Val Asn Gly Lys  Trp Leu Gly Gly Ile  Phe Asp Lys Asp Ser  Phe
            1865                1870                1875

gtg gag aca cta  gaa gga tgg gct aga  aca gtt gtt aca gga  agg      5742
```

```
Val Glu Thr Leu  Glu Gly Trp Ala Arg  Thr Val Val Thr Gly  Arg
            1880                 1885                 1890

gca aag ctt gga  gga atc cct gtg gga  att gtt gcg gtg gaa  aca      5787
Ala Lys Leu Gly  Gly Ile Pro Val Gly  Ile Val Ala Val Glu  Thr
            1895                 1900                 1905

caa aca gtt atg  caa ata ata cct gct  gat cca ggt caa ctt  gat      5832
Gln Thr Val Met  Gln Ile Ile Pro Ala  Asp Pro Gly Gln Leu  Asp
            1910                 1915                 1920

tct cac gag agg  gtt gtt cct caa gcc  ggg cag gtg tgg ttt  cct      5877
Ser His Glu Arg  Val Val Pro Gln Ala  Gly Gln Val Trp Phe  Pro
            1925                 1930                 1935

gat tct gcg acc  aag acg gcc caa gcg  ata ttg gat ttc aac  aga      5922
Asp Ser Ala Thr  Lys Thr Ala Gln Ala  Ile Leu Asp Phe Asn  Arg
            1940                 1945                 1950

gaa gaa ctc cca  ctt ttc att atc gca  aac tgg aga ggc ttt  tca      5967
Glu Glu Leu Pro  Leu Phe Ile Ile Ala  Asn Trp Arg Gly Phe  Ser
            1955                 1960                 1965

ggt gga caa agg  gac ctt ttt gaa gga  att ctt cag gct ggt  tcg      6012
Gly Gly Gln Arg  Asp Leu Phe Glu Gly  Ile Leu Gln Ala Gly  Ser
            1970                 1975                 1980

act att gtg gag  aac ctt agg aca tac  aaa cag ccc ata ttt  gta      6057
Thr Ile Val Glu  Asn Leu Arg Thr Tyr  Lys Gln Pro Ile Phe  Val
            1985                 1990                 1995

tac att cca atg  atg ggt gaa ctc cga  ggc ggg gct tgg gtt  gtt      6102
Tyr Ile Pro Met  Met Gly Glu Leu Arg  Gly Gly Ala Trp Val  Val
            2000                 2005                 2010

gtc gac agc cga  atc aac tca gac cac  att gaa atg tat gct  gag      6147
Val Asp Ser Arg  Ile Asn Ser Asp His  Ile Glu Met Tyr Ala  Glu
            2015                 2020                 2025

cga acg gcc aaa  ggt aac gtc ctt gag  ccg gaa gga atg att  gaa      6192
Arg Thr Ala Lys  Gly Asn Val Leu Glu  Pro Glu Gly Met Ile  Glu
            2030                 2035                 2040

atc aaa ttt aga  aca aga gaa ttg ttg  gag tgt atg aga aga  ctt      6237
Ile Lys Phe Arg  Thr Arg Glu Leu Leu  Glu Cys Met Arg Arg  Leu
            2045                 2050                 2055

gat caa caa ttg  att aat ttg aag gaa  aaa ctt tct gaa gcc  aag      6282
Asp Gln Gln Leu  Ile Asn Leu Lys Glu  Lys Leu Ser Glu Ala  Lys
            2060                 2065                 2070

agt aac aag gac  tat ggt gca tat gat  tct ctg cag cag cag  att      6327
Ser Asn Lys Asp  Tyr Gly Ala Tyr Asp  Ser Leu Gln Gln Gln  Ile
            2075                 2080                 2085

aga ttc cgt gag  aaa cag ctt ttg cct  ttg tat act cag ata  gct      6372
Arg Phe Arg Glu  Lys Gln Leu Leu Pro  Leu Tyr Thr Gln Ile  Ala
            2090                 2095                 2100

aca aaa ttt gct  gaa ctc cat gat act  tca tta aga atg aaa  gca      6417
Thr Lys Phe Ala  Glu Leu His Asp Thr  Ser Leu Arg Met Lys  Ala
            2105                 2110                 2115

aag ggt gta atc  aga gaa gtt ctt gat  tgg cgt aag tcg cgt  tct      6462
Lys Gly Val Ile  Arg Glu Val Leu Asp  Trp Arg Lys Ser Arg  Ser
            2120                 2125                 2130

gtc ttc tat cag  aga ctg cac agg aga  atc ggt gag cac tca  ctg      6507
Val Phe Tyr Gln  Arg Leu His Arg Arg  Ile Gly Glu His Ser  Leu
            2135                 2140                 2145

atc aac atc gtg  aga gat gct gct ggt  gac caa ttg tca tat  gtt      6552
Ile Asn Ile Val  Arg Asp Ala Ala Gly  Asp Gln Leu Ser Tyr  Val
            2150                 2155                 2160

tct gcc atg aac  ttg ctc aaa gaa tgg  tat ctg aat tct gat  atc      6597
Ser Ala Met Asn  Leu Leu Lys Glu Trp  Tyr Leu Asn Ser Asp  Ile
            2165                 2170                 2175

gcc aaa ggt aga  gaa gat gct tgg ttg  gac gat gaa gcc ttc  ttc      6642
```

```
Ala Lys Gly Arg  Glu Asp Ala Trp Leu  Asp Asp Glu Ala Phe  Phe
            2180                 2185                 2190

aga tgg agg gat  gat cca gca aac tac  gag gat aaa cta aag  gaa      6687
Arg Trp Arg Asp  Asp Pro Ala Asn Tyr  Glu Asp Lys Leu Lys  Glu
            2195                 2200                 2205

ttg cgc gtc cag  aga ctg ttg ctt cag  ttg aca aat att ggc  gac      6732
Leu Arg Val Gln  Arg Leu Leu Leu Gln  Leu Thr Asn Ile Gly  Asp
            2210                 2215                 2220

tcg gct cta gat  tta caa gct cta cct  caa ggt ctt gcc gcc  ctt      6777
Ser Ala Leu Asp  Leu Gln Ala Leu Pro  Gln Gly Leu Ala Ala  Leu
            2225                 2230                 2235

tta agc aag ttg  gaa gca tca agt cgc  gat aag ttg atc agt  gaa      6822
Leu Ser Lys Leu  Glu Ala Ser Ser Arg  Asp Lys Leu Ile Ser  Glu
            2240                 2245                 2250

ctt cgc aaa gta  ctc ggt tag tagacagtga atgctcctgt gatctgccca       6873
Leu Arg Lys Val  Leu Gly
            2255

tgcactcatg ttgtagtgtt cacgtcgttg atacatgacc atatagaaat gtatccattt   6933

tacgatgtta tcatcaaagt agcagcatcc ctcggaaaat ggactttcac ttgagggatc   6993

aactgtaaat gacttcggtc ttggatagat atttaattta tgcagttaga ggatcataac   7053

cagcatcacc atgtttggtc tatttatttg ctggttgatt gattctttgc gtgtatctga   7113

ataaacatgt aataatttgt aacattgatt attttttatg aaaaacaaag ttttgggcac   7173

tc                                                                  7175


<210> SEQ ID NO 37
<211> LENGTH: 2257
<212> TYPE: PRT
<213> ORGANISM: Medicago sativa

<400> SEQUENCE: 37

Met Ala Ser Val Gly Arg Gly Asn Gly Tyr Leu Asn Ser Val Leu Pro
1               5                   10                  15

Ser Arg His Pro Ala Thr Thr Thr Glu Val Asp Glu Tyr Cys Asn Ala
            20                  25                  30

Leu Gly Gly Asn Lys Pro Ile His Ser Ile Leu Ile Ala Asn Asn Gly
        35                  40                  45

Met Ala Ala Val Lys Phe Ile Arg Ser Val Arg Ser Trp Ala Tyr Glu
    50                  55                  60

Thr Phe Gly Thr Glu Lys Ala Ile Leu Leu Val Ala Met Ala Thr Pro
65                  70                  75                  80

Glu Asp Met Arg Ile Asn Ala Glu His Ile Arg Ile Ala Asp Gln Phe
                85                  90                  95

Val Glu Val Pro Gly Gly Thr Asn Asn Asn Asn Tyr Ala Asn Val Gln
            100                 105                 110

Leu Ile Leu Glu Ile Ala Glu Ile Thr His Val Asp Ala Val Trp Pro
        115                 120                 125

Gly Trp Gly His Ala Ser Glu Asn Pro Glu Leu Pro Asp Ala Leu Lys
    130                 135                 140

Ala Lys Gly Ile Val Phe Leu Gly Pro Pro Ala Ile Ser Met Ala Ala
145                 150                 155                 160

Leu Gly Asp Lys Ile Gly Ser Ser Leu Ile Ala Gln Ala Ala Glu Val
                165                 170                 175

Pro Thr Leu Pro Trp Ser Gly Ser His Val Lys Ile Pro Pro Glu Ser
            180                 185                 190

Asp Leu Ile Thr Ile Pro Asp Glu Ile Tyr Arg Ala Ala Cys Val Tyr
```

-continued

```
        195                 200                 205

Thr Thr Glu Glu Ala Ile Ala Ser Cys Gln Val Val Gly Tyr Pro Ala
    210                 215                 220

Met Ile Lys Ala Ser Trp Gly Gly Gly Gly Lys Gly Ile Arg Lys Val
225                 230                 235                 240

His Asn Asp Asp Glu Val Arg Ala Leu Phe Lys Gln Val Gln Gly Glu
                245                 250                 255

Val Pro Gly Ser Pro Ile Phe Ile Met Lys Val Ala Ser Gln Ser Arg
            260                 265                 270

His Leu Glu Val Gln Leu Ile Cys Asp Gln His Gly Asn Phe Ala Ala
        275                 280                 285

Leu His Ser Arg Asp Cys Ser Val Gln Arg Arg His Gln Lys Ile Ile
    290                 295                 300

Glu Glu Gly Pro Ile Thr Val Ala Pro Pro Glu Thr Val Lys Glu Leu
305                 310                 315                 320

Glu Gln Ala Ala Arg Arg Leu Ala Lys Ser Val Asn Tyr Val Gly Ala
                325                 330                 335

Ala Thr Val Glu Tyr Leu Tyr Ser Met Glu Thr Gly Glu Tyr Tyr Phe
            340                 345                 350

Leu Glu Leu Asn Pro Arg Leu Gln Val Glu His Pro Val Thr Glu Trp
        355                 360                 365

Ile Ala Glu Ile Asn Leu Pro Ala Ala Gln Val Ala Val Gly Met Gly
    370                 375                 380

Ile Pro Leu Trp Gln Ile Pro Glu Ile Arg Arg Phe Tyr Gly Met Glu
385                 390                 395                 400

His Gly Gly Gly Asn Asp Gly Trp Lys Lys Thr Ser Val Leu Ala Thr
                405                 410                 415

Pro Phe Asp Phe Asp Glu Ala Gln Ser Thr Lys Pro Lys Gly His Cys
            420                 425                 430

Val Ala Val Arg Val Thr Ser Glu Asp Pro Asp Asp Gly Phe Thr Pro
        435                 440                 445

Thr Gly Gly Lys Val Gln Glu Leu Ser Phe Lys Ser Lys Pro Asn Val
    450                 455                 460

Trp Ala Tyr Phe Ser Val Lys Ser Gly Gly Gly Ile His Glu Phe Ser
465                 470                 475                 480

Asp Ser Gln Phe Gly His Val Phe Ala Phe Gly Glu Ser Arg Ala Leu
                485                 490                 495

Ala Ile Ala Asn Met Val Leu Gly Leu Lys Glu Ile Gln Ile Arg Gly
            500                 505                 510

Glu Ile Arg Thr Asn Val Asp Tyr Thr Ile Asp Leu Leu Asn Ala Ser
        515                 520                 525

Asp Tyr Arg Asp Asn Lys Ile His Thr Gly Trp Leu Asp Ser Arg Ile
    530                 535                 540

Ala Met Arg Val Arg Ala Glu Arg Pro Pro Trp Tyr Leu Ser Val Val
545                 550                 555                 560

Gly Gly Ala Leu Tyr Lys Ala Ser Ala Ser Ser Ala Ala Leu Val Ser
                565                 570                 575

Asp Tyr Val Gly Tyr Leu Glu Lys Gly Gln Ile Pro Pro Lys His Ile
            580                 585                 590

Ser Leu Val His Ser Gln Val Ser Leu Ser Ile Glu Gly Ser Lys Tyr
        595                 600                 605

Thr Ile Asp Met Val Arg Gly Gly Pro Gly Ser Tyr Lys Leu Lys Leu
    610                 615                 620
```

-continued

Asn Gln Ser Glu Ile Glu Ala Glu Ile His Thr Leu Arg Asp Gly Gly
625 630 635 640

Leu Leu Met Gln Leu Asp Gly Asn Ser His Val Ile Tyr Ala Glu Glu
645 650 655

Glu Ala Ala Gly Thr Arg Leu Leu Ile Asp Gly Arg Thr Cys Leu Leu
660 665 670

Gln Asn Asp Asp Asp Pro Ser Lys Leu Ile Gly Glu Thr Pro Cys Lys
675 680 685

Leu Leu Arg Tyr Leu Val Ala Asp Asp Ser Gln Ile Asp Ala Asp Thr
690 695 700

Pro Tyr Ala Glu Val Glu Val Met Lys Met Cys Met Pro Leu Leu Ser
705 710 715 720

Pro Ala Ser Gly Ile Ile His Phe Arg Met Ala Glu Gly Gln Ala Met
725 730 735

Gln Ala Gly Glu Leu Ile Ala Lys Leu Asp Leu Asp Asp Gly Ser Ala
740 745 750

Val Arg Lys Ala Glu Pro Phe Thr Gly Ser Phe Pro Ile Leu Gly Pro
755 760 765

Pro Thr Ala Ile Ser Gly Lys Val His Gln Lys Cys Ala Ala Ser Leu
770 775 780

Asn Ala Ala Arg Met Ile Leu Ala Gly Tyr Glu His Asn Ile Asp Glu
785 790 795 800

Val Val Val Lys Ser Leu Leu Asn Cys Leu Asp Ser Pro Glu Leu Pro
805 810 815

Phe Leu Gln Trp Gln Glu Cys Phe Ala Val Leu Ala Thr Arg Leu Pro
820 825 830

Lys Asp Leu Arg Asn Glu Leu Glu Ala Lys Tyr Lys Glu Phe Glu Ile
835 840 845

Ile Ser Ser Ser Gln Thr Ile Asp Phe Pro Ala Lys Leu Leu Lys Ala
850 855 860

Ile Leu Glu Ala His Leu Ser Ser Cys Pro Glu Asn Glu Lys Gly Ala
865 870 875 880

Leu Glu Arg Leu Val Glu Pro Leu Thr Ser Leu Val Lys Ser Tyr Glu
885 890 895

Gly Gly Arg Glu Ser His Ala His Lys Ile Val Gln Ser Leu Phe Glu
900 905 910

Glu Tyr Leu Ser Val Glu Glu Leu Phe Ser Asp Asn Ile Gln Ala Asp
915 920 925

Val Ile Glu Arg Leu Arg Leu Gln Tyr Lys Lys Asp Leu Leu Lys Ile
930 935 940

Val Asp Ile Val Leu Ser His Gln Gly Val Lys Ser Lys Asn Lys Leu
945 950 955 960

Ile Leu Arg Leu Met Asp Lys Leu Val Tyr Pro Asn Pro Ala Ala Tyr
965 970 975

Arg Asp Gln Leu Ile Arg Phe Ser Gln Leu Asn His Ile Val Tyr Ser
980 985 990

Glu Leu Ala Leu Lys Ala Ser Gln Leu Leu Glu Gln Thr Lys Leu Ser
995 1000 1005

Glu Leu Arg Ser Ser Ile Ala Arg Ser Leu Ser Glu Leu Glu Met
1010 1015 1020

Phe Thr Glu Asp Gly Glu Asn Ile Asp Thr Pro Lys Arg Lys Ser
1025 1030 1035

Ala Ile Asn Asp Arg Met Glu Asp Leu Val Ser Ala Pro Leu Ala
1040 1045 1050

```
Val Glu  Asp Ala Leu Val Gly  Leu Phe Asp His Ser  Asp His Thr
    1055                 1060                 1065

Leu Gln  Arg Arg Val Val Glu  Thr Tyr Ile Arg Arg  Leu Tyr Gln
    1070                 1075                 1080

Pro Tyr  Leu Val Lys Asp Ser  Ile Arg Met Gln Trp  His Arg Ser
    1085                 1090                 1095

Gly Leu  Ile Ala Thr Trp Glu  Phe Leu Glu Glu Tyr  Val Glu Arg
    1100                 1105                 1110

Lys Asn  Gly Val Glu Asp Lys  Thr Leu Val Glu Lys  His Ser Glu
    1115                 1120                 1125

Lys Lys  Trp Gly Val Met Val  Val Ile Lys Ser Leu  Gln Phe Leu
    1130                 1135                 1140

Pro Ala  Ile Ile Ser Ala Ala  Leu Arg Glu Ala Thr  Asn Asn Phe
    1145                 1150                 1155

His Asp  Pro Leu Lys Ser Gly  Ser Gly Asp Ser Ser  Asn His Gly
    1160                 1165                 1170

Asn Met  Met His Ile Gly Leu  Val Gly Ile Asn Asn  Gln Met Ser
    1175                 1180                 1185

Leu Leu  Gln Asp Ser Gly Asp  Glu Asp Gln Ala Gln  Glu Arg Ile
    1190                 1195                 1200

Asp Lys  Leu Ala Lys Ile Leu  Arg Glu Gln Glu Ile  Gly Ser Ile
    1205                 1210                 1215

Ile His  Ala Ala Gly Val Gly  Asp Ile Ser Cys Ile  Ile Gln Arg
    1220                 1225                 1230

Asp Glu  Gly Arg Ala Pro Met  Arg His Ser Phe His  Trp Ser Ser
    1235                 1240                 1245

Glu Lys  Leu Tyr Tyr Val Glu  Glu Pro Leu Leu Leu  His Leu Glu
    1250                 1255                 1260

Pro Pro  Leu Ser Ile Tyr Leu  Glu Leu Asp Lys Leu  Lys Cys Tyr
    1265                 1270                 1275

Glu Asn  Ile Arg Tyr Thr Pro  Ser Arg Asp Arg Gln  Trp His Leu
    1280                 1285                 1290

Tyr Thr  Val Val Asp Thr Lys  Pro Gln Pro Ile Gln  Arg Met Phe
    1295                 1300                 1305

Leu Arg  Thr Leu Ile Arg Gln  Pro Thr Thr Asn Glu  Gly Tyr Ser
    1310                 1315                 1320

Ser Tyr  Gln Arg Leu Asp Ala  Glu Thr Ser Arg Thr  Gln Leu Ala
    1325                 1330                 1335

Met Ser  Tyr Thr Ser Arg Ser  Ile Phe Arg Ser Leu  Met Gly Ala
    1340                 1345                 1350

Met Glu  Glu Leu Glu Leu Asn  Ser His Asn Thr Thr  Ile Lys Ser
    1355                 1360                 1365

Glu His  Ala His Met Tyr Leu  Tyr Ile Ile Arg Glu  Gln Gln Ile
    1370                 1375                 1380

Asp Asp  Leu Val Pro Tyr Ser  Lys Lys Ile Asn Ile  Glu Ala Gly
    1385                 1390                 1395

Gln Glu  Glu Thr Thr Val Glu  Ala Ile Leu Glu Glu  Leu Ala Gln
    1400                 1405                 1410

Glu Ile  His Ser Ser Val Gly  Val Arg Met His Arg  Leu Gly Val
    1415                 1420                 1425

Phe Val  Trp Glu Ile Lys Leu  Trp Ile Thr Ala Cys  Gly Gln Ala
    1430                 1435                 1440

Asn Gly  Ala Trp Arg Val Ile  Val Asn Asn Val Thr  Gly His Thr
```

-continued 1445 1450 1455

Cys Thr Val His Ile Tyr Arg Glu Met Glu Asp Ala Thr Thr His
1460 1465 1470

Lys Val Val Tyr Ser Ser Val Thr Val Lys Gly Pro Leu His Gly
1475 1480 1485

Val Pro Val Asn Glu Asn Tyr Gln Pro Leu Gly Gly Ile Asp Arg
1490 1495 1500

Lys Arg Leu Ala Ala Arg Lys Asn Ser Thr Thr Tyr Cys Tyr Asp
1505 1510 1515

Phe Pro Leu Ala Phe Gln Thr Ser Leu Glu Gln Ser Trp Ser Ile
1520 1525 1530

Gln Gln Thr Gly Ile Gln Arg Ala Asn Asp Lys Asp Leu Leu Lys
1535 1540 1545

Val Thr Glu Leu Lys Phe Ser Glu Lys Ala Gly Ser Trp Gly Thr
1550 1555 1560

Ser Leu Val Pro Ala Glu Arg Leu Pro Gly Leu Asn Asp Val Gly
1565 1570 1575

Met Val Ala Trp Leu Met Glu Met Cys Thr Pro Lys Phe Pro Ser
1580 1585 1590

Gly Arg Thr Ile Leu Val Val Ser Asn Asp Val Thr Phe Lys Ala
1595 1600 1605

Gly Ser Phe Gly Pro Arg Glu Asp Ala Phe Phe Arg Ala Val Thr
1610 1615 1620

Asp Leu Ala Cys Ala Lys Lys Ile Pro Leu Ile Tyr Leu Ala Ala
1625 1630 1635

Asn Ser Gly Ala Arg Leu Gly Val Ala Glu Glu Val Lys Ala Cys
1640 1645 1650

Phe Lys Val Gly Trp Ser Glu Glu Ser Lys Pro Glu His Gly Phe
1655 1660 1665

Gln Tyr Val Tyr Leu Thr Pro Glu Asp Tyr Ala Arg Ile Gly Ser
1670 1675 1680

Ser Val Met Ala His Glu Leu Lys Leu Glu Ser Gly Glu Thr Arg
1685 1690 1695

Trp Val Ile Asp Thr Ile Val Gly Lys Glu Asp Gly Leu Gly Val
1700 1705 1710

Glu Asn Leu Ser Gly Ser Gly Ala Ile Ala Gly Ala Tyr Ser Arg
1715 1720 1725

Ala Tyr Lys Glu Thr Phe Thr Leu Thr Tyr Val Thr Gly Arg Thr
1730 1735 1740

Val Gly Ile Gly Ala Tyr Leu Ala Arg Leu Gly Met Arg Cys Ile
1745 1750 1755

Gln Arg Leu Asp Gln Pro Ile Ile Leu Thr Gly Phe Ser Ala Leu
1760 1765 1770

Asn Lys Leu Leu Gly Arg Glu Val Tyr Ser Ser His Met Gln Leu
1775 1780 1785

Gly Gly Pro Lys Ile Met Ala Thr Asn Gly Val Val His Leu Thr
1790 1795 1800

Val Ser Asp Asp Leu Glu Gly Val Ser Ser Ile Leu Lys Trp Leu
1805 1810 1815

Ser Tyr Val Pro Ser His Val Gly Gly Ala Leu Pro Ile Val Lys
1820 1825 1830

Pro Leu Asp Pro Pro Glu Arg Glu Val Glu Tyr Leu Pro Glu Asn
1835 1840 1845

Ser Cys Asp Pro Arg Ala Ala Ile Ser Gly Thr Leu Asp Val Asn
1850 1855 1860

Gly Lys Trp Leu Gly Gly Ile Phe Asp Lys Asp Ser Phe Val Glu
1865 1870 1875

Thr Leu Glu Gly Trp Ala Arg Thr Val Val Thr Gly Arg Ala Lys
1880 1885 1890

Leu Gly Gly Ile Pro Val Gly Ile Val Ala Val Glu Thr Gln Thr
1895 1900 1905

Val Met Gln Ile Ile Pro Ala Asp Pro Gly Gln Leu Asp Ser His
1910 1915 1920

Glu Arg Val Val Pro Gln Ala Gly Gln Val Trp Phe Pro Asp Ser
1925 1930 1935

Ala Thr Lys Thr Ala Gln Ala Ile Leu Asp Phe Asn Arg Glu Glu
1940 1945 1950

Leu Pro Leu Phe Ile Ile Ala Asn Trp Arg Gly Phe Ser Gly Gly
1955 1960 1965

Gln Arg Asp Leu Phe Glu Gly Ile Leu Gln Ala Gly Ser Thr Ile
1970 1975 1980

Val Glu Asn Leu Arg Thr Tyr Lys Gln Pro Ile Phe Val Tyr Ile
1985 1990 1995

Pro Met Met Gly Glu Leu Arg Gly Gly Ala Trp Val Val Val Asp
2000 2005 2010

Ser Arg Ile Asn Ser Asp His Ile Glu Met Tyr Ala Glu Arg Thr
2015 2020 2025

Ala Lys Gly Asn Val Leu Glu Pro Glu Gly Met Ile Glu Ile Lys
2030 2035 2040

Phe Arg Thr Arg Glu Leu Leu Glu Cys Met Arg Arg Leu Asp Gln
2045 2050 2055

Gln Leu Ile Asn Leu Lys Glu Lys Leu Ser Glu Ala Lys Ser Asn
2060 2065 2070

Lys Asp Tyr Gly Ala Tyr Asp Ser Leu Gln Gln Gln Ile Arg Phe
2075 2080 2085

Arg Glu Lys Gln Leu Leu Pro Leu Tyr Thr Gln Ile Ala Thr Lys
2090 2095 2100

Phe Ala Glu Leu His Asp Thr Ser Leu Arg Met Lys Ala Lys Gly
2105 2110 2115

Val Ile Arg Glu Val Leu Asp Trp Arg Lys Ser Arg Ser Val Phe
2120 2125 2130

Tyr Gln Arg Leu His Arg Arg Ile Gly Glu His Ser Leu Ile Asn
2135 2140 2145

Ile Val Arg Asp Ala Ala Gly Asp Gln Leu Ser Tyr Val Ser Ala
2150 2155 2160

Met Asn Leu Leu Lys Glu Trp Tyr Leu Asn Ser Asp Ile Ala Lys
2165 2170 2175

Gly Arg Glu Asp Ala Trp Leu Asp Asp Glu Ala Phe Phe Arg Trp
2180 2185 2190

Arg Asp Asp Pro Ala Asn Tyr Glu Asp Lys Leu Lys Glu Leu Arg
2195 2200 2205

Val Gln Arg Leu Leu Leu Gln Leu Thr Asn Ile Gly Asp Ser Ala
2210 2215 2220

Leu Asp Leu Gln Ala Leu Pro Gln Gly Leu Ala Ala Leu Leu Ser
2225 2230 2235

Lys Leu Glu Ala Ser Ser Arg Asp Lys Leu Ile Ser Glu Leu Arg
2240 2245 2250

```
Lys Val  Leu Gly
    2255


<210> SEQ ID NO 38
<211> LENGTH: 1497
<212> TYPE: DNA
<213> ORGANISM: Trichoderma harzianum
<220> FEATURE:
<221> NAME/KEY: CDS
<222> LOCATION: (49)..(1320)
<223> OTHER INFORMATION: chit42=endochitinase

<400> SEQUENCE: 38

cgttgctgtc gagcttgaac aatctaccaa catcacaagc aattcacc atg ttg agc      57
                                                     Met Leu Ser
                                                     1

ttc ctc gga aaa tcc gta gcc ttg ctg gct gcg ctg cag gct act ctc      105
Phe Leu Gly Lys Ser Val Ala Leu Leu Ala Ala Leu Gln Ala Thr Leu
    5                   10                  15

agc tct ccg aag cct ggc cac aga aga gcg tct gtt gag aag aga gcc      153
Ser Ser Pro Lys Pro Gly His Arg Arg Ala Ser Val Glu Lys Arg Ala
20                  25                  30                  35

aac gga tac gca aac tcc gtc tat ttc acc aac tgg ggc atc tac gac      201
Asn Gly Tyr Ala Asn Ser Val Tyr Phe Thr Asn Trp Gly Ile Tyr Asp
                40                  45                  50

cgc aac ttc cag cct gcc gat ttg gtg gca tca gat gtc act cat gtc      249
Arg Asn Phe Gln Pro Ala Asp Leu Val Ala Ser Asp Val Thr His Val
            55                  60                  65

atc tac tcc ttc atg aac ctc cag gca gac ggc aca gtt atc tct ggc      297
Ile Tyr Ser Phe Met Asn Leu Gln Ala Asp Gly Thr Val Ile Ser Gly
        70                  75                  80

gat acc tac gct gat tac gag aag cac tat gcc gat gat tct tgg aat      345
Asp Thr Tyr Ala Asp Tyr Glu Lys His Tyr Ala Asp Asp Ser Trp Asn
    85                  90                  95

gat gtc ggc acc aat gcc tac ggc tgt gtc aag cag ctg ttc aag gtc      393
Asp Val Gly Thr Asn Ala Tyr Gly Cys Val Lys Gln Leu Phe Lys Val
100                 105                 110                 115

aag aag gcc aac cga ggc ctc aag gtt ctg ctc tcc atc ggt ggc tgg      441
Lys Lys Ala Asn Arg Gly Leu Lys Val Leu Leu Ser Ile Gly Gly Trp
                120                 125                 130

act tgg tcc acc aac ttc cct tct gca gca agc acg gat gcc aac cga      489
Thr Trp Ser Thr Asn Phe Pro Ser Ala Ala Ser Thr Asp Ala Asn Arg
            135                 140                 145

aag aac ttt gcg aaa act gcc att acc ttt atg aag gat tgg ggt ttc      537
Lys Asn Phe Ala Lys Thr Ala Ile Thr Phe Met Lys Asp Trp Gly Phe
        150                 155                 160

gat ggt att gat atc gac tgg gag tac cct gca gac gcc acc cag gcc      585
Asp Gly Ile Asp Ile Asp Trp Glu Tyr Pro Ala Asp Ala Thr Gln Ala
    165                 170                 175

tcc aac atg att ctt ctg ctg aag gaa gtc cga tct cag cgt gat gct      633
Ser Asn Met Ile Leu Leu Leu Lys Glu Val Arg Ser Gln Arg Asp Ala
180                 185                 190                 195

tat gct gcc cag tat gcc cct ggc tac cac ttc ctc ctc acc att gcc      681
Tyr Ala Ala Gln Tyr Ala Pro Gly Tyr His Phe Leu Leu Thr Ile Ala
                200                 205                 210

gcc cca gct ggc aag gac aac tac tcc aag ctg cgc ctg gct gat ctt      729
Ala Pro Ala Gly Lys Asp Asn Tyr Ser Lys Leu Arg Leu Ala Asp Leu
            215                 220                 225

ggc caa gtc ctc gac tac atc aac ctc atg gcc tac gac tac gcc gga      777
Gly Gln Val Leu Asp Tyr Ile Asn Leu Met Ala Tyr Asp Tyr Ala Gly
        230                 235                 240
```

-continued

```
tcc ttc agc ccc ctc acc ggt cac gac gcc aac ctg ttt aac aac ccg      825
Ser Phe Ser Pro Leu Thr Gly His Asp Ala Asn Leu Phe Asn Asn Pro
    245                 250                 255

tcc aac ccc aat gcc acc ccc ttc aac acc gat tcc gct gtc aag gat      873
Ser Asn Pro Asn Ala Thr Pro Phe Asn Thr Asp Ser Ala Val Lys Asp
260                 265                 270                 275

tat atc aat gga ggt gtt ccc gcc aac aag att gtt ctc ggc atg ccc      921
Tyr Ile Asn Gly Gly Val Pro Ala Asn Lys Ile Val Leu Gly Met Pro
                280                 285                 290

atc tac gga aga tca ttc cag aac acc gct ggt att ggc cag act tac      969
Ile Tyr Gly Arg Ser Phe Gln Asn Thr Ala Gly Ile Gly Gln Thr Tyr
            295                 300                 305

aat ggt gtt gga agt gga agc tgg gag gcc ggt atc tgg gat tac aag     1017
Asn Gly Val Gly Ser Gly Ser Trp Glu Ala Gly Ile Trp Asp Tyr Lys
        310                 315                 320

gct ctt ccc aag gct ggc gcc acc gtc cag tac gat tct gtc gca aag     1065
Ala Leu Pro Lys Ala Gly Ala Thr Val Gln Tyr Asp Ser Val Ala Lys
    325                 330                 335

ggc tac tac agc tac aac tcc gcc acc aag gag ctc atc tct ttc gat     1113
Gly Tyr Tyr Ser Tyr Asn Ser Ala Thr Lys Glu Leu Ile Ser Phe Asp
340                 345                 350                 355

acc ccc gac atg atc aac acc aag gtt gcc tat ctc aag tct ctc ggc     1161
Thr Pro Asp Met Ile Asn Thr Lys Val Ala Tyr Leu Lys Ser Leu Gly
                360                 365                 370

ctg gga ggt agc atg ttc tgg gag gcc tca gcc gac aag aag gga gct     1209
Leu Gly Gly Ser Met Phe Trp Glu Ala Ser Ala Asp Lys Lys Gly Ala
            375                 380                 385

gac tct gtg att gga aca agc cac aga gct ctt gga ggc ctg gac aca     1257
Asp Ser Val Ile Gly Thr Ser His Arg Ala Leu Gly Gly Leu Asp Thr
        390                 395                 400

act caa aac ctg ctg agc tac ccc aac tcc aag tat gat aac atc aag     1305
Thr Gln Asn Leu Leu Ser Tyr Pro Asn Ser Lys Tyr Asp Asn Ile Lys
    405                 410                 415

aat ggt ctg aac tag gctgcctgtt ttgaggcgcc ttatggacat tgaagtcgtc     1360
Asn Gly Leu Asn
420

gcggggaaat cgtcttggag gagcagggtc atgaagtaaa tatttgttta aatacctgta   1420

catagccaca ttagcatata gatgcatgaa tagtatctga gtttattata aaaaaaaaaa   1480

aaaaaaaaaa aaaaaaa                                                  1497


<210> SEQ ID NO 39
<211> LENGTH: 423
<212> TYPE: PRT
<213> ORGANISM: Trichoderma harzianum

<400> SEQUENCE: 39

Met Leu Ser Phe Leu Gly Lys Ser Val Ala Leu Leu Ala Ala Leu Gln
1               5                   10                  15

Ala Thr Leu Ser Ser Pro Lys Pro Gly His Arg Arg Ala Ser Val Glu
            20                  25                  30

Lys Arg Ala Asn Gly Tyr Ala Asn Ser Val Tyr Phe Thr Asn Trp Gly
        35                  40                  45

Ile Tyr Asp Arg Asn Phe Gln Pro Ala Asp Leu Val Ala Ser Asp Val
    50                  55                  60

Thr His Val Ile Tyr Ser Phe Met Asn Leu Gln Ala Asp Gly Thr Val
65                  70                  75                  80

Ile Ser Gly Asp Thr Tyr Ala Asp Tyr Glu Lys His Tyr Ala Asp Asp
                85                  90                  95
```

-continued

```
Ser Trp Asn Asp Val Gly Thr Asn Ala Tyr Gly Cys Val Lys Gln Leu
            100                 105                 110

Phe Lys Val Lys Lys Ala Asn Arg Gly Leu Lys Val Leu Leu Ser Ile
        115                 120                 125

Gly Gly Trp Thr Trp Ser Thr Asn Phe Pro Ser Ala Ala Ser Thr Asp
    130                 135                 140

Ala Asn Arg Lys Asn Phe Ala Lys Thr Ala Ile Thr Phe Met Lys Asp
145                 150                 155                 160

Trp Gly Phe Asp Gly Ile Asp Ile Asp Trp Glu Tyr Pro Ala Asp Ala
                165                 170                 175

Thr Gln Ala Ser Asn Met Ile Leu Leu Leu Lys Glu Val Arg Ser Gln
            180                 185                 190

Arg Asp Ala Tyr Ala Ala Gln Tyr Ala Pro Gly Tyr His Phe Leu Leu
        195                 200                 205

Thr Ile Ala Ala Pro Ala Gly Lys Asp Asn Tyr Ser Lys Leu Arg Leu
    210                 215                 220

Ala Asp Leu Gly Gln Val Leu Asp Tyr Ile Asn Leu Met Ala Tyr Asp
225                 230                 235                 240

Tyr Ala Gly Ser Phe Ser Pro Leu Thr Gly His Asp Ala Asn Leu Phe
                245                 250                 255

Asn Asn Pro Ser Asn Pro Asn Ala Thr Pro Phe Asn Thr Asp Ser Ala
            260                 265                 270

Val Lys Asp Tyr Ile Asn Gly Gly Val Pro Ala Asn Lys Ile Val Leu
        275                 280                 285

Gly Met Pro Ile Tyr Gly Arg Ser Phe Gln Asn Thr Ala Gly Ile Gly
    290                 295                 300

Gln Thr Tyr Asn Gly Val Gly Ser Gly Ser Trp Glu Ala Gly Ile Trp
305                 310                 315                 320

Asp Tyr Lys Ala Leu Pro Lys Ala Gly Ala Thr Val Gln Tyr Asp Ser
                325                 330                 335

Val Ala Lys Gly Tyr Tyr Ser Tyr Asn Ser Ala Thr Lys Glu Leu Ile
            340                 345                 350

Ser Phe Asp Thr Pro Asp Met Ile Asn Thr Lys Val Ala Tyr Leu Lys
        355                 360                 365

Ser Leu Gly Leu Gly Gly Ser Met Phe Trp Glu Ala Ser Ala Asp Lys
    370                 375                 380

Lys Gly Ala Asp Ser Val Ile Gly Thr Ser His Arg Ala Leu Gly Gly
385                 390                 395                 400

Leu Asp Thr Thr Gln Asn Leu Leu Ser Tyr Pro Asn Ser Lys Tyr Asp
                405                 410                 415

Asn Ile Lys Asn Gly Leu Asn
            420
```

<210> SEQ ID NO 40
<211> LENGTH: 2099
<212> TYPE: DNA
<213> ORGANISM: Sorghum bicolor
<220> FEATURE:
<221> NAME/KEY: CDS
<222> LOCATION: (184)..(1860)
<223> OTHER INFORMATION: Sorghum bicolor N-hydroxylating,
      multifunctional cytochrome P-450

<400> SEQUENCE: 40

```
ctagctagct catcgggtga tcgatcagtg agctctctct ttggcctagc tagctgctag      60

cagtgcaggt agccaatcaa agcagaagaa ctcgatcgat cgatcatcac gatcgctgct     120
```

-continued

```
agctagctag ctgctcgctc tcacactagc tacgtgtttt tgttaatttg atatatatat    180

ata atg gcg aca atg gag gta gag gcc gcg gcc gcc acg gtg ctg gcc      228
    Met Ala Thr Met Glu Val Glu Ala Ala Ala Ala Thr Val Leu Ala
    1               5                   10                  15

gcg ccc ttg ctg tcc tcc tcc gcg atc ctc aaa ctg ctg cta ttc gta      276
Ala Pro Leu Leu Ser Ser Ser Ala Ile Leu Lys Leu Leu Leu Phe Val
                20                  25                  30

gtg acg ctc tcg tac ctg gcc cga gcc ctg agg cgg cca cgc aaa agc      324
Val Thr Leu Ser Tyr Leu Ala Arg Ala Leu Arg Arg Pro Arg Lys Ser
            35                  40                  45

acc acc aag tgc agc agc aca acg tgc gcc tcg ccc ccg gcc ggc gtt      372
Thr Thr Lys Cys Ser Ser Thr Thr Cys Ala Ser Pro Pro Ala Gly Val
        50                  55                  60

ggc aac ccg ccg ctc cca ccg ggt ccc gtg ccg tgg ccc gtc gtc ggc      420
Gly Asn Pro Pro Leu Pro Pro Gly Pro Val Pro Trp Pro Val Val Gly
    65                  70                  75

aac ctg ccg gag atg ctg ctg aac aag ccg gca ttc cgc tgg atc cac      468
Asn Leu Pro Glu Met Leu Leu Asn Lys Pro Ala Phe Arg Trp Ile His
80                  85                  90                  95

cag atg atg cgc gag atg ggc acg gac atc gcc tgc gtc aag ctt ggc      516
Gln Met Met Arg Glu Met Gly Thr Asp Ile Ala Cys Val Lys Leu Gly
                100                 105                 110

ggc gtc cac gtc gtg tcc atc acc tgc ccg gag atc gcg cgg gag gtg      564
Gly Val His Val Val Ser Ile Thr Cys Pro Glu Ile Ala Arg Glu Val
            115                 120                 125

ctc cgg aag cag gac gcc aac ttc ata tcc cgc ccg ctc acc ttc gcc      612
Leu Arg Lys Gln Asp Ala Asn Phe Ile Ser Arg Pro Leu Thr Phe Ala
        130                 135                 140

tcc gag acg ttc agc ggc ggg tac cgg aac gcc gtg ctc tcg ccc tac      660
Ser Glu Thr Phe Ser Gly Gly Tyr Arg Asn Ala Val Leu Ser Pro Tyr
    145                 150                 155

ggc gac cag tgg aag aag atg cgc cgc gtc ctc acc tcc gag atc atc      708
Gly Asp Gln Trp Lys Lys Met Arg Arg Val Leu Thr Ser Glu Ile Ile
160                 165                 170                 175

tgc ccg tcc cgc cac gcc tgg ctc cac gac aag cgc acc gac gag gcc      756
Cys Pro Ser Arg His Ala Trp Leu His Asp Lys Arg Thr Asp Glu Ala
                180                 185                 190

gac aac ctc acc cgc tac gtc tac aac ctc gcc acc aaa gcc gcc acc      804
Asp Asn Leu Thr Arg Tyr Val Tyr Asn Leu Ala Thr Lys Ala Ala Thr
            195                 200                 205

ggc gac gtc gcc gtc gac gtc agg cac gtc gct cgt cac tat tgc ggc      852
Gly Asp Val Ala Val Asp Val Arg His Val Ala Arg His Tyr Cys Gly
        210                 215                 220

aac gtt atc cgc cgc ctc atg ttc aac agg cgc tac ttc ggc gag ccc      900
Asn Val Ile Arg Arg Leu Met Phe Asn Arg Arg Tyr Phe Gly Glu Pro
    225                 230                 235

cag gct gac ggc ggt ccg ggg ccg atg gag gtg ctg cat atg gac gcc      948
Gln Ala Asp Gly Gly Pro Gly Pro Met Glu Val Leu His Met Asp Ala
240                 245                 250                 255

gtg ttc acc tcc ctc ggc ctc ctc tac gcc ttc tgc gtc tcc gac tac      996
Val Phe Thr Ser Leu Gly Leu Leu Tyr Ala Phe Cys Val Ser Asp Tyr
                260                 265                 270

ctc ccc tgg ctg cgg ggc ctc gac ctc gac ggc cac gag aag atc gtc     1044
Leu Pro Trp Leu Arg Gly Leu Asp Leu Asp Gly His Glu Lys Ile Val
            275                 280                 285

aag gag gct aac gtg gcg gtg aac agg ctc cac gac acg gtc atc gac     1092
Lys Glu Ala Asn Val Ala Val Asn Arg Leu His Asp Thr Val Ile Asp
        290                 295                 300

gac cgg tgg agg cag tgg aag agc ggc gag cgg cag gag atg gag gac     1140
Asp Arg Trp Arg Gln Trp Lys Ser Gly Glu Arg Gln Glu Met Glu Asp
```

```
    305                 310                 315

ttc ctg gat gtg ctc atc act ctc aag gac gcc cag ggc aac ccg ctg     1188
Phe Leu Asp Val Leu Ile Thr Leu Lys Asp Ala Gln Gly Asn Pro Leu
320                 325                 330                 335

ctg acc atc gag gag gtc aaa gcg cag tca cag gac atc acg ttc gcg     1236
Leu Thr Ile Glu Glu Val Lys Ala Gln Ser Gln Asp Ile Thr Phe Ala
                340                 345                 350

gcg gtg gac aac ccg tcg aac gcc gtg gag tgg gcg ctg gca gag atg     1284
Ala Val Asp Asn Pro Ser Asn Ala Val Glu Trp Ala Leu Ala Glu Met
            355                 360                 365

gtg aac aac ccg gag gtg atg gcg aag gcg atg gag gag ctg gac cgc     1332
Val Asn Asn Pro Glu Val Met Ala Lys Ala Met Glu Glu Leu Asp Arg
        370                 375                 380

gtc gtc gga cgg gag agg cta gtg cag gag tcg gac att ccg aag ctc     1380
Val Val Gly Arg Glu Arg Leu Val Gln Glu Ser Asp Ile Pro Lys Leu
    385                 390                 395

aac tac gtg aag gcc tgc atc cgg gag gct ttc cgt ctg cac ccg gtg     1428
Asn Tyr Val Lys Ala Cys Ile Arg Glu Ala Phe Arg Leu His Pro Val
400                 405                 410                 415

gcg ccc ttc aac gtg ccc cac gtc gcg ctc gcc gac acc acc atc gcc     1476
Ala Pro Phe Asn Val Pro His Val Ala Leu Ala Asp Thr Thr Ile Ala
                420                 425                 430

ggc tac cgc gtt ccc aag ggc agc cac gtg atc ctg agc cgc acg ggg     1524
Gly Tyr Arg Val Pro Lys Gly Ser His Val Ile Leu Ser Arg Thr Gly
            435                 440                 445

ctg ggc cgc aac ccg cgc gtg tgg gac gag ccc ctg cgc ttc tac ccg     1572
Leu Gly Arg Asn Pro Arg Val Trp Asp Glu Pro Leu Arg Phe Tyr Pro
        450                 455                 460

gac cga cac ctc gcc acc gcc gcg tcc gac gtc gcg ctc acc gag aac     1620
Asp Arg His Leu Ala Thr Ala Ala Ser Asp Val Ala Leu Thr Glu Asn
    465                 470                 475

gac ctg cgg ttc atc tcc ttc agc acc ggc cgc cgc ggc tgc atc gcc     1668
Asp Leu Arg Phe Ile Ser Phe Ser Thr Gly Arg Arg Gly Cys Ile Ala
480                 485                 490                 495

gcg tcg ctc ggc acc gcc atg agc gtc atg ctc ttc gga agg ctc ctg     1716
Ala Ser Leu Gly Thr Ala Met Ser Val Met Leu Phe Gly Arg Leu Leu
                500                 505                 510

cag ggg ttc acc tgg agc aag ccc gcc ggg gtg gag gcc gtg gac ctc     1764
Gln Gly Phe Thr Trp Ser Lys Pro Ala Gly Val Glu Ala Val Asp Leu
            515                 520                 525

agc gag tcc aag agc gac acc ttc atg gcc acc ccg ctg gtg ctg cac     1812
Ser Glu Ser Lys Ser Asp Thr Phe Met Ala Thr Pro Leu Val Leu His
        530                 535                 540

gct gag ccc agg ctg ccg gcg cac ctc tac ccg tcc atc tcc atc tga     1860
Ala Glu Pro Arg Leu Pro Ala His Leu Tyr Pro Ser Ile Ser Ile
    545                 550                 555

ttaaacgtac ggccggtcgt cattatattg tatgcatata attaaagacg agcgagcctg   1920

ctggtcacac ttgcattgca tgtatcatca gcagggggct atgcaataag tttttttttt   1980

ccgcgcttga tttcgtggtg ctgtgcgtat tctgcgcaca ccgactgtac gtacgacggc   2040

gttcagcttt gtattgtacc gagttaaaaa gtattattat tattatcatc gacaataat    2099


<210> SEQ ID NO 41
<211> LENGTH: 558
<212> TYPE: PRT
<213> ORGANISM: Sorghum bicolor

<400> SEQUENCE: 41

Met Ala Thr Met Glu Val Glu Ala Ala Ala Ala Thr Val Leu Ala Ala
1               5                   10                  15
```

-continued

```
Pro Leu Leu Ser Ser Ser Ala Ile Leu Lys Leu Leu Leu Phe Val Val
            20                  25                  30

Thr Leu Ser Tyr Leu Ala Arg Ala Leu Arg Arg Pro Arg Lys Ser Thr
        35                  40                  45

Thr Lys Cys Ser Ser Thr Thr Cys Ala Ser Pro Pro Ala Gly Val Gly
    50                  55                  60

Asn Pro Pro Leu Pro Pro Gly Pro Val Pro Trp Pro Val Val Gly Asn
65                  70                  75                  80

Leu Pro Glu Met Leu Leu Asn Lys Pro Ala Phe Arg Trp Ile His Gln
                85                  90                  95

Met Met Arg Glu Met Gly Thr Asp Ile Ala Cys Val Lys Leu Gly Gly
            100                 105                 110

Val His Val Val Ser Ile Thr Cys Pro Glu Ile Ala Arg Glu Val Leu
        115                 120                 125

Arg Lys Gln Asp Ala Asn Phe Ile Ser Arg Pro Leu Thr Phe Ala Ser
    130                 135                 140

Glu Thr Phe Ser Gly Gly Tyr Arg Asn Ala Val Leu Ser Pro Tyr Gly
145                 150                 155                 160

Asp Gln Trp Lys Lys Met Arg Arg Val Leu Thr Ser Glu Ile Ile Cys
                165                 170                 175

Pro Ser Arg His Ala Trp Leu His Asp Lys Arg Thr Asp Glu Ala Asp
            180                 185                 190

Asn Leu Thr Arg Tyr Val Tyr Asn Leu Ala Thr Lys Ala Ala Thr Gly
        195                 200                 205

Asp Val Ala Val Asp Val Arg His Val Ala Arg His Tyr Cys Gly Asn
    210                 215                 220

Val Ile Arg Arg Leu Met Phe Asn Arg Arg Tyr Phe Gly Glu Pro Gln
225                 230                 235                 240

Ala Asp Gly Gly Pro Gly Pro Met Glu Val Leu His Met Asp Ala Val
                245                 250                 255

Phe Thr Ser Leu Gly Leu Leu Tyr Ala Phe Cys Val Ser Asp Tyr Leu
            260                 265                 270

Pro Trp Leu Arg Gly Leu Asp Leu Asp Gly His Glu Lys Ile Val Lys
        275                 280                 285

Glu Ala Asn Val Ala Val Asn Arg Leu His Asp Thr Val Ile Asp Asp
    290                 295                 300

Arg Trp Arg Gln Trp Lys Ser Gly Glu Arg Gln Glu Met Glu Asp Phe
305                 310                 315                 320

Leu Asp Val Leu Ile Thr Leu Lys Asp Ala Gln Gly Asn Pro Leu Leu
                325                 330                 335

Thr Ile Glu Glu Val Lys Ala Gln Ser Gln Asp Ile Thr Phe Ala Ala
            340                 345                 350

Val Asp Asn Pro Ser Asn Ala Val Glu Trp Ala Leu Ala Glu Met Val
        355                 360                 365

Asn Asn Pro Glu Val Met Ala Lys Ala Met Glu Glu Leu Asp Arg Val
    370                 375                 380

Val Gly Arg Glu Arg Leu Val Gln Glu Ser Asp Ile Pro Lys Leu Asn
385                 390                 395                 400

Tyr Val Lys Ala Cys Ile Arg Glu Ala Phe Arg Leu His Pro Val Ala
                405                 410                 415

Pro Phe Asn Val Pro His Val Ala Leu Ala Asp Thr Thr Ile Ala Gly
            420                 425                 430

Tyr Arg Val Pro Lys Gly Ser His Val Ile Leu Ser Arg Thr Gly Leu
```

```
        435                 440                 445

Gly Arg Asn Pro Arg Val Trp Asp Glu Pro Leu Arg Phe Tyr Pro Asp
    450                 455                 460

Arg His Leu Ala Thr Ala Ala Ser Asp Val Ala Leu Thr Glu Asn Asp
465                 470                 475                 480

Leu Arg Phe Ile Ser Phe Ser Thr Gly Arg Arg Gly Cys Ile Ala Ala
                485                 490                 495

Ser Leu Gly Thr Ala Met Ser Val Met Leu Phe Gly Arg Leu Leu Gln
            500                 505                 510

Gly Phe Thr Trp Ser Lys Pro Ala Gly Val Glu Ala Val Asp Leu Ser
        515                 520                 525

Glu Ser Lys Ser Asp Thr Phe Met Ala Thr Pro Leu Val Leu His Ala
    530                 535                 540

Glu Pro Arg Leu Pro Ala His Leu Tyr Pro Ser Ile Ser Ile
545                 550                 555


<210> SEQ ID NO 42
<211> LENGTH: 1965
<212> TYPE: DNA
<213> ORGANISM: Narcissus pseudonarcissus
<220> FEATURE:
<221> NAME/KEY: CDS
<222> LOCATION: (60)..(1772)
<223> OTHER INFORMATION: phytoene desaturase

<400> SEQUENCE: 42

tttagcttct ctcttggcga taaaggtgcc tcgataaagt ggacttggaa gcagcagcc      59

atg agc att gtt ggg tta gtt tct gtt gtt tgt cca agt gga ggc atc      107
Met Ser Ile Val Gly Leu Val Ser Val Val Cys Pro Ser Gly Gly Ile
1               5                   10                  15

aaa aag aga tat ttt tca aag ggg ttg gac aat ttt caa gga ttt aga      155
Lys Lys Arg Tyr Phe Ser Lys Gly Leu Asp Asn Phe Gln Gly Phe Arg
            20                  25                  30

agc agt gaa tgt ctg gga att caa ttg caa gtg ccg gtt cca ttt tat      203
Ser Ser Glu Cys Leu Gly Ile Gln Leu Gln Val Pro Val Pro Phe Tyr
        35                  40                  45

tca gga att aga cag agc ccg aga gcc act tct ttg cag gtg gtt tgc      251
Ser Gly Ile Arg Gln Ser Pro Arg Ala Thr Ser Leu Gln Val Val Cys
    50                  55                  60

aag gat tgc cca agg cct gaa ctt gaa ggt gct gtg aat ttc tta gaa      299
Lys Asp Cys Pro Arg Pro Glu Leu Glu Gly Ala Val Asn Phe Leu Glu
65                  70                  75                  80

gct gcc caa ttg tcc gcc tct ttt cgc agc tcc cca cga cca gaa aaa      347
Ala Ala Gln Leu Ser Ala Ser Phe Arg Ser Ser Pro Arg Pro Glu Lys
                85                  90                  95

ggt ctt gaa gtt gta gtg gtt ggt gca ggc ttg gct gga cta tct act      395
Gly Leu Glu Val Val Val Val Gly Ala Gly Leu Ala Gly Leu Ser Thr
            100                 105                 110

gca aaa tat ctt gct gac gca ggt cat aaa ccg ata tta ctg gag tca      443
Ala Lys Tyr Leu Ala Asp Ala Gly His Lys Pro Ile Leu Leu Glu Ser
        115                 120                 125

aga gat gtt ctg gga ggc aag att gct gct tgg aaa gat aag gat ggg      491
Arg Asp Val Leu Gly Gly Lys Ile Ala Ala Trp Lys Asp Lys Asp Gly
    130                 135                 140

gat tgg tat gag aca ggc ctc cat ata ttc ttt gga gct tat ccc aac      539
Asp Trp Tyr Glu Thr Gly Leu His Ile Phe Phe Gly Ala Tyr Pro Asn
145                 150                 155                 160

gtg cag aat ttg ttt ggg gaa ctt ggg att aac gat cgt ttg caa tgg      587
Val Gln Asn Leu Phe Gly Glu Leu Gly Ile Asn Asp Arg Leu Gln Trp
                165                 170                 175
```

-continued

```
aaa gag cat tct atg att ttt gca atg cca aac aaa cca gga gaa ttc      635
Lys Glu His Ser Met Ile Phe Ala Met Pro Asn Lys Pro Gly Glu Phe
            180                 185                 190

agc cgt ttt gat ttc cca gag gtt ctt ccc gca ccc tta aat gga ata      683
Ser Arg Phe Asp Phe Pro Glu Val Leu Pro Ala Pro Leu Asn Gly Ile
        195                 200                 205

tgg gct atc ttg agg aac aac gaa atg ttg act tgg cct gag aaa gtg      731
Trp Ala Ile Leu Arg Asn Asn Glu Met Leu Thr Trp Pro Glu Lys Val
    210                 215                 220

cga ttt gcc att gga ctt ttg ccg gcc atg gtt gga gga cag gct tat      779
Arg Phe Ala Ile Gly Leu Leu Pro Ala Met Val Gly Gly Gln Ala Tyr
225                 230                 235                 240

gtt gag gct cag gat ggg tta act gtt acc gag tgg atg aga agg cag      827
Val Glu Ala Gln Asp Gly Leu Thr Val Thr Glu Trp Met Arg Arg Gln
                245                 250                 255

ggt gta cct gat cga gtg aat gat gaa gtt ttc ata gca atg tcc aag      875
Gly Val Pro Asp Arg Val Asn Asp Glu Val Phe Ile Ala Met Ser Lys
            260                 265                 270

gct ctt aac ttc ata aat ccg gat gaa ctt tcc atg cag tgt att cta      923
Ala Leu Asn Phe Ile Asn Pro Asp Glu Leu Ser Met Gln Cys Ile Leu
        275                 280                 285

att gct ctt aat cgc ttc ctt cag gaa aaa cac ggg tct aaa atg gca      971
Ile Ala Leu Asn Arg Phe Leu Gln Glu Lys His Gly Ser Lys Met Ala
    290                 295                 300

ttt tta gat ggc aac cct cct gag aga cta tgc atg ccc att gtt gat     1019
Phe Leu Asp Gly Asn Pro Pro Glu Arg Leu Cys Met Pro Ile Val Asp
305                 310                 315                 320

cac att caa tca cta ggt ggt cgt gcc caa ctt aat tca cgt ctg caa     1067
His Ile Gln Ser Leu Gly Gly Arg Ala Gln Leu Asn Ser Arg Leu Gln
                325                 330                 335

aaa att gaa ctt aat cct gat gga acc gtg aaa cac ttt gta ctc ggg     1115
Lys Ile Glu Leu Asn Pro Asp Gly Thr Val Lys His Phe Val Leu Gly
            340                 345                 350

aat ggg aat atc atc act gga gat gct tat gta gtt gcg gca cct gtt     1163
Asn Gly Asn Ile Ile Thr Gly Asp Ala Tyr Val Val Ala Ala Pro Val
        355                 360                 365

gat ata ttg aag ctt ctg ttg cct caa gaa tgg agg gaa att cct tat     1211
Asp Ile Leu Lys Leu Leu Leu Pro Gln Glu Trp Arg Glu Ile Pro Tyr
    370                 375                 380

ttc cag aaa ttg gat aaa tta gta gga gtt cct gtg att aat gtg cat     1259
Phe Gln Lys Leu Asp Lys Leu Val Gly Val Pro Val Ile Asn Val His
385                 390                 395                 400

ata tgg ttt gac agg aaa ctg aaa aac act tac gat cac ctc ctt ttc     1307
Ile Trp Phe Asp Arg Lys Leu Lys Asn Thr Tyr Asp His Leu Leu Phe
                405                 410                 415

acg agg agc ccc ctg cta agt gtc tat gct gac atg tca gta acg tgc     1355
Thr Arg Ser Pro Leu Leu Ser Val Tyr Ala Asp Met Ser Val Thr Cys
            420                 425                 430

aag gaa tat tat gac cct aac cgc tct atg cta gag tta gtg ttt gct     1403
Lys Glu Tyr Tyr Asp Pro Asn Arg Ser Met Leu Glu Leu Val Phe Ala
        435                 440                 445

cct gca gag gaa tgg atc tca cgc agt gac agt gaa ata att gaa cgt     1451
Pro Ala Glu Glu Trp Ile Ser Arg Ser Asp Ser Glu Ile Ile Glu Arg
    450                 455                 460

aca atg aag gaa ctt gca aaa tta ttc ccc gac gaa att gct gca gat     1499
Thr Met Lys Glu Leu Ala Lys Leu Phe Pro Asp Glu Ile Ala Ala Asp
465                 470                 475                 480

cag agt aaa gcc aaa att ctg aag tat cat gtt gtc aaa aca cca agg     1547
Gln Ser Lys Ala Lys Ile Leu Lys Tyr His Val Val Lys Thr Pro Arg
                485                 490                 495
```

```
tct gtt tac aaa acc ata ccc gac tgt gag cca tgt cgt cct tta caa     1595
Ser Val Tyr Lys Thr Ile Pro Asp Cys Glu Pro Cys Arg Pro Leu Gln
            500                 505                 510

aga tcc cca att gaa ggg ttt tat ttg gct ggt gat tac aca aat cag     1643
Arg Ser Pro Ile Glu Gly Phe Tyr Leu Ala Gly Asp Tyr Thr Asn Gln
        515                 520                 525

aaa tat tta gct tct atg gag ggt gct gtt ttg tct ggg aag ctt tgt     1691
Lys Tyr Leu Ala Ser Met Glu Gly Ala Val Leu Ser Gly Lys Leu Cys
    530                 535                 540

gca cag tct att gta cag gat tac gag ttg ctc gtt cgt cga agc aag     1739
Ala Gln Ser Ile Val Gln Asp Tyr Glu Leu Leu Val Arg Arg Ser Lys
545                 550                 555                 560

aaa gcg tct aca gcc gag atg act gtt gtc tag ttgaaacttg aaaacccaat   1792
Lys Ala Ser Thr Ala Glu Met Thr Val Val
            565                 570

acagaatttt tttcggggtc acttgtgttg ttgattcctc catatagaag atgatcatgt   1852

ctgtaacttg ttaaaatact cttgagttat agaaaattag ttataggttg tattctcaga   1912

tattgttcag aaatgaaagc taggtccaat tctgtcaaaa aaaaaaaaaa aaa          1965
```

<210> SEQ ID NO 43
<211> LENGTH: 570
<212> TYPE: PRT
<213> ORGANISM: Narcissus pseudonarcissus

<400> SEQUENCE: 43

```
Met Ser Ile Val Gly Leu Val Ser Val Val Cys Pro Ser Gly Gly Ile
1               5                   10                  15

Lys Lys Arg Tyr Phe Ser Lys Gly Leu Asp Asn Phe Gln Gly Phe Arg
            20                  25                  30

Ser Ser Glu Cys Leu Gly Ile Gln Leu Gln Val Pro Val Pro Phe Tyr
        35                  40                  45

Ser Gly Ile Arg Gln Ser Pro Arg Ala Thr Ser Leu Gln Val Val Cys
    50                  55                  60

Lys Asp Cys Pro Arg Pro Glu Leu Glu Gly Ala Val Asn Phe Leu Glu
65                  70                  75                  80

Ala Ala Gln Leu Ser Ala Ser Phe Arg Ser Ser Pro Arg Pro Glu Lys
                85                  90                  95

Gly Leu Glu Val Val Val Val Gly Ala Gly Leu Ala Gly Leu Ser Thr
            100                 105                 110

Ala Lys Tyr Leu Ala Asp Ala Gly His Lys Pro Ile Leu Leu Glu Ser
        115                 120                 125

Arg Asp Val Leu Gly Gly Lys Ile Ala Ala Trp Lys Asp Lys Asp Gly
    130                 135                 140

Asp Trp Tyr Glu Thr Gly Leu His Ile Phe Phe Gly Ala Tyr Pro Asn
145                 150                 155                 160

Val Gln Asn Leu Phe Gly Glu Leu Gly Ile Asn Asp Arg Leu Gln Trp
                165                 170                 175

Lys Glu His Ser Met Ile Phe Ala Met Pro Asn Lys Pro Gly Glu Phe
            180                 185                 190

Ser Arg Phe Asp Phe Pro Glu Val Leu Pro Ala Pro Leu Asn Gly Ile
        195                 200                 205

Trp Ala Ile Leu Arg Asn Asn Glu Met Leu Thr Trp Pro Glu Lys Val
    210                 215                 220

Arg Phe Ala Ile Gly Leu Leu Pro Ala Met Val Gly Gly Gln Ala Tyr
225                 230                 235                 240
```

```
Val Glu Ala Gln Asp Gly Leu Thr Val Thr Glu Trp Met Arg Arg Gln
                245                 250                 255

Gly Val Pro Asp Arg Val Asn Asp Glu Val Phe Ile Ala Met Ser Lys
            260                 265                 270

Ala Leu Asn Phe Ile Asn Pro Asp Glu Leu Ser Met Gln Cys Ile Leu
        275                 280                 285

Ile Ala Leu Asn Arg Phe Leu Gln Glu Lys His Gly Ser Lys Met Ala
    290                 295                 300

Phe Leu Asp Gly Asn Pro Pro Glu Arg Leu Cys Met Pro Ile Val Asp
305                 310                 315                 320

His Ile Gln Ser Leu Gly Gly Arg Ala Gln Leu Asn Ser Arg Leu Gln
                325                 330                 335

Lys Ile Glu Leu Asn Pro Asp Gly Thr Val Lys His Phe Val Leu Gly
            340                 345                 350

Asn Gly Asn Ile Ile Thr Gly Asp Ala Tyr Val Val Ala Ala Pro Val
        355                 360                 365

Asp Ile Leu Lys Leu Leu Leu Pro Gln Glu Trp Arg Glu Ile Pro Tyr
    370                 375                 380

Phe Gln Lys Leu Asp Lys Leu Val Gly Val Pro Val Ile Asn Val His
385                 390                 395                 400

Ile Trp Phe Asp Arg Lys Leu Lys Asn Thr Tyr Asp His Leu Leu Phe
                405                 410                 415

Thr Arg Ser Pro Leu Leu Ser Val Tyr Ala Asp Met Ser Val Thr Cys
            420                 425                 430

Lys Glu Tyr Tyr Asp Pro Asn Arg Ser Met Leu Glu Leu Val Phe Ala
        435                 440                 445

Pro Ala Glu Glu Trp Ile Ser Arg Ser Asp Ser Glu Ile Ile Glu Arg
    450                 455                 460

Thr Met Lys Glu Leu Ala Lys Leu Phe Pro Asp Glu Ile Ala Ala Asp
465                 470                 475                 480

Gln Ser Lys Ala Lys Ile Leu Lys Tyr His Val Val Lys Thr Pro Arg
                485                 490                 495

Ser Val Tyr Lys Thr Ile Pro Asp Cys Glu Pro Cys Arg Pro Leu Gln
            500                 505                 510

Arg Ser Pro Ile Glu Gly Phe Tyr Leu Ala Gly Asp Tyr Thr Asn Gln
        515                 520                 525

Lys Tyr Leu Ala Ser Met Glu Gly Ala Val Leu Ser Gly Lys Leu Cys
    530                 535                 540

Ala Gln Ser Ile Val Gln Asp Tyr Glu Leu Leu Val Arg Arg Ser Lys
545                 550                 555                 560

Lys Ala Ser Thr Ala Glu Met Thr Val Val
                565                 570


<210> SEQ ID NO 44
<211> LENGTH: 1915
<212> TYPE: DNA
<213> ORGANISM: Arabidopsis thaliana
<220> FEATURE:
<221> NAME/KEY: CDS
<222> LOCATION: (23)..(1567)
<223> OTHER INFORMATION: monosaccharide transporter

<400> SEQUENCE: 44

ttgagtgtct ctctaggtaa ac atg gta gca gaa gaa gca aga aaa gaa gcc      52
                         Met Val Ala Glu Glu Ala Arg Lys Glu Ala
                         1               5                   10

atg gct aaa tca gta tct ggc ggg aag att act tat ttt gtg gtg gct      100
```

-continued

```
Met Ala Lys Ser Val Ser Gly Gly Lys Ile Thr Tyr Phe Val Val Ala
                15                  20                  25

tca tgt gtc atg gcc gcc atg ggc ggt gtc atc ttc ggc tac gac atc      148
Ser Cys Val Met Ala Ala Met Gly Gly Val Ile Phe Gly Tyr Asp Ile
            30                  35                  40

ggg gtt tca ggt gga gtg atg tca atg ggg cca ttt cta aaa aga ttt      196
Gly Val Ser Gly Gly Val Met Ser Met Gly Pro Phe Leu Lys Arg Phe
        45                  50                  55

ttc cca aaa gtg tat aag ctc caa gaa gaa gat aga aga aga aga ggc      244
Phe Pro Lys Val Tyr Lys Leu Gln Glu Glu Asp Arg Arg Arg Arg Gly
    60                  65                  70

aat agc aat aac cac tac tgc ctt ttc aat agc caa ctt ctt aca tcc      292
Asn Ser Asn Asn His Tyr Cys Leu Phe Asn Ser Gln Leu Leu Thr Ser
75                  80                  85                  90

ttc aca tct tct cta tac gtt tcc ggt ctc atc gct act ctg tta gct      340
Phe Thr Ser Ser Leu Tyr Val Ser Gly Leu Ile Ala Thr Leu Leu Ala
                95                  100                 105

tcg tcc gtg act cgt tca tgg ggt cgc aag ccc tct ata ttt ctt ggc      388
Ser Ser Val Thr Arg Ser Trp Gly Arg Lys Pro Ser Ile Phe Leu Gly
            110                 115                 120

ggt gtg tcc ttt ctc gcc ggc gct gct ctt ggt ggc tct gct caa aac      436
Gly Val Ser Phe Leu Ala Gly Ala Ala Leu Gly Gly Ser Ala Gln Asn
        125                 130                 135

gtt gct atg ctc att att gcg cgt ctc ttg ctc ggc gta gga gtt gga      484
Val Ala Met Leu Ile Ile Ala Arg Leu Leu Leu Gly Val Gly Val Gly
    140                 145                 150

ttc gct aac cag tcg gtt cct ctg tat ctc tcc gag atg gcg ccg gca      532
Phe Ala Asn Gln Ser Val Pro Leu Tyr Leu Ser Glu Met Ala Pro Ala
155                 160                 165                 170

aaa tac aga gga gca atc agc aat ggt ttc cag ctc tgt atc gga att      580
Lys Tyr Arg Gly Ala Ile Ser Asn Gly Phe Gln Leu Cys Ile Gly Ile
                175                 180                 185

gga ttt cta tct gca aat gta ata aac tac gaa acc caa aat atc aaa      628
Gly Phe Leu Ser Ala Asn Val Ile Asn Tyr Glu Thr Gln Asn Ile Lys
            190                 195                 200

cat ggt tgg aga atc tct tta gcc aca gct gca ata cct gct tca atc      676
His Gly Trp Arg Ile Ser Leu Ala Thr Ala Ala Ile Pro Ala Ser Ile
        205                 210                 215

ctc act tta gga tca ctg ttt ctc ccg gaa acg ccg aat agt atc atc      724
Leu Thr Leu Gly Ser Leu Phe Leu Pro Glu Thr Pro Asn Ser Ile Ile
    220                 225                 230

cag acc acc gga gat gtt cac aag acc gag ctt atg ctt cgc cgt gtc      772
Gln Thr Thr Gly Asp Val His Lys Thr Glu Leu Met Leu Arg Arg Val
235                 240                 245                 250

cgt gga act aac gac gtt caa gat gag ctt act gat ctc gtt gaa gcg      820
Arg Gly Thr Asn Asp Val Gln Asp Glu Leu Thr Asp Leu Val Glu Ala
                255                 260                 265

agt tct ggt tct gat aca gat tca aac gcg ttt ttg aaa ctg ctt caa      868
Ser Ser Gly Ser Asp Thr Asp Ser Asn Ala Phe Leu Lys Leu Leu Gln
            270                 275                 280

aga aaa tat agg cct gag tta gtg atg gct ttg gtg ata cct ttc ttt      916
Arg Lys Tyr Arg Pro Glu Leu Val Met Ala Leu Val Ile Pro Phe Phe
        285                 290                 295

cag caa gtt act gga atc aat gtt gtt gct ttc tac gca ccg gtt ttg      964
Gln Gln Val Thr Gly Ile Asn Val Val Ala Phe Tyr Ala Pro Val Leu
    300                 305                 310

tat aga acc gtt ggg ttt gga gag agt ggt tcg ttg atg tcg acc ctc     1012
Tyr Arg Thr Val Gly Phe Gly Glu Ser Gly Ser Leu Met Ser Thr Leu
315                 320                 325                 330

gtg act gga atc gtg gga acc tcg tcg acg ttg ttg tcg atg ctt gtc     1060
```

-continued

```
Val Thr Gly Ile Val Gly Thr Ser Ser Thr Leu Leu Ser Met Leu Val
                335                 340                 345

gtt gac aga atc ggt aga aag act ctg ttt ttg att gga ggg tta cag     1108
Val Asp Arg Ile Gly Arg Lys Thr Leu Phe Leu Ile Gly Gly Leu Gln
            350                 355                 360

atg ctc gtg tcg caa gtt acc att ggt gtg atc gtt atg gtg gct gat     1156
Met Leu Val Ser Gln Val Thr Ile Gly Val Ile Val Met Val Ala Asp
        365                 370                 375

gtt cac gac ggt gtg atc aag gaa ggg tat ggt tac gcg gtt gtg gtt     1204
Val His Asp Gly Val Ile Lys Glu Gly Tyr Gly Tyr Ala Val Val Val
    380                 385                 390

ttg gtg tgt gtc tac gtg gcc ggg ttt ggt tgg tct tgg ggt cca tta     1252
Leu Val Cys Val Tyr Val Ala Gly Phe Gly Trp Ser Trp Gly Pro Leu
395                 400                 405                 410

gga tgg ctt gta ccg agt gag att ttt ccg ttg gag ata aga tcg gtg     1300
Gly Trp Leu Val Pro Ser Glu Ile Phe Pro Leu Glu Ile Arg Ser Val
                415                 420                 425

gcg cag agt gta act gtg gca gtg agt ttt gtg ttt act ttt gcg gtg     1348
Ala Gln Ser Val Thr Val Ala Val Ser Phe Val Phe Thr Phe Ala Val
            430                 435                 440

gct caa agt gca cca ccg atg ttg tgt aag ttt cga gct ggg att ttc     1396
Ala Gln Ser Ala Pro Pro Met Leu Cys Lys Phe Arg Ala Gly Ile Phe
        445                 450                 455

ttc ttt tat gga ggg tgg ttg gtg gta atg acg gta gcg gtg cag ctg     1444
Phe Phe Tyr Gly Gly Trp Leu Val Val Met Thr Val Ala Val Gln Leu
    460                 465                 470

ttt ttg ccg gag act aag aat gtt cca atc gag aag gtg gtt gga ctt     1492
Phe Leu Pro Glu Thr Lys Asn Val Pro Ile Glu Lys Val Val Gly Leu
475                 480                 485                 490

tgg gag aag cat tgg ttt tgg agg aga atg acg agc aag cgt gat atc     1540
Trp Glu Lys His Trp Phe Trp Arg Arg Met Thr Ser Lys Arg Asp Ile
                495                 500                 505

caa gaa acc acc att ctt agc cat tga aaacaataaa aaaaccagca          1587
Gln Glu Thr Thr Ile Leu Ser His
            510

cctcatgatt tgagatgaga cgcatctttt gttgccaaaa aaattattgc atataagttt   1647

taaaatttc aaagttcaaa ctaaattaag gatatttttt tactattcac gtaacaataa    1707

tcaaatcaca tgatccaaga ttcgattatt gttcaaatta ttttgtaaat ttagccatag   1767

tttcattttt tcacttatat gtttgtgaaa taacgatttg tgtttggaat taaaattagg   1827

ggtgttttat aaatatagta aaactaggat agtgataatg taatatattg aacgttaaag   1887

gacaaagatg ggaaaaaaaa aaaaaaaa                                       1915


<210> SEQ ID NO 45
<211> LENGTH: 514
<212> TYPE: PRT
<213> ORGANISM: Arabidopsis thaliana

<400> SEQUENCE: 45

Met Val Ala Glu Glu Ala Arg Lys Glu Ala Met Ala Lys Ser Val Ser
1               5                   10                  15

Gly Gly Lys Ile Thr Tyr Phe Val Val Ala Ser Cys Val Met Ala Ala
            20                  25                  30

Met Gly Gly Val Ile Phe Gly Tyr Asp Ile Gly Val Ser Gly Gly Val
        35                  40                  45

Met Ser Met Gly Pro Phe Leu Lys Arg Phe Phe Pro Lys Val Tyr Lys
    50                  55                  60

Leu Gln Glu Glu Asp Arg Arg Arg Arg Gly Asn Ser Asn Asn His Tyr
```

-continued

```
65                  70                  75                  80

Cys Leu Phe Asn Ser Gln Leu Leu Thr Ser Phe Thr Ser Ser Leu Tyr
                85                  90                  95

Val Ser Gly Leu Ile Ala Thr Leu Leu Ala Ser Ser Val Thr Arg Ser
            100                 105                 110

Trp Gly Arg Lys Pro Ser Ile Phe Leu Gly Gly Val Ser Phe Leu Ala
        115                 120                 125

Gly Ala Ala Leu Gly Gly Ser Ala Gln Asn Val Ala Met Leu Ile Ile
    130                 135                 140

Ala Arg Leu Leu Leu Gly Val Gly Val Gly Phe Ala Asn Gln Ser Val
145                 150                 155                 160

Pro Leu Tyr Leu Ser Glu Met Ala Pro Ala Lys Tyr Arg Gly Ala Ile
                165                 170                 175

Ser Asn Gly Phe Gln Leu Cys Ile Gly Ile Gly Phe Leu Ser Ala Asn
            180                 185                 190

Val Ile Asn Tyr Glu Thr Gln Asn Ile Lys His Gly Trp Arg Ile Ser
        195                 200                 205

Leu Ala Thr Ala Ala Ile Pro Ala Ser Ile Leu Thr Leu Gly Ser Leu
    210                 215                 220

Phe Leu Pro Glu Thr Pro Asn Ser Ile Ile Gln Thr Thr Gly Asp Val
225                 230                 235                 240

His Lys Thr Glu Leu Met Leu Arg Arg Val Arg Gly Thr Asn Asp Val
                245                 250                 255

Gln Asp Glu Leu Thr Asp Leu Val Glu Ala Ser Ser Gly Ser Asp Thr
            260                 265                 270

Asp Ser Asn Ala Phe Leu Lys Leu Leu Gln Arg Lys Tyr Arg Pro Glu
        275                 280                 285

Leu Val Met Ala Leu Val Ile Pro Phe Phe Gln Gln Val Thr Gly Ile
    290                 295                 300

Asn Val Val Ala Phe Tyr Ala Pro Val Leu Tyr Arg Thr Val Gly Phe
305                 310                 315                 320

Gly Glu Ser Gly Ser Leu Met Ser Thr Leu Val Thr Gly Ile Val Gly
                325                 330                 335

Thr Ser Ser Thr Leu Leu Ser Met Leu Val Val Asp Arg Ile Gly Arg
            340                 345                 350

Lys Thr Leu Phe Leu Ile Gly Gly Leu Gln Met Leu Val Ser Gln Val
        355                 360                 365

Thr Ile Gly Val Ile Val Met Val Ala Asp Val His Asp Gly Val Ile
    370                 375                 380

Lys Glu Gly Tyr Gly Tyr Ala Val Val Val Leu Val Cys Val Tyr Val
385                 390                 395                 400

Ala Gly Phe Gly Trp Ser Trp Gly Pro Leu Gly Trp Leu Val Pro Ser
                405                 410                 415

Glu Ile Phe Pro Leu Glu Ile Arg Ser Val Ala Gln Ser Val Thr Val
            420                 425                 430

Ala Val Ser Phe Val Phe Thr Phe Ala Val Ala Gln Ser Ala Pro Pro
        435                 440                 445

Met Leu Cys Lys Phe Arg Ala Gly Ile Phe Phe Phe Tyr Gly Gly Trp
    450                 455                 460

Leu Val Val Met Thr Val Ala Val Gln Leu Phe Leu Pro Glu Thr Lys
465                 470                 475                 480

Asn Val Pro Ile Glu Lys Val Val Gly Leu Trp Glu Lys His Trp Phe
                485                 490                 495
```

-continued

Trp Arg Arg Met Thr Ser Lys Arg Asp Ile Gln Glu Thr Thr Ile Leu
500 505 510

Ser His

<210> SEQ ID NO 46
<211> LENGTH: 1344
<212> TYPE: DNA
<213> ORGANISM: Caenorhabditis elegans
<220> FEATURE:
<221> NAME/KEY: CDS
<222> LOCATION: (1)..(1344)
<223> OTHER INFORMATION: delta 5 fatty acid desaturase

<400> SEQUENCE: 46 atg gta tta cga gag caa gag cat gag cca ttc ttc att aaa att gat 48
Met Val Leu Arg Glu Gln Glu His Glu Pro Phe Phe Ile Lys Ile Asp
1 5 10 15 gga aaa tgg tgt caa att gac gat gct gtc ctg aga tca cat cca ggt 96
Gly Lys Trp Cys Gln Ile Asp Asp Ala Val Leu Arg Ser His Pro Gly
20 25 30 ggt agt gca att act acc tat aaa aat atg gat gcc act acc gta ttc 144
Gly Ser Ala Ile Thr Thr Tyr Lys Asn Met Asp Ala Thr Thr Val Phe
35 40 45 cac aca ttc cat act ggt tct aaa gaa gcg tat caa tgg ctg aca gaa 192
His Thr Phe His Thr Gly Ser Lys Glu Ala Tyr Gln Trp Leu Thr Glu
50 55 60 ttg aaa aaa gag tgc cct aca caa gaa cca gag atc cca gat att aag 240
Leu Lys Lys Glu Cys Pro Thr Gln Glu Pro Glu Ile Pro Asp Ile Lys
65 70 75 80 gat gac cca atc aaa gga att gat gat gtg aac atg gga act ttc aat 288
Asp Asp Pro Ile Lys Gly Ile Asp Asp Val Asn Met Gly Thr Phe Asn
85 90 95 att tct gag aaa cga tct gcc caa ata aat aaa agt ttc act gat cta 336
Ile Ser Glu Lys Arg Ser Ala Gln Ile Asn Lys Ser Phe Thr Asp Leu
100 105 110 cgt atg cga gtt cgt gca gaa gga ctt atg gat gga tct cct ttg ttc 384
Arg Met Arg Val Arg Ala Glu Gly Leu Met Asp Gly Ser Pro Leu Phe
115 120 125 tac att aga aaa att ctt gaa aca atc ttc aca att ctt ttt gca ttc 432
Tyr Ile Arg Lys Ile Leu Glu Thr Ile Phe Thr Ile Leu Phe Ala Phe
130 135 140 tac ctt caa tac cac aca tat tat ctt cca tca gct att cta atg gga 480
Tyr Leu Gln Tyr His Thr Tyr Tyr Leu Pro Ser Ala Ile Leu Met Gly
145 150 155 160 gtt gcg tgg caa caa ttg gga tgg tta atc cat gaa ttc gca cat cat 528
Val Ala Trp Gln Gln Leu Gly Trp Leu Ile His Glu Phe Ala His His
165 170 175 cag ttg ttc aaa aac aga tac tac aat gat ttg gcc agc tat ttc gtt 576
Gln Leu Phe Lys Asn Arg Tyr Tyr Asn Asp Leu Ala Ser Tyr Phe Val
180 185 190 gga aac ttt tta caa gga ttc tca tct ggt ggt tgg aaa gag cag cac 624
Gly Asn Phe Leu Gln Gly Phe Ser Ser Gly Gly Trp Lys Glu Gln His
195 200 205 aat gtg cat cac gca gcc aca aat gtt gtt gga cga gac gga gat ctt 672
Asn Val His His Ala Ala Thr Asn Val Val Gly Arg Asp Gly Asp Leu
210 215 220 gat tta gtc cca ttc tat gct aca gtg gca gaa cat ctc aac aat tat 720
Asp Leu Val Pro Phe Tyr Ala Thr Val Ala Glu His Leu Asn Asn Tyr
225 230 235 240 tct cag gat tca tgg gtt atg act cta ttc aga tgg caa cat gtt cat 768
Ser Gln Asp Ser Trp Val Met Thr Leu Phe Arg Trp Gln His Val His
245 250 255

```
tgg aca ttc atg tta cca ttc ctc cgt ctc tcg tgg ctt ctt cag tca      816
Trp Thr Phe Met Leu Pro Phe Leu Arg Leu Ser Trp Leu Leu Gln Ser
            260                 265                 270

atc att ttt gtt agt cag atg cca act cat tat tat gac tat tac aga      864
Ile Ile Phe Val Ser Gln Met Pro Thr His Tyr Tyr Asp Tyr Tyr Arg
        275                 280                 285

aat act gcg att tat gaa cag gtt ggt ctc tct ttg cac tgg gct tgg      912
Asn Thr Ala Ile Tyr Glu Gln Val Gly Leu Ser Leu His Trp Ala Trp
    290                 295                 300

tca ttg ggt caa ttg tat ttc cta ccc gat tgg tca act aga ata atg      960
Ser Leu Gly Gln Leu Tyr Phe Leu Pro Asp Trp Ser Thr Arg Ile Met
305                 310                 315                 320

ttc ttc ctt gtt tct cat ctt gtt gga ggt ttc ctg ctc tct cat gta     1008
Phe Phe Leu Val Ser His Leu Val Gly Gly Phe Leu Leu Ser His Val
                325                 330                 335

gtt act ttc aat cat tat tca gtg gag aag ttt gca ttg agc tcg aac     1056
Val Thr Phe Asn His Tyr Ser Val Glu Lys Phe Ala Leu Ser Ser Asn
            340                 345                 350

atc atg tca aat tac gct tgt ctt caa atc atg acc aca aga aat atg     1104
Ile Met Ser Asn Tyr Ala Cys Leu Gln Ile Met Thr Thr Arg Asn Met
        355                 360                 365

aga cct gga aga ttc att gac tgg ctt tgg gga ggt ctt aac tat cag     1152
Arg Pro Gly Arg Phe Ile Asp Trp Leu Trp Gly Gly Leu Asn Tyr Gln
    370                 375                 380

att gag cac cat ctt ttc cca acg atg cca cga cac aac ttg aac act     1200
Ile Glu His His Leu Phe Pro Thr Met Pro Arg His Asn Leu Asn Thr
385                 390                 395                 400

gtt atg cca ctt gtt aag gag ttt gca gca gca aat ggt tta cca tac     1248
Val Met Pro Leu Val Lys Glu Phe Ala Ala Ala Asn Gly Leu Pro Tyr
                405                 410                 415

atg gtc gac gat tat ttc aca gga ttc tgg ctt gaa att gag caa ttc     1296
Met Val Asp Asp Tyr Phe Thr Gly Phe Trp Leu Glu Ile Glu Gln Phe
            420                 425                 430

cga aat att gca aat gtt gct gct aaa ttg act aaa aag att gcc tag     1344
Arg Asn Ile Ala Asn Val Ala Ala Lys Leu Thr Lys Lys Ile Ala
        435                 440                 445


<210> SEQ ID NO 47
<211> LENGTH: 447
<212> TYPE: PRT
<213> ORGANISM: Caenorhabditis elegans

<400> SEQUENCE: 47

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125
```

```
Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
                165                 170                 175

Gln Leu Phe Lys Asn Arg Tyr Tyr Asn Asp Leu Ala Ser Tyr Phe Val
            180                 185                 190

Gly Asn Phe Leu Gln Gly Phe Ser Ser Gly Gly Trp Lys Glu Gln His
        195                 200                 205

Asn Val His His Ala Ala Thr Asn Val Val Gly Arg Asp Gly Asp Leu
    210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
                245                 250                 255

Trp Thr Phe Met Leu Pro Phe Leu Arg Leu Ser Trp Leu Leu Gln Ser
            260                 265                 270

Ile Ile Phe Val Ser Gln Met Pro Thr His Tyr Tyr Asp Tyr Tyr Arg
        275                 280                 285

Asn Thr Ala Ile Tyr Glu Gln Val Gly Leu Ser Leu His Trp Ala Trp
    290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Leu Ser His Val
                325                 330                 335

Val Thr Phe Asn His Tyr Ser Val Glu Lys Phe Ala Leu Ser Ser Asn
            340                 345                 350

Ile Met Ser Asn Tyr Ala Cys Leu Gln Ile Met Thr Thr Arg Asn Met
        355                 360                 365

Arg Pro Gly Arg Phe Ile Asp Trp Leu Trp Gly Gly Leu Asn Tyr Gln
    370                 375                 380

Ile Glu His His Leu Phe Pro Thr Met Pro Arg His Asn Leu Asn Thr
385                 390                 395                 400

Val Met Pro Leu Val Lys Glu Phe Ala Ala Ala Asn Gly Leu Pro Tyr
                405                 410                 415

Met Val Asp Asp Tyr Phe Thr Gly Phe Trp Leu Glu Ile Glu Gln Phe
            420                 425                 430

Arg Asn Ile Ala Asn Val Ala Ala Lys Leu Thr Lys Lys Ile Ala
        435                 440                 445
```

```
<210> SEQ ID NO 48
<211> LENGTH: 570
<212> TYPE: DNA
<213> ORGANISM: Bertholletia excelsa
<220> FEATURE:
<221> NAME/KEY: CDS
<222> LOCATION: (8)..(187)
<223> OTHER INFORMATION: Bertholletia excelsa gene for 2S albumin
<220> FEATURE:
<221> NAME/KEY: CDS
<222> LOCATION: (277)..(534)
<223> OTHER INFORMATION: Bertholletia excelsa gene for 2S albumin

<400> SEQUENCE: 48

aatcacc atg gcg aag att tca gtt gcg gca gca gca ctc ctt gtc ctc       49
        Met Ala Lys Ile Ser Val Ala Ala Ala Ala Leu Leu Val Leu
        1               5                   10
```

```
atg gcc ctc ggc cac gcc acc gcc ttc cgg gcc acc gtc acc acc aca       97
Met Ala Leu Gly His Ala Thr Ala Phe Arg Ala Thr Val Thr Thr Thr
15                  20                  25                  30

gtg gtg gag gag gag aac cag gag gag tgt cgc gag cag atg cag aga      145
Val Val Glu Glu Glu Asn Gln Glu Glu Cys Arg Glu Gln Met Gln Arg
                35                  40                  45

cag cag atg ctc agc cac tgc cgg atg tac atg aga cag cag              187
Gln Gln Met Leu Ser His Cys Arg Met Tyr Met Arg Gln Gln
            50                  55                  60

gttagttatt atacaaaaga atatggaatc tcttttatat ttcttaattt aatgccttat    247

atcttgatgc gaaatgaacc ctggtgcag atg gag gag agc ccg tac cag acc      300
                                Met Glu Glu Ser Pro Tyr Gln Thr
                                65

atg ccc agg cgg gga atg gag ccg cat atg agc gag tgc tgc gag cag      348
Met Pro Arg Arg Gly Met Glu Pro His Met Ser Glu Cys Cys Glu Gln
    70                  75                  80

ctg gag ggg atg gac gag agc tgc aga tgc gaa ggc tta agg atg atg      396
Leu Glu Gly Met Asp Glu Ser Cys Arg Cys Glu Gly Leu Arg Met Met
85                  90                  95                  100

atg agg atg atg caa cag aag gag atg caa ccc cga ggg gag cag atg      444
Met Arg Met Met Gln Gln Lys Glu Met Gln Pro Arg Gly Glu Gln Met
                105                 110                 115

cga agg atg atg agg ctg gcc gag aat atc cct tcc cgc tgc aac ctc      492
Arg Arg Met Met Arg Leu Ala Glu Asn Ile Pro Ser Arg Cys Asn Leu
            120                 125                 130

agt ccc atg aga tgc ccc atg ggt ggc tcc att gcc ggg ttc              534
Ser Pro Met Arg Cys Pro Met Gly Gly Ser Ile Ala Gly Phe
        135                 140                 145

tgaatctgcc actagccagt gctgtaaatg ttaata                              570


<210> SEQ ID NO 49
<211> LENGTH: 146
<212> TYPE: PRT
<213> ORGANISM: Bertholletia excelsa

<400> SEQUENCE: 49

Met Ala Lys Ile Ser Val Ala Ala Ala Ala Leu Leu Val Leu Met Ala
1               5                   10                  15

Leu Gly His Ala Thr Ala Phe Arg Ala Thr Val Thr Thr Thr Val Val
            20                  25                  30

Glu Glu Glu Asn Gln Glu Glu Cys Arg Glu Gln Met Gln Arg Gln Gln
        35                  40                  45

Met Leu Ser His Cys Arg Met Tyr Met Arg Gln Gln Met Glu Glu Ser
    50                  55                  60

Pro Tyr Gln Thr Met Pro Arg Arg Gly Met Glu Pro His Met Ser Glu
65                  70                  75                  80

Cys Cys Glu Gln Leu Glu Gly Met Asp Glu Ser Cys Arg Cys Glu Gly
                85                  90                  95

Leu Arg Met Met Met Arg Met Met Gln Gln Lys Glu Met Gln Pro Arg
            100                 105                 110

Gly Glu Gln Met Arg Arg Met Met Arg Leu Ala Glu Asn Ile Pro Ser
        115                 120                 125

Arg Cys Asn Leu Ser Pro Met Arg Cys Pro Met Gly Gly Ser Ile Ala
    130                 135                 140

Gly Phe
145
```

<210> SEQ ID NO 50
<211> LENGTH: 2012
<212> TYPE: DNA
<213> ORGANISM: Physcomitrella patens
<220> FEATURE:
<221> NAME/KEY: CDS
<222> LOCATION: (319)..(1896)
<223> OTHER INFORMATION: delta6-acyl-lipid desaturase

<400> SEQUENCE: 50

```
ccgagtcgcg gatcagccat cgcccgccca gggccgcctg cattgtgtgg gacggtgttg      60

gaggaggagg cagatgcgcg ggcgttggtg gagtcgtcat ccgaggatct actgcggcaa     120

tacctccggg ttttggagcg ggcaaactct gttgcggctc ggaaggctat aggttcggca     180

ggagactgtt gattttatgt cgggggcatt gccattgtgg agagcggggg agactcagga     240

tctgtgagtg tgcgtgcagc gccccgactg ccgcagagcg tctgtgtatg acgaggttgt     300

tgtggagcgg cttttgaa atg gta ttc gcg ggc ggt gga ctt cag cag ggc       351
                    Met Val Phe Ala Gly Gly Gly Leu Gln Gln Gly
                    1               5                   10

tct ctc gaa gaa aac atc gac gtc gag cac att gcc agt atg tct ctc       399
Ser Leu Glu Glu Asn Ile Asp Val Glu His Ile Ala Ser Met Ser Leu
            15                  20                  25

ttc agc gac ttc ttc agt tat gtg tct tca act gtt ggt tcg tgg agc       447
Phe Ser Asp Phe Phe Ser Tyr Val Ser Ser Thr Val Gly Ser Trp Ser
        30                  35                  40

gta cac agt ata caa cct ttg aag cgc ctg acg agt aag aag cgt gtt       495
Val His Ser Ile Gln Pro Leu Lys Arg Leu Thr Ser Lys Lys Arg Val
    45                  50                  55

tcg gaa agc gct gcc gtg caa tgt ata tca gct gaa gtt cag aga aat       543
Ser Glu Ser Ala Ala Val Gln Cys Ile Ser Ala Glu Val Gln Arg Asn
60                  65                  70                  75

tcg agt acc cag gga act gcg gag gca ctc gca gaa tca gtc gtg aag       591
Ser Ser Thr Gln Gly Thr Ala Glu Ala Leu Ala Glu Ser Val Val Lys
                80                  85                  90

ccc acg aga cga agg tca tct cag tgg aag aag tcg aca cac ccc cta       639
Pro Thr Arg Arg Arg Ser Ser Gln Trp Lys Lys Ser Thr His Pro Leu
            95                  100                 105

tca gaa gta gca gta cac aac aag cca agc gat tgc tgg att gtt gta       687
Ser Glu Val Ala Val His Asn Lys Pro Ser Asp Cys Trp Ile Val Val
        110                 115                 120

aaa aac aag gtg tat gat gtt tcc aat ttt gcg gac gag cat ccc gga       735
Lys Asn Lys Val Tyr Asp Val Ser Asn Phe Ala Asp Glu His Pro Gly
    125                 130                 135

gga tca gtt att agt act tat ttt gga cga gac ggc aca gat gtt ttc       783
Gly Ser Val Ile Ser Thr Tyr Phe Gly Arg Asp Gly Thr Asp Val Phe
140                 145                 150                 155

tct agt ttt cat gca gct tct aca tgg aaa att ctt caa gac ttt tac       831
Ser Ser Phe His Ala Ala Ser Thr Trp Lys Ile Leu Gln Asp Phe Tyr
                160                 165                 170

att ggt gac gtg gag agg gtg gag ccg act cca gag ctg ctg aaa gat       879
Ile Gly Asp Val Glu Arg Val Glu Pro Thr Pro Glu Leu Leu Lys Asp
            175                 180                 185

ttc cga gaa atg aga gct ctt ttc ctg agg gag caa ctt ttc aaa agt       927
Phe Arg Glu Met Arg Ala Leu Phe Leu Arg Glu Gln Leu Phe Lys Ser
        190                 195                 200

tcg aaa ttg tac tat gtt atg aag ctg ctc acg aat gtt gct att ttt       975
Ser Lys Leu Tyr Tyr Val Met Lys Leu Leu Thr Asn Val Ala Ile Phe
    205                 210                 215

gct gcg agc att gca ata ata tgt tgg agc aag act att tca gcg gtt      1023
Ala Ala Ser Ile Ala Ile Ile Cys Trp Ser Lys Thr Ile Ser Ala Val
220                 225                 230                 235
```

-continued

```
ttg gct tca gct tgt atg atg gct ctg tgt ttc caa cag tgc gga tgg      1071
Leu Ala Ser Ala Cys Met Met Ala Leu Cys Phe Gln Gln Cys Gly Trp
                240                 245                 250

cta tcc cat gat ttt ctc cac aat cag gtg ttt gag aca cgc tgg ctt      1119
Leu Ser His Asp Phe Leu His Asn Gln Val Phe Glu Thr Arg Trp Leu
            255                 260                 265

aat gaa gtt gtc ggg tat gtg atc ggc aac gcc gtt ctg ggg ttt agt      1167
Asn Glu Val Val Gly Tyr Val Ile Gly Asn Ala Val Leu Gly Phe Ser
        270                 275                 280

aca ggg tgg tgg aag gag aag cat aac ctt cat cat gct gct cca aat      1215
Thr Gly Trp Trp Lys Glu Lys His Asn Leu His His Ala Ala Pro Asn
    285                 290                 295

gaa tgc gat cag act tac caa cca att gat gaa gat att gat act ctc      1263
Glu Cys Asp Gln Thr Tyr Gln Pro Ile Asp Glu Asp Ile Asp Thr Leu
300                 305                 310                 315

ccc ctc att gcc tgg agc aag gac ata ctg gcc aca gtt gag aat aag      1311
Pro Leu Ile Ala Trp Ser Lys Asp Ile Leu Ala Thr Val Glu Asn Lys
                320                 325                 330

aca ttc ttg cga atc ctc caa tac cag cat ctg ttc ttc atg ggt ctg      1359
Thr Phe Leu Arg Ile Leu Gln Tyr Gln His Leu Phe Phe Met Gly Leu
            335                 340                 345

tta ttt ttc gcc cgt ggt agt tgg ctc ttt tgg agc tgg aga tat acc      1407
Leu Phe Phe Ala Arg Gly Ser Trp Leu Phe Trp Ser Trp Arg Tyr Thr
        350                 355                 360

tct aca gca gtg ctc tca cct gtc gac agg ttg ttg gag aag gga act      1455
Ser Thr Ala Val Leu Ser Pro Val Asp Arg Leu Leu Glu Lys Gly Thr
    365                 370                 375

gtt ctg ttt cac tac ttt tgg ttc gtc ggg aca gcg tgc tat ctt ctc      1503
Val Leu Phe His Tyr Phe Trp Phe Val Gly Thr Ala Cys Tyr Leu Leu
380                 385                 390                 395

cct ggt tgg aag cca tta gta tgg atg gcg gtg act gag ctc atg tcc      1551
Pro Gly Trp Lys Pro Leu Val Trp Met Ala Val Thr Glu Leu Met Ser
                400                 405                 410

ggc atg ctg ctg ggc ttt gta ttt gta ctt agc cac aat ggg atg gag      1599
Gly Met Leu Leu Gly Phe Val Phe Val Leu Ser His Asn Gly Met Glu
            415                 420                 425

gtt tat aat tcg tct aaa gaa ttc gtg agt gca cag atc gta tcc aca      1647
Val Tyr Asn Ser Ser Lys Glu Phe Val Ser Ala Gln Ile Val Ser Thr
        430                 435                 440

cgg gat atc aaa gga aac ata ttc aac gac tgg ttc act ggt ggc ctt      1695
Arg Asp Ile Lys Gly Asn Ile Phe Asn Asp Trp Phe Thr Gly Gly Leu
    445                 450                 455

aac agg caa ata gag cat cat ctt ttc cca aca atg ccc agg cat aat      1743
Asn Arg Gln Ile Glu His His Leu Phe Pro Thr Met Pro Arg His Asn
460                 465                 470                 475

tta aac aaa ata gca cct aga gtg gag gtg ttc tgt aag aaa cac ggt      1791
Leu Asn Lys Ile Ala Pro Arg Val Glu Val Phe Cys Lys Lys His Gly
                480                 485                 490

ctg gtg tac gaa gac gta tct att gct acc ggc act tgc aag gtt ttg      1839
Leu Val Tyr Glu Asp Val Ser Ile Ala Thr Gly Thr Cys Lys Val Leu
            495                 500                 505

aaa gca ttg aag gaa gtc gcg gag gct gcg gca gag cag cat gct acc      1887
Lys Ala Leu Lys Glu Val Ala Glu Ala Ala Ala Glu Gln His Ala Thr
        510                 515                 520

acc agt taa cagtctttgg aaagcttggc aattgatctt tattctccac              1936
Thr Ser
    525

ggcagttgct tgtttgtttt ggggtgaatg accgaatgta ctggcatcca ttcttctgta   1996

gccatcaatt ttgaac                                                    2012
```

<210> SEQ ID NO 51
<211> LENGTH: 525
<212> TYPE: PRT
<213> ORGANISM: Physcomitrella patens

<400> SEQUENCE: 51

```
Met Val Phe Ala Gly Gly Gly Leu Gln Gln Gly Ser Leu Glu Glu Asn
1               5                   10                  15

Ile Asp Val Glu His Ile Ala Ser Met Ser Leu Phe Ser Asp Phe Phe
            20                  25                  30

Ser Tyr Val Ser Ser Thr Val Gly Ser Trp Ser Val His Ser Ile Gln
        35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Val Lys Asn Lys Val Tyr
        115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
            180                 185                 190

Ala Leu Phe Leu Arg Glu Gln Leu Phe Lys Ser Ser Lys Leu Tyr Tyr
        195                 200                 205

Val Met Lys Leu Leu Thr Asn Val Ala Ile Phe Ala Ala Ser Ile Ala
    210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
        275                 280                 285

Glu Lys His Asn Leu His His Ala Ala Pro Asn Glu Cys Asp Gln Thr
    290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
        355                 360                 365

Ser Pro Val Asp Arg Leu Leu Glu Lys Gly Thr Val Leu Phe His Tyr
    370                 375                 380
```

-continued

Phe Trp Phe Val Gly Thr Ala Cys Tyr Leu Leu Pro Gly Trp Lys Pro
385 390 395 400

Leu Val Trp Met Ala Val Thr Glu Leu Met Ser Gly Met Leu Leu Gly
405 410 415

Phe Val Phe Val Leu Ser His Asn Gly Met Glu Val Tyr Asn Ser Ser
420 425 430

Lys Glu Phe Val Ser Ala Gln Ile Val Ser Thr Arg Asp Ile Lys Gly
435 440 445

Asn Ile Phe Asn Asp Trp Phe Thr Gly Gly Leu Asn Arg Gln Ile Glu
450 455 460

His His Leu Phe Pro Thr Met Pro Arg His Asn Leu Asn Lys Ile Ala
465 470 475 480

Pro Arg Val Glu Val Phe Cys Lys Lys His Gly Leu Val Tyr Glu Asp
485 490 495

Val Ser Ile Ala Thr Gly Thr Cys Lys Val Leu Lys Ala Leu Lys Glu
500 505 510

Val Ala Glu Ala Ala Ala Glu Gln His Ala Thr Thr Ser
515 520 525

<210> SEQ ID NO 52
<211> LENGTH: 1804
<212> TYPE: DNA
<213> ORGANISM: Perilla frutescens
<220> FEATURE:
<221> NAME/KEY: CDS
<222> LOCATION: (42)..(1613)
<223> OTHER INFORMATION: flavonoid 3'-hydroxylase

<400> SEQUENCE: 52
aattcggcac gagcaaaaat taaaggcaca ccccacatgc a atg atc agt gcc gcc 56
Met Ile Ser Ala Ala
1 5 gta agt ttg atc ata tgc act tcc att tta ggg gta ctg gtt tat ttt 104
Val Ser Leu Ile Ile Cys Thr Ser Ile Leu Gly Val Leu Val Tyr Phe
10 15 20 ttg ttc ctc agg cgg ggc ggc ggc agt aat ggg cgg cct ctg cct cca 152
Leu Phe Leu Arg Arg Gly Gly Gly Ser Asn Gly Arg Pro Leu Pro Pro
25 30 35 ggg ccg agg ccg tgg ccg att gtc ggc aac ctt ccg cag ctg ggg ccg 200
Gly Pro Arg Pro Trp Pro Ile Val Gly Asn Leu Pro Gln Leu Gly Pro
40 45 50 aag ccc cac cag tcg atg gca gcc ttg gcc cgg gtg cat ggc ccc ctc 248
Lys Pro His Gln Ser Met Ala Ala Leu Ala Arg Val His Gly Pro Leu
55 60 65 atg cat ctc aag atg ggg ttc gtg cat gtt gtg gtg gcc gcc tcc gcc 296
Met His Leu Lys Met Gly Phe Val His Val Val Val Ala Ala Ser Ala
70 75 80 85 acc gtg gcg gag aag ttc ttg aag gtg cac gac acc aac ttc ttg agc 344
Thr Val Ala Glu Lys Phe Leu Lys Val His Asp Thr Asn Phe Leu Ser
90 95 100 cgc ccg ccc aac tcc ggc gcc gag cac att gct tac aac tac aac gac 392
Arg Pro Pro Asn Ser Gly Ala Glu His Ile Ala Tyr Asn Tyr Asn Asp
105 110 115 ttg gtt ttt gct ccc cac ggc ccg cgg tgg cgg ttg ctt cgg aaa att 440
Leu Val Phe Ala Pro His Gly Pro Arg Trp Arg Leu Leu Arg Lys Ile
120 125 130 tgt gcc ctc cac ctc ttc tcc tcc aag gcc tta gat gac ttc cgc cat 488
Cys Ala Leu His Leu Phe Ser Ser Lys Ala Leu Asp Asp Phe Arg His
135 140 145

-continued

```
gtt aga gag gaa gaa gtg ggg atc ctc att cgc aac cta gca agt gtg      536
Val Arg Glu Glu Glu Val Gly Ile Leu Ile Arg Asn Leu Ala Ser Val
150                 155                 160                 165

gga gaa atg cct gca agt ata ggt caa atg atg tat gtg tgt gcc aca      584
Gly Glu Met Pro Ala Ser Ile Gly Gln Met Met Tyr Val Cys Ala Thr
                170                 175                 180

aac gca ata tct cga gtc atg tta ggg cgg cac gtg ttg ggc gac gaa      632
Asn Ala Ile Ser Arg Val Met Leu Gly Arg His Val Leu Gly Asp Glu
            185                 190                 195

cac cgc ggc gcc gcc ggt ggt gga gat acc acg gcg gag gag ttc aag      680
His Arg Gly Ala Ala Gly Gly Gly Asp Thr Thr Ala Glu Glu Phe Lys
        200                 205                 210

gcg atg gtg gtg gaa ctg atg gcg ttg gcc gga gta ttc aac gta ggg      728
Ala Met Val Val Glu Leu Met Ala Leu Ala Gly Val Phe Asn Val Gly
    215                 220                 225

gat ttt att cca cca ctc aag ggc ctg gac ttg caa gga gtg gtg gct      776
Asp Phe Ile Pro Pro Leu Lys Gly Leu Asp Leu Gln Gly Val Val Ala
230                 235                 240                 245

aag atg aag aaa ctt cat caa cgt ttc gac gct ttc ttc agc ggt atc      824
Lys Met Lys Lys Leu His Gln Arg Phe Asp Ala Phe Phe Ser Gly Ile
                250                 255                 260

ctt cat gat cac aag atc aac ggc tct aat gcc gct gag ggc cac gtg      872
Leu His Asp His Lys Ile Asn Gly Ser Asn Ala Ala Glu Gly His Val
            265                 270                 275

gac tta ctc act acg ttg att tct ttg aaa gac gtt gac aat aat ggt      920
Asp Leu Leu Thr Thr Leu Ile Ser Leu Lys Asp Val Asp Asn Asn Gly
        280                 285                 290

gag gga ggg aag ctc acc gat act gaa att aaa gca ttg ctt ttg aac      968
Glu Gly Gly Lys Leu Thr Asp Thr Glu Ile Lys Ala Leu Leu Leu Asn
    295                 300                 305

ttg ttt act gca gga aca gac acg aca tct agc acg gtg gaa tgg gcc     1016
Leu Phe Thr Ala Gly Thr Asp Thr Thr Ser Ser Thr Val Glu Trp Ala
310                 315                 320                 325

ata acg gag ctc atc cgt aac cca aat att ttg gct cga gtt cga aag     1064
Ile Thr Glu Leu Ile Arg Asn Pro Asn Ile Leu Ala Arg Val Arg Lys
                330                 335                 340

gag ctc gac tta ata gta ggc aag gat aaa ttg gtt aaa gaa tcc gat     1112
Glu Leu Asp Leu Ile Val Gly Lys Asp Lys Leu Val Lys Glu Ser Asp
            345                 350                 355

tta ggc caa ttg acc tac ctc caa gcc gtg atc aag gag aac ttt cgc     1160
Leu Gly Gln Leu Thr Tyr Leu Gln Ala Val Ile Lys Glu Asn Phe Arg
        360                 365                 370

ctc cac cct tcg act cca ctt tct cta cca aga gtc gca caa gag agc     1208
Leu His Pro Ser Thr Pro Leu Ser Leu Pro Arg Val Ala Gln Glu Ser
    375                 380                 385

tgt gag atc aac ggc tac tac atc cct aaa gat tcg acc cta ctc gtc     1256
Cys Glu Ile Asn Gly Tyr Tyr Ile Pro Lys Asp Ser Thr Leu Leu Val
390                 395                 400                 405

aat gtt tgg gcc atc ggc cgc gat cca aat gta tgg ccc gat cca ctt     1304
Asn Val Trp Ala Ile Gly Arg Asp Pro Asn Val Trp Pro Asp Pro Leu
                410                 415                 420

gaa ttt cgg ccc gaa cga ttc ttg atg ggc ggg gaa aag ccc aat gtt     1352
Glu Phe Arg Pro Glu Arg Phe Leu Met Gly Gly Glu Lys Pro Asn Val
            425                 430                 435

gat gtg aga gga aat gat ttc gaa ttg att ccg ttc ggg tcg ggc cgt     1400
Asp Val Arg Gly Asn Asp Phe Glu Leu Ile Pro Phe Gly Ser Gly Arg
        440                 445                 450

aga att tgt gca gga atg aac ttg gga att cgt atg gtg cag ctg ctg     1448
Arg Ile Cys Ala Gly Met Asn Leu Gly Ile Arg Met Val Gln Leu Leu
    455                 460                 465
```

```
att gct aca atg gtt cat gcg ttt gat ttt gaa ttg gct aat gga cag     1496
Ile Ala Thr Met Val His Ala Phe Asp Phe Glu Leu Ala Asn Gly Gln
470                 475                 480                 485

ttg gcc aaa gac tta aat atg gag gaa gct tac ggg att acg ttg caa     1544
Leu Ala Lys Asp Leu Asn Met Glu Glu Ala Tyr Gly Ile Thr Leu Gln
                490                 495                 500

cgg gcc gac ccg ttg gtg gtc cat cca agg ccc aga ctg gcc cga cat     1592
Arg Ala Asp Pro Leu Val Val His Pro Arg Pro Arg Leu Ala Arg His
            505                 510                 515

gtt tat caa gct caa gta tga tgcacaaatt gcgaacagga tcctccgatc        1643
Val Tyr Gln Ala Gln Val
        520

cattccaact tggtatttcc atctcgtatt ttaactatta gatgtatgtc atatgcattt   1703

aattttttt agtggtaaat tatttaatta tttaaataca catgttatac atttaatgct    1763

tgaaatacga gatgaaaaat caaaaaaaaa aaaaaaaaaa a                       1804


<210> SEQ ID NO 53
<211> LENGTH: 523
<212> TYPE: PRT
<213> ORGANISM: Perilla frutescens

<400> SEQUENCE: 53

Met Ile Ser Ala Ala Val Ser Leu Ile Ile Cys Thr Ser Ile Leu Gly
1               5                   10                  15

Val Leu Val Tyr Phe Leu Phe Leu Arg Arg Gly Gly Gly Ser Asn Gly
            20                  25                  30

Arg Pro Leu Pro Pro Gly Pro Arg Pro Trp Pro Ile Val Gly Asn Leu
        35                  40                  45

Pro Gln Leu Gly Pro Lys Pro His Gln Ser Met Ala Ala Leu Ala Arg
    50                  55                  60

Val His Gly Pro Leu Met His Leu Lys Met Gly Phe Val His Val Val
65                  70                  75                  80

Val Ala Ala Ser Ala Thr Val Ala Glu Lys Phe Leu Lys Val His Asp
                85                  90                  95

Thr Asn Phe Leu Ser Arg Pro Pro Asn Ser Gly Ala Glu His Ile Ala
            100                 105                 110

Tyr Asn Tyr Asn Asp Leu Val Phe Ala Pro His Gly Pro Arg Trp Arg
        115                 120                 125

Leu Leu Arg Lys Ile Cys Ala Leu His Leu Phe Ser Ser Lys Ala Leu
    130                 135                 140

Asp Asp Phe Arg His Val Arg Glu Glu Glu Val Gly Ile Leu Ile Arg
145                 150                 155                 160

Asn Leu Ala Ser Val Gly Glu Met Pro Ala Ser Ile Gly Gln Met Met
                165                 170                 175

Tyr Val Cys Ala Thr Asn Ala Ile Ser Arg Val Met Leu Gly Arg His
            180                 185                 190

Val Leu Gly Asp Glu His Arg Gly Ala Ala Gly Gly Gly Asp Thr Thr
        195                 200                 205

Ala Glu Glu Phe Lys Ala Met Val Val Glu Leu Met Ala Leu Ala Gly
    210                 215                 220

Val Phe Asn Val Gly Asp Phe Ile Pro Pro Leu Lys Gly Leu Asp Leu
225                 230                 235                 240

Gln Gly Val Val Ala Lys Met Lys Lys Leu His Gln Arg Phe Asp Ala
                245                 250                 255

Phe Phe Ser Gly Ile Leu His Asp His Lys Ile Asn Gly Ser Asn Ala
            260                 265                 270
```

```
Ala Glu Gly His Val Asp Leu Leu Thr Thr Leu Ile Ser Leu Lys Asp
        275                 280                 285

Val Asp Asn Asn Gly Glu Gly Gly Lys Leu Thr Asp Thr Glu Ile Lys
    290                 295                 300

Ala Leu Leu Leu Asn Leu Phe Thr Ala Gly Thr Asp Thr Thr Ser Ser
305                 310                 315                 320

Thr Val Glu Trp Ala Ile Thr Glu Leu Ile Arg Asn Pro Asn Ile Leu
                325                 330                 335

Ala Arg Val Arg Lys Glu Leu Asp Leu Ile Val Gly Lys Asp Lys Leu
            340                 345                 350

Val Lys Glu Ser Asp Leu Gly Gln Leu Thr Tyr Leu Gln Ala Val Ile
        355                 360                 365

Lys Glu Asn Phe Arg Leu His Pro Ser Thr Pro Leu Ser Leu Pro Arg
    370                 375                 380

Val Ala Gln Glu Ser Cys Glu Ile Asn Gly Tyr Tyr Ile Pro Lys Asp
385                 390                 395                 400

Ser Thr Leu Leu Val Asn Val Trp Ala Ile Gly Arg Asp Pro Asn Val
                405                 410                 415

Trp Pro Asp Pro Leu Glu Phe Arg Pro Glu Arg Phe Leu Met Gly Gly
            420                 425                 430

Glu Lys Pro Asn Val Asp Val Arg Gly Asn Asp Phe Glu Leu Ile Pro
        435                 440                 445

Phe Gly Ser Gly Arg Arg Ile Cys Ala Gly Met Asn Leu Gly Ile Arg
    450                 455                 460

Met Val Gln Leu Leu Ile Ala Thr Met Val His Ala Phe Asp Phe Glu
465                 470                 475                 480

Leu Ala Asn Gly Gln Leu Ala Lys Asp Leu Asn Met Glu Glu Ala Tyr
                485                 490                 495

Gly Ile Thr Leu Gln Arg Ala Asp Pro Leu Val Val His Pro Arg Pro
            500                 505                 510

Arg Leu Ala Arg His Val Tyr Gln Ala Gln Val
        515                 520


<210> SEQ ID NO 54
<211> LENGTH: 1190
<212> TYPE: DNA
<213> ORGANISM: Cymbidium hybrid
<220> FEATURE:
<221> NAME/KEY: CDS
<222> LOCATION: (11)..(1072)
<223> OTHER INFORMATION: dihydroflavonol-4-reductase

<400> SEQUENCE: 54

gaaagaagaa atg gag act gag agg aag ggt cca gtg gtg gtg act gga        49
           Met Glu Thr Glu Arg Lys Gly Pro Val Val Val Thr Gly
           1               5                   10

gcc agt ggc tat gtg ggt tca tgg ctg gtg atg aag ctt ctt caa aag       97
Ala Ser Gly Tyr Val Gly Ser Trp Leu Val Met Lys Leu Leu Gln Lys
    15                  20                  25

ggt tat gag gtc agg gct gcg gtc aga gat tca aca aat ttt gaa aag      145
Gly Tyr Glu Val Arg Ala Ala Val Arg Asp Ser Thr Asn Phe Glu Lys
30                  35                  40                  45

gtg aag ccg ctg ctg gat ctc ccg ggc tcg aat gaa ctg ctc agc att      193
Val Lys Pro Leu Leu Asp Leu Pro Gly Ser Asn Glu Leu Leu Ser Ile
                50                  55                  60

tgg aag gca gat ctc aat gac att gac gaa acc ttc gac gag gtg aca      241
Trp Lys Ala Asp Leu Asn Asp Ile Asp Glu Thr Phe Asp Glu Val Thr
            65                  70                  75
```

```
cgt ggc agt gtt ggg ttg ttc cac gtt gcc act ccc atg aat ttt caa      289
Arg Gly Ser Val Gly Leu Phe His Val Ala Thr Pro Met Asn Phe Gln
        80                  85                  90

tcc gaa gac ccc gag aat gaa gtc ata aaa ccg aca att agc ggt tta      337
Ser Glu Asp Pro Glu Asn Glu Val Ile Lys Pro Thr Ile Ser Gly Leu
    95                  100                 105

ctg gga atc ttg agg tcc tgc aaa agg gtc ggc act gta aag cga gtg      385
Leu Gly Ile Leu Arg Ser Cys Lys Arg Val Gly Thr Val Lys Arg Val
110                 115                 120                 125

ata ttc aca tct tcg gca gga aca gtg aac gtg gag gaa cac caa gca      433
Ile Phe Thr Ser Ser Ala Gly Thr Val Asn Val Glu Glu His Gln Ala
                130                 135                 140

acg gtc tac gac gag agc tcc tgg agc gac ctc gac ttc gtc acc cga      481
Thr Val Tyr Asp Glu Ser Ser Trp Ser Asp Leu Asp Phe Val Thr Arg
            145                 150                 155

gta aag atg acc ggc tgg atg tac ttc gtg tca aaa acg ctt gcg gag      529
Val Lys Met Thr Gly Trp Met Tyr Phe Val Ser Lys Thr Leu Ala Glu
        160                 165                 170

aag gct gct tgg gag ttt gta agc gat aat gat att cac ttt ata acc      577
Lys Ala Ala Trp Glu Phe Val Ser Asp Asn Asp Ile His Phe Ile Thr
    175                 180                 185

att att cca act ttg gtg gtc ggt tcc ttc tta ata tct cga atg cca      625
Ile Ile Pro Thr Leu Val Val Gly Ser Phe Leu Ile Ser Arg Met Pro
190                 195                 200                 205

cca agt ttg atc act gct tta tcg tta att aca gga aat gag gcc cat      673
Pro Ser Leu Ile Thr Ala Leu Ser Leu Ile Thr Gly Asn Glu Ala His
                210                 215                 220

tat tca ata tta agg caa gct caa ttt gtt cat ttg gat gac tta tgt      721
Tyr Ser Ile Leu Arg Gln Ala Gln Phe Val His Leu Asp Asp Leu Cys
            225                 230                 235

gat gct cac att ttt ctt ttt gag cat cac aaa gca aat ggc aga tat      769
Asp Ala His Ile Phe Leu Phe Glu His His Lys Ala Asn Gly Arg Tyr
        240                 245                 250

att tgc tct tct cat gac tca aca att tat agc ttg gca aaa atg ctg      817
Ile Cys Ser Ser His Asp Ser Thr Ile Tyr Ser Leu Ala Lys Met Leu
    255                 260                 265

aag aac aga tat gcc aca tat gac att cct ctg aag ttt aag gaa atc      865
Lys Asn Arg Tyr Ala Thr Tyr Asp Ile Pro Leu Lys Phe Lys Glu Ile
270                 275                 280                 285

gat cca aac att gag agc gtg agc ttc tct tct aag aag ttg ttg gac      913
Asp Pro Asn Ile Glu Ser Val Ser Phe Ser Ser Lys Lys Leu Leu Asp
                290                 295                 300

ctt ggg ttc aag tac aag tac aag tac acc atg gag gag atg ttt gat      961
Leu Gly Phe Lys Tyr Lys Tyr Lys Tyr Thr Met Glu Glu Met Phe Asp
            305                 310                 315

gat gct att aag act tgc agg gat aag aat ctc ata cca ctc cac act     1009
Asp Ala Ile Lys Thr Cys Arg Asp Lys Asn Leu Ile Pro Leu His Thr
        320                 325                 330

gag gaa atg gtc tca gct aat gag aaa ttt gat gaa gta aaa gaa caa     1057
Glu Glu Met Val Ser Ala Asn Glu Lys Phe Asp Glu Val Lys Glu Gln
    335                 340                 345

att gct gtt aag tga atagggaatg agcaaggaga aatgttgtgt gaaattttca     1112
Ile Ala Val Lys
350

tttgtattgt cctattaatt gtctatgtac tttattatct atggagacat ctcaatttat   1172

tcttctaaaa aaaaaaaa                                                  1190
```

<210> SEQ ID NO 55
<211> LENGTH: 353

<212> TYPE: PRT
<213> ORGANISM: Cymbidium hybrid

<400> SEQUENCE: 55

```
Met Glu Thr Glu Arg Lys Gly Pro Val Val Val Thr Gly Ala Ser Gly
1               5                   10                  15

Tyr Val Gly Ser Trp Leu Val Met Lys Leu Leu Gln Lys Gly Tyr Glu
            20                  25                  30

Val Arg Ala Ala Val Arg Asp Ser Thr Asn Phe Glu Lys Val Lys Pro
        35                  40                  45

Leu Leu Asp Leu Pro Gly Ser Asn Glu Leu Leu Ser Ile Trp Lys Ala
    50                  55                  60

Asp Leu Asn Asp Ile Asp Glu Thr Phe Asp Glu Val Thr Arg Gly Ser
65                  70                  75                  80

Val Gly Leu Phe His Val Ala Thr Pro Met Asn Phe Gln Ser Glu Asp
                85                  90                  95

Pro Glu Asn Glu Val Ile Lys Pro Thr Ile Ser Gly Leu Leu Gly Ile
            100                 105                 110

Leu Arg Ser Cys Lys Arg Val Gly Thr Val Lys Arg Val Ile Phe Thr
        115                 120                 125

Ser Ser Ala Gly Thr Val Asn Val Glu Glu His Gln Ala Thr Val Tyr
    130                 135                 140

Asp Glu Ser Ser Trp Ser Asp Leu Asp Phe Val Thr Arg Val Lys Met
145                 150                 155                 160

Thr Gly Trp Met Tyr Phe Val Ser Lys Thr Leu Ala Glu Lys Ala Ala
                165                 170                 175

Trp Glu Phe Val Ser Asp Asn Asp Ile His Phe Ile Thr Ile Ile Pro
            180                 185                 190

Thr Leu Val Val Gly Ser Phe Leu Ile Ser Arg Met Pro Pro Ser Leu
        195                 200                 205

Ile Thr Ala Leu Ser Leu Ile Thr Gly Asn Glu Ala His Tyr Ser Ile
    210                 215                 220

Leu Arg Gln Ala Gln Phe Val His Leu Asp Asp Leu Cys Asp Ala His
225                 230                 235                 240

Ile Phe Leu Phe Glu His His Lys Ala Asn Gly Arg Tyr Ile Cys Ser
                245                 250                 255

Ser His Asp Ser Thr Ile Tyr Ser Leu Ala Lys Met Leu Lys Asn Arg
            260                 265                 270

Tyr Ala Thr Tyr Asp Ile Pro Leu Lys Phe Lys Glu Ile Asp Pro Asn
        275                 280                 285

Ile Glu Ser Val Ser Phe Ser Ser Lys Lys Leu Leu Asp Leu Gly Phe
    290                 295                 300

Lys Tyr Lys Tyr Lys Tyr Thr Met Glu Glu Met Phe Asp Asp Ala Ile
305                 310                 315                 320

Lys Thr Cys Arg Asp Lys Asn Leu Ile Pro Leu His Thr Glu Glu Met
                325                 330                 335

Val Ser Ala Asn Glu Lys Phe Asp Glu Val Lys Glu Gln Ile Ala Val
            340                 345                 350

Lys
```

<210> SEQ ID NO 56
<211> LENGTH: 819
<212> TYPE: DNA
<213> ORGANISM: Glycine max
<220> FEATURE:
<221> NAME/KEY: CDS

```
<222> LOCATION: (27)..(683)
<223> OTHER INFORMATION: chalcone isomerase

<400> SEQUENCE: 56

gttaaataga aaagaggagt ttgaga atg gca acg atc agc gcg gtt cag gtg      53
                             Met Ala Thr Ile Ser Ala Val Gln Val
                             1               5

gag ttc ctg gag ttt cca gcg gtg gtt act tca cca gcc tcc ggc aag      101
Glu Phe Leu Glu Phe Pro Ala Val Val Thr Ser Pro Ala Ser Gly Lys
10                  15                  20                  25

acc tat ttc ctc ggc ggc gca ggg gag aga gga ttg acg att gag ggg      149
Thr Tyr Phe Leu Gly Gly Ala Gly Glu Arg Gly Leu Thr Ile Glu Gly
                30                  35                  40

aag ttc ata aag ttc aca ggc ata gga gta tac ttg gag gat aag gcg      197
Lys Phe Ile Lys Phe Thr Gly Ile Gly Val Tyr Leu Glu Asp Lys Ala
            45                  50                  55

gtg cca tca ctc gcc gct aag tgg aag ggt aaa act tca gag gag tta      245
Val Pro Ser Leu Ala Ala Lys Trp Lys Gly Lys Thr Ser Glu Glu Leu
        60                  65                  70

gtt cac acc ctc cac ttc tac agg gat atc att tca ggg ccg ttt gaa      293
Val His Thr Leu His Phe Tyr Arg Asp Ile Ile Ser Gly Pro Phe Glu
    75                  80                  85

aag cta att aga ggg tcg aag att ctg cca ttg gct ggc gct gaa tac      341
Lys Leu Ile Arg Gly Ser Lys Ile Leu Pro Leu Ala Gly Ala Glu Tyr
90                  95                  100                 105

tca aag aag gtg atg gaa aac tgc gtg gca cac atg aag tct gtt ggg      389
Ser Lys Lys Val Met Glu Asn Cys Val Ala His Met Lys Ser Val Gly
                110                 115                 120

act tac ggt gat gct gaa gcc gca gcc att gaa aag ttt gct gaa gcc      437
Thr Tyr Gly Asp Ala Glu Ala Ala Ala Ile Glu Lys Phe Ala Glu Ala
            125                 130                 135

ttc aag aat gtg aat ttt gca cct ggt gcc tct gtt ttc tac aga caa      485
Phe Lys Asn Val Asn Phe Ala Pro Gly Ala Ser Val Phe Tyr Arg Gln
        140                 145                 150

tca cct gat gga atc ttg ggg ctt agt ttc tct gaa gat gca aca ata      533
Ser Pro Asp Gly Ile Leu Gly Leu Ser Phe Ser Glu Asp Ala Thr Ile
    155                 160                 165

cca gaa aag gag gct gca gtg ata gag aac aag gct gta tca gcg gcg      581
Pro Glu Lys Glu Ala Ala Val Ile Glu Asn Lys Ala Val Ser Ala Ala
170                 175                 180                 185

gtc ttg gag acc atg att ggt gaa cat gct gtt tcc cct gac tta aaa      629
Val Leu Glu Thr Met Ile Gly Glu His Ala Val Ser Pro Asp Leu Lys
                190                 195                 200

cgc agt ttg gct tct cga ttg cct gcg gta ttg agc cac ggc att ata      677
Arg Ser Leu Ala Ser Arg Leu Pro Ala Val Leu Ser His Gly Ile Ile
            205                 210                 215

gtc tga gaaatgagaa ggatcaactt taccttttc aaatattctt gtttttctcc      733
Val

tttctttctt gtcgcttgtc atgtatttct actgttttat taaataataa aattgagttc    793

tgttagagtt ggtgaaaaaa aaaaaa                                         819


<210> SEQ ID NO 57
<211> LENGTH: 218
<212> TYPE: PRT
<213> ORGANISM: Glycine max

<400> SEQUENCE: 57

Met Ala Thr Ile Ser Ala Val Gln Val Glu Phe Leu Glu Phe Pro Ala
1               5                   10                  15

Val Val Thr Ser Pro Ala Ser Gly Lys Thr Tyr Phe Leu Gly Gly Ala
```

```
            20                  25                  30

Gly Glu Arg Gly Leu Thr Ile Glu Gly Lys Phe Ile Lys Phe Thr Gly
        35                  40                  45

Ile Gly Val Tyr Leu Glu Asp Lys Ala Val Pro Ser Leu Ala Ala Lys
    50                  55                  60

Trp Lys Gly Lys Thr Ser Glu Glu Leu Val His Thr Leu His Phe Tyr
65                  70                  75                  80

Arg Asp Ile Ile Ser Gly Pro Phe Glu Lys Leu Ile Arg Gly Ser Lys
                85                  90                  95

Ile Leu Pro Leu Ala Gly Ala Glu Tyr Ser Lys Lys Val Met Glu Asn
            100                 105                 110

Cys Val Ala His Met Lys Ser Val Gly Thr Tyr Gly Asp Ala Glu Ala
        115                 120                 125

Ala Ala Ile Glu Lys Phe Ala Glu Ala Phe Lys Asn Val Asn Phe Ala
    130                 135                 140

Pro Gly Ala Ser Val Phe Tyr Arg Gln Ser Pro Asp Gly Ile Leu Gly
145                 150                 155                 160

Leu Ser Phe Ser Glu Asp Ala Thr Ile Pro Glu Lys Glu Ala Ala Val
                165                 170                 175

Ile Glu Asn Lys Ala Val Ser Ala Ala Val Leu Glu Thr Met Ile Gly
            180                 185                 190

Glu His Ala Val Ser Pro Asp Leu Lys Arg Ser Leu Ala Ser Arg Leu
        195                 200                 205

Pro Ala Val Leu Ser His Gly Ile Ile Val
    210                 215


<210> SEQ ID NO 58
<211> LENGTH: 1290
<212> TYPE: DNA
<213> ORGANISM: Humulus lupulus
<220> FEATURE:
<221> NAME/KEY: CDS
<222> LOCATION: (1)..(189)
<223> OTHER INFORMATION: chalcone synthase
<220> FEATURE:
<221> NAME/KEY: CDS
<222> LOCATION: (280)..(1287)
<223> OTHER INFORMATION: chalcone synthase

<400> SEQUENCE: 58

atg tcc tcc tcc ata act gtg gat caa atc cga aag gct cag cgg gct       48
Met Ser Ser Ser Ile Thr Val Asp Gln Ile Arg Lys Ala Gln Arg Ala
1               5                   10                  15

gag ggt ccg gcc acg atc ctc gcc att ggc acg gcc act cct gcc aac       96
Glu Gly Pro Ala Thr Ile Leu Ala Ile Gly Thr Ala Thr Pro Ala Asn
            20                  25                  30

ttc atc atc caa gct gat tat cct gac tac tac ttc cgc gtc acc aaa      144
Phe Ile Ile Gln Ala Asp Tyr Pro Asp Tyr Tyr Phe Arg Val Thr Lys
        35                  40                  45

agc gaa cac atg act aac ctc aaa aaa cga ttc caa cga ata tgt          189
Ser Glu His Met Thr Asn Leu Lys Lys Arg Phe Gln Arg Ile Cys
    50                  55                  60

atatatactc ttctcctctt catgaacttt atatatattc atatatatat ataattataa    249

atgtatgtgc ttgcatatga tattgcaggt gat aga acc atg ata aag aaa cgt     303
                                 Asp Arg Thr Met Ile Lys Lys Arg
                                 65                  70

cac ctg gtc ttg agc gaa gac cac ctg aag gag aac cca aac atg tgc      351
His Leu Val Leu Ser Glu Asp His Leu Lys Glu Asn Pro Asn Met Cys
            75                  80                  85
```

-continued

```
gag ttc atg gcg ccg tcc ctg gac gta cgt caa gac ata ttg gtg gtc      399
Glu Phe Met Ala Pro Ser Leu Asp Val Arg Gln Asp Ile Leu Val Val
        90                  95                  100

gag gtt ccc aag ctt gga aag gag gct tgc atg aag gcc atc aag gag      447
Glu Val Pro Lys Leu Gly Lys Glu Ala Cys Met Lys Ala Ile Lys Glu
    105                 110                 115

tgg gac cag cca aag tcc aag atc acc cat ttc atc ttc gcc acc acc      495
Trp Asp Gln Pro Lys Ser Lys Ile Thr His Phe Ile Phe Ala Thr Thr
120                 125                 130                 135

tcc ggt gtc gac atg cct ggc gcc gac tac caa tgt gcc aag ctt ctc      543
Ser Gly Val Asp Met Pro Gly Ala Asp Tyr Gln Cys Ala Lys Leu Leu
                140                 145                 150

gga ctc agc tcc tcc gtg aag cgt gtg atg atg tat caa caa ggt tgt      591
Gly Leu Ser Ser Ser Val Lys Arg Val Met Met Tyr Gln Gln Gly Cys
            155                 160                 165

ttc gcc ggt gga act gtt ctc cgc atc gcc aag gac ata gcg gaa aac      639
Phe Ala Gly Gly Thr Val Leu Arg Ile Ala Lys Asp Ile Ala Glu Asn
        170                 175                 180

aac aag ggt gcc cga gtt ctt gcc ttg tgt tct gag atc acg act tgc      687
Asn Lys Gly Ala Arg Val Leu Ala Leu Cys Ser Glu Ile Thr Thr Cys
    185                 190                 195

atg ttt cat ggc cca aca gaa tct cat ctg gac tcc atg gtg gga caa      735
Met Phe His Gly Pro Thr Glu Ser His Leu Asp Ser Met Val Gly Gln
200                 205                 210                 215

gct ttg ttc gga gat ggg gct tct gcg gtc atc gta ggt gcg gaa ccg      783
Ala Leu Phe Gly Asp Gly Ala Ser Ala Val Ile Val Gly Ala Glu Pro
                220                 225                 230

gat gag tcg gcc ggg gaa cga ccg atc tat gag ttg gtg tca gct gcg      831
Asp Glu Ser Ala Gly Glu Arg Pro Ile Tyr Glu Leu Val Ser Ala Ala
            235                 240                 245

cag acg att ctg cca aac tca gaa gga gcg atc gat ggg cat ttg atg      879
Gln Thr Ile Leu Pro Asn Ser Glu Gly Ala Ile Asp Gly His Leu Met
        250                 255                 260

gaa acg agg cta acg ttt cac tta ctc aag gac gtg ccc ggg ttg atc      927
Glu Thr Arg Leu Thr Phe His Leu Leu Lys Asp Val Pro Gly Leu Ile
    265                 270                 275

tct aac aac atc gag aag agt ttg att gag gcc ttc act ccg atc ggg      975
Ser Asn Asn Ile Glu Lys Ser Leu Ile Glu Ala Phe Thr Pro Ile Gly
280                 285                 290                 295

att aat gac tgg aac tcc ata ttc tgg gtt aca cac cca ggt gga ccg     1023
Ile Asn Asp Trp Asn Ser Ile Phe Trp Val Thr His Pro Gly Gly Pro
                300                 305                 310

gcc att ttg gac gag gtg gag gcc aaa ctg gaa ctg aag aag gaa aag     1071
Ala Ile Leu Asp Glu Val Glu Ala Lys Leu Glu Leu Lys Lys Glu Lys
            315                 320                 325

cta gca atc tca cgc cat gtg ttg agt gag tac ggg aac atg tcg agt     1119
Leu Ala Ile Ser Arg His Val Leu Ser Glu Tyr Gly Asn Met Ser Ser
        330                 335                 340

gca agc gtt ttc ttc gta atg gac gag ttg aga aag agg tcg ttg gag     1167
Ala Ser Val Phe Phe Val Met Asp Glu Leu Arg Lys Arg Ser Leu Glu
    345                 350                 355

gaa ggg aag tcg acc acc gga gat gga ttg gat tgg ggt gtt ctc ttc     1215
Glu Gly Lys Ser Thr Thr Gly Asp Gly Leu Asp Trp Gly Val Leu Phe
360                 365                 370                 375

ggc ttc gga ccc ggt ttg acg gtg gag atg gtg gtc ttg cat agc gtt     1263
Gly Phe Gly Pro Gly Leu Thr Val Glu Met Val Val Leu His Ser Val
                380                 385                 390

gaa aac aag gtc aaa agt gag act tga                                 1290
Glu Asn Lys Val Lys Ser Glu Thr
            395
```

<210> SEQ ID NO 59
<211> LENGTH: 399
<212> TYPE: PRT
<213> ORGANISM: Humulus lupulus

<400> SEQUENCE: 59

```
Met Ser Ser Ser Ile Thr Val Asp Gln Ile Arg Lys Ala Gln Arg Ala
1               5                   10                  15

Glu Gly Pro Ala Thr Ile Leu Ala Ile Gly Thr Ala Thr Pro Ala Asn
            20                  25                  30

Phe Ile Ile Gln Ala Asp Tyr Pro Asp Tyr Tyr Phe Arg Val Thr Lys
        35                  40                  45

Ser Glu His Met Thr Asn Leu Lys Lys Arg Phe Gln Arg Ile Cys Asp
    50                  55                  60

Arg Thr Met Ile Lys Lys Arg His Leu Val Leu Ser Glu Asp His Leu
65                  70                  75                  80

Lys Glu Asn Pro Asn Met Cys Glu Phe Met Ala Pro Ser Leu Asp Val
                85                  90                  95

Arg Gln Asp Ile Leu Val Val Glu Val Pro Lys Leu Gly Lys Glu Ala
            100                 105                 110

Cys Met Lys Ala Ile Lys Glu Trp Asp Gln Pro Lys Ser Lys Ile Thr
        115                 120                 125

His Phe Ile Phe Ala Thr Thr Ser Gly Val Asp Met Pro Gly Ala Asp
    130                 135                 140

Tyr Gln Cys Ala Lys Leu Leu Gly Leu Ser Ser Ser Val Lys Arg Val
145                 150                 155                 160

Met Met Tyr Gln Gln Gly Cys Phe Ala Gly Gly Thr Val Leu Arg Ile
                165                 170                 175

Ala Lys Asp Ile Ala Glu Asn Asn Lys Gly Ala Arg Val Leu Ala Leu
            180                 185                 190

Cys Ser Glu Ile Thr Thr Cys Met Phe His Gly Pro Thr Glu Ser His
        195                 200                 205

Leu Asp Ser Met Val Gly Gln Ala Leu Phe Gly Asp Gly Ala Ser Ala
    210                 215                 220

Val Ile Val Gly Ala Glu Pro Asp Glu Ser Ala Gly Glu Arg Pro Ile
225                 230                 235                 240

Tyr Glu Leu Val Ser Ala Ala Gln Thr Ile Leu Pro Asn Ser Glu Gly
                245                 250                 255

Ala Ile Asp Gly His Leu Met Glu Thr Arg Leu Thr Phe His Leu Leu
            260                 265                 270

Lys Asp Val Pro Gly Leu Ile Ser Asn Asn Ile Glu Lys Ser Leu Ile
        275                 280                 285

Glu Ala Phe Thr Pro Ile Gly Ile Asn Asp Trp Asn Ser Ile Phe Trp
    290                 295                 300

Val Thr His Pro Gly Gly Pro Ala Ile Leu Asp Glu Val Glu Ala Lys
305                 310                 315                 320

Leu Glu Leu Lys Lys Glu Lys Leu Ala Ile Ser Arg His Val Leu Ser
                325                 330                 335

Glu Tyr Gly Asn Met Ser Ser Ala Ser Val Phe Phe Val Met Asp Glu
            340                 345                 350

Leu Arg Lys Arg Ser Leu Glu Glu Gly Lys Ser Thr Thr Gly Asp Gly
        355                 360                 365

Leu Asp Trp Gly Val Leu Phe Gly Phe Gly Pro Gly Leu Thr Val Glu
    370                 375                 380
```

```
Met Val Val Leu His Ser Val Glu Asn Lys Val Lys Ser Glu Thr
385                 390                 395


<210> SEQ ID NO 60
<211> LENGTH: 1513
<212> TYPE: DNA
<213> ORGANISM: Dianthus caryophyllus
<220> FEATURE:
<221> NAME/KEY: CDS
<222> LOCATION: (137)..(1234)
<223> OTHER INFORMATION: naringenin,2-oxoglutarate 3-dioxygenase

<400> SEQUENCE: 60

cacaacatta taacataagc ttcaaaataa cattattccg atatttacgt aatataatac     60

gtatcatatt agggtacatt cattttatca actacgactg catattgtta gacagtctca    120

tatatacgca taaaaa atg gtc gct gaa aaa ccc aaa acg ctc act tca cta    172
                  Met Val Ala Glu Lys Pro Lys Thr Leu Thr Ser Leu
                  1               5                   10

gaa ggg gac gat aaa ttg aac tcg aat ttt gtt agg gac gag gat gaa      220
Glu Gly Asp Asp Lys Leu Asn Ser Asn Phe Val Arg Asp Glu Asp Glu
        15                  20                  25

cgt ccg aaa gtg gcg tat aat gag ttt agc aat gat att ccg gtg ata      268
Arg Pro Lys Val Ala Tyr Asn Glu Phe Ser Asn Asp Ile Pro Val Ile
    30                  35                  40

tct ctt gct ggt ata gat ggt gaa aaa agg ggt gaa ata tgt cgg aag      316
Ser Leu Ala Gly Ile Asp Gly Glu Lys Arg Gly Glu Ile Cys Arg Lys
45                  50                  55                  60

att gtt gag gcg tgt gaa gat tgg ggg att ttt caa gtg gtt gat cac      364
Ile Val Glu Ala Cys Glu Asp Trp Gly Ile Phe Gln Val Val Asp His
                65                  70                  75

ggt gtt ggt gac gat ctt att gct gat atg act cgg ttg gct cgt gaa      412
Gly Val Gly Asp Asp Leu Ile Ala Asp Met Thr Arg Leu Ala Arg Glu
            80                  85                  90

ttt ttc gct ctc ccg gca gaa gag aag ctc cga ttt gat atg tct ggt      460
Phe Phe Ala Leu Pro Ala Glu Glu Lys Leu Arg Phe Asp Met Ser Gly
        95                  100                 105

ggt aaa aag ggc ggt ttt atc gtg tcg agt cat ctt cag gga gaa gta      508
Gly Lys Lys Gly Gly Phe Ile Val Ser Ser His Leu Gln Gly Glu Val
    110                 115                 120

gtg cag gac tgg agg gaa atc gtg acg tat ttc tca tac ccg acg aac      556
Val Gln Asp Trp Arg Glu Ile Val Thr Tyr Phe Ser Tyr Pro Thr Asn
125                 130                 135                 140

tca agg gac tac aca aga tgg cca gac aaa cca gag ggt tgg ata aag      604
Ser Arg Asp Tyr Thr Arg Trp Pro Asp Lys Pro Glu Gly Trp Ile Lys
                145                 150                 155

gtc aca gag gaa tac agc aac aag tta atg acc tta gca tgt aca ctt      652
Val Thr Glu Glu Tyr Ser Asn Lys Leu Met Thr Leu Ala Cys Thr Leu
            160                 165                 170

tta ggt gta ctt tct gaa gcc atg ggt tta gaa tta gag gca ctt act      700
Leu Gly Val Leu Ser Glu Ala Met Gly Leu Glu Leu Glu Ala Leu Thr
        175                 180                 185

aaa gct tgt gtt gat atg gac caa aag att gtg gtt aat tac tac cct      748
Lys Ala Cys Val Asp Met Asp Gln Lys Ile Val Val Asn Tyr Tyr Pro
    190                 195                 200

aag tgc cct caa cct gac ctt act tta ggg ctc aag agg cac acc gac      796
Lys Cys Pro Gln Pro Asp Leu Thr Leu Gly Leu Lys Arg His Thr Asp
205                 210                 215                 220

ccc ggg act ata acc ctc ctc ctt cag gac caa gtc ggc ggt ctt cag      844
Pro Gly Thr Ile Thr Leu Leu Leu Gln Asp Gln Val Gly Gly Leu Gln
                225                 230                 235

gcc act cgt gac ggt ggt aaa act tgg att acc gtg cag ccg gtt ccc      892
```

-continued

```
Ala Thr Arg Asp Gly Gly Lys Thr Trp Ile Thr Val Gln Pro Val Pro
            240                 245                 250

ggt gcc ttc gtt gtt aac ctt ggt gat cat ggt cat ttt ttg agc aat      940
Gly Ala Phe Val Val Asn Leu Gly Asp His Gly His Phe Leu Ser Asn
        255                 260                 265

ggg aga ttc aaa aat gcg gat cac caa gcg gtg gtg aac tcg gaa tgc      988
Gly Arg Phe Lys Asn Ala Asp His Gln Ala Val Val Asn Ser Glu Cys
    270                 275                 280

agc cgc cta tca atc gca acg ttt caa aac ccg tca cca gac gcg acg     1036
Ser Arg Leu Ser Ile Ala Thr Phe Gln Asn Pro Ser Pro Asp Ala Thr
285                 290                 295                 300

gtc tac cca ttg gca ata aga gaa ggt gag aat tca att atg gaa gaa     1084
Val Tyr Pro Leu Ala Ile Arg Glu Gly Glu Asn Ser Ile Met Glu Glu
                305                 310                 315

cca ata act ttc gcc gat ttg tat cgg cga aaa atg gcc aaa gac ctt     1132
Pro Ile Thr Phe Ala Asp Leu Tyr Arg Arg Lys Met Ala Lys Asp Leu
            320                 325                 330

gag atc gcc cgt cat aag agg ctt gct aaa gag gaa atg cct ttt aaa     1180
Glu Ile Ala Arg His Lys Arg Leu Ala Lys Glu Glu Met Pro Phe Lys
        335                 340                 345

gag ttg gac gag gcc aag ttt gag tcc aaa tct att gac caa ata ctt     1228
Glu Leu Asp Glu Ala Lys Phe Glu Ser Lys Ser Ile Asp Gln Ile Leu
    350                 355                 360

gct tag atgggcttgg tttggtttca ttatattaaa tttattatta ttattattta      1284
Ala
365

ttgcatttga tatgatatga ttggaaataa aagagagatt gtttgtgata atttgtgtga   1344

ttattatatc actaagttat ggctttaatt tgtggtatgt tgggaattat atatttagtt   1404

ttgtgtgaag aatatatgat ttaaagttaa aaaaaaaaat gatttgttat atgatttact   1464

tgtaaggtta taaggttata tttattgttc gagtttgcgt ataaaaaaa               1513


<210> SEQ ID NO 61
<211> LENGTH: 365
<212> TYPE: PRT
<213> ORGANISM: Dianthus caryophyllus

<400> SEQUENCE: 61

Met Val Ala Glu Lys Pro Lys Thr Leu Thr Ser Leu Glu Gly Asp Asp
1               5                   10                  15

Lys Leu Asn Ser Asn Phe Val Arg Asp Glu Asp Glu Arg Pro Lys Val
            20                  25                  30

Ala Tyr Asn Glu Phe Ser Asn Asp Ile Pro Val Ile Ser Leu Ala Gly
        35                  40                  45

Ile Asp Gly Glu Lys Arg Gly Glu Ile Cys Arg Lys Ile Val Glu Ala
    50                  55                  60

Cys Glu Asp Trp Gly Ile Phe Gln Val Val Asp His Gly Val Gly Asp
65                  70                  75                  80

Asp Leu Ile Ala Asp Met Thr Arg Leu Ala Arg Glu Phe Phe Ala Leu
                85                  90                  95

Pro Ala Glu Glu Lys Leu Arg Phe Asp Met Ser Gly Gly Lys Lys Gly
            100                 105                 110

Gly Phe Ile Val Ser Ser His Leu Gln Gly Glu Val Val Gln Asp Trp
        115                 120                 125

Arg Glu Ile Val Thr Tyr Phe Ser Tyr Pro Thr Asn Ser Arg Asp Tyr
    130                 135                 140

Thr Arg Trp Pro Asp Lys Pro Glu Gly Trp Ile Lys Val Thr Glu Glu
145                 150                 155                 160
```

```
Tyr Ser Asn Lys Leu Met Thr Leu Ala Cys Thr Leu Leu Gly Val Leu
                165                 170                 175

Ser Glu Ala Met Gly Leu Glu Leu Glu Ala Leu Thr Lys Ala Cys Val
            180                 185                 190

Asp Met Asp Gln Lys Ile Val Val Asn Tyr Tyr Pro Lys Cys Pro Gln
        195                 200                 205

Pro Asp Leu Thr Leu Gly Leu Lys Arg His Thr Asp Pro Gly Thr Ile
    210                 215                 220

Thr Leu Leu Leu Gln Asp Gln Val Gly Gly Leu Gln Ala Thr Arg Asp
225                 230                 235                 240

Gly Gly Lys Thr Trp Ile Thr Val Gln Pro Val Pro Gly Ala Phe Val
                245                 250                 255

Val Asn Leu Gly Asp His Gly His Phe Leu Ser Asn Gly Arg Phe Lys
            260                 265                 270

Asn Ala Asp His Gln Ala Val Val Asn Ser Glu Cys Ser Arg Leu Ser
        275                 280                 285

Ile Ala Thr Phe Gln Asn Pro Ser Pro Asp Ala Thr Val Tyr Pro Leu
    290                 295                 300

Ala Ile Arg Glu Gly Glu Asn Ser Ile Met Glu Glu Pro Ile Thr Phe
305                 310                 315                 320

Ala Asp Leu Tyr Arg Arg Lys Met Ala Lys Asp Leu Glu Ile Ala Arg
                325                 330                 335

His Lys Arg Leu Ala Lys Glu Glu Met Pro Phe Lys Glu Leu Asp Glu
            340                 345                 350

Ala Lys Phe Glu Ser Lys Ser Ile Asp Gln Ile Leu Ala
        355                 360                 365


<210> SEQ ID NO 62
<211> LENGTH: 1770
<212> TYPE: DNA
<213> ORGANISM: Perilla frutescens
<220> FEATURE:
<221> NAME/KEY: CDS
<222> LOCATION: (21)..(1541)
<223> OTHER INFORMATION: flavone synthase II

<400> SEQUENCE: 62

tgtcgacgga gcaagtggaa atg gca ctg tac gcc gcc ctc ttc ctc ctg tcc      53
                      Met Ala Leu Tyr Ala Ala Leu Phe Leu Leu Ser
                      1               5                   10

gcc gcc gtg gtc cgc tcc gtt ctg gat cga aaa cgc ggg cgg ccg ccc       101
Ala Ala Val Val Arg Ser Val Leu Asp Arg Lys Arg Gly Arg Pro Pro
            15                  20                  25

tac cct ccc ggg ccg ttc cct ctt ccc atc atc ggc cac tta cac ctc       149
Tyr Pro Pro Gly Pro Phe Pro Leu Pro Ile Ile Gly His Leu His Leu
        30                  35                  40

ctc ggg ccg aga ctc cac caa acc ttc cac gat ctg tcc caa cgg tac       197
Leu Gly Pro Arg Leu His Gln Thr Phe His Asp Leu Ser Gln Arg Tyr
    45                  50                  55

ggg ccc tta atg cag ctc cgc ctc ggg tcc atc cgc tgc gtc att gct       245
Gly Pro Leu Met Gln Leu Arg Leu Gly Ser Ile Arg Cys Val Ile Ala
60                  65                  70                  75

gcc tcg ccg gag ctc gcc aag gaa tgc ctc aag aca cac gag ctc gtc       293
Ala Ser Pro Glu Leu Ala Lys Glu Cys Leu Lys Thr His Glu Leu Val
                80                  85                  90

ttc tcc tcc cgc aaa cac tcc acc gcc att gat atc gtc acc tac gat       341
Phe Ser Ser Arg Lys His Ser Thr Ala Ile Asp Ile Val Thr Tyr Asp
            95                  100                 105
```

-continued

```
tca tcc ttc gct ttc tct ccc tac ggg cct tac tgg aaa ttc atc aag      389
Ser Ser Phe Ala Phe Ser Pro Tyr Gly Pro Tyr Trp Lys Phe Ile Lys
        110                 115                 120

aaa tta tgc acc tac gag ctg ctc ggg gcc cga aat ctc gcc cac ttt      437
Lys Leu Cys Thr Tyr Glu Leu Leu Gly Ala Arg Asn Leu Ala His Phe
    125                 130                 135

cag ccc atc agg act ctc gaa gtc aag tct ttc ctc caa att ctt atg      485
Gln Pro Ile Arg Thr Leu Glu Val Lys Ser Phe Leu Gln Ile Leu Met
140                 145                 150                 155

cgc aag ggt gaa tcg ggg gag agc ttc aac gtg act gag gag ctc gtg      533
Arg Lys Gly Glu Ser Gly Glu Ser Phe Asn Val Thr Glu Glu Leu Val
                160                 165                 170

aag ctg acg agc aac gtc ata tcg cat atg atg ctg agc ata cgg tgt      581
Lys Leu Thr Ser Asn Val Ile Ser His Met Met Leu Ser Ile Arg Cys
            175                 180                 185

tca gag acg gag tcg gag gcg gag gcg gcg agg acg gtg att cgg gag      629
Ser Glu Thr Glu Ser Glu Ala Glu Ala Ala Arg Thr Val Ile Arg Glu
        190                 195                 200

gtc acg cag ata ttt ggg gag ttc gac gtc tcc gac atc ata tgg ctt      677
Val Thr Gln Ile Phe Gly Glu Phe Asp Val Ser Asp Ile Ile Trp Leu
    205                 210                 215

tgt aag aac ttc gat ttc caa ggt ata agg aag cgg tcc gag gat atc      725
Cys Lys Asn Phe Asp Phe Gln Gly Ile Arg Lys Arg Ser Glu Asp Ile
220                 225                 230                 235

cag agg aga tat gat gct ctg ctg gag aag atc atc acc gac aga gag      773
Gln Arg Arg Tyr Asp Ala Leu Leu Glu Lys Ile Ile Thr Asp Arg Glu
                240                 245                 250

aag cag agg cgg acc cac ggc ggc ggt ggc ggc ggc ggg gaa gcc aag      821
Lys Gln Arg Arg Thr His Gly Gly Gly Gly Gly Gly Gly Glu Ala Lys
            255                 260                 265

gat ttt ctt gac atg ttc ctc gac ata atg gag agc ggg aaa gcc gaa      869
Asp Phe Leu Asp Met Phe Leu Asp Ile Met Glu Ser Gly Lys Ala Glu
        270                 275                 280

gtt aaa ttc acg agg gag cat ctc aaa gct ttg att ctg gat ttc ttc      917
Val Lys Phe Thr Arg Glu His Leu Lys Ala Leu Ile Leu Asp Phe Phe
    285                 290                 295

acc gcc ggc acc gac acg acg gcg atc gtg tgt gaa tgg gcg ata gca      965
Thr Ala Gly Thr Asp Thr Thr Ala Ile Val Cys Glu Trp Ala Ile Ala
300                 305                 310                 315

gaa gtg atc aac aat cca aat gtg ttg aag aaa gct caa gaa gag att     1013
Glu Val Ile Asn Asn Pro Asn Val Leu Lys Lys Ala Gln Glu Glu Ile
                320                 325                 330

gcc aac atc gtc gga ttc gac aga att ctg caa gaa tcc gac gcc cca     1061
Ala Asn Ile Val Gly Phe Asp Arg Ile Leu Gln Glu Ser Asp Ala Pro
            335                 340                 345

aat ctg ccc tac ctt caa gcc ctc atc aaa gaa aca ttc cgg ctc cac     1109
Asn Leu Pro Tyr Leu Gln Ala Leu Ile Lys Glu Thr Phe Arg Leu His
        350                 355                 360

cct cca atc cca atg ctg gcg agg aaa tcg atc tcc gac tgc gtc atc     1157
Pro Pro Ile Pro Met Leu Ala Arg Lys Ser Ile Ser Asp Cys Val Ile
    365                 370                 375

gac ggc tac atg att ccg gcc aac acg ctg ctc ttc gtc aac ctc tgg     1205
Asp Gly Tyr Met Ile Pro Ala Asn Thr Leu Leu Phe Val Asn Leu Trp
380                 385                 390                 395

tcc atg ggg cgg aac cct aaa atc tgg gac tac ccg acg gcg ttc cag     1253
Ser Met Gly Arg Asn Pro Lys Ile Trp Asp Tyr Pro Thr Ala Phe Gln
                400                 405                 410

ccg gag agg ttt ctg gag aag gaa aag gcc gcc atc gat gtt aaa ggg     1301
Pro Glu Arg Phe Leu Glu Lys Glu Lys Ala Ala Ile Asp Val Lys Gly
            415                 420                 425
```

-continued

```
cag cat ttt gag ctg cta ccg ttc gga acg ggc agg aga ggc tgc cca      1349
Gln His Phe Glu Leu Leu Pro Phe Gly Thr Gly Arg Arg Gly Cys Pro
        430                 435                 440

ggg atg ctt tta gcc att cag gag gtg gtc atc ata att ggg acg atg      1397
Gly Met Leu Leu Ala Ile Gln Glu Val Val Ile Ile Ile Gly Thr Met
    445                 450                 455

att caa tgc ttc gat tgg aag ctg ccc gac ggc tcc ggc cat gtt gat      1445
Ile Gln Cys Phe Asp Trp Lys Leu Pro Asp Gly Ser Gly His Val Asp
460                 465                 470                 475

atg gca gaa cgg cca ggg ctc acg gca ccg cga gag acc gat ttg ttt      1493
Met Ala Glu Arg Pro Gly Leu Thr Ala Pro Arg Glu Thr Asp Leu Phe
                480                 485                 490

tgc cgt gtg gtg ccg cga gtt gat ccg ttg gtt gtt tcc acc cag tga      1541
Cys Arg Val Val Pro Arg Val Asp Pro Leu Val Val Ser Thr Gln
            495                 500                 505

tcaccccctt taaatttatt aatgatatat ttttattttg agaaaaaata aaaatgctaa    1601

ttgttttgtt tcatgatgta attgttaatt agtttctatt gtgcgctgtc gcgtgtcgcg    1661

tggcttaaga taagattgta tcattggtac ctaggatgta ttttcatttt caataaatta    1721

ttttgtgctg tgtatattaa aaaaaaaaaa gaaaaaaaaa aaaaaaaaa                1770


<210> SEQ ID NO 63
<211> LENGTH: 506
<212> TYPE: PRT
<213> ORGANISM: Perilla frutescens

<400> SEQUENCE: 63

Met Ala Leu Tyr Ala Ala Leu Phe Leu Leu Ser Ala Ala Val Val Arg
1               5                   10                  15

Ser Val Leu Asp Arg Lys Arg Gly Arg Pro Pro Tyr Pro Pro Gly Pro
            20                  25                  30

Phe Pro Leu Pro Ile Ile Gly His Leu His Leu Leu Gly Pro Arg Leu
        35                  40                  45

His Gln Thr Phe His Asp Leu Ser Gln Arg Tyr Gly Pro Leu Met Gln
    50                  55                  60

Leu Arg Leu Gly Ser Ile Arg Cys Val Ile Ala Ala Ser Pro Glu Leu
65                  70                  75                  80

Ala Lys Glu Cys Leu Lys Thr His Glu Leu Val Phe Ser Ser Arg Lys
                85                  90                  95

His Ser Thr Ala Ile Asp Ile Val Thr Tyr Asp Ser Ser Phe Ala Phe
            100                 105                 110

Ser Pro Tyr Gly Pro Tyr Trp Lys Phe Ile Lys Lys Leu Cys Thr Tyr
        115                 120                 125

Glu Leu Leu Gly Ala Arg Asn Leu Ala His Phe Gln Pro Ile Arg Thr
    130                 135                 140

Leu Glu Val Lys Ser Phe Leu Gln Ile Leu Met Arg Lys Gly Glu Ser
145                 150                 155                 160

Gly Glu Ser Phe Asn Val Thr Glu Glu Leu Val Lys Leu Thr Ser Asn
                165                 170                 175

Val Ile Ser His Met Met Leu Ser Ile Arg Cys Ser Glu Thr Glu Ser
            180                 185                 190

Glu Ala Glu Ala Ala Arg Thr Val Ile Arg Glu Val Thr Gln Ile Phe
        195                 200                 205

Gly Glu Phe Asp Val Ser Asp Ile Ile Trp Leu Cys Lys Asn Phe Asp
    210                 215                 220

Phe Gln Gly Ile Arg Lys Arg Ser Glu Asp Ile Gln Arg Arg Tyr Asp
225                 230                 235                 240
```

```
Ala Leu Leu Glu Lys Ile Ile Thr Asp Arg Glu Lys Gln Arg Arg Thr
                245                 250                 255

His Gly Gly Gly Gly Gly Gly Gly Glu Ala Lys Asp Phe Leu Asp Met
            260                 265                 270

Phe Leu Asp Ile Met Glu Ser Gly Lys Ala Glu Val Lys Phe Thr Arg
        275                 280                 285

Glu His Leu Lys Ala Leu Ile Leu Asp Phe Phe Thr Ala Gly Thr Asp
    290                 295                 300

Thr Thr Ala Ile Val Cys Glu Trp Ala Ile Ala Glu Val Ile Asn Asn
305                 310                 315                 320

Pro Asn Val Leu Lys Lys Ala Gln Glu Glu Ile Ala Asn Ile Val Gly
                325                 330                 335

Phe Asp Arg Ile Leu Gln Glu Ser Asp Ala Pro Asn Leu Pro Tyr Leu
            340                 345                 350

Gln Ala Leu Ile Lys Glu Thr Phe Arg Leu His Pro Pro Ile Pro Met
        355                 360                 365

Leu Ala Arg Lys Ser Ile Ser Asp Cys Val Ile Asp Gly Tyr Met Ile
    370                 375                 380

Pro Ala Asn Thr Leu Leu Phe Val Asn Leu Trp Ser Met Gly Arg Asn
385                 390                 395                 400

Pro Lys Ile Trp Asp Tyr Pro Thr Ala Phe Gln Pro Glu Arg Phe Leu
                405                 410                 415

Glu Lys Glu Lys Ala Ala Ile Asp Val Lys Gly Gln His Phe Glu Leu
            420                 425                 430

Leu Pro Phe Gly Thr Gly Arg Arg Gly Cys Pro Gly Met Leu Leu Ala
        435                 440                 445

Ile Gln Glu Val Val Ile Ile Ile Gly Thr Met Ile Gln Cys Phe Asp
    450                 455                 460

Trp Lys Leu Pro Asp Gly Ser Gly His Val Asp Met Ala Glu Arg Pro
465                 470                 475                 480

Gly Leu Thr Ala Pro Arg Glu Thr Asp Leu Phe Cys Arg Val Val Pro
                485                 490                 495

Arg Val Asp Pro Leu Val Val Ser Thr Gln
            500                 505
```

<210> SEQ ID NO 64
<211> LENGTH: 1393
<212> TYPE: DNA
<213> ORGANISM: Artificial Sequence
<220> FEATURE:
<223> OTHER INFORMATION: Sequence 3 from patent US 6169226
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (1150)..(1150)
<223> OTHER INFORMATION: n is a, c, g, or t

<400> SEQUENCE: 64

```
tctgccaaat aatgtggatg gttctcctgc aattcctcat gggtccagag tgaagatacg      60
```

-continued

```
tatggacact ccatcaggtg ttaaggattc cattcctgct tggatcaact actctttaca    120

gcttcctgat gaaattccat ataatggaat atattatgat ccacccgaag aggagaggta    180

tatcttccaa cacccacggc caaagaaacc aaagtcgctg agaatatatg aatctcatat    240

tggaatgagt agtccggagc ctaaaattaa ctcatacgtg aattttagag atgaagttct    300

tcctcgcata aaaaagcttg ggtacaatgc ggtgcaaatt atggctattc aagagcattc    360

ttattatgct agttttggtt atcatgtcac aaattttttn gcaccaagca gccgttttga    420

aacncccgac gaccttaagt ctttgattga taaagctcat gagctaggaa ttgttgttct    480

catggacatt gttcacagcc atgcatcaaa taatacttta gatggactga acatgtttga    540

cggcacagat agttgttact ttcactctgg agctcgtggt tatcattgga tgtgggattc    600

ccgcctcttt aactatggaa actgggaggt acttaggtat cttctctcaa atgcgagatg    660

gtggttggat gagttcaaat ttgatggatt tagatttgat ggtgtgacat caatgatgta    720

tactcaccac ggattatcgg tgggattcac tgggaactac gaggaatact ttggactcgc    780

aactgatgtg gatgctgttg tgtatctgat gctggtcaac gatcttattc atgggctttt    840

cccagatgca attaccattg gtgaagatgt tagcggaatg ccgacatttt ntattcccgt    900

tcaagatggg ggtgttggct ttgactatcg gctgcatatg gcaattgctg ataaatggat    960

tgagttgctc aagaaacggg atgaggattg gagagtgggt gatattgttc atacactgac   1020

aaatagaaga tggtcggaaa agtgtgtttc atacgctgaa agtcatgatc aagctctagt   1080

cggtgataaa actatagcat tctggctgat ggacaaggat atgtatgatt ttatggctct   1140

ggatagaccn tcaacatcat taatagatcg tgggatagca ttgcacaaga tgattaggct   1200

tgtaactatg ggattaggag gagaagggta cctaaatttc atgggaaatg aattcggcca   1260

ccctgagtgg attgatttcc ctagggctga acaacacctc tctgatggct cagtaattcc   1320

cggaaaccaa ttcagttatg ataaatgcag acggagattt gacctgggag atgcagaata   1380

tttaagatac cgt                                                       1393
```

<210> SEQ ID NO 65
<211> LENGTH: 615
<212> TYPE: DNA
<213> ORGANISM: Streptomyces hygroscopicus
<220> FEATURE:
<221> NAME/KEY: CDS
<222> LOCATION: (31)..(582)
<223> OTHER INFORMATION: phosphinothricin acetyltransferase

<400> SEQUENCE: 65

```
gaattcgagc tcggtacccg ggatctacc atg agc cca gaa cga cgc ccg gcc       54
                                Met Ser Pro Glu Arg Arg Pro Ala
                                1               5

gac atc cgc cgt gcc acc gag gcg gac atg ccg gcg gtc tgc acc atc      102
Asp Ile Arg Arg Ala Thr Glu Ala Asp Met Pro Ala Val Cys Thr Ile
    10                  15                  20

gtc aac cac tac atc gag aca agc acg gtc aac ttc cgt acc gag ccg      150
Val Asn His Tyr Ile Glu Thr Ser Thr Val Asn Phe Arg Thr Glu Pro
25                  30                  35                  40

cag gaa ccg cag gag tgg acg gac gac ctc gtc cgt ctg cgg gag cgc      198
Gln Glu Pro Gln Glu Trp Thr Asp Asp Leu Val Arg Leu Arg Glu Arg
                45                  50                  55

tat ccc tgg ctc gtc gcc gag gtg gac ggc gag gtc gcc ggc atc gcc      246
Tyr Pro Trp Leu Val Ala Glu Val Asp Gly Glu Val Ala Gly Ile Ala
            60                  65                  70

tac gcg ggc ccc tgg aag gca cgc aac gcc tac gac tgg acg gcc gag      294
Tyr Ala Gly Pro Trp Lys Ala Arg Asn Ala Tyr Asp Trp Thr Ala Glu
```

```
        75                  80                  85

tcg acc gtg tac gtc tcc ccc cgc cac cag cgg acg gga ctg ggc tcc      342
Ser Thr Val Tyr Val Ser Pro Arg His Gln Arg Thr Gly Leu Gly Ser
    90                  95                  100

acg ctc tac acc cac ctg ctg aag tcc ctg gag gca cag ggc ttc aag      390
Thr Leu Tyr Thr His Leu Leu Lys Ser Leu Glu Ala Gln Gly Phe Lys
105                 110                 115                 120

agc gtg gtc gct gtc atc ggg ctg ccc aac gac ccg agc gtg cgc atg      438
Ser Val Val Ala Val Ile Gly Leu Pro Asn Asp Pro Ser Val Arg Met
                125                 130                 135

cac gag gcg ctc gga tat gcc ccc cgc ggc atg ctg cgg gcg gcc ggc      486
His Glu Ala Leu Gly Tyr Ala Pro Arg Gly Met Leu Arg Ala Ala Gly
            140                 145                 150

ttc aag cac ggg aac tgg cat gac gtg ggt ttc tgg cag ctg gac ttc      534
Phe Lys His Gly Asn Trp His Asp Val Gly Phe Trp Gln Leu Asp Phe
        155                 160                 165

agc ctg ccg gta ccg ccc cgt ccg gtc ctg ccc gtc acc gag atc tga      582
Ser Leu Pro Val Pro Pro Arg Pro Val Leu Pro Val Thr Glu Ile
    170                 175                 180

tgacccgggg gatccctgca ggcatgcaag ctt                                 615


<210> SEQ ID NO 66
<211> LENGTH: 183
<212> TYPE: PRT
<213> ORGANISM: Streptomyces hygroscopicus

<400> SEQUENCE: 66

Met Ser Pro Glu Arg Arg Pro Ala Asp Ile Arg Arg Ala Thr Glu Ala
1               5                   10                  15

Asp Met Pro Ala Val Cys Thr Ile Val Asn His Tyr Ile Glu Thr Ser
            20                  25                  30

Thr Val Asn Phe Arg Thr Glu Pro Gln Glu Pro Gln Glu Trp Thr Asp
        35                  40                  45

Asp Leu Val Arg Leu Arg Glu Arg Tyr Pro Trp Leu Val Ala Glu Val
    50                  55                  60

Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
        115                 120                 125

Pro Asn Asp Pro Ser Val Arg Met His Glu Ala Leu Gly Tyr Ala Pro
    130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                165                 170                 175

Val Leu Pro Val Thr Glu Ile
            180


<210> SEQ ID NO 67
<211> LENGTH: 835
<212> TYPE: DNA
<213> ORGANISM: Streptomyces hygroscopicus
<220> FEATURE:
<221> NAME/KEY: CDS
<222> LOCATION: (160)..(711)
```

<223> OTHER INFORMATION: bar gene product

<400> SEQUENCE: 67

```
gctcgctgtc attttcgaga cgccatcttt ggaagcggtg gccgaatccg tactgcgcgg      60

actcgacgac gcgtaaaacg atcgaccacg tacacgagtc cggacacggg gcgaggaggc     120

ccggttccgg caccgaggaa gaccgaagga agaccacac gtg agc cca gaa cga       174
                                           Val Ser Pro Glu Arg
                                           1               5

cgc ccg gcc gac atc cgc cgt gcc acc gag gcg gac atg ccg gcg gtc       222
Arg Pro Ala Asp Ile Arg Arg Ala Thr Glu Ala Asp Met Pro Ala Val
                10                  15                  20

tgc acc atc gtc aac cac tac atc gag aca agc acg gtc aac ttc cgt       270
Cys Thr Ile Val Asn His Tyr Ile Glu Thr Ser Thr Val Asn Phe Arg
            25                  30                  35

acc gag ccg cag gaa ccg cag gag tgg acg gac gac ctc gtc cgt ctg       318
Thr Glu Pro Gln Glu Pro Gln Glu Trp Thr Asp Asp Leu Val Arg Leu
        40                  45                  50

cgg gag cgc tat ccc tgg ctc gtc gcc gag gtg gac ggc gag gtc gcc       366
Arg Glu Arg Tyr Pro Trp Leu Val Ala Glu Val Asp Gly Glu Val Ala
    55                  60                  65

ggc atc gcc tac gcg ggc ccc tgg aag gca cgc aac gcc tac gac tgg       414
Gly Ile Ala Tyr Ala Gly Pro Trp Lys Ala Arg Asn Ala Tyr Asp Trp
70                  75                  80                  85

acg gcc gag tcg acc gtg tac gtc tcc ccc cgc cac cag cgg acg gga       462
Thr Ala Glu Ser Thr Val Tyr Val Ser Pro Arg His Gln Arg Thr Gly
                90                  95                  100

ctg ggc tcc acg ctc tac acc cac ctg ctg aag tcc ctg gag gca cag       510
Leu Gly Ser Thr Leu Tyr Thr His Leu Leu Lys Ser Leu Glu Ala Gln
            105                 110                 115

ggc ttc aag agc gtg gtc gct gtc atc ggg ctg ccc aac gac ccg agc       558
Gly Phe Lys Ser Val Val Ala Val Ile Gly Leu Pro Asn Asp Pro Ser
        120                 125                 130

gtg cgc atg cac gag gcg ctc gga tat gcc ccc cgc ggc atg ctg cgg       606
Val Arg Met His Glu Ala Leu Gly Tyr Ala Pro Arg Gly Met Leu Arg
    135                 140                 145

gcg gcc ggc ttc aag cac ggg aac tgg cat gac gtg ggt ttc tgg cag       654
Ala Ala Gly Phe Lys His Gly Asn Trp His Asp Val Gly Phe Trp Gln
150                 155                 160                 165

ctg gac ttc agc ctg ccg gta ccg ccc cgt ccg gtc ctg ccc gtc acc       702
Leu Asp Phe Ser Leu Pro Val Pro Pro Arg Pro Val Leu Pro Val Thr
                170                 175                 180

gag atc tga acggagtgcg cgtgggcatc gcccgagttg gagctggtac               751
Glu Ile

gggaactcat cgaactcaac tggcataccc gcaatggtga ggtggaaccg cggcggatcg     811

cgtacgaccg tgcccaggag gcct                                            835
```

<210> SEQ ID NO 68
<211> LENGTH: 183
<212> TYPE: PRT
<213> ORGANISM: Streptomyces hygroscopicus

<400> SEQUENCE: 68

```
Val Ser Pro Glu Arg Arg Pro Ala Asp Ile Arg Arg Ala Thr Glu Ala
1               5                   10                  15

Asp Met Pro Ala Val Cys Thr Ile Val Asn His Tyr Ile Glu Thr Ser
            20                  25                  30

Thr Val Asn Phe Arg Thr Glu Pro Gln Glu Pro Gln Glu Trp Thr Asp
        35                  40                  45
```

-continued

```
Asp Leu Val Arg Leu Arg Glu Arg Tyr Pro Trp Leu Val Ala Glu Val
    50                  55                  60

Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
        115                 120                 125

Pro Asn Asp Pro Ser Val Arg Met His Glu Ala Leu Gly Tyr Ala Pro
    130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                165                 170                 175

Val Leu Pro Val Thr Glu Ile
            180
```

<210> SEQ ID NO 69
<211> LENGTH: 1312
<212> TYPE: DNA
<213> ORGANISM: Streptomyces viridochromogenes

<400> SEQUENCE: 69

```
agatctggag cgacgtcctg ggggccggtc cggtgctgcc cggggacgac ttcttctccc      60

tcggcggcac ctccatctcg gcgttgcggg tggtctcgcg catccgcaag gaactcggcg     120

tgccactccg gctcgccgtg atcttcgaga cgccgtccct ggaagcggtg gccgaatccg     180

tactccgcga actgaagggg acgtagtaaa gaggtgcccg ccacccgctt tcgcagaaca     240

ccgaaggaag accacacgtg agcccagaac gacgcccggt cgagatccgt cccgccaccg     300

ccgccgacat ggcggcggtc tgcgacatcg tcaatcacta catcgagacg agcacggtca     360

acttccgtac ggagccgcag actccgcagg agtggatcga cgacctggag cgcctccagg     420

accgctaccc ctggctcgtc gccgaggtgg agggcgtcgt cgccggcatc gcctacgccg     480

gcccctggaa ggcccgcaac gcctacgact ggaccgtcga gtcgacggtg tacgtctccc     540

accggcacca gcggctcgga ctgggctcca ccctctacac ccacctgctg aagtccatgg     600

aggcccaggg cttcaagagc gtggtcgccg tcatcggact gcccaacgac ccgagcgtgc     660

gcctgcacga ggcgctcgga tacaccgcgc gcgggacgct gcgggcagcc ggctacaagc     720

acgggggctg gcacgacgtg gggttctggc agcgcgactt cgagctgccg gccccgcccc     780

gccccgtccg gcccgtcaca cagatctgag cggagagcgc atggcatcgt cggagttgga     840

gctggtgcgg gaactgatcg ggctcaactg gcacacccgc aacggcgatg tggagccacg     900

ccgggtggcc tacgaccgag cccaggaggc cttcgggcac ctgggcctgc cccccggcga     960

gaccgtcgtg atcggcgact gctcggcgga gtgggtacgg cccgcccagg aggacggcag    1020

gaccctgctg tacctgcacg gcggttcgta cgccctcgga tcgccgcagt cgcaccgcca    1080

tctgtccagc gcgctgggcg cggcggccgg ggcggcggtg ctcgccctgc actaccgcag    1140

gccgcccgag tctcccttcc cggcggcggt ggaggacgcc gtggcggcct accggatgct    1200

gcgggagcgg ggcctgccgc cggggcggat caccttcgcc ggtgactcgg ccggcgcggg    1260

cctcgccgtc gccgccctcc aggtgctgcg cgacgccggg gacccgctgc cg            1312
```

```
<210> SEQ ID NO 70
<211> LENGTH: 1335
<212> TYPE: DNA
<213> ORGANISM: Zea mays
<220> FEATURE:
<221> NAME/KEY: CDS
<222> LOCATION: (1)..(1335)
<223> OTHER INFORMATION: 3-phosphoshikimate 1-carboxyvinyltransferase

<400> SEQUENCE: 70

gcg ggt gcc gag gag atc gtg ctg cag ccc atc aag gag atc tcc ggc       48
Ala Gly Ala Glu Glu Ile Val Leu Gln Pro Ile Lys Glu Ile Ser Gly
1               5                   10                  15

acc gtc aag ctg ccg ggg tcc aag tcg ctt tcc aac cgg atc ctc cta       96
Thr Val Lys Leu Pro Gly Ser Lys Ser Leu Ser Asn Arg Ile Leu Leu
            20                  25                  30

ctc gcc gcc ctg tcc gag ggg aca aca gtg gtt gat aac ctg ctg aac      144
Leu Ala Ala Leu Ser Glu Gly Thr Thr Val Val Asp Asn Leu Leu Asn
        35                  40                  45

agt gag gat gtc cac tac atg ctc ggg gcc ttg agg act ctt ggt ctc      192
Ser Glu Asp Val His Tyr Met Leu Gly Ala Leu Arg Thr Leu Gly Leu
    50                  55                  60

tct gtc gaa gcg gac aaa gct gcc aaa aga gct gta gtt gtt ggc tgt      240
Ser Val Glu Ala Asp Lys Ala Ala Lys Arg Ala Val Val Val Gly Cys
65                  70                  75                  80

ggt gga aag ttc cca gtt gag gat gct aaa gag gaa gtg cag ctc ttc      288
Gly Gly Lys Phe Pro Val Glu Asp Ala Lys Glu Glu Val Gln Leu Phe
                85                  90                  95

ttg ggg aat gct gga act gca atg cgg cca ttg aca gca gct gtt act      336
Leu Gly Asn Ala Gly Thr Ala Met Arg Pro Leu Thr Ala Ala Val Thr
            100                 105                 110

gct gct ggt gga aat gca act tac gtg ctt gat gga gta cca aga atg      384
Ala Ala Gly Gly Asn Ala Thr Tyr Val Leu Asp Gly Val Pro Arg Met
        115                 120                 125

agg gag aga ccc att ggc gac ttg gtt gtc gga ttg aag cag ctt ggt      432
Arg Glu Arg Pro Ile Gly Asp Leu Val Val Gly Leu Lys Gln Leu Gly
    130                 135                 140

gca gat gtt gat tgt ttc ctt ggc act gac tgc cca cct gtt cgt gtc      480
Ala Asp Val Asp Cys Phe Leu Gly Thr Asp Cys Pro Pro Val Arg Val
145                 150                 155                 160

aat gga atc gga ggg cta cct ggt ggc aag gtc aag ctg tct ggc tcc      528
Asn Gly Ile Gly Gly Leu Pro Gly Gly Lys Val Lys Leu Ser Gly Ser
                165                 170                 175

atc agc agt cag tac ttg agt gcc ttg ctg atg gct gct cct ttg gct      576
Ile Ser Ser Gln Tyr Leu Ser Ala Leu Leu Met Ala Ala Pro Leu Ala
            180                 185                 190

ctt ggg gat gtg gag att gaa atc att gat aaa tta atc tcc att ccg      624
Leu Gly Asp Val Glu Ile Glu Ile Ile Asp Lys Leu Ile Ser Ile Pro
        195                 200                 205

tac gtc gaa atg aca ttg aga ttg atg gag cgt ttt ggt gtg aaa gca      672
Tyr Val Glu Met Thr Leu Arg Leu Met Glu Arg Phe Gly Val Lys Ala
    210                 215                 220

gag cat tct gat agc tgg gac aga ttc tac att aag gga ggt caa aaa      720
Glu His Ser Asp Ser Trp Asp Arg Phe Tyr Ile Lys Gly Gly Gln Lys
225                 230                 235                 240

tac aag tcc cct aaa aat gcc tat gtt gaa ggt gat gcc tca agc gca      768
Tyr Lys Ser Pro Lys Asn Ala Tyr Val Glu Gly Asp Ala Ser Ser Ala
                245                 250                 255

agc tat ttc ttg gct ggt gct gca att act gga ggg act gtg act gtg      816
Ser Tyr Phe Leu Ala Gly Ala Ala Ile Thr Gly Gly Thr Val Thr Val
            260                 265                 270

gaa ggt tgt ggc acc acc agt ttg cag ggt gat gtg aag ttt gct gag      864
```

```
Glu Gly Cys Gly Thr Thr Ser Leu Gln Gly Asp Val Lys Phe Ala Glu
        275                 280                 285

gta ctg gag atg atg gga gcg aag gtt aca tgg acc gag act agc gta      912
Val Leu Glu Met Met Gly Ala Lys Val Thr Trp Thr Glu Thr Ser Val
    290                 295                 300

act gtt act ggc cca ccg cgg gag cca ttt ggg agg aaa cac ctc aag      960
Thr Val Thr Gly Pro Pro Arg Glu Pro Phe Gly Arg Lys His Leu Lys
305                 310                 315                 320

gcg att gat gtc aac atg aac aag atg cct gat gtc gcc atg act ctt     1008
Ala Ile Asp Val Asn Met Asn Lys Met Pro Asp Val Ala Met Thr Leu
                325                 330                 335

gct gtg gtt gcc ctc ttt gcc gat ggc ccg aca gcc atc aga gac gtg     1056
Ala Val Val Ala Leu Phe Ala Asp Gly Pro Thr Ala Ile Arg Asp Val
            340                 345                 350

gct tcc tgg aga gta aag gag acc gag agg atg gtt gcg atc cgg acg     1104
Ala Ser Trp Arg Val Lys Glu Thr Glu Arg Met Val Ala Ile Arg Thr
        355                 360                 365

gag cta acc aag ctg gga gca tct gtt gag gaa ggg ccg gac tac tgc     1152
Glu Leu Thr Lys Leu Gly Ala Ser Val Glu Glu Gly Pro Asp Tyr Cys
    370                 375                 380

atc atc acg ccg ccg gag aag ctg aac gtg acg gcg atc gac acg tac     1200
Ile Ile Thr Pro Pro Glu Lys Leu Asn Val Thr Ala Ile Asp Thr Tyr
385                 390                 395                 400

gac gac cac agg atg gcc atg gcc ttc tcc ctt gcc gcc tgt gcc gag     1248
Asp Asp His Arg Met Ala Met Ala Phe Ser Leu Ala Ala Cys Ala Glu
                405                 410                 415

gtc ccc gtc acc atc cgg gac cct ggg tgc acc cgg aag acc ttc ccc     1296
Val Pro Val Thr Ile Arg Asp Pro Gly Cys Thr Arg Lys Thr Phe Pro
            420                 425                 430

gac tac ttc gat gtg ctg agc act ttc gtc aag aat taa                 1335
Asp Tyr Phe Asp Val Leu Ser Thr Phe Val Lys Asn
        435                 440


<210> SEQ ID NO 71
<211> LENGTH: 444
<212> TYPE: PRT
<213> ORGANISM: Zea mays

<400> SEQUENCE: 71

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160
```

-continued

```
Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440


<210> SEQ ID NO 72
<211> LENGTH: 1332
<212> TYPE: DNA
<213> ORGANISM: Salmonella typhimurium
<220> FEATURE:
<221> NAME/KEY: CDS
<222> LOCATION: (27)..(1310)
<223> OTHER INFORMATION: 5-enolpyruvylshikimate-3-phosphate synthase

<400> SEQUENCE: 72

tttctgtttt ttgagagttg agtttc atg gaa tcc ctg acg tta caa ccc atc      53
                             Met Glu Ser Leu Thr Leu Gln Pro Ile
                             1               5

gcg cgg gtc gat ggc gcc att aat tta cct ggc tcc aaa agt gtt tca      101
Ala Arg Val Asp Gly Ala Ile Asn Leu Pro Gly Ser Lys Ser Val Ser
10                  15                  20                  25

aac cgt gct ttg ctc ctg gcg gct tta cct tgt ggt aaa acc gct ctg      149
Asn Arg Ala Leu Leu Leu Ala Ala Leu Pro Cys Gly Lys Thr Ala Leu
                30                  35                  40

acg aat ctg ctg gat agc gat gac gtc cgc cat atg ctc aat gcc ctg      197
```

-continued

```
Thr Asn Leu Leu Asp Ser Asp Asp Val Arg His Met Leu Asn Ala Leu
            45                  50                  55

agc gcg ttg ggg atc aat tac acc ctt tct gcc gat cgc acc cgc tgt      245
Ser Ala Leu Gly Ile Asn Tyr Thr Leu Ser Ala Asp Arg Thr Arg Cys
        60                  65                  70

gat atc acg ggt aat ggc ggc gca tta cgt gcg cca ggc gct ctg gaa      293
Asp Ile Thr Gly Asn Gly Gly Ala Leu Arg Ala Pro Gly Ala Leu Glu
    75                  80                  85

ctg ttt ctc ggt aat gcc gga acc gcg atg cgt ccg tta gcg gca gcg      341
Leu Phe Leu Gly Asn Ala Gly Thr Ala Met Arg Pro Leu Ala Ala Ala
90                  95                  100                 105

cta tgt ctg ggg caa aat gag ata gtg tta acc ggc gaa ccg cgt atg      389
Leu Cys Leu Gly Gln Asn Glu Ile Val Leu Thr Gly Glu Pro Arg Met
                110                 115                 120

aaa gag cgt ccg ata ggc cat ctg gtc gat tcg ctg cgt cag ggc ggg      437
Lys Glu Arg Pro Ile Gly His Leu Val Asp Ser Leu Arg Gln Gly Gly
            125                 130                 135

gcg aat att gat tac ctg gag cag gaa aac tat ccg ccc ctg cgt ctg      485
Ala Asn Ile Asp Tyr Leu Glu Gln Glu Asn Tyr Pro Pro Leu Arg Leu
        140                 145                 150

cgc ggc ggt ttt acc ggc ggc gac att gag gtt gat ggt agc gtt tcc      533
Arg Gly Gly Phe Thr Gly Gly Asp Ile Glu Val Asp Gly Ser Val Ser
    155                 160                 165

agc cag ttc ctg acc gct ctg ctg atg acg gcg ccg ctg gcc cct aaa      581
Ser Gln Phe Leu Thr Ala Leu Leu Met Thr Ala Pro Leu Ala Pro Lys
170                 175                 180                 185

gac aca att att cgc gtt aaa ggc gaa ctg gta tca aaa cct tac atc      629
Asp Thr Ile Ile Arg Val Lys Gly Glu Leu Val Ser Lys Pro Tyr Ile
                190                 195                 200

gat atc acg cta aat tta atg aaa acc ttt ggc gtg gag ata gcg aac      677
Asp Ile Thr Leu Asn Leu Met Lys Thr Phe Gly Val Glu Ile Ala Asn
            205                 210                 215

cac cac tac caa caa ttt gtc gtg aag gga ggt caa cag tat cac tct      725
His His Tyr Gln Gln Phe Val Val Lys Gly Gly Gln Gln Tyr His Ser
        220                 225                 230

cca ggt cgc tat ctg gtc gag ggc gat gcc tcg tca gcg tcc tat ttt      773
Pro Gly Arg Tyr Leu Val Glu Gly Asp Ala Ser Ser Ala Ser Tyr Phe
    235                 240                 245

ctc gcc gct ggg gcg ata aaa ggc ggc acg gta aaa gtg acc gga att      821
Leu Ala Ala Gly Ala Ile Lys Gly Gly Thr Val Lys Val Thr Gly Ile
250                 255                 260                 265

ggc cgc aaa agt atg cag ggc gat att cgt ttt gcc gat gtg ctg gag      869
Gly Arg Lys Ser Met Gln Gly Asp Ile Arg Phe Ala Asp Val Leu Glu
                270                 275                 280

aaa atg ggc gcg acc att acc tgg ggc gat gat ttt att gcc tgc acg      917
Lys Met Gly Ala Thr Ile Thr Trp Gly Asp Asp Phe Ile Ala Cys Thr
            285                 290                 295

cgc ggt gaa ttg cac gcc ata gat atg gat atg aac cat att ccg gat      965
Arg Gly Glu Leu His Ala Ile Asp Met Asp Met Asn His Ile Pro Asp
        300                 305                 310

gcg gcg atg acg att gcc acc acg gcg ctg ttt gcg aaa gga acc acg     1013
Ala Ala Met Thr Ile Ala Thr Thr Ala Leu Phe Ala Lys Gly Thr Thr
    315                 320                 325

acg ttg cgc aat att tat aac tgg cga gtg aaa gaa acc gat cgc ctg     1061
Thr Leu Arg Asn Ile Tyr Asn Trp Arg Val Lys Glu Thr Asp Arg Leu
330                 335                 340                 345

ttc gcg atg gcg acc gag cta cgt aaa gtg ggc gct gaa gtc gaa gaa     1109
Phe Ala Met Ala Thr Glu Leu Arg Lys Val Gly Ala Glu Val Glu Glu
                350                 355                 360

ggg cac gac tat att cgt atc acg ccg ccg gcg aag ctc caa cac gcg     1157
```

```
Gly His Asp Tyr Ile Arg Ile Thr Pro Pro Ala Lys Leu Gln His Ala
            365                 370                 375

gat att ggc acg tac aac gac cac cgt atg gcg atg tgc ttc tca ctg     1205
Asp Ile Gly Thr Tyr Asn Asp His Arg Met Ala Met Cys Phe Ser Leu
        380                 385                 390

gtc gca ctg tcc gat acg cca gtt acg atc ctg gac cct aaa tgt acc     1253
Val Ala Leu Ser Asp Thr Pro Val Thr Ile Leu Asp Pro Lys Cys Thr
    395                 400                 405

gca aaa acg ttc cct gat tat ttc gaa caa ctg gcg cga atg agt acg     1301
Ala Lys Thr Phe Pro Asp Tyr Phe Glu Gln Leu Ala Arg Met Ser Thr
410                 415                 420                 425

cct gcc taa gtcttctgtt gcgccagtcg ac                                 1332
Pro Ala


<210> SEQ ID NO 73
<211> LENGTH: 427
<212> TYPE: PRT
<213> ORGANISM: Salmonella typhimurium

<400> SEQUENCE: 73

Met Glu Ser Leu Thr Leu Gln Pro Ile Ala Arg Val Asp Gly Ala Ile
1               5                   10                  15

Asn Leu Pro Gly Ser Lys Ser Val Ser Asn Arg Ala Leu Leu Leu Ala
            20                  25                  30

Ala Leu Pro Cys Gly Lys Thr Ala Leu Thr Asn Leu Leu Asp Ser Asp
        35                  40                  45

Asp Val Arg His Met Leu Asn Ala Leu Ser Ala Leu Gly Ile Asn Tyr
    50                  55                  60

Thr Leu Ser Ala Asp Arg Thr Arg Cys Asp Ile Thr Gly Asn Gly Gly
65                  70                  75                  80

Ala Leu Arg Ala Pro Gly Ala Leu Glu Leu Phe Leu Gly Asn Ala Gly
                85                  90                  95

Thr Ala Met Arg Pro Leu Ala Ala Ala Leu Cys Leu Gly Gln Asn Glu
            100                 105                 110

Ile Val Leu Thr Gly Glu Pro Arg Met Lys Glu Arg Pro Ile Gly His
        115                 120                 125

Leu Val Asp Ser Leu Arg Gln Gly Gly Ala Asn Ile Asp Tyr Leu Glu
    130                 135                 140

Gln Glu Asn Tyr Pro Pro Leu Arg Leu Arg Gly Gly Phe Thr Gly Gly
145                 150                 155                 160

Asp Ile Glu Val Asp Gly Ser Val Ser Ser Gln Phe Leu Thr Ala Leu
                165                 170                 175

Leu Met Thr Ala Pro Leu Ala Pro Lys Asp Thr Ile Ile Arg Val Lys
            180                 185                 190

Gly Glu Leu Val Ser Lys Pro Tyr Ile Asp Ile Thr Leu Asn Leu Met
        195                 200                 205

Lys Thr Phe Gly Val Glu Ile Ala Asn His His Tyr Gln Gln Phe Val
    210                 215                 220

Val Lys Gly Gly Gln Gln Tyr His Ser Pro Gly Arg Tyr Leu Val Glu
225                 230                 235                 240

Gly Asp Ala Ser Ser Ala Ser Tyr Phe Leu Ala Ala Gly Ala Ile Lys
                245                 250                 255

Gly Gly Thr Val Lys Val Thr Gly Ile Gly Arg Lys Ser Met Gln Gly
            260                 265                 270

Asp Ile Arg Phe Ala Asp Val Leu Glu Lys Met Gly Ala Thr Ile Thr
        275                 280                 285
```

-continued

```
Trp Gly Asp Asp Phe Ile Ala Cys Thr Arg Gly Glu Leu His Ala Ile
    290                 295                 300

Asp Met Asp Met Asn His Ile Pro Asp Ala Ala Met Thr Ile Ala Thr
305                 310                 315                 320

Thr Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Ala Lys Leu Gln His Ala Asp Ile Gly Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Met Ser Thr Pro Ala
            420                 425
```

<210> SEQ ID NO 74
<211> LENGTH: 912
<212> TYPE: DNA
<213> ORGANISM: Artificial Sequence
<220> FEATURE:
<223> OTHER INFORMATION: Sequence 3 from Patent WO9927116

<400> SEQUENCE: 74

```
atggatagga gagcccacac aatgaccaac cctgcatact ttccgcaact ttcccagctt     60

gatgtgtctg gagaaatgga atcgacctat gaagatattc gcctaacgtt acgcgtgcct    120

tgggtcgcct tcggttgccg agtgcttgct acatttccag gttacctgcc acttgcatgg    180

cgcgcgagcg cagaagcact cattacccgc tacgctgagc aagccgctga cgagctgcgc    240

gagcgctccc tactcaacat cggtccattg ccgaacttaa aagaacggtt gtacgctgca    300

ggattcgatg acggagaaat tgagaaggtt agacgcgtgc tttatgcgtt taactatggt    360

aatccaaaat atctgttgct cattaccgcg ttgagtgaaa gcatgcagat gcggccggtg    420

ggaggagctg aggtttcgtc cgagcttcga gcatccatcc cgaaggggca tccaaaaggt    480

atggatccgc ttttgccgct tgtcgatgcc accaaggcat ccaccgaggt tcaagggctc    540

cttaagcggg tggctgacct tcactatcat cacggtccgg caagtgattt ccaagcgctg    600

gccaattggc cgaaggtact gcagattgtt acagatgaag tgctcgcacc ggttgcccgc    660

accgagcagt atgatgccaa gtcacgggag ctggtaaccc gggcgcggga actggtgcgt    720

ggactgcccg gctctgctgg tgttcagcgg tcggagctaa tgtccatgct gacaccgaac    780

gagcttgccg gtctgactgg tgtcctattc atgtatcagc gcttcatcgc tgacatcaca    840

attagcatca ttcatataac agagtgtttg gacggcgcgg aagcagcgtc taagtcgcct    900

tttcctatct aa                                                        912
```

<210> SEQ ID NO 75
<211> LENGTH: 1170
<212> TYPE: DNA
<213> ORGANISM: Artificial Sequence
<220> FEATURE:
<223> OTHER INFORMATION: Sequence 1 from Patent WO9927116

<400> SEQUENCE: 75

```
cccgcgaaat taatacgact cactataggg agaccacaac ggtttccctc tagggaattc     60
```

atggacaggc gcgcccacac catgaccaac ccagcctact ttccacagct ttctcaactc 120
gacgtgtctg gggagatgga gtctacctac gaggacatca ggctcaccct cagggtgcca 180
tgggtcgcct ttgggtgcag ggtgctcgcc acctttccag ggtacttgcc actcgcctgg 240
cgcaggtccg ccgaggccct catcaccagg tacgccgagc aagccgccga cgagttgagg 300
gagaggtccc tcctcaacat cgggccattg ccaaacttga aggagaggtt gtacgccgcc 360
gggtttgacg acggggagat cgagaaggtg cgcagggtgc tctacgcctt taactacggg 420
aacccaaagt acctcttgct catcaccgcc ttgtctgagt ctatgcagat gaggccagtg 480 ggggggggccg aggtgtcttc tgagctccgc gcctctatcc caaaggggca cccaaagggg 540
atggacccac tcctcccact cgtggacgcc accaaggcct ctaccgaggt gcaagggctc 600
ctcaagaggg tggccgacct ccactaccac cacgggccag cctctgactt tcaggccttg 660
gccaactggc caaaggtgct ccaaatcgtg accgacgagg tgctcgcccc agtggcccgc 720
accgagcaat acgacgccaa gtccagggag ctcgctaccc gcgccaggga gctggtgagg 780
ggcctcccca ggtccgccgg ggtgcaaagg tctgaactta tgtccatgct caccccaaac 840
gagctcgccg ggctcaccgg ggtgctcttt atgtaccaac gctttatcgc cgacatcacc 900
atcagcatca tccacatcac cgagtgcttg gacggggccg aggccgcctc taagtctcca 960
tttccaatct gagtcgacgg atccgagctt gagtattcta tagtgtcacc taaatcccag 1020
cttgatccgg ctgctaacaa agcccgaaag gaagctgagt tggctgctgc caccgctgag 1080
caataactag cataacccct tggggcctct aaacgggtct tgaggggttt tttgctgaaa 1140
ggaggaacta tatccggata acctggcgta 1170

<210> SEQ ID NO 76
<211> LENGTH: 1047
<212> TYPE: DNA
<213> ORGANISM: Klebsiella pneumoniae

<400> SEQUENCE: 76
atggacacca ctttcaaagc agccgctgtt caggccgaac cggtatggat ggatgccgct 60
gcaacagccg ataagaccgt gacgctagta gctaaagccg cagcggctgg cgcgcagctc 120
gtcgcatttc ccgaattgtg gattccgggc tacccaggat tcatgctcac gcacaaccaa 180
accgaaaccc taccattcat cattaaatac cgcaagcagg caatcgccgc cgatggacca 240
gaaatcgaaa aaattcgctg cgcggctcag gagcataaca ttgcgctctc ctttgggtac 300
agcgaacggg ctggccgtac gctctacatg tcacaaatgc ttatcgatgc cgatggcatc 360
accaaaattc gtcgtcgaaa gctcaaacca acccgctttg aacgagaact ctttggcgaa 420
ggtgacggat cggacttaca ggtcgcccaa actagcgttg gtcgggtggg tgccctcaac 480
tgcgcggaga atttgcagtc gctaaacaag tttgcgcttg ctgccgaggg tgaacagata 540
catatctccg cctggccatt cacgcttgga agccctgtgc tcgtcggaga ctccatcggc 600
gccatcaacc aggtctacgc ggccgagacg gggaccttcg ttctcatgtc gacgcaggtg 660
gttggaccga ccggcatcgc cgccttcgag atcgaagaca ggtacaaccc gaatcagtat 720
cttggtggtg ggtacgcgcg gatctacggg cctgacatgc agttgaagag caagtcgttg 780
tcaccgaccg aagagggcat cgtctacgcc gagatcgacc tgtcgatgct tgaggcagca 840
aagtactcgc tcgatcccac gggccactat tcgcgccctg atgtgttcag cgtgtcgatt 900
aaccggcaac ggcagcctgc ggtgtcagaa gttatcgact caaacggtga cgaggacccg 960
agagcagcat gcgagcccga cgagggggat cgtgaggtcg taatctctac ggcaataggg 1020

```
gttctacccc gttattgcgg acattcc                                          1047


<210> SEQ ID NO 77
<211> LENGTH: 1212
<212> TYPE: DNA
<213> ORGANISM: Klebsiella pneumoniae
<220> FEATURE:
<221> NAME/KEY: CDS
<222> LOCATION: (66)..(1115)
<223> OTHER INFORMATION: bromoxynil-specific nitrilase

<400> SEQUENCE: 77

ctgcaggata gtaggggctt gaagagatac gctgtttgtc gagccatcaa aataagggga        60

ttttc atg gac acc act ttc aaa gca gcc gct gtt cag gcc gaa ccg gta      110
      Met Asp Thr Thr Phe Lys Ala Ala Ala Val Gln Ala Glu Pro Val
      1               5                   10                  15

tgg atg gat gcc gct gca aca gcc gat aag acc gtg acg cta gta gct        158
Trp Met Asp Ala Ala Ala Thr Ala Asp Lys Thr Val Thr Leu Val Ala
                20                  25                  30

aaa gcc gca gcg gct ggc gcg cag ctc gtc gca ttt ccc gaa ttg tgg        206
Lys Ala Ala Ala Ala Gly Ala Gln Leu Val Ala Phe Pro Glu Leu Trp
            35                  40                  45

att ccg ggc tac cca gga ttc atg ctc acg cac aac caa acc gaa acc        254
Ile Pro Gly Tyr Pro Gly Phe Met Leu Thr His Asn Gln Thr Glu Thr
        50                  55                  60

cta cca ttc atc att aaa tac cgc aag cag gca atc gcc gcc gat gga        302
Leu Pro Phe Ile Ile Lys Tyr Arg Lys Gln Ala Ile Ala Ala Asp Gly
    65                  70                  75

cca gaa atc gaa aaa att cgc tgc gcg gct cag gag cat aac att gcg        350
Pro Glu Ile Glu Lys Ile Arg Cys Ala Ala Gln Glu His Asn Ile Ala
80                  85                  90                  95

ctc tcc ttt ggg tac agc gaa cgg gct ggc cgt acg ctc tac atg tca        398
Leu Ser Phe Gly Tyr Ser Glu Arg Ala Gly Arg Thr Leu Tyr Met Ser
                100                 105                 110

caa atg ctt atc gat gcc gat ggc atc acc aaa att cgt cgt cga aag        446
Gln Met Leu Ile Asp Ala Asp Gly Ile Thr Lys Ile Arg Arg Arg Lys
            115                 120                 125

ctc aaa cca acc cgc ttt gaa cga gaa ctc ttt ggc gaa ggt gac gga        494
Leu Lys Pro Thr Arg Phe Glu Arg Glu Leu Phe Gly Glu Gly Asp Gly
        130                 135                 140

tcg gac tta cag gtc gcc caa act agc gtt ggt cgg gtg ggt gcc ctc        542
Ser Asp Leu Gln Val Ala Gln Thr Ser Val Gly Arg Val Gly Ala Leu
    145                 150                 155

aac tgc gcg gag aat ttg cag tcg cta aac aag ttt gcg ctt gct gcc        590
Asn Cys Ala Glu Asn Leu Gln Ser Leu Asn Lys Phe Ala Leu Ala Ala
160                 165                 170                 175

gag ggt gaa cag ata cat atc tcc gcc tgg cca ttc acg ctt gga agc        638
Glu Gly Glu Gln Ile His Ile Ser Ala Trp Pro Phe Thr Leu Gly Ser
                180                 185                 190

cct gtg ctc gtc gga gac tcc atc ggc gcc atc aac cag gtc tac gcg        686
Pro Val Leu Val Gly Asp Ser Ile Gly Ala Ile Asn Gln Val Tyr Ala
            195                 200                 205

gcc gag acg ggg acc ttc gtt ctc atg tcg acg cag gtg gtt gga ccg        734
Ala Glu Thr Gly Thr Phe Val Leu Met Ser Thr Gln Val Val Gly Pro
        210                 215                 220

acc ggc atc gcc gcc ttc gag atc gaa gac agg tac aac ccg aat cag        782
Thr Gly Ile Ala Ala Phe Glu Ile Glu Asp Arg Tyr Asn Pro Asn Gln
    225                 230                 235

tat ctt ggt ggt ggg tac gcg cgg atc tac ggg cct gac atg cag ttg        830
Tyr Leu Gly Gly Gly Tyr Ala Arg Ile Tyr Gly Pro Asp Met Gln Leu
240                 245                 250                 255
```

```
aag agc aag tcg ttg tca ccg acc gaa gag ggc atc gtc tac gcc gag      878
Lys Ser Lys Ser Leu Ser Pro Thr Glu Glu Gly Ile Val Tyr Ala Glu
                260                 265                 270

atc gac ctg tcg atg ctt gag gca gca aag tac tcg ctc gat ccc acg      926
Ile Asp Leu Ser Met Leu Glu Ala Ala Lys Tyr Ser Leu Asp Pro Thr
            275                 280                 285

ggc cac tat tcg cgc cct gat gtg ttc agc gtg tcg att aac cgg caa      974
Gly His Tyr Ser Arg Pro Asp Val Phe Ser Val Ser Ile Asn Arg Gln
        290                 295                 300

cgg cag cct gcg gtg tca gaa gtt atc gac tca aac ggt gac gag gac     1022
Arg Gln Pro Ala Val Ser Glu Val Ile Asp Ser Asn Gly Asp Glu Asp
    305                 310                 315

ccg aga gca gca tgc gag ccc gac gag ggg gat cgt gag gtc gta atc     1070
Pro Arg Ala Ala Cys Glu Pro Asp Glu Gly Asp Arg Glu Val Val Ile
320                 325                 330                 335

tct acg gca ata ggg gtt cta ccc cgt tat tgc gga cat tcc taa         1115
Ser Thr Ala Ile Gly Val Leu Pro Arg Tyr Cys Gly His Ser
                340                 345

taaaaagaga cacgttgtac caaaggggtg ttcatgtcca gacgcagaaa atatagccca   1175

gagttaaaac gcgaagccat cgctttaacc cgtcaac                            1212


<210> SEQ ID NO 78
<211> LENGTH: 349
<212> TYPE: PRT
<213> ORGANISM: Klebsiella pneumoniae

<400> SEQUENCE: 78

Met Asp Thr Thr Phe Lys Ala Ala Ala Val Gln Ala Glu Pro Val Trp
1               5                   10                  15

Met Asp Ala Ala Ala Thr Ala Asp Lys Thr Val Thr Leu Val Ala Lys
            20                  25                  30

Ala Ala Ala Ala Gly Ala Gln Leu Val Ala Phe Pro Glu Leu Trp Ile
        35                  40                  45

Pro Gly Tyr Pro Gly Phe Met Leu Thr His Asn Gln Thr Glu Thr Leu
    50                  55                  60

Pro Phe Ile Ile Lys Tyr Arg Lys Gln Ala Ile Ala Ala Asp Gly Pro
65                  70                  75                  80

Glu Ile Glu Lys Ile Arg Cys Ala Ala Gln Glu His Asn Ile Ala Leu
                85                  90                  95

Ser Phe Gly Tyr Ser Glu Arg Ala Gly Arg Thr Leu Tyr Met Ser Gln
            100                 105                 110

Met Leu Ile Asp Ala Asp Gly Ile Thr Lys Ile Arg Arg Arg Lys Leu
        115                 120                 125

Lys Pro Thr Arg Phe Glu Arg Glu Leu Phe Gly Glu Gly Asp Gly Ser
    130                 135                 140

Asp Leu Gln Val Ala Gln Thr Ser Val Gly Arg Val Gly Ala Leu Asn
145                 150                 155                 160

Cys Ala Glu Asn Leu Gln Ser Leu Asn Lys Phe Ala Leu Ala Ala Glu
                165                 170                 175

Gly Glu Gln Ile His Ile Ser Ala Trp Pro Phe Thr Leu Gly Ser Pro
            180                 185                 190

Val Leu Val Gly Asp Ser Ile Gly Ala Ile Asn Gln Val Tyr Ala Ala
        195                 200                 205

Glu Thr Gly Thr Phe Val Leu Met Ser Thr Gln Val Val Gly Pro Thr
    210                 215                 220

Gly Ile Ala Ala Phe Glu Ile Glu Asp Arg Tyr Asn Pro Asn Gln Tyr
```

```
225                 230                 235                 240

Leu Gly Gly Gly Tyr Ala Arg Ile Tyr Gly Pro Asp Met Gln Leu Lys
                245                 250                 255

Ser Lys Ser Leu Ser Pro Thr Glu Glu Gly Ile Val Tyr Ala Glu Ile
            260                 265                 270

Asp Leu Ser Met Leu Glu Ala Ala Lys Tyr Ser Leu Asp Pro Thr Gly
        275                 280                 285

His Tyr Ser Arg Pro Asp Val Phe Ser Val Ser Ile Asn Arg Gln Arg
    290                 295                 300

Gln Pro Ala Val Ser Glu Val Ile Asp Ser Asn Gly Asp Glu Asp Pro
305                 310                 315                 320

Arg Ala Ala Cys Glu Pro Asp Glu Gly Asp Arg Glu Val Val Ile Ser
                325                 330                 335

Thr Ala Ile Gly Val Leu Pro Arg Tyr Cys Gly His Ser
            340                 345


<210> SEQ ID NO 79
<211> LENGTH: 3046
<212> TYPE: DNA
<213> ORGANISM: Artificial Sequence
<220> FEATURE:
<223> OTHER INFORMATION: Minitransposon mTn5-GNm

<400> SEQUENCE: 79

ctgactctta tacacaagtg cggccgcgcg aattgatccg gtgattgatt gagcaagcta     60

attccggacc agtattatta tcttaatgag gagtccctta tgttacgtcc tgtagaaacc    120

ccaacccgtg aaatcaaaaa actcgacggc ctgtgggcat tcagtctgga tcgcgaaaac    180

tgtggaattg atcagcgttg gtgggaaagc gcgttacaag aaagccgggc aattgctgtg    240

ccaggcagtt ttaacgatca gttcgccgat gcagatattc gtaattatgc gggcaacgtc    300

tggtatcagc gcgaagtctt tataccgaaa ggttgggcag gccagcgtat cgtgctgcgt    360

ttcgatgcgg tcactcatta cggcaaagtg tgggtcaata atcaggaagt gatggagcat    420

cagggcggct atacgccatt tgaagccgat gtcacgccgt atgttattgc cgggaaaagt    480

gtacgtatca ccgtttgtgt gaacaacgaa ctgaactggc agactatccc gccgggaatg    540

gtgattaccg acgaaaacgg caagaaaaag cagtcttact tccatgattt ctttaactat    600

gccgggatcc atcgcagcgt aatgctctac accacgccga acacctgggt ggacgatatc    660

accgtggtga cgcatgtcgc gcaagactgt aaccacgcgt ctgttgactg gcaggtggtg    720

gccaatggtg atgtcagcgt tgaactgcgt gatgcggatc aacaggtggt tgcaactgga    780

caaggcacta gcgggacttt gcaagtggtg aatccgcacc tctggcaacc gggtgaaggt    840

tatctctatg aactgtgcgt cacagccaaa agccagacag agtgtgatat ctacccgctt    900

cgcgtcggca tccggtcagt ggcagtgaag ggcgaacagt tcctgattaa ccacaaaccg    960

ttctacttta ctggctttgg tcgtcatgaa gatgcggact tacgtggcaa aggattcgat   1020

aacgtgctga tggtgcacga ccacgcatta atggactgga ttggggccaa ctcctaccgt   1080

acctcgcatt acccttacgc tgaagagatg ctcgactggg cagatgaaca tggcatcgtg   1140

gtgattgatg aaactgctgc tgtcggcttt aacctctctt taggcattgg tttcgaagcg   1200

ggcaacaagc cgaaagaact gtacagcgaa gaggcagtca acggggaaac tcagcaagcg   1260

cacttacagg cgattaaaga gctgatagcg cgtgacaaaa accacccaag cgtggtgatg   1320

tggagtattg ccaacgaacc ggatacccgt ccgcaagtgc acgggaatat ttcgccactg   1380

gcggaagcaa cgcgtaaact cgacccgacg cgtccgatca cctgcgtcaa tgtaatgttc   1440
```

```
tgcgacgctc acaccgatac catcagcgat ctctttgatg tgctgtgcct gaaccgttat   1500

tacggatggt atgtccaaag cggcgatttg gaaacggcag agaaggtact ggaaaaagaa   1560

cttctggcct ggcaggagaa actgcatcag ccgattatca tcaccgaata cggcgtggat   1620

acgttagccg ggctgcactc aatgtacacc gacatgtgga gtgaagagta tcagtgtgca   1680

tggctggata tgtatcaccg cgtctttgat cgcgtcagcg ccgtcgtcgg tgaacaggta   1740

tggaatttcg ccgattttgc gacctcgcaa ggcatattgc gcgttggcgg taacaagaaa   1800

gggatcttca ctcgcgaccg caaaccgaag tcggcggctt ttctgctgca aaaacgctgg   1860

actggcatga acttcggtga aaaaccgcag cagggaggca aacaatgaat caacaactct   1920

cctggcgcac catcgtcggc tacagcctcg gtgaagctag cttactcccc atccccctgt   1980

tgacaattaa tcatcggctc gtataattgt ggaattgtga gcggataaca atttcacaca   2040

ggaaacagga tcgatcaaga gacaggatga ggatcgtttc gcatgattga acaagatgga   2100

ttgcacgcag gttctccggc cgcttgggtg gagaggctat tcggctatga ctgggcacaa   2160

cagacaatcg gctgctctga tgccgccgtg ttccggctgt cagcgcaggg gcgcccggtt   2220

ctttttgtca agaccgacct gtccggtgcc ctgaatgaac tgcaggacga ggcagcgcgg   2280

ctatcgtggc tggccacgac gggcgttcct tgcgcagctg tgctcgacgt tgtcactgaa   2340

gcgggaaggg actggctgct attgggcgaa gtgccggggc aggatctcct gtcatctcac   2400

cttgctcctg ccgagaaagt atccatcatg gctgatgcaa tgcggcggct gcatacgctt   2460

gatccggcta cctgcccatt cgaccaccaa gcgaaacatc gcatcgagcg agcacgtact   2520

cggatggaag ccggtcttgt cgatcaggat gatctggacg aagagcatca ggggctcgcg   2580

ccagccgaac tgttcgccag gctcaaggcg cgcatgcccg acggcgagga tctcgtcgtg   2640

acccatggcg atgcctgctt gccgaatatc atggtggaaa atggccgctt ttctggattc   2700

atcgactgtg gccggctggg tgtggcggac cgctatcagg acatagcgtt ggctacccgt   2760

gatattgctg aagagcttgg cggcgaatgg gctgaccgct tcctcgtgct ttacggtatc   2820

gccgctcccg attcgcagcg catcgccttc tatcgccttc ttgacgagtt cttctgagcg   2880

ggactctggg gttcgaattg atccggtgat tgattgagca agctgatccg tcgatcgacc   2940

tgcatctagc ccgcctaatg agcgggcttt tttttagatg cagccaagct agcttgcggc   3000

cagcttgcgg ccgcggccta ggcggccaga tctgatcaag agacag                  3046
```

<210> SEQ ID NO 80
<211> LENGTH: 1107
<212> TYPE: DNA
<213> ORGANISM: Artificial Sequence
<220> FEATURE:
<223> OTHER INFORMATION: Minitransposon mTn5-Nm
<220> FEATURE:
<221> NAME/KEY: CDS
<222> LOCATION: (157)..(951)
<223> OTHER INFORMATION: aminoglycoside-3'-O-phosphotransferase

<400> SEQUENCE: 80

```
ctgactctta tacacaagtg cggccgcaag ctagcttact ccccatcccc ctgttgacaa     60

ttaatcatcg gctcgtataa ttgtggaatt gtgagcggat aacaatttca cacaggaaac    120

aggatcgatc aagagacagg atgaggatcg tttcgc atg att gaa caa gat gga      174
                                        Met Ile Glu Gln Asp Gly
                                        1               5

ttg cac gca ggt tct ccg gcc gct tgg gtg gag agg cta ttc ggc tat      222
Leu His Ala Gly Ser Pro Ala Ala Trp Val Glu Arg Leu Phe Gly Tyr
            10                  15                  20
```

-continued

```
gac tgg gca caa cag aca atc ggc tgc tct gat gcc gcc gtg ttc cgg      270
Asp Trp Ala Gln Gln Thr Ile Gly Cys Ser Asp Ala Ala Val Phe Arg
        25                  30                  35

ctg tca gcg cag ggg cgc ccg gtt ctt ttt gtc aag acc gac ctg tcc      318
Leu Ser Ala Gln Gly Arg Pro Val Leu Phe Val Lys Thr Asp Leu Ser
    40                  45                  50

ggt gcc ctg aat gaa ctg cag gac gag gca gcg cgg cta tcg tgg ctg      366
Gly Ala Leu Asn Glu Leu Gln Asp Glu Ala Ala Arg Leu Ser Trp Leu
55                  60                  65                  70

gcc acg acg ggc gtt cct tgc gca gct gtg ctc gac gtt gtc act gaa      414
Ala Thr Thr Gly Val Pro Cys Ala Ala Val Leu Asp Val Val Thr Glu
                75                  80                  85

gcg gga agg gac tgg ctg cta ttg ggc gaa gtg ccg ggg cag gat ctc      462
Ala Gly Arg Asp Trp Leu Leu Leu Gly Glu Val Pro Gly Gln Asp Leu
            90                  95                  100

ctg tca tct cac ctt gct cct gcc gag aaa gta tcc atc atg gct gat      510
Leu Ser Ser His Leu Ala Pro Ala Glu Lys Val Ser Ile Met Ala Asp
        105                 110                 115

gca atg cgg cgg ctg cat acg ctt gat ccg gct acc tgc cca ttc gac      558
Ala Met Arg Arg Leu His Thr Leu Asp Pro Ala Thr Cys Pro Phe Asp
    120                 125                 130

cac caa gcg aaa cat cgc atc gag cga gca cgt act cgg atg gaa gcc      606
His Gln Ala Lys His Arg Ile Glu Arg Ala Arg Thr Arg Met Glu Ala
135                 140                 145                 150

ggt ctt gtc gat cag gat gat ctg gac gaa gag cat cag ggg ctc gcg      654
Gly Leu Val Asp Gln Asp Asp Leu Asp Glu Glu His Gln Gly Leu Ala
                155                 160                 165

cca gcc gaa ctg ttc gcc agg ctc aag gcg cgc atg ccc gac ggc gag      702
Pro Ala Glu Leu Phe Ala Arg Leu Lys Ala Arg Met Pro Asp Gly Glu
            170                 175                 180

gat ctc gtc gtg acc cat ggc gat gcc tgc ttg ccg aat atc atg gtg      750
Asp Leu Val Val Thr His Gly Asp Ala Cys Leu Pro Asn Ile Met Val
        185                 190                 195

gaa aat ggc cgc ttt tct gga ttc atc gac tgt ggc cgg ctg ggt gtg      798
Glu Asn Gly Arg Phe Ser Gly Phe Ile Asp Cys Gly Arg Leu Gly Val
    200                 205                 210

gcg gac cgc tat cag gac ata gcg ttg gct acc cgt gat att gct gaa      846
Ala Asp Arg Tyr Gln Asp Ile Ala Leu Ala Thr Arg Asp Ile Ala Glu
215                 220                 225                 230

gag ctt ggc ggc gaa tgg gct gac cgc ttc ctc gtg ctt tac ggt atc      894
Glu Leu Gly Gly Glu Trp Ala Asp Arg Phe Leu Val Leu Tyr Gly Ile
                235                 240                 245

gcc gct ccc gat tcg cag cgc atc gcc ttc tat cgc ctt ctt gac gag      942
Ala Ala Pro Asp Ser Gln Arg Ile Ala Phe Tyr Arg Leu Leu Asp Glu
            250                 255                 260

ttc ttc tga gcgggactct ggggttcgaa ttgatccggt gattgattga              991
Phe Phe

gcaagctgat ccgtcgacct gcatctagcc cgcctaatga gcgggctttt ttttagatgc   1051

agccaagcta attcgcgcgg ccgcggccta ggcggccaga tctgatcaag agacag       1107
```

<210> SEQ ID NO 81
<211> LENGTH: 264
<212> TYPE: PRT
<213> ORGANISM: Artificial Sequence
<220> FEATURE:
<223> OTHER INFORMATION: Synthetic Construct

<400> SEQUENCE: 81

```
Met Ile Glu Gln Asp Gly Leu His Ala Gly Ser Pro Ala Ala Trp Val
1               5                   10                  15
```

```
Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 82
<211> LENGTH: 2365
<212> TYPE: DNA
<213> ORGANISM: Arabidopsis thaliana
<220> FEATURE:
<221> NAME/KEY: CDS
<222> LOCATION: (309)..(2321)
<223> OTHER INFORMATION: precursor acetolactate synthase

<400> SEQUENCE: 82

```
cttgtatcca ttctcttaac caataaaaaa agaaagaaag atcaatttga taaatttctc      60

agccacaaat tctacattta ggttttagca tatcgaaggc tcaatcacaa atacaataga     120

tagactagag attccagcgt cacgtgagtt ttatctataa ataaaggacc aaaaatcaaa     180

tcccgagggc attttcgtaa tccaacataa aacccttaaa cttcaagtct catttttaaa     240

caaatcatgt tcacaagtct cttcttcttc tctgtttctc tatctcttgc tcatctttct     300

cctgaacc atg gcg gcg gca aca aca aca aca aca aca tct tct tcg atc      350
         Met Ala Ala Ala Thr Thr Thr Thr Thr Thr Ser Ser Ser Ile
         1               5                   10

tcc ttc tcc acc aaa cca tct cct tcc tcc tcc aaa tca cca tta cca       398
Ser Phe Ser Thr Lys Pro Ser Pro Ser Ser Ser Lys Ser Pro Leu Pro
15                  20                  25                  30

atc tcc aga ttc tcc ctc cca ttc tcc cta aac ccc aac aaa tca tcc       446
```

```
Ile Ser Arg Phe Ser Leu Pro Phe Ser Leu Asn Pro Asn Lys Ser Ser
                35                  40                  45

tcc tcc tcc cgc cgc cgc ggt atc aaa tcc agc tct ccc tcc tcc atc      494
Ser Ser Ser Arg Arg Arg Gly Ile Lys Ser Ser Ser Pro Ser Ser Ile
            50                  55                  60

tcc gcc gtg ctc aac aca acc acc aat gtc aca acc act ccc tct cca      542
Ser Ala Val Leu Asn Thr Thr Thr Asn Val Thr Thr Thr Pro Ser Pro
        65                  70                  75

acc aaa cct acc aaa ccc gaa aca ttc atc tcc cga ttc gct cca gat      590
Thr Lys Pro Thr Lys Pro Glu Thr Phe Ile Ser Arg Phe Ala Pro Asp
    80                  85                  90

caa ccc cgc aaa ggc gct gat atc ctc gtc gaa gct tta gaa cgt caa      638
Gln Pro Arg Lys Gly Ala Asp Ile Leu Val Glu Ala Leu Glu Arg Gln
95                  100                 105                 110

ggc gta gaa acc gta ttc gct tac cct gga ggt gca tca atg gag att      686
Gly Val Glu Thr Val Phe Ala Tyr Pro Gly Gly Ala Ser Met Glu Ile
                115                 120                 125

cac caa gcc tta acc cgc tct tcc tca atc cgt aac gtc ctt cct cgt      734
His Gln Ala Leu Thr Arg Ser Ser Ser Ile Arg Asn Val Leu Pro Arg
            130                 135                 140

cac gaa caa gga ggt gta ttc gca gca gaa gga tac gct cga tcc tca      782
His Glu Gln Gly Gly Val Phe Ala Ala Glu Gly Tyr Ala Arg Ser Ser
        145                 150                 155

ggt aaa cca ggt atc tgt ata gcc act tca ggt ccc gga gct aca aat      830
Gly Lys Pro Gly Ile Cys Ile Ala Thr Ser Gly Pro Gly Ala Thr Asn
    160                 165                 170

ctc gtt agc gga tta gcc gat gcg ttg tta gat agt gtt cct ctt gta      878
Leu Val Ser Gly Leu Ala Asp Ala Leu Leu Asp Ser Val Pro Leu Val
175                 180                 185                 190

gca atc aca gga caa gtc cct cgt cgt atg att ggt aca gat gcg ttt      926
Ala Ile Thr Gly Gln Val Pro Arg Arg Met Ile Gly Thr Asp Ala Phe
                195                 200                 205

caa gag act ccg att gtt gag gta acg cgt tcg att acg aag cat aac      974
Gln Glu Thr Pro Ile Val Glu Val Thr Arg Ser Ile Thr Lys His Asn
            210                 215                 220

tat ctt gtg atg gat gtt gaa gat atc cct agg att att gag gaa gct     1022
Tyr Leu Val Met Asp Val Glu Asp Ile Pro Arg Ile Ile Glu Glu Ala
        225                 230                 235

ttc ttt tta gct act tct ggt aga cct gga cct gtt ttg gtt gat gtt     1070
Phe Phe Leu Ala Thr Ser Gly Arg Pro Gly Pro Val Leu Val Asp Val
    240                 245                 250

cct aaa gat att caa caa cag ctt gcg att cct aat tgg gaa cag gct     1118
Pro Lys Asp Ile Gln Gln Gln Leu Ala Ile Pro Asn Trp Glu Gln Ala
255                 260                 265                 270

atg aga tta cct ggt tat atg tct agg atg cct aaa cct ccg gaa gat     1166
Met Arg Leu Pro Gly Tyr Met Ser Arg Met Pro Lys Pro Pro Glu Asp
                275                 280                 285

tct cat ttg gag cag att gtt agg ttg att tct gag tct aag aag cct     1214
Ser His Leu Glu Gln Ile Val Arg Leu Ile Ser Glu Ser Lys Lys Pro
            290                 295                 300

gtg ttg tat gtt ggt ggt ggt tgt ttg aat tct agc gat gaa ttg ggt     1262
Val Leu Tyr Val Gly Gly Gly Cys Leu Asn Ser Ser Asp Glu Leu Gly
        305                 310                 315

agg ttt gtt gag ctt acg ggg atc cct gtt gcg agt acg ttg atg ggg     1310
Arg Phe Val Glu Leu Thr Gly Ile Pro Val Ala Ser Thr Leu Met Gly
    320                 325                 330

ctg gga tct tat cct tgt gat gat gag ttg tcg tta cat atg ctt gga     1358
Leu Gly Ser Tyr Pro Cys Asp Asp Glu Leu Ser Leu His Met Leu Gly
335                 340                 345                 350

atg cat ggg act gtg tat gca aat tac gct gtg gag cat agt gat ttg     1406
```

-continued

```
Met His Gly Thr Val Tyr Ala Asn Tyr Ala Val Glu His Ser Asp Leu
                355                 360                 365

ttg ttg gcg ttt ggg gta agg ttt gat gat cgt gtc acg ggt aag ctt      1454
Leu Leu Ala Phe Gly Val Arg Phe Asp Asp Arg Val Thr Gly Lys Leu
            370                 375                 380

gag gct ttt gct agt agg gct aag att gtt cat att gat att gac tcg      1502
Glu Ala Phe Ala Ser Arg Ala Lys Ile Val His Ile Asp Ile Asp Ser
        385                 390                 395

gct gag att ggg aag aat aag act cct cat gtg tct gtg tgt ggt gat      1550
Ala Glu Ile Gly Lys Asn Lys Thr Pro His Val Ser Val Cys Gly Asp
    400                 405                 410

gtt aag ctg gct ttg caa ggg atg aat aag gtt ctt gag aac cga gcg      1598
Val Lys Leu Ala Leu Gln Gly Met Asn Lys Val Leu Glu Asn Arg Ala
415                 420                 425                 430

gag gag ctt aag ctt gat ttt gga gtt tgg agg aat gag ttg aac gta      1646
Glu Glu Leu Lys Leu Asp Phe Gly Val Trp Arg Asn Glu Leu Asn Val
                435                 440                 445

cag aaa cag aag ttt ccg ttg agc ttt aag acg ttt ggg gaa gct att      1694
Gln Lys Gln Lys Phe Pro Leu Ser Phe Lys Thr Phe Gly Glu Ala Ile
            450                 455                 460

cct cca cag tat gcg att aag gtc ctt gat gag ttg act gat gga aaa      1742
Pro Pro Gln Tyr Ala Ile Lys Val Leu Asp Glu Leu Thr Asp Gly Lys
        465                 470                 475

gcc ata ata agt act ggt gtc ggg caa cat caa atg tgg gcg gcg cag      1790
Ala Ile Ile Ser Thr Gly Val Gly Gln His Gln Met Trp Ala Ala Gln
    480                 485                 490

ttc tac aat tac aag aaa cca agg cag tgg cta tca tca gga ggc ctt      1838
Phe Tyr Asn Tyr Lys Lys Pro Arg Gln Trp Leu Ser Ser Gly Gly Leu
495                 500                 505                 510

gga gct atg gga ttt gga ctt cct gct gcg att gga gcg tct gtt gct      1886
Gly Ala Met Gly Phe Gly Leu Pro Ala Ala Ile Gly Ala Ser Val Ala
                515                 520                 525

aac cct gat gcg ata gtt gtg gat att gac gga gat gga agc ttt ata      1934
Asn Pro Asp Ala Ile Val Val Asp Ile Asp Gly Asp Gly Ser Phe Ile
            530                 535                 540

atg aat gtg caa gag cta gcc act att cgt gta gag aat ctt cca gtg      1982
Met Asn Val Gln Glu Leu Ala Thr Ile Arg Val Glu Asn Leu Pro Val
        545                 550                 555

aag gta ctt tta tta aac aac cag cat ctt ggc atg gtt atg caa tgg      2030
Lys Val Leu Leu Leu Asn Asn Gln His Leu Gly Met Val Met Gln Trp
    560                 565                 570

gaa gat cgg ttc tac aaa gct aac cga gct cac aca ttt ctc ggg gat      2078
Glu Asp Arg Phe Tyr Lys Ala Asn Arg Ala His Thr Phe Leu Gly Asp
575                 580                 585                 590

ccg gct cag gag gac gag ata ttc ccg aac atg ttg ctg ttt gca gca      2126
Pro Ala Gln Glu Asp Glu Ile Phe Pro Asn Met Leu Leu Phe Ala Ala
                595                 600                 605

gct tgc ggg att cca gcg gcg agg gtg aca aag aaa gca gat ctc cga      2174
Ala Cys Gly Ile Pro Ala Ala Arg Val Thr Lys Lys Ala Asp Leu Arg
            610                 615                 620

gaa gct att cag aca atg ctg gat aca cca gga cct tac ctg ttg gat      2222
Glu Ala Ile Gln Thr Met Leu Asp Thr Pro Gly Pro Tyr Leu Leu Asp
        625                 630                 635

gtg att tgt ccg cac caa gaa cat gtg ttg ccg atg atc ccg aat ggt      2270
Val Ile Cys Pro His Gln Glu His Val Leu Pro Met Ile Pro Asn Gly
    640                 645                 650

ggc act ttc aac gat gtc ata acg gaa gga gat ggc cgg att aaa tac      2318
Gly Thr Phe Asn Asp Val Ile Thr Glu Gly Asp Gly Arg Ile Lys Tyr
655                 660                 665                 670

tga gagatgaaac cggtgattat cagaaccttt tatggtcttt gtat                 2365
```

<210> SEQ ID NO 83
<211> LENGTH: 670
<212> TYPE: PRT
<213> ORGANISM: Arabidopsis thaliana

<400> SEQUENCE: 83

```
Met Ala Ala Ala Thr Thr Thr Thr Thr Thr Ser Ser Ser Ile Ser Phe
1               5                   10                  15

Ser Thr Lys Pro Ser Pro Ser Ser Ser Lys Ser Pro Leu Pro Ile Ser
            20                  25                  30

Arg Phe Ser Leu Pro Phe Ser Leu Asn Pro Asn Lys Ser Ser Ser Ser
        35                  40                  45

Ser Arg Arg Arg Gly Ile Lys Ser Ser Ser Pro Ser Ser Ile Ser Ala
    50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
        115                 120                 125

Ala Leu Thr Arg Ser Ser Ser Ile Arg Asn Val Leu Pro Arg His Glu
    130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
            180                 185                 190

Thr Gly Gln Val Pro Arg Arg Met Ile Gly Thr Asp Ala Phe Gln Glu
        195                 200                 205

Thr Pro Ile Val Glu Val Thr Arg Ser Ile Thr Lys His Asn Tyr Leu
    210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
            260                 265                 270

Leu Pro Gly Tyr Met Ser Arg Met Pro Lys Pro Pro Glu Asp Ser His
        275                 280                 285

Leu Glu Gln Ile Val Arg Leu Ile Ser Glu Ser Lys Lys Pro Val Leu
    290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
                325                 330                 335

Ser Tyr Pro Cys Asp Asp Glu Leu Ser Leu His Met Leu Gly Met His
            340                 345                 350

Gly Thr Val Tyr Ala Asn Tyr Ala Val Glu His Ser Asp Leu Leu Leu
        355                 360                 365

Ala Phe Gly Val Arg Phe Asp Asp Arg Val Thr Gly Lys Leu Glu Ala
    370                 375                 380
```

```
Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
                405                 410                 415

Leu Ala Leu Gln Gly Met Asn Lys Val Leu Glu Asn Arg Ala Glu Glu
            420                 425                 430

Leu Lys Leu Asp Phe Gly Val Trp Arg Asn Glu Leu Asn Val Gln Lys
        435                 440                 445

Gln Lys Phe Pro Leu Ser Phe Lys Thr Phe Gly Glu Ala Ile Pro Pro
    450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Ser Gly Gly Leu Gly Ala
            500                 505                 510

Met Gly Phe Gly Leu Pro Ala Ala Ile Gly Ala Ser Val Ala Asn Pro
        515                 520                 525

Asp Ala Ile Val Val Asp Ile Asp Gly Asp Gly Ser Phe Ile Met Asn
    530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Glu Asp
                565                 570                 575

Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
        595                 600                 605

Gly Ile Pro Ala Ala Arg Val Thr Lys Lys Ala Asp Leu Arg Glu Ala
    610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Asn Gly Gly Thr
                645                 650                 655

Phe Asn Asp Val Ile Thr Glu Gly Asp Gly Arg Ile Lys Tyr
            660                 665                 670
```

<210> SEQ ID NO 84
<211> LENGTH: 2279
<212> TYPE: DNA
<213> ORGANISM: Oryza sativa
<220> FEATURE:
<221> NAME/KEY: CDS
<222> LOCATION: (32)..(1966)
<223> OTHER INFORMATION: acetolactate synthase

<400> SEQUENCE: 84

```
ctcgccgccg ccgccgccgc caccacccac c atg gct acg acc gcc gcg gcc        52
                                   Met Ala Thr Thr Ala Ala Ala
                                   1               5

gcg gcc gcc gcc ctg tcc gcc gcc gcg acg gcc aag acc ggc cgt aag       100
Ala Ala Ala Ala Leu Ser Ala Ala Ala Thr Ala Lys Thr Gly Arg Lys
        10                  15                  20

aac cac cag cga cac cac gtc ctt ccc gct cga ggc cgg gtg ggg gcg       148
Asn His Gln Arg His His Val Leu Pro Ala Arg Gly Arg Val Gly Ala
    25                  30                  35

gcg gcg gtc agg tgc tcg gcg gtg tcc ccg gtc acc ccg ccg tcc ccg       196
```

```
Ala Ala Val Arg Cys Ser Ala Val Ser Pro Val Thr Pro Pro Ser Pro
40                  45                  50                  55

gcg ccg ccg gcc acg ccg ctc cgg ccg tgg ggg ccg gcc gag ccc cgc      244
Ala Pro Pro Ala Thr Pro Leu Arg Pro Trp Gly Pro Ala Glu Pro Arg
                60                  65                  70

aag ggc gcg gac atc ctc gtg gag gcg ctg gag cgg tgc ggc gtc agc      292
Lys Gly Ala Asp Ile Leu Val Glu Ala Leu Glu Arg Cys Gly Val Ser
            75                  80                  85

gac gtg ttc gcc tac ccg ggc ggc gcg tcc atg gag atc cac cag gcg      340
Asp Val Phe Ala Tyr Pro Gly Gly Ala Ser Met Glu Ile His Gln Ala
        90                  95                  100

ctg acg cgc tcc ccg gtc atc acc aac cac ctc ttc cgc cac gag cag      388
Leu Thr Arg Ser Pro Val Ile Thr Asn His Leu Phe Arg His Glu Gln
    105                 110                 115

ggc gag gcg ttc gcg gcg tcc ggg tac gcg cgc gcg tcc ggc cgc gtc      436
Gly Glu Ala Phe Ala Ala Ser Gly Tyr Ala Arg Ala Ser Gly Arg Val
120                 125                 130                 135

ggg gtc tgc gtc gcc acc tcc ggc ccc ggg gca acc aac ctc gtg tcc      484
Gly Val Cys Val Ala Thr Ser Gly Pro Gly Ala Thr Asn Leu Val Ser
                140                 145                 150

gcg ctc gcc gac gcg ctg ctc gac tcc gtc ccg atg gtc gcc atc acg      532
Ala Leu Ala Asp Ala Leu Leu Asp Ser Val Pro Met Val Ala Ile Thr
            155                 160                 165

ggc cag gtc ccc cgc cgc atg atc ggc acc gac gcc ttc cag gag acg      580
Gly Gln Val Pro Arg Arg Met Ile Gly Thr Asp Ala Phe Gln Glu Thr
        170                 175                 180

ccc ata gtc gag gtc acc cgc tcc atc acc aag cac aat tac ctt gtc      628
Pro Ile Val Glu Val Thr Arg Ser Ile Thr Lys His Asn Tyr Leu Val
    185                 190                 195

ctt gat gtg gag gac atc ccc cgc gtc ata cag gaa gcc ttc ttc ctc      676
Leu Asp Val Glu Asp Ile Pro Arg Val Ile Gln Glu Ala Phe Phe Leu
200                 205                 210                 215

gcg tcc tcg ggc cgt cct ggc ccg gtg ctg gtc gac atc ccc aag gac      724
Ala Ser Ser Gly Arg Pro Gly Pro Val Leu Val Asp Ile Pro Lys Asp
                220                 225                 230

atc cag cag cag atg gcc gtg ccg gtc tgg gac acc tcg atg aat cta      772
Ile Gln Gln Gln Met Ala Val Pro Val Trp Asp Thr Ser Met Asn Leu
            235                 240                 245

cca ggg tac atc gca cgc ctg ccc aag cca ccc gcg aca gaa ttg ctt      820
Pro Gly Tyr Ile Ala Arg Leu Pro Lys Pro Pro Ala Thr Glu Leu Leu
        250                 255                 260

gag cag gtc ttg cgt ctg gtt ggc gag tca cgg cgc ccg att ctc tat      868
Glu Gln Val Leu Arg Leu Val Gly Glu Ser Arg Arg Pro Ile Leu Tyr
    265                 270                 275

gtc ggt ggt ggc tgc tct gca tct ggt gac gaa ttg cgc tgg ttt gtt      916
Val Gly Gly Gly Cys Ser Ala Ser Gly Asp Glu Leu Arg Trp Phe Val
280                 285                 290                 295

gag ctg act ggt atc cca gtt aca acc act ctg atg ggc ctc ggc aat      964
Glu Leu Thr Gly Ile Pro Val Thr Thr Thr Leu Met Gly Leu Gly Asn
                300                 305                 310

ttc ccc agt gac gac ccg ttg tcc ctg cgc atg ctt ggg atg cat ggc     1012
Phe Pro Ser Asp Asp Pro Leu Ser Leu Arg Met Leu Gly Met His Gly
            315                 320                 325

acg gtg tac gca aat tat gcc gtg gat aag gct gac ctg ttg ctt gcg     1060
Thr Val Tyr Ala Asn Tyr Ala Val Asp Lys Ala Asp Leu Leu Leu Ala
        330                 335                 340

ttt ggt gtg cgg ttt gat gat cgt gtg aca ggg aaa att gag gct ttt     1108
Phe Gly Val Arg Phe Asp Asp Arg Val Thr Gly Lys Ile Glu Ala Phe
    345                 350                 355

gca agc agg gcc aag att gtg cac att gac att gat cca gca gag att     1156
```

```
Ala Ser Arg Ala Lys Ile Val His Ile Asp Ile Asp Pro Ala Glu Ile
360                 365                 370                 375

gga aag aac aag caa cca cat gtg tca att tgc gca gat gtt aag ctt     1204
Gly Lys Asn Lys Gln Pro His Val Ser Ile Cys Ala Asp Val Lys Leu
                380                 385                 390

gct tta cag ggc ttg aat gct ctg cta caa cag agc aca aca aag aca     1252
Ala Leu Gln Gly Leu Asn Ala Leu Leu Gln Gln Ser Thr Thr Lys Thr
            395                 400                 405

agt tct gat ttt agt gca tgg cac aat gag ttg gac cag cag aag agg     1300
Ser Ser Asp Phe Ser Ala Trp His Asn Glu Leu Asp Gln Gln Lys Arg
        410                 415                 420

gag ttt cct ctg ggg tac aaa act ttt ggt gaa gag atc cca ccg caa     1348
Glu Phe Pro Leu Gly Tyr Lys Thr Phe Gly Glu Glu Ile Pro Pro Gln
    425                 430                 435

tat gcc att cag gtg ctg gat gag ctg acg aaa ggt gag gca atc atc     1396
Tyr Ala Ile Gln Val Leu Asp Glu Leu Thr Lys Gly Glu Ala Ile Ile
440                 445                 450                 455

gct act ggt gtt ggg cag cac cag atg tgg gcg gca caa tat tac acc     1444
Ala Thr Gly Val Gly Gln His Gln Met Trp Ala Ala Gln Tyr Tyr Thr
                460                 465                 470

tac aag cgg cca cgg cag tgg ctg tct tcg gct ggt ctg ggc gca atg     1492
Tyr Lys Arg Pro Arg Gln Trp Leu Ser Ser Ala Gly Leu Gly Ala Met
            475                 480                 485

gga ttt ggg ctg cct gct gca gct ggt gct tct gtg gct aac cca ggt     1540
Gly Phe Gly Leu Pro Ala Ala Ala Gly Ala Ser Val Ala Asn Pro Gly
        490                 495                 500

gtc aca gtt gtt gat att gat ggg gat ggt agc ttc ctc atg aac att     1588
Val Thr Val Val Asp Ile Asp Gly Asp Gly Ser Phe Leu Met Asn Ile
    505                 510                 515

cag gag ctg gca ttg atc cgc att gag aac ctc cct gtg aag gtg atg     1636
Gln Glu Leu Ala Leu Ile Arg Ile Glu Asn Leu Pro Val Lys Val Met
520                 525                 530                 535

gtg ttg aac aac caa cat ttg ggt atg gtg gtg caa ttg gag gat agg     1684
Val Leu Asn Asn Gln His Leu Gly Met Val Val Gln Leu Glu Asp Arg
                540                 545                 550

ttt tac aag gcg aat agg gcg cat aca tac ttg ggc aac ccg gaa tgt     1732
Phe Tyr Lys Ala Asn Arg Ala His Thr Tyr Leu Gly Asn Pro Glu Cys
            555                 560                 565

gag agc gag ata tat cca gat ttt gtg act att gct aag ggg ttc aat     1780
Glu Ser Glu Ile Tyr Pro Asp Phe Val Thr Ile Ala Lys Gly Phe Asn
        570                 575                 580

att cct gca gtc cgt gta aca aag aag agt gaa gtc cgt gcc gcc atc     1828
Ile Pro Ala Val Arg Val Thr Lys Lys Ser Glu Val Arg Ala Ala Ile
    585                 590                 595

aag aag atg ctc gag act cca ggg cca tac ttg ttg gat atc atc gtc     1876
Lys Lys Met Leu Glu Thr Pro Gly Pro Tyr Leu Leu Asp Ile Ile Val
600                 605                 610                 615

ccg cac cag gag cat gtg ctg cct atg atc cca att ggg ggc gca ttc     1924
Pro His Gln Glu His Val Leu Pro Met Ile Pro Ile Gly Gly Ala Phe
                620                 625                 630

aag gac atg atc ctg gat ggt gat ggc agg act gtg tat taa             1966
Lys Asp Met Ile Leu Asp Gly Asp Gly Arg Thr Val Tyr
            635                 640

tctataatct gtatgttggc aaagcaccag cccggcctat gtttgacctg aatgacccat   2026

aaagagtggt atgcctatga tgtttgtatg tgctctatca ataactaagg tgtcaactat   2086

gaaccatatg ctcttctgtt ttacttgttt gatgtgcttg gcatggtaat cctaattagc   2146

ttcctgctgt ctaggtttgt agtgtgttgt tttctgtagg catatgcatc acaagatatc   2206

atgtaagttt cttgtcctac atatcaataa taagagaata aagtacttct atgtaaaaaa   2266
```

aaaaaaaaaa aaa 2279

<210> SEQ ID NO 85
<211> LENGTH: 644
<212> TYPE: PRT
<213> ORGANISM: Oryza sativa

<400> SEQUENCE: 85

Met Ala Thr Thr Ala Ala Ala Ala Ala Ala Ala Leu Ser Ala Ala Ala
1 5 10 15

Thr Ala Lys Thr Gly Arg Lys Asn His Gln Arg His His Val Leu Pro
20 25 30

Ala Arg Gly Arg Val Gly Ala Ala Ala Val Arg Cys Ser Ala Val Ser
35 40 45

Pro Val Thr Pro Pro Ser Pro Ala Pro Pro Ala Thr Pro Leu Arg Pro
50 55 60

Trp Gly Pro Ala Glu Pro Arg Lys Gly Ala Asp Ile Leu Val Glu Ala
65 70 75 80

Leu Glu Arg Cys Gly Val Ser Asp Val Phe Ala Tyr Pro Gly Gly Ala
85 90 95

Ser Met Glu Ile His Gln Ala Leu Thr Arg Ser Pro Val Ile Thr Asn
100 105 110

His Leu Phe Arg His Glu Gln Gly Glu Ala Phe Ala Ala Ser Gly Tyr
115 120 125

Ala Arg Ala Ser Gly Arg Val Gly Val Cys Val Ala Thr Ser Gly Pro
130 135 140

Gly Ala Thr Asn Leu Val Ser Ala Leu Ala Asp Ala Leu Leu Asp Ser
145 150 155 160

Val Pro Met Val Ala Ile Thr Gly Gln Val Pro Arg Arg Met Ile Gly
165 170 175

Thr Asp Ala Phe Gln Glu Thr Pro Ile Val Glu Val Thr Arg Ser Ile
180 185 190

Thr Lys His Asn Tyr Leu Val Leu Asp Val Glu Asp Ile Pro Arg Val
195 200 205

Ile Gln Glu Ala Phe Phe Leu Ala Ser Ser Gly Arg Pro Gly Pro Val
210 215 220

Leu Val Asp Ile Pro Lys Asp Ile Gln Gln Gln Met Ala Val Pro Val
225 230 235 240

Trp Asp Thr Ser Met Asn Leu Pro Gly Tyr Ile Ala Arg Leu Pro Lys
245 250 255

Pro Pro Ala Thr Glu Leu Leu Glu Gln Val Leu Arg Leu Val Gly Glu
260 265 270

Ser Arg Arg Pro Ile Leu Tyr Val Gly Gly Gly Cys Ser Ala Ser Gly
275 280 285

Asp Glu Leu Arg Trp Phe Val Glu Leu Thr Gly Ile Pro Val Thr Thr
290 295 300

Thr Leu Met Gly Leu Gly Asn Phe Pro Ser Asp Asp Pro Leu Ser Leu
305 310 315 320

Arg Met Leu Gly Met His Gly Thr Val Tyr Ala Asn Tyr Ala Val Asp
325 330 335

Lys Ala Asp Leu Leu Leu Ala Phe Gly Val Arg Phe Asp Asp Arg Val
340 345 350

Thr Gly Lys Ile Glu Ala Phe Ala Ser Arg Ala Lys Ile Val His Ile
355 360 365

```
Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
    530                 535                 540

Val Val Gln Leu Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ile Gly Gly Ala Phe Lys Asp Met Ile Leu Asp Gly Asp Gly
625                 630                 635                 640

Arg Thr Val Tyr


<210> SEQ ID NO 86
<211> LENGTH: 2227
<212> TYPE: DNA
<213> ORGANISM: Bassia scoparia
<220> FEATURE:
<221> NAME/KEY: CDS
<222> LOCATION: (1)..(2001)
<223> OTHER INFORMATION: herbicide resistant acetolactate synthase

<400> SEQUENCE: 86

atg gcg tct act tgt gca aat ccc act ttt acc cct ttc acc agt aaa       48
Met Ala Ser Thr Cys Ala Asn Pro Thr Phe Thr Pro Phe Thr Ser Lys
1               5                   10                  15

ccc ctt aaa ccc cgt tct ccc ttt cac tct ttc cca ttt ccc tca aac       96
Pro Leu Lys Pro Arg Ser Pro Phe His Ser Phe Pro Phe Pro Ser Asn
            20                  25                  30

ccc aaa acc cct tcc tct tca ttt cgc aac ctc aaa atc aca tct tct      144
Pro Lys Thr Pro Ser Ser Ser Phe Arg Asn Leu Lys Ile Thr Ser Ser
        35                  40                  45

ctc tct tct tca caa ccc ccg aaa cca cct tcc gcc gtc aaa acc cac      192
Leu Ser Ser Ser Gln Pro Pro Lys Pro Pro Ser Ala Val Lys Thr His
    50                  55                  60
```

```
tca cca cct tcc cct ctc aca acc gac gaa ccc ccg caa ggt ttt gtt      240
Ser Pro Pro Ser Pro Leu Thr Thr Asp Glu Pro Pro Gln Gly Phe Val
65                  70                  75                  80

tcc cga ttt gcc cct gac caa ccc aga aaa ggc tgc gat gtc ctc gtt      288
Ser Arg Phe Ala Pro Asp Gln Pro Arg Lys Gly Cys Asp Val Leu Val
                85                  90                  95

gag gcc ctc gag cgg gag ggc gtc acc gac gtg ttc gct tat cct ggt      336
Glu Ala Leu Glu Arg Glu Gly Val Thr Asp Val Phe Ala Tyr Pro Gly
            100                 105                 110

ggc gca tca atg gag att cat caa gct ctg act cgc tct gat tcc ata      384
Gly Ala Ser Met Glu Ile His Gln Ala Leu Thr Arg Ser Asp Ser Ile
        115                 120                 125

cgc aac gtc ctg cct cgc cac gag caa ggc ggg atc ttt gcc gcg gag      432
Arg Asn Val Leu Pro Arg His Glu Gln Gly Gly Ile Phe Ala Ala Glu
    130                 135                 140

ggg tat gct cgt gcc acg ggc cgt gtt ggt gtc tgc att gcg aca tct      480
Gly Tyr Ala Arg Ala Thr Gly Arg Val Gly Val Cys Ile Ala Thr Ser
145                 150                 155                 160

ggc cct ggc gct acg aac ctc gtg tcc ggg ttt gct gat gct ttg ctc      528
Gly Pro Gly Ala Thr Asn Leu Val Ser Gly Phe Ala Asp Ala Leu Leu
                165                 170                 175

gat tcc gtt cca ctg gtg gcg atc acg ggg cag gtg ccg cgg cga atg      576
Asp Ser Val Pro Leu Val Ala Ile Thr Gly Gln Val Pro Arg Arg Met
            180                 185                 190

att ggg acg gat gct ttt cag gag act cct att gtt gag gta aca cgg      624
Ile Gly Thr Asp Ala Phe Gln Glu Thr Pro Ile Val Glu Val Thr Arg
        195                 200                 205

tct att acc aag cat aat tat ctg gta tta gat gtt gag gat att cct      672
Ser Ile Thr Lys His Asn Tyr Leu Val Leu Asp Val Glu Asp Ile Pro
    210                 215                 220

aga att gtt aag gag gct ttc ttt ttg gct aat tct ggt aga cct gga      720
Arg Ile Val Lys Glu Ala Phe Phe Leu Ala Asn Ser Gly Arg Pro Gly
225                 230                 235                 240

cct gtt ttg att gat att cct aag gat att cag cag caa ttg gtt gtg      768
Pro Val Leu Ile Asp Ile Pro Lys Asp Ile Gln Gln Gln Leu Val Val
                245                 250                 255

cct gat tgg gat cag ggg gtt agg tta ggt ggg tat gtg tct agg ttg      816
Pro Asp Trp Asp Gln Gly Val Arg Leu Gly Gly Tyr Val Ser Arg Leu
            260                 265                 270

ccg aaa tcg gtg ttt tcg gcc aat gat gag ggg ctt ctt gag cag att      864
Pro Lys Ser Val Phe Ser Ala Asn Asp Glu Gly Leu Leu Glu Gln Ile
        275                 280                 285

gtg agg ttg atg agt gag gct aag aag cct gtg ttg tat gtg gga ggc      912
Val Arg Leu Met Ser Glu Ala Lys Lys Pro Val Leu Tyr Val Gly Gly
    290                 295                 300

ggg tgt ttg aat tct ggg gag gag ttg agg aaa ttc gtc gag ttg act      960
Gly Cys Leu Asn Ser Gly Glu Glu Leu Arg Lys Phe Val Glu Leu Thr
305                 310                 315                 320

ggg att ccg gtg gct agt act tta atg ggt ttg ggc gct tat ccc tgt     1008
Gly Ile Pro Val Ala Ser Thr Leu Met Gly Leu Gly Ala Tyr Pro Cys
                325                 330                 335

aat gat gac ttg tct ctt cat atg ttg ggt atg cac ggg acc gtg tat     1056
Asn Asp Asp Leu Ser Leu His Met Leu Gly Met His Gly Thr Val Tyr
            340                 345                 350

gct aat tat gct gtt gat aag gca gat ttg ttg ctt gcc ttt ggg gtt     1104
Ala Asn Tyr Ala Val Asp Lys Ala Asp Leu Leu Leu Ala Phe Gly Val
        355                 360                 365

agg ttt gat gat cgt gtg aca ggg aag ctt gag gcg ttt gct agc cgg     1152
Arg Phe Asp Asp Arg Val Thr Gly Lys Leu Glu Ala Phe Ala Ser Arg
    370                 375                 380
```

-continued

```
gct aag atc gtg cat att gat att gat tct gct gag att ggg aag aat      1200
Ala Lys Ile Val His Ile Asp Ile Asp Ser Ala Glu Ile Gly Lys Asn
385                 390                 395                 400

aag caa ccc cat gtg tca ata tgt gct gat gtc aag tat gcg ttg aag      1248
Lys Gln Pro His Val Ser Ile Cys Ala Asp Val Lys Tyr Ala Leu Lys
                405                 410                 415

ggt atg aat aag att ttg gag tct agg aaa ggg aag ttg aaa tta aat      1296
Gly Met Asn Lys Ile Leu Glu Ser Arg Lys Gly Lys Leu Lys Leu Asn
            420                 425                 430

tac tct agc tgg agg gag gaa ttg ggt gag caa aag aag aaa ttc cca      1344
Tyr Ser Ser Trp Arg Glu Glu Leu Gly Glu Gln Lys Lys Lys Phe Pro
        435                 440                 445

ttg tct ttt aag acc ttc ggg gaa gcg att cct cct cag tat gcc att      1392
Leu Ser Phe Lys Thr Phe Gly Glu Ala Ile Pro Pro Gln Tyr Ala Ile
    450                 455                 460

cag atg ctt gat gag ctg acc aat ggt aac gct att att agt act ggt      1440
Gln Met Leu Asp Glu Leu Thr Asn Gly Asn Ala Ile Ile Ser Thr Gly
465                 470                 475                 480

gtt ggg caa cat caa atg tgg gct gct cag cat tac aag tac aga aac      1488
Val Gly Gln His Gln Met Trp Ala Ala Gln His Tyr Lys Tyr Arg Asn
                485                 490                 495

cct cgc caa tgg ctg acc tca ggt ggg ttg ggt gcc atg ggt ttt ggt      1536
Pro Arg Gln Trp Leu Thr Ser Gly Gly Leu Gly Ala Met Gly Phe Gly
            500                 505                 510

cta cca gcc gcc att gga gct gct gtg gct cga cct gat gca gtg gtg      1584
Leu Pro Ala Ala Ile Gly Ala Ala Val Ala Arg Pro Asp Ala Val Val
        515                 520                 525

gtt gat att gat ggc gat ggg agt ttc att atg aat gtt caa gag ttg      1632
Val Asp Ile Asp Gly Asp Gly Ser Phe Ile Met Asn Val Gln Glu Leu
    530                 535                 540

gct act att agg gtg gaa aat ctc cct gtt aag ata atg ctt ttg aat      1680
Ala Thr Ile Arg Val Glu Asn Leu Pro Val Lys Ile Met Leu Leu Asn
545                 550                 555                 560

aac caa cat tta ggt atg gtg gtt caa ttg gaa gat agg ttt tat aaa      1728
Asn Gln His Leu Gly Met Val Val Gln Leu Glu Asp Arg Phe Tyr Lys
                565                 570                 575

gcc aat agg gca cat act tac ctt gga aac cct tca aaa gag tct gaa      1776
Ala Asn Arg Ala His Thr Tyr Leu Gly Asn Pro Ser Lys Glu Ser Glu
            580                 585                 590

atc ttc ccg gat atg ctt aaa ttt gct gag gcg tgt gat att cct gct      1824
Ile Phe Pro Asp Met Leu Lys Phe Ala Glu Ala Cys Asp Ile Pro Ala
        595                 600                 605

gct cgt gtc acc aag gtt gga gat ttg agg gcg gcc atg cag aca atg      1872
Ala Arg Val Thr Lys Val Gly Asp Leu Arg Ala Ala Met Gln Thr Met
    610                 615                 620

ttg gat act ccg gga cct tac ctg ctt gat gtg att gta cct cat cag      1920
Leu Asp Thr Pro Gly Pro Tyr Leu Leu Asp Val Ile Val Pro His Gln
625                 630                 635                 640

gag cat gtg ctg cct atg att cct agt ggt gca gcc ttc aag gat atc      1968
Glu His Val Leu Pro Met Ile Pro Ser Gly Ala Ala Phe Lys Asp Ile
                645                 650                 655

att aac gaa ggt gat gga aga aca agt tat tga tgttcgtatc gatggttgaa    2021
Ile Asn Glu Gly Asp Gly Arg Thr Ser Tyr
            660                 665

agcatctata gagggggaag caaaataaga ataataatct gtatgtataa tagtatgttc    2081

cttttaaatt tttagcgtct gtttacttgt ttttttagtt ttctagttag tttgtcgttg    2141

ttatgttgct tgttactttg agaatgcttt tttgtagttt tcaagagacg agtatggatg    2201

atcttcctat attgttgaaa gatttc                                         2227
```

<210> SEQ ID NO 87
<211> LENGTH: 666
<212> TYPE: PRT
<213> ORGANISM: Bassia scoparia

<400> SEQUENCE: 87

```
Met Ala Ser Thr Cys Ala Asn Pro Thr Phe Thr Pro Phe Thr Ser Lys
1               5                   10                  15

Pro Leu Lys Pro Arg Ser Pro Phe His Ser Phe Pro Phe Pro Ser Asn
            20                  25                  30

Pro Lys Thr Pro Ser Ser Ser Phe Arg Asn Leu Lys Ile Thr Ser Ser
        35                  40                  45

Leu Ser Ser Ser Gln Pro Pro Lys Pro Pro Ser Ala Val Lys Thr His
    50                  55                  60

Ser Pro Pro Ser Pro Leu Thr Thr Asp Glu Pro Pro Gln Gly Phe Val
65                  70                  75                  80

Ser Arg Phe Ala Pro Asp Gln Pro Arg Lys Gly Cys Asp Val Leu Val
                85                  90                  95

Glu Ala Leu Glu Arg Glu Gly Val Thr Asp Val Phe Ala Tyr Pro Gly
            100                 105                 110

Gly Ala Ser Met Glu Ile His Gln Ala Leu Thr Arg Ser Asp Ser Ile
        115                 120                 125

Arg Asn Val Leu Pro Arg His Glu Gln Gly Gly Ile Phe Ala Ala Glu
    130                 135                 140

Gly Tyr Ala Arg Ala Thr Gly Arg Val Gly Val Cys Ile Ala Thr Ser
145                 150                 155                 160

Gly Pro Gly Ala Thr Asn Leu Val Ser Gly Phe Ala Asp Ala Leu Leu
                165                 170                 175

Asp Ser Val Pro Leu Val Ala Ile Thr Gly Gln Val Pro Arg Arg Met
            180                 185                 190

Ile Gly Thr Asp Ala Phe Gln Glu Thr Pro Ile Val Glu Val Thr Arg
        195                 200                 205

Ser Ile Thr Lys His Asn Tyr Leu Val Leu Asp Val Glu Asp Ile Pro
    210                 215                 220

Arg Ile Val Lys Glu Ala Phe Phe Leu Ala Asn Ser Gly Arg Pro Gly
225                 230                 235                 240

Pro Val Leu Ile Asp Ile Pro Lys Asp Ile Gln Gln Gln Leu Val Val
                245                 250                 255

Pro Asp Trp Asp Gln Gly Val Arg Leu Gly Gly Tyr Val Ser Arg Leu
            260                 265                 270

Pro Lys Ser Val Phe Ser Ala Asn Asp Glu Gly Leu Leu Glu Gln Ile
        275                 280                 285

Val Arg Leu Met Ser Glu Ala Lys Lys Pro Val Leu Tyr Val Gly Gly
    290                 295                 300

Gly Cys Leu Asn Ser Gly Glu Glu Leu Arg Lys Phe Val Glu Leu Thr
305                 310                 315                 320

Gly Ile Pro Val Ala Ser Thr Leu Met Gly Leu Gly Ala Tyr Pro Cys
                325                 330                 335

Asn Asp Asp Leu Ser Leu His Met Leu Gly Met His Gly Thr Val Tyr
            340                 345                 350

Ala Asn Tyr Ala Val Asp Lys Ala Asp Leu Leu Leu Ala Phe Gly Val
        355                 360                 365

Arg Phe Asp Asp Arg Val Thr Gly Lys Leu Glu Ala Phe Ala Ser Arg
    370                 375                 380
```

```
Ala Lys Ile Val His Ile Asp Ile Asp Ser Ala Glu Ile Gly Lys Asn
385                 390                 395                 400

Lys Gln Pro His Val Ser Ile Cys Ala Asp Val Lys Tyr Ala Leu Lys
                405                 410                 415

Gly Met Asn Lys Ile Leu Glu Ser Arg Lys Gly Lys Leu Lys Leu Asn
            420                 425                 430

Tyr Ser Ser Trp Arg Glu Glu Leu Gly Glu Gln Lys Lys Lys Phe Pro
        435                 440                 445

Leu Ser Phe Lys Thr Phe Gly Glu Ala Ile Pro Pro Gln Tyr Ala Ile
    450                 455                 460

Gln Met Leu Asp Glu Leu Thr Asn Gly Asn Ala Ile Ile Ser Thr Gly
465                 470                 475                 480

Val Gly Gln His Gln Met Trp Ala Ala Gln His Tyr Lys Tyr Arg Asn
                485                 490                 495

Pro Arg Gln Trp Leu Thr Ser Gly Gly Leu Gly Ala Met Gly Phe Gly
            500                 505                 510

Leu Pro Ala Ala Ile Gly Ala Ala Val Ala Arg Pro Asp Ala Val Val
        515                 520                 525

Val Asp Ile Asp Gly Asp Gly Ser Phe Ile Met Asn Val Gln Glu Leu
    530                 535                 540

Ala Thr Ile Arg Val Glu Asn Leu Pro Val Lys Ile Met Leu Leu Asn
545                 550                 555                 560

Asn Gln His Leu Gly Met Val Val Gln Leu Glu Asp Arg Phe Tyr Lys
                565                 570                 575

Ala Asn Arg Ala His Thr Tyr Leu Gly Asn Pro Ser Lys Glu Ser Glu
            580                 585                 590

Ile Phe Pro Asp Met Leu Lys Phe Ala Glu Ala Cys Asp Ile Pro Ala
        595                 600                 605

Ala Arg Val Thr Lys Val Gly Asp Leu Arg Ala Ala Met Gln Thr Met
    610                 615                 620

Leu Asp Thr Pro Gly Pro Tyr Leu Leu Asp Val Ile Val Pro His Gln
625                 630                 635                 640

Glu His Val Leu Pro Met Ile Pro Ser Gly Ala Ala Phe Lys Asp Ile
                645                 650                 655

Ile Asn Glu Gly Asp Gly Arg Thr Ser Tyr
            660                 665


<210> SEQ ID NO 88
<211> LENGTH: 2461
<212> TYPE: DNA
<213> ORGANISM: Nicotiana tabacum
<220> FEATURE:
<221> NAME/KEY: CDS
<222> LOCATION: (415)..(2409)
<223> OTHER INFORMATION: acetolactate synthase; herbicide resistance

<400> SEQUENCE: 88

tatttcttag cttgtttttt ttttgttcta tattgttact ttgagctata tttcataaca      60

gcattcacat tctttttcca tagtcttttt tccctttttat attttaattt actgaagtaa    120

caaatacttc cacttctttc ttcttcccac cctcctaaat atatccaaca tctcattttt    180

cttttcccca attctcagac attttaatct ttcttttcta tttattttct tcatattttg    240

atctctcttc catttgttct catccatttt cgctattcac gtgaattcaa tcaagtagga    300

ccctttcagt ttcgtggcgc tctcgtcttc tcagcttaat ataaaaccaa ccacacacca    360

tctacattgc cctttccttt cagtttcgtc tctcactgct ctcattcaac aata atg      417
```

-continued

```
                                                            Met
                                                            1

gcg gcg gct gcg gcg gct cca tct ccc tct ttc tcc aaa acc cta tcg      465
Ala Ala Ala Ala Ala Ala Pro Ser Pro Ser Phe Ser Lys Thr Leu Ser
            5                   10                  15

tcc tcc tcc tcc aaa tcc tcc acc ctc ctc cct aga tcc acc ttc cct      513
Ser Ser Ser Ser Lys Ser Ser Thr Leu Leu Pro Arg Ser Thr Phe Pro
        20                  25                  30

ttc ccc cac cac ccc cac aaa acc acc cca cca ccc ctc cac ctc acc      561
Phe Pro His His Pro His Lys Thr Thr Pro Pro Pro Leu His Leu Thr
    35                  40                  45

ccc acc cac att cac agc caa cgc cgt cgt ttc acc atc tcc aat gtc      609
Pro Thr His Ile His Ser Gln Arg Arg Arg Phe Thr Ile Ser Asn Val
50                  55                  60                  65

att tcc act acc caa aaa gtt tcc gag acc caa aaa gcc gaa act ttc      657
Ile Ser Thr Thr Gln Lys Val Ser Glu Thr Gln Lys Ala Glu Thr Phe
                70                  75                  80

gtt tcc cgt ttt gcc cct gac gaa ccc aga aag ggt tcc gac gtt ctc      705
Val Ser Arg Phe Ala Pro Asp Glu Pro Arg Lys Gly Ser Asp Val Leu
            85                  90                  95

gtg gag gcc ctc gaa aga gaa ggg gtt acg gac gtt ttt gcg tac cca      753
Val Glu Ala Leu Glu Arg Glu Gly Val Thr Asp Val Phe Ala Tyr Pro
        100                 105                 110

ggc ggc gct tcc atg gag att cac caa gct ttg acg cgc tca agc atc      801
Gly Gly Ala Ser Met Glu Ile His Gln Ala Leu Thr Arg Ser Ser Ile
    115                 120                 125

atc cgc aac gtg cta cca cgt cac gag cag ggt ggt gtc ttc gcc gct      849
Ile Arg Asn Val Leu Pro Arg His Glu Gln Gly Gly Val Phe Ala Ala
130                 135                 140                 145

gag ggt tac gca cgc gcc acc ggc ttc ccc ggc gtt tgc att gcc acc      897
Glu Gly Tyr Ala Arg Ala Thr Gly Phe Pro Gly Val Cys Ile Ala Thr
                150                 155                 160

tcc ggc cct ggc gcc acc aat ctc gtc agt ggc ctc gcg gac gcc cta      945
Ser Gly Pro Gly Ala Thr Asn Leu Val Ser Gly Leu Ala Asp Ala Leu
            165                 170                 175

ctg gat agc gtc ccc att gtt gct ata acc ggt caa gtg cca cgt agg      993
Leu Asp Ser Val Pro Ile Val Ala Ile Thr Gly Gln Val Pro Arg Arg
        180                 185                 190

atg atc ggt act gat gct ttt cag gaa act ccg att gtt gag gta act     1041
Met Ile Gly Thr Asp Ala Phe Gln Glu Thr Pro Ile Val Glu Val Thr
    195                 200                 205

aga tcg att acc aag cat aat tat ctc gtt atg gac gta gag gat att     1089
Arg Ser Ile Thr Lys His Asn Tyr Leu Val Met Asp Val Glu Asp Ile
210                 215                 220                 225

cct agg gtt gta cgt gag gct ttt ttc ctt gcg aga tcg ggc cgg cct     1137
Pro Arg Val Val Arg Glu Ala Phe Phe Leu Ala Arg Ser Gly Arg Pro
                230                 235                 240

ggc cct gtt ttg att gat gta cct aag gat att cag caa caa ttg gtg     1185
Gly Pro Val Leu Ile Asp Val Pro Lys Asp Ile Gln Gln Gln Leu Val
            245                 250                 255

ata cct gac tgg gat cag cca atg agg ttg cct ggt tac atg tct agg     1233
Ile Pro Asp Trp Asp Gln Pro Met Arg Leu Pro Gly Tyr Met Ser Arg
        260                 265                 270

tta cct aaa ttg ccc aat gag atg ctt tta gaa caa att gtt agg ctt     1281
Leu Pro Lys Leu Pro Asn Glu Met Leu Leu Glu Gln Ile Val Arg Leu
    275                 280                 285

att tct gag tca aag aag cct gtt ttg tat gtg ggg ggt ggg tgt tcg     1329
Ile Ser Glu Ser Lys Lys Pro Val Leu Tyr Val Gly Gly Gly Cys Ser
290                 295                 300                 305

caa tcg agt gag gag ttg aga cga ttc gtg gag ctc acc ggt atc ccc     1377
```

```
Gln Ser Ser Glu Glu Leu Arg Arg Phe Val Glu Leu Thr Gly Ile Pro
                310                 315                 320

gtg gca agt act ttg atg ggt ctt gga gct ttt cca act ggg gat gag      1425
Val Ala Ser Thr Leu Met Gly Leu Gly Ala Phe Pro Thr Gly Asp Glu
            325                 330                 335

ctt tcc ctt tca atg ttg ggt atg cat ggt act gtt tat gct aat tat      1473
Leu Ser Leu Ser Met Leu Gly Met His Gly Thr Val Tyr Ala Asn Tyr
        340                 345                 350

gct gtg gac agt agt gat tta ttg ctc gca ttt ggg gtg agg ttt gat      1521
Ala Val Asp Ser Ser Asp Leu Leu Leu Ala Phe Gly Val Arg Phe Asp
    355                 360                 365

gat aga gtt act gga aag tta gaa gct ttt gct agc cga gcg aaa att      1569
Asp Arg Val Thr Gly Lys Leu Glu Ala Phe Ala Ser Arg Ala Lys Ile
370                 375                 380                 385

gtt cac att gat att gat tca gct gag att gga aag aac aag cag cct      1617
Val His Ile Asp Ile Asp Ser Ala Glu Ile Gly Lys Asn Lys Gln Pro
                390                 395                 400

cat gtt tcc att tgt gcg gat atc aag ttg gcg tta cag ggt ttg aat      1665
His Val Ser Ile Cys Ala Asp Ile Lys Leu Ala Leu Gln Gly Leu Asn
            405                 410                 415

tcg ata ttg gag agt aag gaa ggt aaa ctg aag ttg gat ttt tct gct      1713
Ser Ile Leu Glu Ser Lys Glu Gly Lys Leu Lys Leu Asp Phe Ser Ala
        420                 425                 430

tgg agg cag gag ttg acg gtg cag aaa gtg aag tac ccg ttg aat ttt      1761
Trp Arg Gln Glu Leu Thr Val Gln Lys Val Lys Tyr Pro Leu Asn Phe
    435                 440                 445

aaa act ttt ggt gat gct att cct ccg caa tat gct atc cag gtt cta      1809
Lys Thr Phe Gly Asp Ala Ile Pro Pro Gln Tyr Ala Ile Gln Val Leu
450                 455                 460                 465

gat gag tta act aat ggg agt gct att ata agt acc ggt gtt ggg cag      1857
Asp Glu Leu Thr Asn Gly Ser Ala Ile Ile Ser Thr Gly Val Gly Gln
                470                 475                 480

cac cag atg tgg gct gct caa tat tat aag tac aga aag cca cgc caa      1905
His Gln Met Trp Ala Ala Gln Tyr Tyr Lys Tyr Arg Lys Pro Arg Gln
            485                 490                 495

tgg ttg aca tct ggt gga tta gga gcg atg gga ttt ggt ttg ccc gct      1953
Trp Leu Thr Ser Gly Gly Leu Gly Ala Met Gly Phe Gly Leu Pro Ala
        500                 505                 510

gct att ggt gcg gct gtt gga aga cct gat gaa gtt gtg gtt gac att      2001
Ala Ile Gly Ala Ala Val Gly Arg Pro Asp Glu Val Val Val Asp Ile
    515                 520                 525

gat ggt gat ggc agt ttc atc atg aat gtg cag gag cta gca act att      2049
Asp Gly Asp Gly Ser Phe Ile Met Asn Val Gln Glu Leu Ala Thr Ile
530                 535                 540                 545

aag gtg gag aat ctc cca gtt aag att atg tta ctg aat aat caa cac      2097
Lys Val Glu Asn Leu Pro Val Lys Ile Met Leu Leu Asn Asn Gln His
                550                 555                 560

ttg gga atg gtg gtt caa tgg gag gat cgg ttc tat aag gct aac aga      2145
Leu Gly Met Val Val Gln Trp Glu Asp Arg Phe Tyr Lys Ala Asn Arg
            565                 570                 575

gca cac aca tac ctg ggg aat cct tct aat gag gcg gag atc ttt cct      2193
Ala His Thr Tyr Leu Gly Asn Pro Ser Asn Glu Ala Glu Ile Phe Pro
        580                 585                 590

aat atg ttg aaa ttt gca gag gct tgt ggc gta cct gct gcg aga gtg      2241
Asn Met Leu Lys Phe Ala Glu Ala Cys Gly Val Pro Ala Ala Arg Val
    595                 600                 605

aca cac agg gat gat ctt aga gcg gct att caa aag atg tta gac act      2289
Thr His Arg Asp Asp Leu Arg Ala Ala Ile Gln Lys Met Leu Asp Thr
610                 615                 620                 625

cct ggg cca tac ttg ttg gat gtg att gta cct cat cag gaa cat gtt      2337
```

```
Pro Gly Pro Tyr Leu Leu Asp Val Ile Val Pro His Gln Glu His Val
                630                 635                 640

cta cct atg att ccc agt ggc ggg gct ttc aaa gat gtg atc aca gag     2385
Leu Pro Met Ile Pro Ser Gly Gly Ala Phe Lys Asp Val Ile Thr Glu
            645                 650                 655

ggt gac ggg aga agt tcc tat tga ctttgaggtg ctacagagct agattctagg    2439
Gly Asp Gly Arg Ser Ser Tyr
        660

ccttgtatta tctaaaataa ac                                            2461


<210> SEQ ID NO 89
<211> LENGTH: 664
<212> TYPE: PRT
<213> ORGANISM: Nicotiana tabacum

<400> SEQUENCE: 89

Met Ala Ala Ala Ala Ala Ala Pro Ser Pro Ser Phe Ser Lys Thr Leu
1               5                   10                  15

Ser Ser Ser Ser Ser Lys Ser Ser Thr Leu Leu Pro Arg Ser Thr Phe
            20                  25                  30

Pro Phe Pro His His Pro His Lys Thr Thr Pro Pro Pro Leu His Leu
        35                  40                  45

Thr Pro Thr His Ile His Ser Gln Arg Arg Arg Phe Thr Ile Ser Asn
    50                  55                  60

Val Ile Ser Thr Thr Gln Lys Val Ser Glu Thr Gln Lys Ala Glu Thr
65                  70                  75                  80

Phe Val Ser Arg Phe Ala Pro Asp Glu Pro Arg Lys Gly Ser Asp Val
                85                  90                  95

Leu Val Glu Ala Leu Glu Arg Glu Gly Val Thr Asp Val Phe Ala Tyr
            100                 105                 110

Pro Gly Gly Ala Ser Met Glu Ile His Gln Ala Leu Thr Arg Ser Ser
        115                 120                 125

Ile Ile Arg Asn Val Leu Pro Arg His Glu Gln Gly Gly Val Phe Ala
    130                 135                 140

Ala Glu Gly Tyr Ala Arg Ala Thr Gly Phe Pro Gly Val Cys Ile Ala
145                 150                 155                 160

Thr Ser Gly Pro Gly Ala Thr Asn Leu Val Ser Gly Leu Ala Asp Ala
                165                 170                 175

Leu Leu Asp Ser Val Pro Ile Val Ala Ile Thr Gly Gln Val Pro Arg
            180                 185                 190

Arg Met Ile Gly Thr Asp Ala Phe Gln Glu Thr Pro Ile Val Glu Val
        195                 200                 205

Thr Arg Ser Ile Thr Lys His Asn Tyr Leu Val Met Asp Val Glu Asp
    210                 215                 220

Ile Pro Arg Val Val Arg Glu Ala Phe Phe Leu Ala Arg Ser Gly Arg
225                 230                 235                 240

Pro Gly Pro Val Leu Ile Asp Val Pro Lys Asp Ile Gln Gln Gln Leu
                245                 250                 255

Val Ile Pro Asp Trp Asp Gln Pro Met Arg Leu Pro Gly Tyr Met Ser
            260                 265                 270

Arg Leu Pro Lys Leu Pro Asn Glu Met Leu Leu Glu Gln Ile Val Arg
        275                 280                 285

Leu Ile Ser Glu Ser Lys Lys Pro Val Leu Tyr Val Gly Gly Gly Cys
    290                 295                 300

Ser Gln Ser Ser Glu Glu Leu Arg Arg Phe Val Glu Leu Thr Gly Ile
305                 310                 315                 320
```

-continued

```
Pro Val Ala Ser Thr Leu Met Gly Leu Gly Ala Phe Pro Thr Gly Asp
                325                 330                 335

Glu Leu Ser Leu Ser Met Leu Gly Met His Gly Thr Val Tyr Ala Asn
            340                 345                 350

Tyr Ala Val Asp Ser Ser Asp Leu Leu Leu Ala Phe Gly Val Arg Phe
        355                 360                 365

Asp Asp Arg Val Thr Gly Lys Leu Glu Ala Phe Ala Ser Arg Ala Lys
    370                 375                 380

Ile Val His Ile Asp Ile Asp Ser Ala Glu Ile Gly Lys Asn Lys Gln
385                 390                 395                 400

Pro His Val Ser Ile Cys Ala Asp Ile Lys Leu Ala Leu Gln Gly Leu
                405                 410                 415

Asn Ser Ile Leu Glu Ser Lys Glu Gly Lys Leu Lys Leu Asp Phe Ser
            420                 425                 430

Ala Trp Arg Gln Glu Leu Thr Val Gln Lys Val Lys Tyr Pro Leu Asn
        435                 440                 445

Phe Lys Thr Phe Gly Asp Ala Ile Pro Pro Gln Tyr Ala Ile Gln Val
    450                 455                 460

Leu Asp Glu Leu Thr Asn Gly Ser Ala Ile Ile Ser Thr Gly Val Gly
465                 470                 475                 480

Gln His Gln Met Trp Ala Ala Gln Tyr Tyr Lys Tyr Arg Lys Pro Arg
                485                 490                 495

Gln Trp Leu Thr Ser Gly Gly Leu Gly Ala Met Gly Phe Gly Leu Pro
            500                 505                 510

Ala Ala Ile Gly Ala Ala Val Gly Arg Pro Asp Glu Val Val Val Asp
        515                 520                 525

Ile Asp Gly Asp Gly Ser Phe Ile Met Asn Val Gln Glu Leu Ala Thr
    530                 535                 540

Ile Lys Val Glu Asn Leu Pro Val Lys Ile Met Leu Leu Asn Asn Gln
545                 550                 555                 560

His Leu Gly Met Val Val Gln Trp Glu Asp Arg Phe Tyr Lys Ala Asn
                565                 570                 575

Arg Ala His Thr Tyr Leu Gly Asn Pro Ser Asn Glu Ala Glu Ile Phe
            580                 585                 590

Pro Asn Met Leu Lys Phe Ala Glu Ala Cys Gly Val Pro Ala Ala Arg
        595                 600                 605

Val Thr His Arg Asp Asp Leu Arg Ala Ala Ile Gln Lys Met Leu Asp
    610                 615                 620

Thr Pro Gly Pro Tyr Leu Leu Asp Val Ile Val Pro His Gln Glu His
625                 630                 635                 640

Val Leu Pro Met Ile Pro Ser Gly Gly Ala Phe Lys Asp Val Ile Thr
                645                 650                 655

Glu Gly Asp Gly Arg Ser Ser Tyr
            660
```

<210> SEQ ID NO 90
<211> LENGTH: 2468
<212> TYPE: DNA
<213> ORGANISM: Nicotiana tabacum
<220> FEATURE:
<221> NAME/KEY: CDS
<222> LOCATION: (413)..(2416)
<223> OTHER INFORMATION: acetolactate synthase; herbicide resistance

<400> SEQUENCE: 90

```
ccactgggca aattagcgtg tattagatac actttggaaa ggttgagtgt gtaatgtgat      60
```

-continued

```
ttttgttcgc aaaaagtgtg taatagggat ttagtccata gtttaggggg taacttatgt    120

atttataggt taaatgatgg cgactaaata gagcgcccgt gcaattttta ctattaaagt    180

agtattaaat tttcatacga ccctatatct atggctggca ccaaatttct tcacatttgg    240

atccctcttt catttgttct catccatttt tgcgattcat gtgcatttaa tcagtaggac    300

cccttttag cttagtagtg ctctcatgtt ctcaacttaa tattaaacca accacactcc    360

atctgcatta ccctccttcc agtttcgtct ctccctgccc tccccttcaa ca atg gcg    418
                                                           Met Ala
                                                           1

gcg gcg gct cca tct ccc tct tct tcc gct ttc tcc aaa acc cta tcg      466
Ala Ala Ala Pro Ser Pro Ser Ser Ser Ala Phe Ser Lys Thr Leu Ser
        5                   10                  15

cct tcc tcc tcc aca tcc tcc acc ctc ctc cct aga tca acc ttc cct      514
Pro Ser Ser Ser Thr Ser Ser Thr Leu Leu Pro Arg Ser Thr Phe Pro
    20                  25                  30

ttc ccc cac cac ccc cac aag acc acc cca cca ccc ctc cac ctc acc      562
Phe Pro His His Pro His Lys Thr Thr Pro Pro Pro Leu His Leu Thr
35                  40                  45                  50

cac act cac att cac att cac agc caa cgc cgt cgt ttc acc ata tcc      610
His Thr His Ile His Ile His Ser Gln Arg Arg Arg Phe Thr Ile Ser
                55                  60                  65

aat gtc att tcc act aac caa aaa gtt tcc cag acc gaa aaa acc gaa      658
Asn Val Ile Ser Thr Asn Gln Lys Val Ser Gln Thr Glu Lys Thr Glu
            70                  75                  80

act ttc gtt tcc cgt ttt gct cct gac gaa ccc aga aag ggt tcc gac      706
Thr Phe Val Ser Arg Phe Ala Pro Asp Glu Pro Arg Lys Gly Ser Asp
        85                  90                  95

gtt ctc gtg gag gct ctc gaa aga gaa ggg gtt acg gac gtc ttt gcg      754
Val Leu Val Glu Ala Leu Glu Arg Glu Gly Val Thr Asp Val Phe Ala
    100                 105                 110

tac cca ggt ggc gct tcc atg gag att cac caa gct ttg acc cgt tca      802
Tyr Pro Gly Gly Ala Ser Met Glu Ile His Gln Ala Leu Thr Arg Ser
115                 120                 125                 130

agc atc atc cgc aac gtg ctg cca cgt cac gag cag ggc ggt gtc ttc      850
Ser Ile Ile Arg Asn Val Leu Pro Arg His Glu Gln Gly Gly Val Phe
                135                 140                 145

gcc gct gag ggt tac gca cgc gcc acc gga ttt ccc ggc gtt tgc att      898
Ala Ala Glu Gly Tyr Ala Arg Ala Thr Gly Phe Pro Gly Val Cys Ile
            150                 155                 160

gcc acc tct ggc ccc ggc gcc acc aat ctc gtc agc ggc ctc gct gac      946
Ala Thr Ser Gly Pro Gly Ala Thr Asn Leu Val Ser Gly Leu Ala Asp
        165                 170                 175

gcg cta ctg gat agc gtc ccc att gtt gct ata aca ggt caa gtg cca      994
Ala Leu Leu Asp Ser Val Pro Ile Val Ala Ile Thr Gly Gln Val Pro
    180                 185                 190

cgt agg atg ata ggt act gat gct ttt cag gaa act cct att gtt gag     1042
Arg Arg Met Ile Gly Thr Asp Ala Phe Gln Glu Thr Pro Ile Val Glu
195                 200                 205                 210

gta act aga tcg att acc aag cat aat tat ctc gtt atg gac gta gag     1090
Val Thr Arg Ser Ile Thr Lys His Asn Tyr Leu Val Met Asp Val Glu
                215                 220                 225

gat att cct agg gtt gta cgt gaa gct ttt ttc ctc gcg aga tcg ggc     1138
Asp Ile Pro Arg Val Val Arg Glu Ala Phe Phe Leu Ala Arg Ser Gly
            230                 235                 240

cgg cct ggc cct att ttg att gat gta cct aag gat att cag caa caa     1186
Arg Pro Gly Pro Ile Leu Ile Asp Val Pro Lys Asp Ile Gln Gln Gln
        245                 250                 255

ttg gtg ata cct gac tgg gat cag cca atg agg tta cct ggt tac atg     1234
```

-continued

```
Leu Val Ile Pro Asp Trp Asp Gln Pro Met Arg Leu Pro Gly Tyr Met
    260                 265                 270

tct agg tta cct aaa ttg ccc aat gag atg ctt tta gaa caa att gtt     1282
Ser Arg Leu Pro Lys Leu Pro Asn Glu Met Leu Leu Glu Gln Ile Val
275                 280                 285                 290

agg ctt att tct gag tca aag aag cct gtt ttg tat gtg ggg ggt ggg     1330
Arg Leu Ile Ser Glu Ser Lys Lys Pro Val Leu Tyr Val Gly Gly Gly
                295                 300                 305

tgt tcg caa tcg agt gag gac ttg aga cga ttc gtg gag ctc acg ggt     1378
Cys Ser Gln Ser Ser Glu Asp Leu Arg Arg Phe Val Glu Leu Thr Gly
            310                 315                 320

atc ccc gtg gca agt act ttg atg ggt ctt gga gct ttt cca act ggg     1426
Ile Pro Val Ala Ser Thr Leu Met Gly Leu Gly Ala Phe Pro Thr Gly
        325                 330                 335

gat gag ctt tcc ctt tca atg ttg ggt atg cat ggt act gtt tat gct     1474
Asp Glu Leu Ser Leu Ser Met Leu Gly Met His Gly Thr Val Tyr Ala
    340                 345                 350

aat tat gct gtg gac agt agt gat ttg ttg ctc gca ttt ggg gtg agg     1522
Asn Tyr Ala Val Asp Ser Ser Asp Leu Leu Leu Ala Phe Gly Val Arg
355                 360                 365                 370

ttt gat gat aga gtt act gga aag tta gaa gct ttt gct agc cga gca     1570
Phe Asp Asp Arg Val Thr Gly Lys Leu Glu Ala Phe Ala Ser Arg Ala
                375                 380                 385

aaa att gtt cac att gat att gat tca gct gag att gga aag aac aag     1618
Lys Ile Val His Ile Asp Ile Asp Ser Ala Glu Ile Gly Lys Asn Lys
            390                 395                 400

cag cct cat gtt tcc att tgt gca gat atc aag ttg gcg tta cag ggt     1666
Gln Pro His Val Ser Ile Cys Ala Asp Ile Lys Leu Ala Leu Gln Gly
        405                 410                 415

ttg aat tcg ata ctg gag agt aag gaa ggt aaa ctg aag ttg gat ttt     1714
Leu Asn Ser Ile Leu Glu Ser Lys Glu Gly Lys Leu Lys Leu Asp Phe
    420                 425                 430

tct gct tgg agg cag gag ttg acg gag cag aaa gtg aag cac cca ttg     1762
Ser Ala Trp Arg Gln Glu Leu Thr Glu Gln Lys Val Lys His Pro Leu
435                 440                 445                 450

aac ttt aaa act ttt ggt gat gca att cct ccg caa tat gct atc cag     1810
Asn Phe Lys Thr Phe Gly Asp Ala Ile Pro Pro Gln Tyr Ala Ile Gln
                455                 460                 465

gtt cta gat gag tta act aat ggg aat gct att ata agt act ggt gtg     1858
Val Leu Asp Glu Leu Thr Asn Gly Asn Ala Ile Ile Ser Thr Gly Val
            470                 475                 480

ggg caa cac cag atg tgg gct gct caa tac tat aag tac aga aag cca     1906
Gly Gln His Gln Met Trp Ala Ala Gln Tyr Tyr Lys Tyr Arg Lys Pro
        485                 490                 495

cgc caa tgg ttg aca tct ggt gga tta gga gca atg gga ttt ggt ttg     1954
Arg Gln Trp Leu Thr Ser Gly Gly Leu Gly Ala Met Gly Phe Gly Leu
    500                 505                 510

ccc gct gct att ggt gcg gct gtt gga aga ccg gat gaa gtt gtg gtt     2002
Pro Ala Ala Ile Gly Ala Ala Val Gly Arg Pro Asp Glu Val Val Val
515                 520                 525                 530

gac att gat ggt gat ggc agt ttc atc atg aat gtg cag gag ctt gca     2050
Asp Ile Asp Gly Asp Gly Ser Phe Ile Met Asn Val Gln Glu Leu Ala
                535                 540                 545

aca att aag gtg gag aat ctc cca gtt aag att atg tta ctg aat aat     2098
Thr Ile Lys Val Glu Asn Leu Pro Val Lys Ile Met Leu Leu Asn Asn
            550                 555                 560

caa cac ttg gga atg gtg gtt caa tgg gag gat cgg ttc tat aag gct     2146
Gln His Leu Gly Met Val Val Gln Trp Glu Asp Arg Phe Tyr Lys Ala
        565                 570                 575

aac aga gca cac aca tac ctg ggg aat cct tct aat gag gcg gag atc     2194
```

```
Asn Arg Ala His Thr Tyr Leu Gly Asn Pro Ser Asn Glu Ala Glu Ile
    580                 585                 590

ttt cct aat atg ctg aaa ttt gca gag gct tgt ggc gta cct gct gca      2242
Phe Pro Asn Met Leu Lys Phe Ala Glu Ala Cys Gly Val Pro Ala Ala
595                 600                 605                 610

aga gtg aca cat agg gat gat ctt aga gct gcc att cag aag atg tta      2290
Arg Val Thr His Arg Asp Asp Leu Arg Ala Ala Ile Gln Lys Met Leu
                615                 620                 625

gac act cct ggg cca tac ttg ttg gat gtg att gta cct cat cag gaa      2338
Asp Thr Pro Gly Pro Tyr Leu Leu Asp Val Ile Val Pro His Gln Glu
            630                 635                 640

cat gtt tta cct atg att ccc agt ggc gga gct ttc aaa gat gtg atc      2386
His Val Leu Pro Met Ile Pro Ser Gly Gly Ala Phe Lys Asp Val Ile
        645                 650                 655

aca gag ggt gac ggg aga agt tcc tat tga gtttgagaag ctacagagct        2436
Thr Glu Gly Asp Gly Arg Ser Ser Tyr
    660                 665

agattctagg ccttgtatta tctaaaataa ac                                  2468


<210> SEQ ID NO 91
<211> LENGTH: 667
<212> TYPE: PRT
<213> ORGANISM: Nicotiana tabacum

<400> SEQUENCE: 91

Met Ala Ala Ala Ala Pro Ser Pro Ser Ser Ser Ala Phe Ser Lys Thr
1               5                   10                  15

Leu Ser Pro Ser Ser Ser Thr Ser Ser Thr Leu Leu Pro Arg Ser Thr
            20                  25                  30

Phe Pro Phe Pro His His Pro His Lys Thr Thr Pro Pro Leu His
        35                  40                  45

Leu Thr His Thr His Ile His Ile His Ser Gln Arg Arg Arg Phe Thr
    50                  55                  60

Ile Ser Asn Val Ile Ser Thr Asn Gln Lys Val Ser Gln Thr Glu Lys
65                  70                  75                  80

Thr Glu Thr Phe Val Ser Arg Phe Ala Pro Asp Glu Pro Arg Lys Gly
                85                  90                  95

Ser Asp Val Leu Val Glu Ala Leu Glu Arg Glu Gly Val Thr Asp Val
            100                 105                 110

Phe Ala Tyr Pro Gly Gly Ala Ser Met Glu Ile His Gln Ala Leu Thr
        115                 120                 125

Arg Ser Ser Ile Ile Arg Asn Val Leu Pro Arg His Glu Gln Gly Gly
    130                 135                 140

Val Phe Ala Ala Glu Gly Tyr Ala Arg Ala Thr Gly Phe Pro Gly Val
145                 150                 155                 160

Cys Ile Ala Thr Ser Gly Pro Gly Ala Thr Asn Leu Val Ser Gly Leu
                165                 170                 175

Ala Asp Ala Leu Leu Asp Ser Val Pro Ile Val Ala Ile Thr Gly Gln
            180                 185                 190

Val Pro Arg Arg Met Ile Gly Thr Asp Ala Phe Gln Glu Thr Pro Ile
        195                 200                 205

Val Glu Val Thr Arg Ser Ile Thr Lys His Asn Tyr Leu Val Met Asp
    210                 215                 220

Val Glu Asp Ile Pro Arg Val Val Arg Glu Ala Phe Phe Leu Ala Arg
225                 230                 235                 240

Ser Gly Arg Pro Gly Pro Ile Leu Ile Asp Val Pro Lys Asp Ile Gln
                245                 250                 255
```

```
Gln Gln Leu Val Ile Pro Asp Trp Asp Gln Pro Met Arg Leu Pro Gly
            260                 265                 270

Tyr Met Ser Arg Leu Pro Lys Leu Pro Asn Glu Met Leu Leu Glu Gln
        275                 280                 285

Ile Val Arg Leu Ile Ser Glu Ser Lys Lys Pro Val Leu Tyr Val Gly
    290                 295                 300

Gly Gly Cys Ser Gln Ser Ser Glu Asp Leu Arg Arg Phe Val Glu Leu
305                 310                 315                 320

Thr Gly Ile Pro Val Ala Ser Thr Leu Met Gly Leu Gly Ala Phe Pro
                325                 330                 335

Thr Gly Asp Glu Leu Ser Leu Ser Met Leu Gly Met His Gly Thr Val
            340                 345                 350

Tyr Ala Asn Tyr Ala Val Asp Ser Ser Asp Leu Leu Leu Ala Phe Gly
        355                 360                 365

Val Arg Phe Asp Asp Arg Val Thr Gly Lys Leu Glu Ala Phe Ala Ser
    370                 375                 380

Arg Ala Lys Ile Val His Ile Asp Ile Asp Ser Ala Glu Ile Gly Lys
385                 390                 395                 400

Asn Lys Gln Pro His Val Ser Ile Cys Ala Asp Ile Lys Leu Ala Leu
                405                 410                 415

Gln Gly Leu Asn Ser Ile Leu Glu Ser Lys Glu Gly Lys Leu Lys Leu
            420                 425                 430

Asp Phe Ser Ala Trp Arg Gln Glu Leu Thr Glu Gln Lys Val Lys His
        435                 440                 445

Pro Leu Asn Phe Lys Thr Phe Gly Asp Ala Ile Pro Pro Gln Tyr Ala
    450                 455                 460

Ile Gln Val Leu Asp Glu Leu Thr Asn Gly Asn Ala Ile Ile Ser Thr
465                 470                 475                 480

Gly Val Gly Gln His Gln Met Trp Ala Ala Gln Tyr Tyr Lys Tyr Arg
                485                 490                 495

Lys Pro Arg Gln Trp Leu Thr Ser Gly Gly Leu Gly Ala Met Gly Phe
            500                 505                 510

Gly Leu Pro Ala Ala Ile Gly Ala Ala Val Gly Arg Pro Asp Glu Val
        515                 520                 525

Val Val Asp Ile Asp Gly Asp Gly Ser Phe Ile Met Asn Val Gln Glu
    530                 535                 540

Leu Ala Thr Ile Lys Val Glu Asn Leu Pro Val Lys Ile Met Leu Leu
545                 550                 555                 560

Asn Asn Gln His Leu Gly Met Val Val Gln Trp Glu Asp Arg Phe Tyr
                565                 570                 575

Lys Ala Asn Arg Ala His Thr Tyr Leu Gly Asn Pro Ser Asn Glu Ala
            580                 585                 590

Glu Ile Phe Pro Asn Met Leu Lys Phe Ala Glu Ala Cys Gly Val Pro
        595                 600                 605

Ala Ala Arg Val Thr His Arg Asp Asp Leu Arg Ala Ala Ile Gln Lys
    610                 615                 620

Met Leu Asp Thr Pro Gly Pro Tyr Leu Leu Asp Val Ile Val Pro His
625                 630                 635                 640

Gln Glu His Val Leu Pro Met Ile Pro Ser Gly Gly Ala Phe Lys Asp
                645                 650                 655

Val Ile Thr Glu Gly Asp Gly Arg Ser Ser Tyr
            660                 665
```

<210> SEQ ID NO 92
<211> LENGTH: 2141
<212> TYPE: DNA
<213> ORGANISM: Artificial Sequence
<220> FEATURE:
<223> OTHER INFORMATION: Synthetic nucleotide mutant acetolactate synthase
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (1737)..(1741)
<223> OTHER INFORMATION: n is a, c, g, or t

<400> SEQUENCE: 92

```
actggccgca ctaccgctgc gcccaaggca ggcgccgcag ccctcctggc cacccgccgc     60
gccctcgccg cgcccatcag gtgctcagcg gcgtcacccg ccatgccgat gcgtcccccg    120
gccaccccgc tccggccgtg ggccccacc gagccccgca agggtgctga catcctcgtc    180
gagtccctcg agcgctgcgg cgtccgcgac gtcttngcct accccggcgg cgcgtccatg    240
gagatccacc aggcactcac ccgctccccc gtcatcgcca accacctctt ccgccacgag    300
caaggggagg cctttcgcgc ctccgcgtac gcgcgctcct cggcgcgcgt cggcgtctgc    360
atcgccacct ccggccccgg cgccaccaac ctagtctccg cgctcgccga cgcgctgctc    420
gattccgtcc ccatggtcgc catcacggga caggtgccgc gacgcatgat tggcaccgac    480
gccttccagg agacgcccat cgtcgaggtc acccgctcca tcaccaagca caactacctg    540
gtcctcgacg tcgacgacat cccccgcgtc gtgcaggagg ctttcttcct cgcctcctct    600
ggtcgaccag ggccggtgct tgtcgacatc cccaaggaca tccagcagca gatggcggtg    660
cctgtctggg acaagcccat gagtctgcct gggtacattg cgcgccttcc caagcccccct    720
gcgactgagt tgcttgagca ggtgctgcgt cttgttggtg aatcgcggcg ccctgttctt    780
tatgtgggcg gtggctgcgc agcatctggt gaggagttgc gacgctttgt ggagctgact    840
ggaatcccgg tcacaactac tcttatgggc ctcggcaact tccccagcga cgacccactg    900
tctctgcgca tgcttggtat gcatggcacg gtgtatgcaa attatgcagt ggataaggcc    960
gatctgttgc ttgcatttgg tgtgcggttt gatgatcgcg tgacagggaa gattgaggct   1020
tttgcaagca gggctaagat tgtgcacgtt gatattgatc ccgctgagat tggcaagaac   1080
aagcagccac atgtgtccat ctgtgcagat gttaagcttg ctttgcaggg catgaatgct   1140
cttcttgaag gaagcacatc aaagaagagc tttgactttg gctcatggaa cgatgagttg   1200
gatcagcaga agagggaatt ccccttggg tataaaacat ctaatgagga gatccagcca   1260
caatatgcta ttcaggttct tgatgagctg acgaaaggcg aggccatcat cggcacaggt   1320
gttgggcagc accagatgtg ggcggcacag tactacactt acaagcggcc aaggcagtgg   1380
ttgtcttcag ctggtcttgg ggctatggga tttggtttgc cggctgctgc tggtgcttct   1440
gtggcaaacc caggtgtcac tgttgttgac atcgatggag atggtagctt tctcatgaac   1500
gttcaggagc tagctatgat ccgaattgag aacctcccgg tgaaggtctt tgtgctaaac   1560
aaccagcacc tggggatggt ggtgcagtgg gaggacaggt tctataaggc caacagagcg   1620
cacacatact tgggaaaccc agagaatgaa agtgagatat atccagattt cgtgacgatc   1680
gccaaagggt tcaacattcc agcggtccgt gtgacaaaga agaacgaagt ccgcgcnnnn   1740
ntaaagaaga tgctcgagac tccagggccg tacctcttgg atataatcgt cccacaccag   1800
gagcatgtgt tgcctatgat ccctagtggt ggggctttca aggatatgat cctggatggt   1860
```

-continued

```
gatggcagga ctgtgtactg atctaaaatc cagcaagcaa ctgatctaaa atccagcaag   1920

caccgcctcc ctgctagtac aagggtgata tgtttttatc tgtgtgatgt tctcctgtgt   1980

tctatctttt tttgtaggcc gtcagctatc tgttatggta atcctatgta gcttccgacc   2040

ttgtaattgt gtagtctgtt gttttccttc tggcatgtgt cataagagat catttaagtg   2100

ccttttgcta catataaata agataataag cactgctatg c                       2141
```

<210> SEQ ID NO 93
<211> LENGTH: 2226
<212> TYPE: DNA
<213> ORGANISM: Artificial Sequence
<220> FEATURE:
<223> OTHER INFORMATION: Synthetic nucleotide mutant acetolactate synthase
<220> FEATURE:
<221> NAME/KEY: misc_feature
<222> LOCATION: (477)..(477)
<223> OTHER INFORMATION: n is a, c, g, or t

<400> SEQUENCE: 93

```
cctcgcgccg cctccgagac agccgccgca accatggcca ccgcggccgc cgcgtctacc     60

ggcctcactg gccgcactac cgctgcgccc aaggcaggcg ccgcagccct cctggccacc    120

cgccgcgccc tcgccgcgcc catcaggtgc tcagcggcgt cacccgccat gccgatgcgt    180

cccccggcca ccccgctccg gccgtggggc cccaccgagc cccgcaaggg tgctgacatc    240

ctcgtcgagt ccctcgagcg ctgcggcgtc cgcgacgtct tcgcctaccc cggcggcgcg    300

tccatggaga tccaccaggc actcacccgc tcccccgtca tcgccaacca cctcttccgc    360

cacgagcaag ggaggccttt tgcgctccgc gtacgcgcgc tcctcggcgc gcgtcggcgt    420

ctgcatcgcc acctccggcc ccggcgccac caacctagtc tccgcgctcg ccgacgnctg    480

ctcgattccg tccccatggt cgccatcacg ggacaggtgc cgcgacgcat gattggcacc    540

gacgccttcc aggagacgcc catcgtcgag gtcacccgct ccatcaccaa gcacaactac    600

ctggtcctcg acgtcgacga catcccccgc gtcgtgcagg aggctttctt cctcgcctcc    660

tctggtcgac cagggccggt gcttgtcgac atccccaagg acatccagca gcagatggcg    720

gtgcctgtct gggacaagcc catgagtctg cctgggtaca ttgcgcgcct tcccaagccc    780

cctgcgactg agttgcttga gcaggtgctg cgtcttgttg gtgaatcgcg gcgccctgtt    840

ctttatgtgg gcggtggctg cgcacgatct ggtgaggagt tgcgacgctt tgtggagctg    900

actggaatcc cggtcacaac tactcttatg ggcctcggca acttccccag cgacgaccca    960

ctgtctctgc gcatgcttgg tatgcatggc acggtgtatg caaattatgc agtggataag   1020

gccgatctgt tgcttgcatt tggtgtgcgg tttgatgatc gcgtgacagg gaagattgag   1080

gcttttgcaa gcagggctaa gattgtgcac gttgatattg atcccgctga gattggcaag   1140

aacaagcagc cacatgtgtc catctgtgca gatgttaagc ttgctttgca gggcatgaat   1200

gctcttcttg aaggaagcac atcaaagaag agctttgact ttggctcatg gaacgatgag   1260

ttggatcagc agaagaggga attccccctt gggtataaaa catctaatga ggagatccag   1320

ccacaatatg ctattcaggt tcttgatgag ctgacgaaag gcgaggccat catcggcaca   1380

ggtgttgggc agcaccagat gtgggcggca cagtactaca cttacaagcg gccaaggcag   1440

tggttgtctt cagctggtct tggggctatg ggatttggtt tgccggctgc tgctggtgct   1500

tctgtggcaa acccaggtgt cactgttgtt gacatcgatg gagatggtag ctttctcatg   1560

aacgttcagg agctagctat gatccgaatt gagaacctcc cggtgaaggt ctttgtgcta   1620

aacaaccagc acctggggat ggtggtgcag tgggaggaca ggttctataa ggccaacaga   1680
```

-continued

```
gcgcacacat acttgggaaa cccagagaat gaaagtgaga tatatccaga tttcgtgacg   1740

atcgccaaag ggttcaacat tccagcggtc cgtgtgacaa agaagaacga agtccgcgca   1800

gcataaagaa gatgctcgag actccagggc cgtacctctt ggatataatc gtcccacacc   1860

aggagcatgt gttgcctatg atccctaatg gtggggcttt caaggatatg atcctggatg   1920

gtgatggcag gactgtgtac tgatctaaaa tccagcaagc aactgatcta aaatccagca   1980

agcaccgcct ccctgctagt acaagggtga tatgttttta tctgtgtgat gttctcctgt   2040

gttctatctt tttttgtagg ccgtcagcta tctgttatgg taatcctatg tagcttccga   2100

ccttgtaatt gtgtagtctg ttgttttcct tctggcatgt gtcataagag atcatttaag   2160

tgccttttgc tacatataaa taagataata agcactgcta tgcagtggtt ctgaaaaaaa   2220

aaaaaa                                                              2226
```

```
<210> SEQ ID NO 94
<211> LENGTH: 2089
<212> TYPE: DNA
<213> ORGANISM: Artificial Sequence
<220> FEATURE:
<223> OTHER INFORMATION: Synthetic nucleotide mutant acetolactate
      synthase
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t

<400> SEQUENCE: 94
```

```
ccctcgcngn gcccatcagg tgctcagcgc gtcacccgcc atcgcgatgg ctcccccggc     60

caccccgctc cggccgtggg gccccaccga gccccgcaag ggtgctgaca tcctcgtcga    120

gtccctcgag cgctgcggcg tccgcgacgt cttcgcctac cccggcggca cgtccatgga    180

gatccaccag gcactcaccc gctcccccgt catcgccaac cacctcttcc gccacgagca    240

aggggaggcc tttgcgctcc gcgtacgcgc gctcctcggc gcgcgtcggc gtctgcatcg    300

ccacctccgg ccccggcgcc accaacctag tctccgcgct cgccgacgcn ctgctcgatt    360

ccgtccccat ggtcgccatc acgggacagg tgccgcgacg catgattggc accgacgcct    420

tccaggagac gcccatcgtc gaggtcaccc gctccatcac caagcacaac tacctggtcc    480

tcgacgtcga cgacatcccc cgcgtcgtgc aggaggcttt cttcctcgcc tcctctggtc    540

gaccagggcc ggtgcttgtc gacatcccca aggacatcca gcagcagatg gcggtgcctg    600

tctgggacaa gcccatgagt ctgcctgggt acattgcgcg ccttcccaag ccccctgcga    660

ctgagttgct tgagcaggtg ctgcgtcttg ttggtgaatc gcggcgccct gttctttatg    720

tgggcggtgg ctgcgcacga tctggtgagg agttgcgacg ctttgtggag ctgactggaa    780

tcccggtcac aactactctt atgggcctcg gcaacttccc cagcgacgac ccactgtctc    840

tgcgcatgct tggtatgcat ggcacggtgt atgcaaatta tgcagtggat aaggccgatc    900

tgttgcttgc atttggtgtg cggtttgatg atcgcgtgac agggaagatt gaggcttttg    960

caagcagggc taagattgtg cacgttgata ttgatcccgc tgagattggc aagaacaagc   1020

agccacatgt gtccatctgt gcagatgtta agcttgcttt gcagggcatg aatgctcttc   1080
```

```
ttgaaggaag cacatcaaag aagagctttg actttggctc atggaacgat gagttggatc   1140

agcagaagag ggaattcccc cttgggtata aaacatctaa tgaggagatc cagccacaat   1200

atgctattca ggttcttgat gagctgacga aaggcgaggc catcatcggc acaggtgttg   1260

ggcagcacca gatgtgggcg gcacagtact acacttacaa gcggccaagg cagtggttgt   1320

cttcagctgg tcttggggct atgggatttg gtttgccggc tgctgctggt gcttctgtgg   1380

caaacccagg tgtcactgtt gttgacatcg atggagatgg tagctttctc atgaacgttc   1440

aggagctagc tatgatccga attgagaacc tcccggtgaa ggtctttgtg ctaaacaacc   1500

agcacctggg gatggtggtg cagtgggagg acaggttcta taaggccaac agagcgcaca   1560

catacttggg aaacccagag aatgaaagtg agatatatcc agatttcgtg acgatcgcca   1620

aagggttcaa cattccagcg gtccgtgtga caaagaagaa cgaagtccgc gcacgataaa   1680

gaagatgctc gagactccag ggccgtacct cttggatata atcgtcccac accaggagca   1740

tgtgttgcct atgatcccta gtggtggggc tttcaaggat atgatcctgg atggtgatgg   1800

caggactgtg tactgatcta aaatccagca agcaactgat ctaaaatcca gcaagcaccg   1860

cctccctgct agtacaaggg tgatatgttt ttatctgtgt gatgttctcc tgtgttctat   1920

cttttttgt aggccgtcag ctatctgtta tggtaatcct atgtagcttc cgaccttgta   1980

attgtgtagt ctgttgtttt ccttctggca tgtgtcataa gagatcattt aagtgccttt   2040

tgctacatat aaataagata ataagcactg ctatgcgatg gttctgaaa              2089


<210> SEQ ID NO 95
<211> LENGTH: 2520
<212> TYPE: DNA
<213> ORGANISM: Artificial Sequence
<220> FEATURE:
<223> OTHER INFORMATION: Sequence 5 from Patent EP 0257993
<220> FEATURE:
<221> NAME/KEY: misc_feature
<222> LOCATION: (2405)..(2406)
<223> OTHER INFORMATION: n is a, c, g, or t
<220> FEATURE:
<221> NAME/KEY: misc_feature
<222> LOCATION: (2452)..(2453)
<223> OTHER INFORMATION: n is a, c, g, or t

<400> SEQUENCE: 95

ggatccctct ttcatttgtt ctcatccatt tttgcgattc atgtgcattt aatcagtagg     60

accccttttt agcttagtag tgctctcatg tttctcaactt aatattaaac caaccacact   120

ccatctgcat taccctcctt ccagtttcgt ctctccctgc cctccccttc aacaatggcg    180

gcggcggctc catctccctc ttcttccgct ttctccaaaa ccctatcgcc ttcctcctcc    240

acatcctcca ccctcctccc tagatcaacc ttccctttcc ccccaccaccc ccacaagacc   300

accccaccac ccctccacct cacccacact cacattcaca ttcacagcca acgccgtcgt    360

ttcaccatat ccaatgtcat ttccactaac caaaaagttt cccagaccga aaaaaccgaa    420

actttcgttt cccgttttgc tcctgacgaa cccagaaagg gttccgacgt tctcgtggag    480

gctctcgaaa gagaaggggt tacggacgtc tttgcgtacc caggtggcgc ttccatggag    540

attcaccaag ctttgacccg ttcaagcatc atccgcaacg tgctgccacg tcacgagcag    600

ggcggtgtct tcgccgctga gggttacgca cgcgccaccg gatttcccgg cgtttgcatt    660

gccacctctg gccccggcgc caccaatctc gtcagcggcc tcgctgacgc gctactggat    720

agcgtcccca ttgttgctat aacaggtcaa gtgcaacgta ggatgatagg tactgatgct    780

tttcaggaaa ctcctattgt tgaggtaact agatcgatta ccaagcataa ttatctcgtt    840
```

```
atggacgtag aggatattcc tagggttgta cgtgaagctt ttttcctcgc gagatcgggc    900

cggcctggcc ctattttgat tgatgtacct aaggatattc agcaacaatt ggtgatacct    960

gactgggatc agccaatgag gttacctggt tacatgtcta ggttgcctaa attgcccaat   1020

gagatgcttt tagaacaaat tgttaggctt atttctgagt caaagaagcc tgttttgtat   1080

gtgggggtg ggtgttcgca atcgagtgag gacttgagac gattcgtgga gctcacgggt   1140

atccccgtgg caagtacttt gatgggtctt ggagcttttc caactgggga tgagctttcc   1200

ctttcaatgt tgggtatgca tggtactgtt tatgctaatt atgctgtgga cagtagtgat   1260

ttgttgctcg catttggggt gaggtttgat gatagagtta ctggaaagtt agaagctttt   1320

gctagccgag caaaaattgt tcacattgat attgattcag ctgagattgg aaagaacaag   1380

cagcctcatg tttccatttg tgcagatatc aagttggcgt tacagggttt gaattcgata   1440

ctggagagta aggaaggtaa actgaagttg gatttttctg cttggaggca ggagttgacg   1500

gagcagaaag tgaagcaccc attgaacttt aaaacttttg gtgatgcaat tcctccgcaa   1560

tatgctatcc aggttctaga tgagttaact aatgggaatg ctattataag tactggtgtg   1620

gggcaacacc agatgtgggc tgctcaatac tataagtaca gaaagccacg ccaatggttg   1680

acatctggtg gattaggagc aatgggattt ggtttgcccg ctgctattgg tgcggctgtt   1740

ggaagaccgg atgaagttgt ggttgacatt gatggtgatg gcagtttcat catgaatgtg   1800

caggagcttg caacaattaa ggtggagaat ctcccagtta agattatgtt actgaataat   1860

caacacttgg gaatggtggt tcaatgggag gatcggttct ataaggctaa cagagcacac   1920

acatacctgg ggaatccttc taatgaggcg gagatctttc ctaatatgct gaaatttgca   1980

gaggcttgtg gcgtacctgc tgcaagagtg acacataggg atgatcttag agctgccatt   2040

cagaagatgt tagacactcc tggccatac ttgttggatg tgattgtacc tcatcaggaa   2100

catgttttac ctatgattcc cagtggcgga gctttcaaag atgtgatcac agagggtgac   2160

gggagaagtt cctattgagt ttgagaagct acagagctag ttctaggcct tgtattatct   2220

aaaataaact tctattaagc caaacatgtt ctgtctatta gtttgttgtt agtttttgct   2280

gtggctttgc tcgttgtcac tgttgtacta ttaagtagtt gatatttatg tttgctttaa   2340

gttttgcatc atctcccttt ggttttgaat gtgaaggatt tcagcaaagt ttcattctct   2400

gtttnnaaca tccacttggt atctggagat taatttctag tggagtagtt tnntgcgata   2460

aaattagctt gttccacatt tttatttcgt aagctatgtt aggctgggtc agattggaac   2520
```

```
<210> SEQ ID NO 96
<211> LENGTH: 2946
<212> TYPE: DNA
<213> ORGANISM: Artificial Sequence
<220> FEATURE:
<223> OTHER INFORMATION: Sequence 2 from Patent EP 0257993
<220> FEATURE:
<221> NAME/KEY: misc_feature
<222> LOCATION: (102)..(102)
<223> OTHER INFORMATION: n is a, c, g, or t

<400> SEQUENCE: 96

ctgcaggtcg actctagtgt acaagattgg gatgtgaagg ctcaaggatg tgaattgata     60

ctctcatcag gggagttaa tacgtgttgt actcttttt cnttacaaga ttttgaccca    120

ctgggtttt cttgcaaggt ttttaacgag gcaaccaaaa ggcgtatttc taaacatgtg    180

tactttttt ccttcactag gatttttttc ctatatgatt ttttcctaat aaggttttaa    240

cgaggcacat tatctatgga catccaaggg ggagtgttat aagaaaaatc aaattatggt    300
```

-continued

```
ggatgtctac tcttcctcca tgatcttctc aaatgcttaa tgacatattc aatgacatat    360
ttctatgctt aatgacatat ttttcttcac ttttcatgcc tatataaagg ccttgtaata    420
gatagaaaaa tacaaataat tgaagaagaa ataaaaatct cttatctcta tatttcttag    480
cttgtttttt ttttgttcta tattgttact ttgagctata tttcataaca gcattcacat    540
tctttttcca tagtcttttt tccctttttat attttaattt actgaagtaa caaatacttc    600
cacttctttc ttcttcccac cctcctaaat atatccaaca tctcattttt cttttcccca    660
attctcagac attttaatct ttcttttcta tttattttct tcatattttg atctctcttc    720
catttgttct catccatttt cgctattcac gtgaattcaa tcaagtagga ccctttcagt    780
ttcgtggcgc tctcgtcttc tcagcttaat ataaaaccaa ccacacacca tctacattgc    840
cctttccttt cagtttcgtc tctcactgct ctcattcaac aataatggcg gcggctgcgg    900
cggctccatc tccctctttc tccaaaaccc tatcgtcctc ctcctccaaa tcctccaccc    960
tcctccctag atccaccttc cctttccccc accaccccca caaaaccacc ccaccacccc   1020
tccacctcac ccccacccac attcacagcc aacgccgtcg tttcaccatc tccaatgtca   1080
tttccactac ccaaaaagtt tccgagaccc aaaaagccga aactttcgtt tcccgttttg   1140
cccctgacga acccagaaag ggttccgacg ttctcgtgga ggccctcgaa agagaagggg   1200
ttacggacgt tttgcgtac ccaggcggcg cttccatgga gattcaccaa gctttgacgc   1260
gctcaagcat catccgcaac gtgctaccac gtcacgagca gggtggtgtc ttcgccgctg   1320
agggttacgc acgcgccacc ggcttccccg gcgtttgcat tgccacctcc ggccctggcg   1380
ccaccaatct cgtcagtggc ctcgcggacg ccctactgga tagcgtcccc attgttgcta   1440
taaccggtca agttgcacgt aggatgatcg gtactgatgc ttttcaggaa actccgattg   1500
ttgaggtaac tagatcgatt accaagcata attatctcgt tatggacgta gaggatattc   1560
ctagggttgt acgtgaggct tttttccttg cgagatcggg ccggcctggc cctgttttga   1620
ttgatgtacc taaggatatt cagcaacaat tggtgatacc tgactgggat cagccaatga   1680
ggttgcctgg ttacatgtct aggttaccta aattgcccaa tgagatcctt ttagaacaaa   1740
ttgttaggct tatttctgag tcaaagaagc ctgttttgta tgtgggggt gggtgttcgc   1800
aatcgagtga ggagttgaga cgattcgtgg agctcaccgg tatccccgtg gcaagtactt   1860
tgatgggtct tggagctttt ccaactgggg atgagctttc cctttcaatg ttgggtatgc   1920
atggtactgt ttatgctaat tatgctgtgg acagtagtga tttattgctc gcatttgggg   1980
tgaggtttga tgatagagtt actggaaagt tagaagcttt tgctagccga gcgaaaattg   2040
ttcacattga tattgattca gctgagattg gaaagaacaa gcagcctcat gtttccattt   2100
gtgcggatat caagttggcg ttacagggtt tgaattcgat attggagagt aaggaaggta   2160
aactgaagtt ggatttttct gcttggaggc aggagttgac ggtgcagaaa gtgaagtacc   2220
cgttgaattt taaaactttt ggtgatgcta ttcctccgca atatgctatc caggttctag   2280
atgagttaac taatgggagt gctattataa gtaccggtgt tgggcagcac cagatgtggg   2340
ctgctcaata ttataagtac agaaagccac gccaatggtt gacatctggt ggattaggag   2400
cgatgggatt tggtttgccc gctgctattg gtgcggctgt tggaagacct gatgaagttg   2460
tggttgacat tgatggtgat ggcagtttca tcatgaatgt gcaggagcta gcaactatta   2520
aggtggagaa tctcccagtt aagattatgt tactgaataa tcaacacttg ggaatggtgg   2580
ttcaattgga ggatcggttc tataacgcta acagagcaca cacatacctg gggaatcctt   2640
ctaatgaggc ggagatcttt cctaatatgt tgaaatttgc agaggcttgt ggcgtacctg   2700
```

-continued ctgcgagagt gacacacagg gatgatctta gagcggctat tcaaaagatg ttagacactc 2760
ctgggccata cttgttggat gtcattgtac ctcatcagga acatgttcta cctatgattc 2820
ccagtcgcgg ggctttcaaa gatgtgatca cagagggtga cgggagaagt tcctattgac 2880
tttgaggtgc tacagagcta gttctaggcc ttgtattatc taaaataaac ttctataaaa 2940
ccaaaa 2946

<210> SEQ ID NO 97
<211> LENGTH: 3102
<212> TYPE: DNA
<213> ORGANISM: Burkholderia pseudomallei

<400> SEQUENCE: 97
ggatctctgc agcccaagct tctgattgaa tgtgtagctc gtggatcgct ggcagactgt 60
atgaagaaga ggcggaagct gctgatgcct ctgccatcct tggtagagga tctagtgact 120
tttggagtgg tgtggctagg ggttcgggag agaagatgga ggagccggct taaccgaaaa 180
gcagctcgaa tgctgattgc caagagtcga acgccgagaa ggcgaaatgc accggacact 240
ggggatgctg ctggaagatg ggccgacaaa ggactcagct gctactgagt cataaatagt 300
tcggattgac ggctgagtcg aaagcgttcg tatatattgg tctgattcac gattcggaag 360
aaattctaca aggttgcgca gctcaggtca tcttaagttt actctcaccg tctcgagtgg 420
cggcagatgt gagtcgtgtg ctacaaaacg tgaatcgaca cgcgcagggc ggaaccaaaa 480 aaaacccccca ccccgctgtc aagttgacaa atcaacacat ttgttacaat ttcaaatcgg 540
gaaatcaaaa attagggcca gatcagcgat caggaatggt aatcgggtaa cagaggtcgc 600
aaaatcgtct agaaagtgga agaagaacgt ggtaactagg agcgaatgct gcaaacttct 660
aaaaaaaaat ctgggcacga tgaaagttgg gctaacgctg acgctcacaa atggcgtggc 720
gaaaggaagc gagacaatcg gaaaattgtt ctctcgggca ccacaaagct gttgtttgtc 780
gctgaagaac aattccaact gattccgccg ccttcctatt gcgtcagcct tgtacctaag 840
ctgccgagta acgtcactca acctctcttt gaatactgct ttgctccgcg aatacttttc 900
ttctatgcgc tcaagaaaat gacacagcac accaagctct gcaaactttc ttcgctcatc 960
tggcgcgaaa tgtgggccat ttcttctcgc ctgcaatggc aatgcgtctg tgcggcgagg 1020
agaatcacga tgcggaatgg gggctggaag ttcatagaga tgctgagttg ttggagcgac 1080
atggtacata agcatgagtc tgtcctgatt tccaccctcc cgtctttcat caactttctc 1140
gtcggaccct tccgatcggc gggcgcagaa ccaggcggta tgcaccgtag ggtggaccca 1200
ccgcggccac tgtcgccagc cttgatcgag gccttcgacg gggtcatgca gctctcgggc 1260
gccccctctc gtggggtcac accaacccca cgagggccag atgctttggg ccggataaca 1320
gatagccgcg gggggtccga ggctggctat aggtttaata tgtgtaatcg ggcagtacca 1380
tcggccgcgc tcccgattgg ggaagtgctt gacattgggg aattcagcgg gaagcggacc 1440
tacctggccg ccgtgcacag ggcccgcgag caagacctgc ctgaaaccga actgcccgct 1500
gttctgcagc cctgcacggg catggcacat gcgatcgctg cggccgatct tagccacacg 1560
agcgggttcg ccccattcgg accgcaagga atgggtcaag agactccatg gcgtgataag 1620
cgcgattgct atttcgatcc ccaggtgtat tattggctct ctcaaatggg cgacacccta 1680
cgggcgtccg tcgcgcaggg tttcgaaaag cggatgcttt gggccgagga ctgccccgaa 1740
gcccggcacc tccggattca cgtaaagggg tccaacgctg ccctgccgga acccggcccc 1800
aaaacgtggg cgggggacgg gagccaagcg gtgtgggcag gccggctgcg tcccacccag 1860
gattcccggt acgtggtcgc cagcatcttc ccctggaggc cgtggtgaac ttgtagggag 1920
cagcaaacgc cctacttcga ggggaggcat ccccagctgg caaaatcgcc ccggtttcgg 1980
gccctaatgg ggcgcacccc tcttgccaaa ctctatcaaa gtttggggga ggggaagggc 2040
gatgatgcgg ctggggcgca gggtcgaggg gacgcccgac ccggagccgg gaatcgtact 2100
gtcgggcgta cacaaatcgc ggcgcggccg accgccgcag aaggccgcgt atctggcccg 2160
ctggaagtac tcgccgatag tggcggccga cccgagggcg ccccagcact cgtgggggaa 2220
tagtagagta gatgccgacc gggagcgggg cagcaccaag acacggaacc ccaacagtcg 2280
tgaggaggtg gtgatctgca tgtccaaatc ctggaacgtg aatcacgaac cacgaatcct 2340
gaatagccaa tttgcgcgaa aatcgctgaa tgccgccaaa ccgagccacc gcgagttgcg 2400
tgaagtaggc gtgaggcaca cccacgactg gcgattgtgg gttggtcgac gacattcggt 2460
acccagacca acactcacga ctttttgggc tagcttgcag gctgagccaa ctttctccct 2520
cactccccgc tttcccctcc atcacgctca ttcctttgaa gtgttcatcc ggtatcatga 2580
gcactatatc atagtgaaac tcgcaacaac ccggtcttcg tcgcgaaagc aaccctccat 2640
cgctgctgcc tcttgcagtg aagaccgcca ccatgcagtc tacgcagtcg aagaccctac 2700
acgtccagtt cgtccattct ggtcctacac attgtatcca cgcacccaag tctgccaacg 2760
tggagtaagt gaaccttttt ttgtcctgtc gaggctcaac gtagatcaca ggctgatcat 2820
ccacactgga ggctcctttg acattacgca gtcgcattct tacccactag agctcctcga 2880
gatgactacc tgtcaatggg ctgcctctct ccgacgtaga gccgcagctt atcgaagacg 2940
ccactggagc ggtgacctcg ctcgatgctg acggccgctt cctcgttgat agcttccgaa 3000
gatggtgtca acgcctctac cgacaccacc caatcgacgc ggaaggcaac ccagcatcac 3060
cggctgtgct tcaatcgctg ctgcgccgcg aagcttagat cc 3102

<210> SEQ ID NO 98
<211> LENGTH: 2843
<212> TYPE: DNA
<213> ORGANISM: Salmonella enterica

<400> SEQUENCE: 98
ggcactgttg caaagttagc gatgaggcag ccttttgtct tattcaaagg ccttacattt 60
caaaaactct gcttaccagg cgcatttcgc ccaggggatc accataataa aatgctgagg 120
cctggccttt gcgtagtgca cgcatcacct caataccttt gatggtggcg taagccgtct 180
tcatggattt aaatcccagc gtggcgccga ttatccgttt cagtttgcca tgatcgcatt 240
caatcacgtt gttccggtac ttaatctgtc ggtgttcaac gtcagacggg caccggcctt 300
cgcgtttgag cagagcaagc gcgcgaccat aggcgggcgc tttatccgtg ttgatgaatc 360
gcgggatctg ccacttcttc acgttgttga ggattttacc cagaaaccgg tatgcagctt 420
tgctgttacg acgggaggag agataaaaat cgacagtgcg gccccggctg tcgacggccc 480
ggtacagata cgcccagcgg ccattgacct tcacgtaggt ttcatccatg tgccacgggc 540
aaagatcgga agggttacgc cagtaccagc gcagccgttt ttccatttca ggcgcataac 600
gctgaaccca gcggtaaatc gtggagtgat cgacattcac tccgcgttca gccagcatct 660
cctgcagctc acggtaactg atgccgtatt tgcagtacca gcgtacggcc cacagaatga 720
tgtcacgctg aaaatgccgg cctttgaatg ggttcatgtg cagctccatc agcaaaaggg 780
gatgataagt ttatcaccac cgactatttg caacagtgcc gtaagctgca cctcaaaccc 840
ccggatcagg ctctccaggc catgcagaaa ggcctgctca ccatcatcac tgtccataat 900

-continued

```
ctgcagcgct tcccgcaata gcggcggcag gttttcgtcc ggtgctgcag ggcggtcggt    960

cagggcggca gtatgctcct gctgctccag tacggcacca agggtaaaat gactgaccgc   1020

tgaaatcgca tataacccgt cgcgcagtga aaagccgttt tctgtcataa agcgtaactg   1080

ggtttccacc gtatcatact gtttttcatc agggcgggtg ccgaggtgca cttttgcccc   1140

gtcacggtaa cgcagcagcg cccggcggaa actcattgca ttattgcgca gaaatgactg   1200

ccaggattcc cccgccgcag gcagtgaata atcatgatga cgcgccagga tctccaccgc   1260

cagcgcatcc agtaacgccc gtttattttt cacatgccag taaagtgtcg gctgttctat   1320

tcccagcttc tgcgccagct tgcgggtcgt cagcccgtca atccctgtct cattcagcag   1380

ttccagtgcc gcatcaataa ccgattctct gttcagccgt gccatgaccg tctcctccga   1440

ttttcagatt gacactctat cattgatagg gatatattcc aactctatca atgataggga   1500

attaacacag gatctgaaaa atgaataaac ccgctgtcat cgcgctggtg attacactgc   1560

tggacgcgat gggaattggt ctgatcatgc cggtattacc gtcactgctg cgggaatatc   1620

tcccggaagc ggatgtggca aaccattacg gcattctgct ggcgctgtat gcggtgatgc   1680

aggtctgttt tgctccgctg ctgggcagat ggtcagataa gctggggcgc agaccggtgc   1740

tgctgttatc cctggcgggt gccgcgtttg attacacact gctggcactg tccaatgtgc   1800

tgtggatgtt gtatctcggg cggattatct ccgggatcac tggtgccacc ggcgcggttg   1860

cggcttcggt agtggcggac agcacggcgg tcagcgagcg taccgcctgg ttcggccgtc   1920

tcggtgcggc ctttggtgcc gggctgattg ccgggccggc tatcggcgga ctggcggggg   1980

atatctcacc gcatctgccg tttgtcattg cggcaatact gaatgcctgc acctttctga   2040

tggtcttttt tatctttaaa ccggcggtac agacagaaga aaaaccggcg gacgagaaac   2100

aagaaagcgc aggtatcagc tttatcacac tgcttaaacc tctggcgctg ttgctgtttg   2160

tctttttttac cgcgcagctt atcgggcaga tcccggccac tgtctgggta ttgtttacgg   2220

agagccgctt tgcctgggac agcgcggcgg tcggtttttc actggcggga ctcggggcga   2280

tgcatgcact gtttcaggcg gtggttgccg ggcgcgctggc aaaacggctg agtgagaaaa   2340

ccattatttt cgccggattt attgccgatg ccaccgcgtt tttactgatg tctgctatca   2400

cttccggatg gatggtgtat ccggtcctga tcctgctggc aggcggcgga attgcactgc   2460

ctgcattgca gggcattatc tctgccgggg catcggcggc aaatcaggga aaactacagg   2520

gtgtgctggt cagcctgacc aatctgaccg gcgtggcggg cccgctgctg tttgctttta   2580

ttttcagtca gacacagcag agtgcggacg gtacggtgtg gctgattggc acggcactgt   2640

acggtctgct gctggcaatc tgtctgctga tcagaaaacc ggcaccggtg gcggccacct   2700

gctgaccggc gctatacagg cagcgctgtt gtgcggtatg gtggacggca ttcgtgctta   2760

tcgcctgcca tgataagcct cagacacaga ggaaccgtta tgaaatcacg cgcacgagtc   2820

gccttcgggc cgggtttacc ctt                                           2843
```

<210> SEQ ID NO 99
<211> LENGTH: 1644
<212> TYPE: DNA
<213> ORGANISM: Bacillus cereus
<220> FEATURE:
<221> NAME/KEY: CDS
<222> LOCATION: (184)..(1560)
<223> OTHER INFORMATION: TET protein, tetracyclin resistance

<400> SEQUENCE: 99

```
tattgttgta taagtgatga aatactgaat ttaaaactta gtttatatgt ggtaaaatgt     60
```

```
tttaatcaag tttaggagga attaattatg aagtgtaatg aatgtaacag ggttcaatta    120

aaagagggaa gcgtatcatt aaccctataa actacgtctg ccctcattat tggagggtga    180

aat gtg aat aca tcc tat tca caa tcg aat tta cga cac aac caa att      228
    Val Asn Thr Ser Tyr Ser Gln Ser Asn Leu Arg His Asn Gln Ile
    1               5                   10                  15

tta att tgg ctt tgc att tta tct ttt ttt agc gta tta aat gaa atg      276
Leu Ile Trp Leu Cys Ile Leu Ser Phe Phe Ser Val Leu Asn Glu Met
                20                  25                  30

gtt ttg aac gtc tca tta cct gat att gca aat gat ttt aat aaa cca      324
Val Leu Asn Val Ser Leu Pro Asp Ile Ala Asn Asp Phe Asn Lys Pro
            35                  40                  45

cct gcg agt aca aac tgg gtg aac aca gcc ttt atg tta acc ttt tcc      372
Pro Ala Ser Thr Asn Trp Val Asn Thr Ala Phe Met Leu Thr Phe Ser
        50                  55                  60

att gga aca gct gta tat gga aag cta tct gat caa tta ggc atc aaa      420
Ile Gly Thr Ala Val Tyr Gly Lys Leu Ser Asp Gln Leu Gly Ile Lys
    65                  70                  75

agg tta ctc cta ttt gga att ata ata aat tgt ttc ggg tcg gta att      468
Arg Leu Leu Leu Phe Gly Ile Ile Ile Asn Cys Phe Gly Ser Val Ile
80                  85                  90                  95

ggg ttt gtt ggc cat tct ttc ttt tcc tta ctt att atg gct cgt ttt      516
Gly Phe Val Gly His Ser Phe Phe Ser Leu Leu Ile Met Ala Arg Phe
                100                 105                 110

att caa ggg gct ggt gca gct gca ttt cca gca ctc gta atg gtt gta      564
Ile Gln Gly Ala Gly Ala Ala Ala Phe Pro Ala Leu Val Met Val Val
            115                 120                 125

gtt gcg cgc tat att cca aag gaa aat agg ggt aaa gca ttt ggt ctt      612
Val Ala Arg Tyr Ile Pro Lys Glu Asn Arg Gly Lys Ala Phe Gly Leu
        130                 135                 140

att gga tcg ata gta gcc atg gga gaa gga gtc ggt cca gcg att ggt      660
Ile Gly Ser Ile Val Ala Met Gly Glu Gly Val Gly Pro Ala Ile Gly
    145                 150                 155

gga atg ata gcc cat tat att cat tgg tcc tat ctt cta ctc att cct      708
Gly Met Ile Ala His Tyr Ile His Trp Ser Tyr Leu Leu Leu Ile Pro
160                 165                 170                 175

atg ata aca att atc act gtt ccg ttt ctt atg aaa tta tta aag aaa      756
Met Ile Thr Ile Ile Thr Val Pro Phe Leu Met Lys Leu Leu Lys Lys
                180                 185                 190

gaa gta agg ata aaa ggt cat ttt gat atc aaa gga att ata cta atg      804
Glu Val Arg Ile Lys Gly His Phe Asp Ile Lys Gly Ile Ile Leu Met
            195                 200                 205

tct gta ggc att gta ttt ttt atg ttg ttt aca aca tca tat agc att      852
Ser Val Gly Ile Val Phe Phe Met Leu Phe Thr Thr Ser Tyr Ser Ile
        210                 215                 220

tct ttt ctt atc gtt agc gtg ctg tca ttc ctg ata ttt gta aaa cat      900
Ser Phe Leu Ile Val Ser Val Leu Ser Phe Leu Ile Phe Val Lys His
    225                 230                 235

atc agg aaa gta aca gat cct ttt gtt gat ccc gga tta ggg aaa aat      948
Ile Arg Lys Val Thr Asp Pro Phe Val Asp Pro Gly Leu Gly Lys Asn
240                 245                 250                 255

ata cct ttt atg att gga gtt ctt tgt ggg gga att ata ttt gga aca      996
Ile Pro Phe Met Ile Gly Val Leu Cys Gly Gly Ile Ile Phe Gly Thr
                260                 265                 270

gta gca ggg ttt gtc tct atg gtt cct tat atg atg aaa gat gtt cac     1044
Val Ala Gly Phe Val Ser Met Val Pro Tyr Met Met Lys Asp Val His
            275                 280                 285

cag cta agt act gcc gaa atc gga agt gta att att ttc cct gga aca     1092
Gln Leu Ser Thr Ala Glu Ile Gly Ser Val Ile Ile Phe Pro Gly Thr
        290                 295                 300
```

```
atg agt gtc att att ttc ggc tac att ggt ggg ata ctt gtt gat aga      1140
Met Ser Val Ile Ile Phe Gly Tyr Ile Gly Gly Ile Leu Val Asp Arg
    305                 310                 315

aga ggt cct tta tac gtg tta aac atc gga gtt aca ttt ctt tct gtt      1188
Arg Gly Pro Leu Tyr Val Leu Asn Ile Gly Val Thr Phe Leu Ser Val
320                 325                 330                 335

agc ttt tta act gct tcc ttt ctt tta gaa aca aca tca tgg ttc atg      1236
Ser Phe Leu Thr Ala Ser Phe Leu Leu Glu Thr Thr Ser Trp Phe Met
                340                 345                 350

aca att ata atc gta ttt gtt tta ggt ggg ctt tcg ttc acc aaa aca      1284
Thr Ile Ile Ile Val Phe Val Leu Gly Gly Leu Ser Phe Thr Lys Thr
            355                 360                 365

gtt ata tca aca att gtt tca agt agc ttg aaa cag cag gaa gct ggt      1332
Val Ile Ser Thr Ile Val Ser Ser Ser Leu Lys Gln Gln Glu Ala Gly
        370                 375                 380

gct gga atg agt ttg ctt aac ttt acc agc ttt tta tca gag gga aca      1380
Ala Gly Met Ser Leu Leu Asn Phe Thr Ser Phe Leu Ser Glu Gly Thr
    385                 390                 395

ggt att gca att gta ggt ggt tta tta tcc ata ccc tta ctt gat caa      1428
Gly Ile Ala Ile Val Gly Gly Leu Leu Ser Ile Pro Leu Leu Asp Gln
400                 405                 410                 415

agg ttg tta cct atg gaa gtt gat cag tca act tat ctg tat agt aat      1476
Arg Leu Leu Pro Met Glu Val Asp Gln Ser Thr Tyr Leu Tyr Ser Asn
                420                 425                 430

ttg tta tta ctt ttt tca gga atc att gtc att agt tgg ctg gtt acc      1524
Leu Leu Leu Leu Phe Ser Gly Ile Ile Val Ile Ser Trp Leu Val Thr
            435                 440                 445

ttg aat gta tat aaa cat tct caa agg gat ttc taa atcgttaagg          1570
Leu Asn Val Tyr Lys His Ser Gln Arg Asp Phe
        450                 455

gatcaacttt gggagagagt tcaaaattga tcctttttttt ataacaggaa ttcaaatctt   1630

tttgttccat taaa                                                      1644


<210> SEQ ID NO 100
<211> LENGTH: 458
<212> TYPE: PRT
<213> ORGANISM: Bacillus cereus

<400> SEQUENCE: 100

Val Asn Thr Ser Tyr Ser Gln Ser Asn Leu Arg His Asn Gln Ile Leu
1               5                   10                  15

Ile Trp Leu Cys Ile Leu Ser Phe Phe Ser Val Leu Asn Glu Met Val
            20                  25                  30

Leu Asn Val Ser Leu Pro Asp Ile Ala Asn Asp Phe Asn Lys Pro Pro
        35                  40                  45

Ala Ser Thr Asn Trp Val Asn Thr Ala Phe Met Leu Thr Phe Ser Ile
    50                  55                  60

Gly Thr Ala Val Tyr Gly Lys Leu Ser Asp Gln Leu Gly Ile Lys Arg
65                  70                  75                  80

Leu Leu Leu Phe Gly Ile Ile Ile Asn Cys Phe Gly Ser Val Ile Gly
                85                  90                  95

Phe Val Gly His Ser Phe Phe Ser Leu Leu Ile Met Ala Arg Phe Ile
            100                 105                 110

Gln Gly Ala Gly Ala Ala Ala Phe Pro Ala Leu Val Met Val Val Val
        115                 120                 125

Ala Arg Tyr Ile Pro Lys Glu Asn Arg Gly Lys Ala Phe Gly Leu Ile
    130                 135                 140

Gly Ser Ile Val Ala Met Gly Glu Gly Val Gly Pro Ala Ile Gly Gly
```

```
145                 150                 155                 160

Met Ile Ala His Tyr Ile His Trp Ser Tyr Leu Leu Leu Ile Pro Met
                165                 170                 175

Ile Thr Ile Ile Thr Val Pro Phe Leu Met Lys Leu Leu Lys Lys Glu
            180                 185                 190

Val Arg Ile Lys Gly His Phe Asp Ile Lys Gly Ile Ile Leu Met Ser
        195                 200                 205

Val Gly Ile Val Phe Phe Met Leu Phe Thr Thr Ser Tyr Ser Ile Ser
    210                 215                 220

Phe Leu Ile Val Ser Val Leu Ser Phe Leu Ile Phe Val Lys His Ile
225                 230                 235                 240

Arg Lys Val Thr Asp Pro Phe Val Asp Pro Gly Leu Gly Lys Asn Ile
                245                 250                 255

Pro Phe Met Ile Gly Val Leu Cys Gly Gly Ile Ile Phe Gly Thr Val
            260                 265                 270

Ala Gly Phe Val Ser Met Val Pro Tyr Met Met Lys Asp Val His Gln
        275                 280                 285

Leu Ser Thr Ala Glu Ile Gly Ser Val Ile Ile Phe Pro Gly Thr Met
    290                 295                 300

Ser Val Ile Ile Phe Gly Tyr Ile Gly Gly Ile Leu Val Asp Arg Arg
305                 310                 315                 320

Gly Pro Leu Tyr Val Leu Asn Ile Gly Val Thr Phe Leu Ser Val Ser
                325                 330                 335

Phe Leu Thr Ala Ser Phe Leu Leu Glu Thr Thr Ser Trp Phe Met Thr
            340                 345                 350

Ile Ile Ile Val Phe Val Leu Gly Gly Leu Ser Phe Thr Lys Thr Val
        355                 360                 365

Ile Ser Thr Ile Val Ser Ser Ser Leu Lys Gln Gln Glu Ala Gly Ala
    370                 375                 380

Gly Met Ser Leu Leu Asn Phe Thr Ser Phe Leu Ser Glu Gly Thr Gly
385                 390                 395                 400

Ile Ala Ile Val Gly Gly Leu Leu Ser Ile Pro Leu Leu Asp Gln Arg
                405                 410                 415

Leu Leu Pro Met Glu Val Asp Gln Ser Thr Tyr Leu Tyr Ser Asn Leu
            420                 425                 430

Leu Leu Leu Phe Ser Gly Ile Ile Val Ile Ser Trp Leu Val Thr Leu
        435                 440                 445

Asn Val Tyr Lys His Ser Gln Arg Asp Phe
    450                 455
```

<210> SEQ ID NO 101
<211> LENGTH: 1374
<212> TYPE: DNA
<213> ORGANISM: Corynebacterium acetoacidophilum
<220> FEATURE:
<221> NAME/KEY: CDS
<222> LOCATION: (231)..(1010)
<223> OTHER INFORMATION: streptomycin adenylyltransferase

<400> SEQUENCE: 101

```
cgactctaga ggatcgatat atttctgatt ctggtgaagt ttcaaatgcg caggccttca     60

ccgttgagca tcatgaaatt gatgcgggaa ttcagcgcta tcttgcagat actgatgcag    120

atcccttgcg tcgagccgaa ccacttctga gtgccatgaa ggcgcttcgt cgacatattt    180

atctagaaga agaaattgtg ttcccgcatc ttcaacaagg cacgttaatc atg acc       236
                                                       Met Thr
                                                       1
```

```
atc gag att tcg aac cag ctc tcg gag gtc ctg agc gtc atc gag cgc      284
Ile Glu Ile Ser Asn Gln Leu Ser Glu Val Leu Ser Val Ile Glu Arg
        5                   10                  15

cat ctg gag tcc acg ttg ctg gcc atg cat ttg tac ggc tcc gca gtg      332
His Leu Glu Ser Thr Leu Leu Ala Met His Leu Tyr Gly Ser Ala Val
    20                  25                  30

gat ggc ggc ctg aag cca tac agc gat att gat ctc ctt gtt act gtg      380
Asp Gly Gly Leu Lys Pro Tyr Ser Asp Ile Asp Leu Leu Val Thr Val
35                  40                  45                  50

gcc gtg aag ctc gat gag acg acg cgc cga gca tta ctc aac gac ttg      428
Ala Val Lys Leu Asp Glu Thr Thr Arg Arg Ala Leu Leu Asn Asp Leu
                55                  60                  65

atg gag gct tcg gct ttc cca ggc gag agc gag acg ctc cga gct atc      476
Met Glu Ala Ser Ala Phe Pro Gly Glu Ser Glu Thr Leu Arg Ala Ile
            70                  75                  80

gag gtc aca ctt gtt gtg cat gac gat atc ata ccg tgg agg tac ccg      524
Glu Val Thr Leu Val Val His Asp Asp Ile Ile Pro Trp Arg Tyr Pro
        85                  90                  95

gct aag cgc gag ctg caa ttc gga gaa tgg cag cgc aac gac att ctg      572
Ala Lys Arg Glu Leu Gln Phe Gly Glu Trp Gln Arg Asn Asp Ile Leu
    100                 105                 110

gcg ggt atc ttc gag cca gcc atg atc gac att gat cta gct atc ctg      620
Ala Gly Ile Phe Glu Pro Ala Met Ile Asp Ile Asp Leu Ala Ile Leu
115                 120                 125                 130

ctt aca aaa gca aga gaa cat agc gtt gcc ttg gta ggt ccg gca gcg      668
Leu Thr Lys Ala Arg Glu His Ser Val Ala Leu Val Gly Pro Ala Ala
                135                 140                 145

gag gaa ttc ttt gac ccg gtt cct gaa cag gat cta ttc gag gcg ctg      716
Glu Glu Phe Phe Asp Pro Val Pro Glu Gln Asp Leu Phe Glu Ala Leu
            150                 155                 160

agg gaa acc ttg aag cta tgg aac tcg cag ccc gac tgg gcc ggc gat      764
Arg Glu Thr Leu Lys Leu Trp Asn Ser Gln Pro Asp Trp Ala Gly Asp
        165                 170                 175

gag cga aat gta gtg ctt acg ttg tcc cgc att tgg tac agc gca ata      812
Glu Arg Asn Val Val Leu Thr Leu Ser Arg Ile Trp Tyr Ser Ala Ile
    180                 185                 190

acc ggc aaa atc gcg ccg aag gat gtc gct gcc gac tgg gca ata aaa      860
Thr Gly Lys Ile Ala Pro Lys Asp Val Ala Ala Asp Trp Ala Ile Lys
195                 200                 205                 210

cgc cta cct gcc cag tat cag ccc gtc tta ctt gaa gct aag caa gct      908
Arg Leu Pro Ala Gln Tyr Gln Pro Val Leu Leu Glu Ala Lys Gln Ala
                215                 220                 225

tat ctg gga caa aaa gaa gat cac ttg gcc tca cgc gca gat cac ttg      956
Tyr Leu Gly Gln Lys Glu Asp His Leu Ala Ser Arg Ala Asp His Leu
            230                 235                 240

gaa gaa ttt att cgc ttt gtg aaa ggc gag atc atc aag tca gtt ggt     1004
Glu Glu Phe Ile Arg Phe Val Lys Gly Glu Ile Ile Lys Ser Val Gly
        245                 250                 255

aaa tga ctttgttcag cggacttgca cttggacgca ctggaaaaac atgcaaccgt      1060
Lys

tgttggagtc cacagaaccc gttggtgaaa caagtaaagc tactgctaaa taacctggat   1120

ctcgctaaaa cattggactg actttcaccg caaagttcgc aaatccacct tccggcatag   1180

tgccgccggc aagcaagtca cgaaccttat cctgctcatc agaagtgagg tccgaatcca   1240

tatgcggata gatgaatgcg ttcttccttc tggttgtgcc gatcaaggag ttgaaggatc   1300

tccgtgcaga tttcttccac ctgagtaggc tcaccgggac gagttgtgca gcgtgtccac   1360

aagcgcatcg atcc                                                     1374
```

<210> SEQ ID NO 102
<211> LENGTH: 259
<212> TYPE: PRT
<213> ORGANISM: Corynebacterium acetoacidophilum

<400> SEQUENCE: 102

```
Met Thr Ile Glu Ile Ser Asn Gln Leu Ser Glu Val Leu Ser Val Ile
1               5                   10                  15

Glu Arg His Leu Glu Ser Thr Leu Leu Ala Met His Leu Tyr Gly Ser
            20                  25                  30

Ala Val Asp Gly Gly Leu Lys Pro Tyr Ser Asp Ile Asp Leu Leu Val
        35                  40                  45

Thr Val Ala Val Lys Leu Asp Glu Thr Thr Arg Arg Ala Leu Leu Asn
    50                  55                  60

Asp Leu Met Glu Ala Ser Ala Phe Pro Gly Glu Ser Glu Thr Leu Arg
65                  70                  75                  80

Ala Ile Glu Val Thr Leu Val Val His Asp Asp Ile Ile Pro Trp Arg
                85                  90                  95

Tyr Pro Ala Lys Arg Glu Leu Gln Phe Gly Glu Trp Gln Arg Asn Asp
            100                 105                 110

Ile Leu Ala Gly Ile Phe Glu Pro Ala Met Ile Asp Ile Asp Leu Ala
        115                 120                 125

Ile Leu Leu Thr Lys Ala Arg Glu His Ser Val Ala Leu Val Gly Pro
    130                 135                 140

Ala Ala Glu Glu Phe Phe Asp Pro Val Pro Glu Gln Asp Leu Phe Glu
145                 150                 155                 160

Ala Leu Arg Glu Thr Leu Lys Leu Trp Asn Ser Gln Pro Asp Trp Ala
                165                 170                 175

Gly Asp Glu Arg Asn Val Val Leu Thr Leu Ser Arg Ile Trp Tyr Ser
            180                 185                 190

Ala Ile Thr Gly Lys Ile Ala Pro Lys Asp Val Ala Ala Asp Trp Ala
        195                 200                 205

Ile Lys Arg Leu Pro Ala Gln Tyr Gln Pro Val Leu Leu Glu Ala Lys
    210                 215                 220

Gln Ala Tyr Leu Gly Gln Lys Glu Asp His Leu Ala Ser Arg Ala Asp
225                 230                 235                 240

His Leu Glu Glu Phe Ile Arg Phe Val Lys Gly Glu Ile Ile Lys Ser
                245                 250                 255

Val Gly Lys
```

<210> SEQ ID NO 103
<211> LENGTH: 3451
<212> TYPE: DNA
<213> ORGANISM: Artificial Sequence
<220> FEATURE:
<223> OTHER INFORMATION: Cloning vector pZEO
<220> FEATURE:
<221> NAME/KEY: CDS
<222> LOCATION: (2884)..(3258)
<223> OTHER INFORMATION: Sh protein

<400> SEQUENCE: 103

```
ggatccgctg tggaatgtgt gtcagttagg gtgtggaaag tccccaggct ccccagcagg      60

cagaagtatg caaagcatgc atctcaatta gtcagcaacc aggtgtggaa agtccccagg     120

ctccccagca ggcagaagta tgcaaagcat gcatctcaat tagtcagcaa ccatagtccc     180

gcccctaact ccgcccatcc cgcccctaac tccgcccagt tccgcccatt ctccgcccca     240
```

-continued

```
tggctgacta atttttttta tttatgcaga ggccgaggcc gcctcggcct ctgagctatt    300
ccagaagtag tgaggaggct tttttggagg cctaggcttt tgcaaaaagc ttattaaccc    360
tcactaaagg gagtactagt accggtacct cgagaattcg aacgcgtgat cagctgttct    420
atagtgtcac ctaaatagct tcgaggtcga cctcgaaact tgtttattgc agcttataat    480
ggttacaaat aaagcaatag catcacaaat ttcacaaata aagcattttt ttcactgcat    540
tctagttgtg gtttgtccaa actcatcaat gtatcttatc atgtctggat ccctcggaga    600
tctgggccca tgcggccgcg gatcgatgct cactcaaagg cggtaatacg gttatccaca    660
gaatcagggg ataacgcagg aaagaacatg tgagcaaaag gccagcaaaa ggccaggaac    720
cgtaaaaagg ccgcgttgct ggcgtttttc cataggctcc gcccccctga cgagcatcac    780
aaaaatcgac gctcaagtca gaggtggcga aacccgacag gactataaag ataccaggcg    840
tttccccctg gaagctccct cgtgcgctct cctgttccga ccctgccgct taccggatac    900
ctgtccgcct ttctcccttc gggaagcgtg gcgctttctc aatgctcacg ctgtaggtat    960
ctcagttcgg tgtaggtcgt tcgctccaag ctgggctgtg tgcacgaacc ccccgttcag   1020
cccgaccgct gcgccttatc cggtaactat cgtcttgagt ccaacccggt aagacacgac   1080
ttatcgccac tggcagcagc cactggtaac aggattagca gagcgaggta tgtaggcggt   1140
gctacagagt tcttgaagtg gtggcctaac tacggctaca ctagaagaac agtatttggt   1200
atctgcgctc tgctgaagcc agttaccttc ggaaaaagag ttggtagctc ttgatccggc   1260
aaacaaacca ccgctggtag cggtggtttt tttgtttgca agcagcagat tacgcgcaga   1320
aaaaaaggat ctcaagaaga tcctttgatc ttttctacgg ggtctgacgc tcagtggaac   1380
gaaaactcac gttaagggat tttggtcatg acattaacct ataaaaatag gcgtatcacg   1440
aggccctttc gtctcgcgcg tttcggtgat gacggtgaaa acctctgaca catgcagctc   1500
ccggagacgg tcacagcttg tctgtaagcg gatgccggga gcagacaagc ccgtcagggc   1560
gcgtcagcgg gtgttggcgg gtgtcggggc tggcttaact atgcggcatc agagcagatt   1620
gtactgagag tgcaccatat gcggtgtgaa ataccgcaca gatgcgtaag gagaaaatac   1680
cgcatcaggc gacgcgccct gtagcggcgc attaagcgcg gcgggtgtgg tggttacgcg   1740
cagcgtgacc gctacacttg ccagcgccct agcgcccgct cctttcgctt tcttcccttc   1800
ctttctcgcc acgttcgccg gctttccccg tcaagctcta aatcgggggc tccctttagg   1860
gttccgattt agagctttac ggcacctcga ccgcaaaaaa cttgatttgg gtgatggttc   1920
acgtagtggg ccatcgccct gatagacggt ttttcgccct ttgacgttgg agtccacgtt   1980
ctttaatagt ggactcttgt tccaaactgg aacaacactc aaccctatct cggtctattc   2040
ttttgattta taagggattt tgccgatttc ggcctattgg ttaaaaaatg agctgattta   2100
acaaatattt aacgcgaatt ttaacaaaat attaacgttt acaatttcca ttcgccattc   2160
aggctgcaac tagatctaga gtccgttaca taacttacgg taaatggccc gcctggctga   2220
ccgcccaacg acccccgccc attgacgtca ataatgacgt atgttcccat agtaacgcca   2280
atagggactt tccattgacg tcaatgggtg gagtatttac ggtaaactgc ccacttggca   2340
gtacatcaag tgtatcatat gccaagtacg ccccctattg acgtcaatga cggtaaatgg   2400
cccgcctggc attatgccca gtacatgacc ttatgggact ttcctacttg gcagtacatc   2460
tacgtattag tcatcgctat taccatggtg atgcggtttt ggcagtacat caatgggcgt   2520
ggatagcggt ttgactcacg gggatttcca agtctccacc ccattgacgt caatgggagt   2580
ttgttttggc accaaaatca acgggacttt ccaaaatgtc gtaacaactc cgccccattg   2640
```

-continued

```
acgcaaatgg gcggtaggcg tgtacggtgg gaggtctata taagcagagc tcgtttagtg   2700

aaccgtcaga tcgcctggag acgccatcca cgctgttttg acctccatag aagacaccgg   2760

gaccgatcca gcctccgcgg ccgggaacgg tgcattggaa cggacctgca gcacgtgttg   2820

acaattaatc atcggcatag tatatcggca tagtataata cgactcacta taggagggcc   2880

acc atg gcc aag ttg acc agt gcc gtt ccg gtg ctc acc gcg cgc gac     2928
    Met Ala Lys Leu Thr Ser Ala Val Pro Val Leu Thr Ala Arg Asp
    1               5                   10                  15

gtc gcc gga gcg gtc gag ttc tgg acc gac cgg ctc ggg ttc tcc cgg     2976
Val Ala Gly Ala Val Glu Phe Trp Thr Asp Arg Leu Gly Phe Ser Arg
                20                  25                  30

gac ttc gtg gag gac gac ttc gcc ggt gtg gtc cgg gac gac gtg acc     3024
Asp Phe Val Glu Asp Asp Phe Ala Gly Val Val Arg Asp Asp Val Thr
            35                  40                  45

ctg ttc atc agc gcg gtc cag gac cag gtg gtg ccg gac aac acc ctg     3072
Leu Phe Ile Ser Ala Val Gln Asp Gln Val Val Pro Asp Asn Thr Leu
        50                  55                  60

gcc tgg gtg tgg gtg cgc ggc ctg gac gag ctg tac gcc gag tgg tcg     3120
Ala Trp Val Trp Val Arg Gly Leu Asp Glu Leu Tyr Ala Glu Trp Ser
    65                  70                  75

gag gtc gtg tcc acg aac ttc cgg gac gcc tcc ggg ccg gcc atg acc     3168
Glu Val Val Ser Thr Asn Phe Arg Asp Ala Ser Gly Pro Ala Met Thr
80                  85                  90                  95

gag atc ggc gag cag ccg tgg ggg cgg gag ttc gcc ctg cgc gac ccg     3216
Glu Ile Gly Glu Gln Pro Trp Gly Arg Glu Phe Ala Leu Arg Asp Pro
                100                 105                 110

gcc ggc aac tgc gtg cac ttc gtg gcc gag gag cag gac tga             3258
Ala Gly Asn Cys Val His Phe Val Ala Glu Glu Gln Asp
            115                 120

ccgacgccga ccaacaccgc cggtccgacg gcggcccacg ggtcccaggg gggtcgacct   3318

cgaaacttgt ttattgcagc ttataatggt tacaaataaa gcaatagcat cacaaatttc   3378

acaaataaag catttttttc actgcattct agttgtggtt tgtccaaact catcaatgta   3438

tcttatcatg tct                                                      3451


<210> SEQ ID NO 104
<211> LENGTH: 124
<212> TYPE: PRT
<213> ORGANISM: Artificial Sequence
<220> FEATURE:
<223> OTHER INFORMATION: Synthetic Construct

<400> SEQUENCE: 104

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
```

```
        115                 120


<210> SEQ ID NO 105
<211> LENGTH: 1997
<212> TYPE: DNA
<213> ORGANISM: Agrobacterium tumefaciens
<220> FEATURE:
<221> NAME/KEY: CDS
<222> LOCATION: (688)..(1410)
<223> OTHER INFORMATION: isopentenyl transferase

<400> SEQUENCE: 105

gatcctgtta caagtattgc acgttttata aattgcatat taatgcaatc ttgatgttta      60

acaacgaagg taatggcgta aaagaaaaaa tgtatgttat tgtattgatc tttcattatg     120

ttgaagtgtg ccataatatg atgtataagt aaaatatcaa ctgtcgcatt tattgaaatg     180

gcactgttat ttcaaccata tctttgattc tgtgacaatg acaacgactg caagaagtaa     240

ataatagacg ccgttgttaa aggattgcta tcatatgtgc ctaactatag ggacatttac     300

gtcaattgtg aaatagtcgc ccttattttg acgtctcacc taatcaaata ttacaaacga     360

tctcactctg tcgccagcaa tggtgtaatc agcgcagaca agtggcagta aagcgcggaa     420

aaacgtcccc gagtggcatg aatagctgcc tctgtattgc tgatttagtc agccttattt     480

gacttaaggg tgccctcgtt agtgacaaat tgctttcaag gagacagcca tgccccacac     540

tgtgttgaaa aacaaattgc cctttgggga gacggtaaag ccagttgctc ttcaataagg     600

aatctcgagg aggcaatata accgcctctg gtagtacact tctctaatcc aaaaatcaat     660

ttgtattcaa gataccgcaa aaaactt atg gat ctg cgt cta att ttc ggt cca     714
                              Met Asp Leu Arg Leu Ile Phe Gly Pro
                              1               5

act tgc aca gga aag acg tcg acc gcg gta gct ctt gcc cag cag act      762
Thr Cys Thr Gly Lys Thr Ser Thr Ala Val Ala Leu Ala Gln Gln Thr
10                  15                  20                  25

ggg ctt cca gtc ctt tcg ctc gat cgg gtc caa tgt tgt cct cag ctg      810
Gly Leu Pro Val Leu Ser Leu Asp Arg Val Gln Cys Cys Pro Gln Leu
                30                  35                  40

tca acc gga agc gga cga cca aca gtg gaa gaa ctg aaa gga acg agc      858
Ser Thr Gly Ser Gly Arg Pro Thr Val Glu Glu Leu Lys Gly Thr Ser
            45                  50                  55

cgt cta tac ctt gat gat cgg cct ctg gtg aag ggt atc atc gca gcc      906
Arg Leu Tyr Leu Asp Asp Arg Pro Leu Val Lys Gly Ile Ile Ala Ala
        60                  65                  70

aag caa gct cat gaa agg ctg atg ggg gag gtg tat aat tat gag gcc      954
Lys Gln Ala His Glu Arg Leu Met Gly Glu Val Tyr Asn Tyr Glu Ala
    75                  80                  85

cac ggc ggg ctt att ctt gag gga gga tct atc tcg ttg ctc aag tgc     1002
His Gly Gly Leu Ile Leu Glu Gly Gly Ser Ile Ser Leu Leu Lys Cys
90                  95                  100                 105

atg gcg caa agc agt tat tgg agt gcg gat ttt cgt tgg cat att att     1050
Met Ala Gln Ser Ser Tyr Trp Ser Ala Asp Phe Arg Trp His Ile Ile
                110                 115                 120

cgc cac gag tta gca cac gag gag acc ttc atg aac gtg gcc aag gcc     1098
Arg His Glu Leu Ala His Glu Glu Thr Phe Met Asn Val Ala Lys Ala
            125                 130                 135

aga gtt aag cag atg tta cgc ccc gct tca ggc ctt tct att atc caa     1146
Arg Val Lys Gln Met Leu Arg Pro Ala Ser Gly Leu Ser Ile Ile Gln
        140                 145                 150

gag ttg gtt gat ctt tgg aaa gag cct cgg ctg agg cgc ata ctg aaa     1194
Glu Leu Val Asp Leu Trp Lys Glu Pro Arg Leu Arg Arg Ile Leu Lys
    155                 160                 165
```

```
gag atc gat gga tat cga tat gcc atg ttg ttt gtt agc cag aac cag     1242
Glu Ile Asp Gly Tyr Arg Tyr Ala Met Leu Phe Val Ser Gln Asn Gln
170                 175                 180                 185

atc aca tcc gat atg cta ttg cag ctt gac gca gat atg gag gat aag     1290
Ile Thr Ser Asp Met Leu Leu Gln Leu Asp Ala Asp Met Glu Asp Lys
                190                 195                 200

ttg att cat ggg atc gct cag gag tat ctc atc cat gca cgc cga caa     1338
Leu Ile His Gly Ile Ala Gln Glu Tyr Leu Ile His Ala Arg Arg Gln
            205                 210                 215

gaa cag aaa ttc cct cga gtt aac gca gcc gct tac gac gga ttc gaa     1386
Glu Gln Lys Phe Pro Arg Val Asn Ala Ala Ala Tyr Asp Gly Phe Glu
        220                 225                 230

ggt cat cca ttc gga atg tat tag tttgcaccag ctccgcgtca cacctgtctt    1440
Gly His Pro Phe Gly Met Tyr
    235                 240

catttgaata agatgttcgc aattgttttt agctttgtct tgttgtggca gggcggcaag   1500

tgcttcagac atcatcctgt tttcaaaatt tatgctggtg aacagcttct taattccttt   1560

ggaaatacta gactgcgtct taaaattacg atgtctagat gaagatgtga ttgtaaaata   1620

acctatttaa gttttcattt agaacataag ttttatgaat gttcttccat tttcgtcatc   1680

gaacgaataa gagtaaatac acctttttta acattataaa aataagttct tatacgttgt   1740

ttatacaccg ggaatcattt ccattatttt cgcgcaaaaa gtcacggata ttcgtgaaag   1800

cgacaaaaac tgcgaaattt gcggggagtg tcttcagttt gcctattaat atttagtttg   1860

acactaattg ttaccattgc agccaagctc agctgtttct tttcttaaaa acgcaggatc   1920

gaaagagcat gactcggcaa ggttggcttg taccatgcat ttctcatgcc aaagatgatc   1980

aactgcaggt cgactct                                                  1997


<210> SEQ ID NO 106
<211> LENGTH: 240
<212> TYPE: PRT
<213> ORGANISM: Agrobacterium tumefaciens

<400> SEQUENCE: 106

Met Asp Leu Arg Leu Ile Phe Gly Pro Thr Cys Thr Gly Lys Thr Ser
1               5                   10                  15

Thr Ala Val Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Ser Arg Leu Tyr Leu Asp Asp Arg
    50                  55                  60

Pro Leu Val Lys Gly Ile Ile Ala Ala Lys Gln Ala His Glu Arg Leu
65                  70                  75                  80

Met Gly Glu Val Tyr Asn Tyr Glu Ala His Gly Gly Leu Ile Leu Glu
                85                  90                  95

Gly Gly Ser Ile Ser Leu Leu Lys Cys Met Ala Gln Ser Ser Tyr Trp
            100                 105                 110

Ser Ala Asp Phe Arg Trp His Ile Ile Arg His Glu Leu Ala His Glu
        115                 120                 125

Glu Thr Phe Met Asn Val Ala Lys Ala Arg Val Lys Gln Met Leu Arg
    130                 135                 140

Pro Ala Ser Gly Leu Ser Ile Ile Gln Glu Leu Val Asp Leu Trp Lys
145                 150                 155                 160

Glu Pro Arg Leu Arg Arg Ile Leu Lys Glu Ile Asp Gly Tyr Arg Tyr
                165                 170                 175
```

-continued

```
Ala Met Leu Phe Val Ser Gln Asn Gln Ile Thr Ser Asp Met Leu Leu
            180                 185                 190

Gln Leu Asp Ala Asp Met Glu Asp Lys Leu Ile His Gly Ile Ala Gln
        195                 200                 205

Glu Tyr Leu Ile His Ala Arg Arg Gln Glu Gln Lys Phe Pro Arg Val
    210                 215                 220

Asn Ala Ala Ala Tyr Asp Gly Phe Glu Gly His Pro Phe Gly Met Tyr
225                 230                 235                 240
```